United States Patent
De Tavernier et al.

(10) Patent No.: US 11,312,788 B2
(45) Date of Patent: Apr. 26, 2022

(54) PSEUDOMONAS AERUGINOSA PCRV BINDING SINGLE VARIABLE DOMAIN ANTIBODIES

(71) Applicant: Ablynx N.V., Ghent-Zwijnaarde (BE)

(72) Inventors: Evelyn De Tavernier, Deurle (BE); Ann Union, Aalter (BE); Bruno Dombrecht, Heusden (BE); Guy Hermans, Merelbeke (BE); Erika Morizzo, Ghent (BE)

(73) Assignee: Ablynx N.V., Zwijnaarde (BE)

( * ) Notice: Subject to any disclaimer, the term of this patent is extended or adjusted under 35 U.S.C. 154(b) by 261 days.

(21) Appl. No.: 16/037,411

(22) Filed: Jul. 17, 2018

(65) Prior Publication Data

US 2019/0055322 A1 Feb. 21, 2019
US 2020/0190217 A9 Jun. 18, 2020

Related U.S. Application Data

(62) Division of application No. 14/382,027, filed as application No. PCT/EP2013/054262 on Mar. 4, 2013, now Pat. No. 10,072,098.

(60) Provisional application No. 61/606,094, filed on Mar. 2, 2012.

(51) Int. Cl.
C07K 16/46 (2006.01)
C07K 16/12 (2006.01)
A61K 39/00 (2006.01)

(52) U.S. Cl.
CPC ........ C07K 16/468 (2013.01); C07K 16/1214 (2013.01); A61K 2039/505 (2013.01); C07K 2317/31 (2013.01); C07K 2317/565 (2013.01); C07K 2317/567 (2013.01); C07K 2317/569 (2013.01); C07K 2317/626 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 10,072,098 B2 * | 9/2018 | De Tavernier | A61P 11/00 |
| 2007/0020685 A1 * | 1/2007 | Yarranton | C07K 16/00 435/7.1 |
| 2010/0129368 A9 | 5/2010 | Lasters et al. | |
| 2014/0302038 A1 * | 10/2014 | Dimasi | C07K 16/22 424/136.1 |
| 2015/0023966 A1 | 1/2015 | Digiandomenico | |

FOREIGN PATENT DOCUMENTS

| | | |
|---|---|---|
| EP | 0527809 A1 | 2/1993 |
| EP | 2248826 A1 | 11/2010 |
| JP | 2009510998 A | 3/2009 |
| JP | 2015-509723 A | 4/2015 |
| WO | WO 2002/064161 A2 | 8/2002 |
| WO | WO 2005/003345 A2 | 1/2005 |
| WO | WO 2006/023144 A2 | 3/2006 |
| WO | WO 2009/073631 A2 | 6/2009 |
| WO | WO 2009/088032 A1 | 7/2009 |
| WO | WO 2010/066835 A2 | 6/2010 |

OTHER PUBLICATIONS

Greenspan et al. 1999 (Defining epitopes: It's not as easy as it seems; Nature Biotechnology, 17:936-937). (Year: 1999).*
Rudikoff et al. 1982 (Single amino acid substitution altering antigen-binding specificity; PNAS, USA, 79(6):1979-1983) (Year: 1982).*
[No Author Listed], Anti-PcrV Program Fact Sheet (KB001). Kalo Bios.
Baer et al., An engineered human antibody Fab fragment specific for Pseudomonas aeruginosa PcrV antigen has potent antibacterial activity. Infect Immun. Mar. 2009;77(3):1083-90. doi: 10.1128/IAI. 00815-08. Epub Dec. 22, 2008.
Davies et al., 'Camelising' human antibody fragments: NMR studies on VH domains. FEBS Lett. Feb. 21, 1994;339(3):285-90.
Davies et al., Antibody VH domains as small recognition units. Biotechnology (N Y). May 1995;13(5):475-9.
Davies et al., Single antibody domains as small recognition units: design and in vitro antigen selection of camelized, human VH domains with improved protein stability. Protein Eng. Jun. 1996;9(6): 531-7.
De Tavernier et al., High throughput combinatorial formatting of PcrV Nanobodies for efficient potency improvement. J Biol Chem. Jul. 15, 2016;291(29):15243-55. doi: 10.1074/jbc.M115.684241. Epub May 20, 2016.
Decanniere et al., A single-domain antibody fragment in complex with RNase A: non-canonical loop structures and nanomolar affinity using two CDR loops. Structure. Apr. 15, 1999;7(4):361-70.
Desmyter et al., Crystal structure of a camel single-domain VH antibody fragment in complex with lysozyme. Nat Struct Biol. Sep. 1996;3(9):803-11.
Doring et al., Vaccines and immunotherapy against Pseudomonas aeruginosa. Vaccine. Feb. 20, 2008;26(8):1011-24. doi: 10.1016/j. vaccine.2007.12.007. Epub Dec. 26, 2007.
El Solh et al., Persistent infection with Pseudomonas aeruginosa in ventilator-associated pneumonia. Am J Respir Crit Care Med. Sep. 1, 2008;178(5):513-9. doi: 10.1164/rccm.200802-239OC. Epub May 8, 2008.
El Solh et al., Update on the treatment of Pseudomonas aeruginosa pneumonia. J Antimicrob Chemother. Aug. 2009;64(2):229-38. doi: 10.1093/jac/dkp201. Epub Jun. 11, 2009.

(Continued)

Primary Examiner — Mary Maille Lyons
(74) Attorney, Agent, or Firm — Wolf, Greenfield & Sacks, P.C.

(57) ABSTRACT

Polypeptides are provided that are capable of significantly inhibiting and/or neutralizing *P. aeruginosa*. The polypeptides comprise two or more immunoglobulin single variable domains that are directed against the PcrV protein of *P. aeruginosa*, wherein the "first" immunoglobulin single variable domain and the "second" immunoglobulin single variable domain have different paratopes.

18 Claims, 14 Drawing Sheets

Figure 1A:
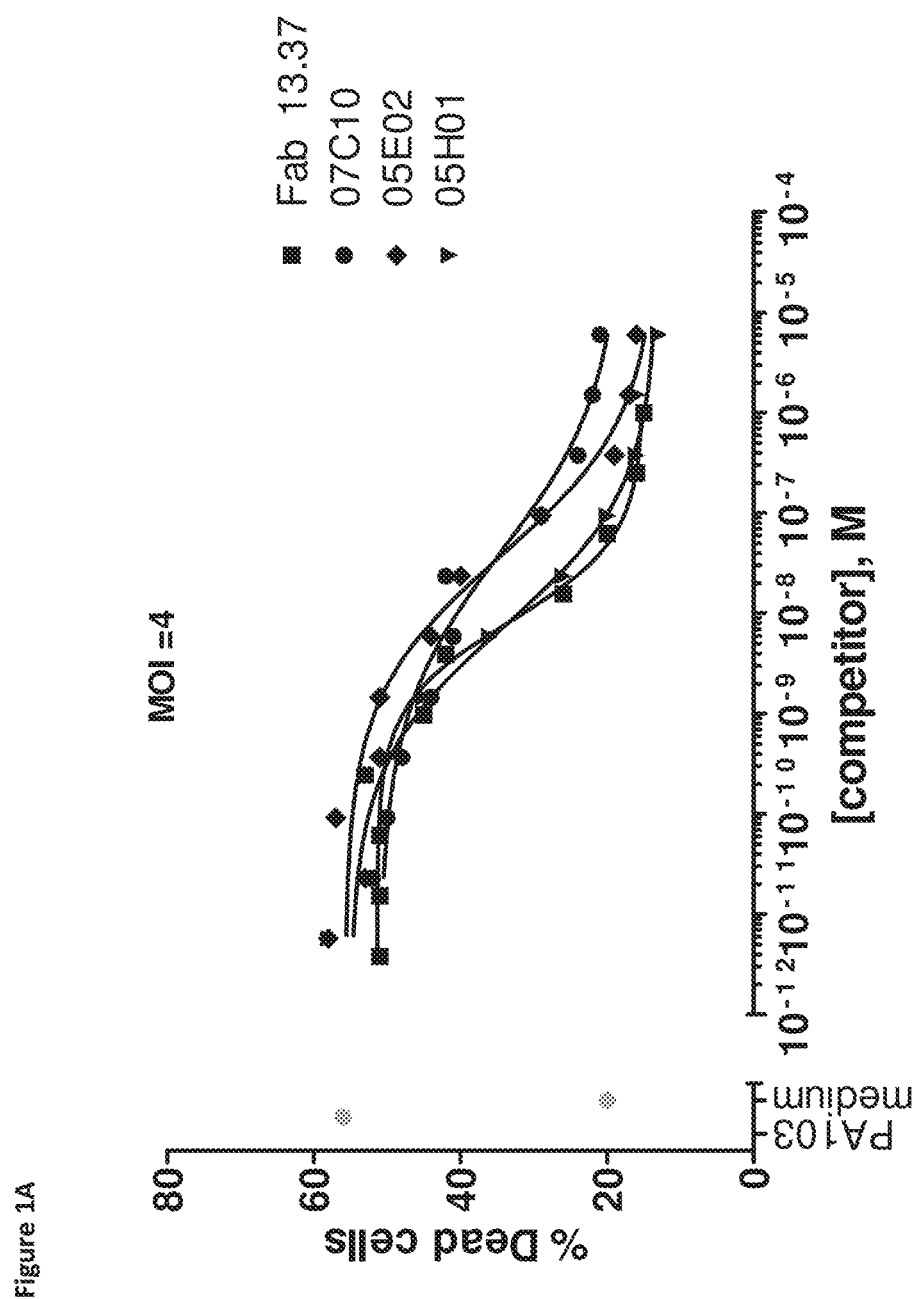
Figure 1B:
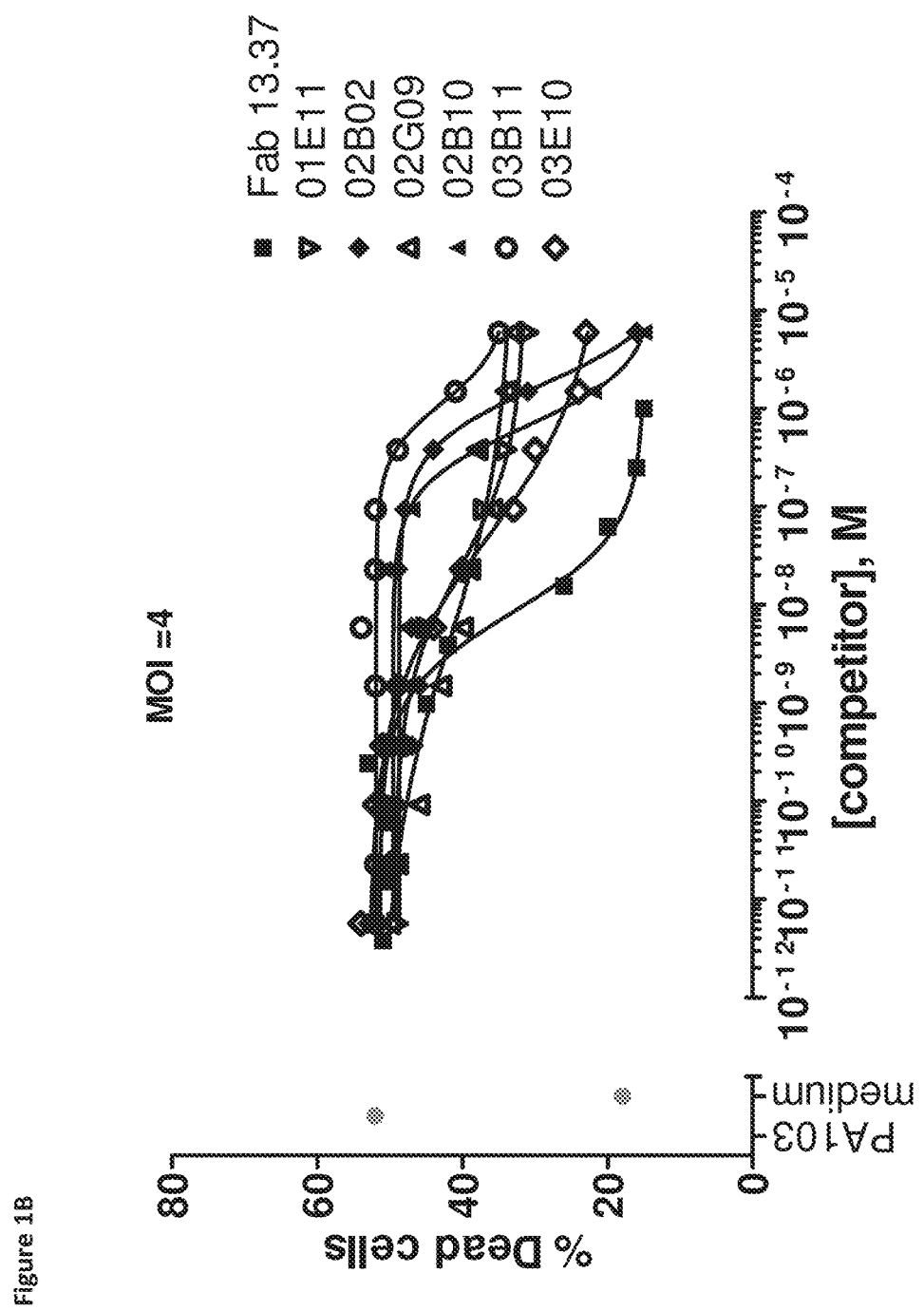
Figure 1C:
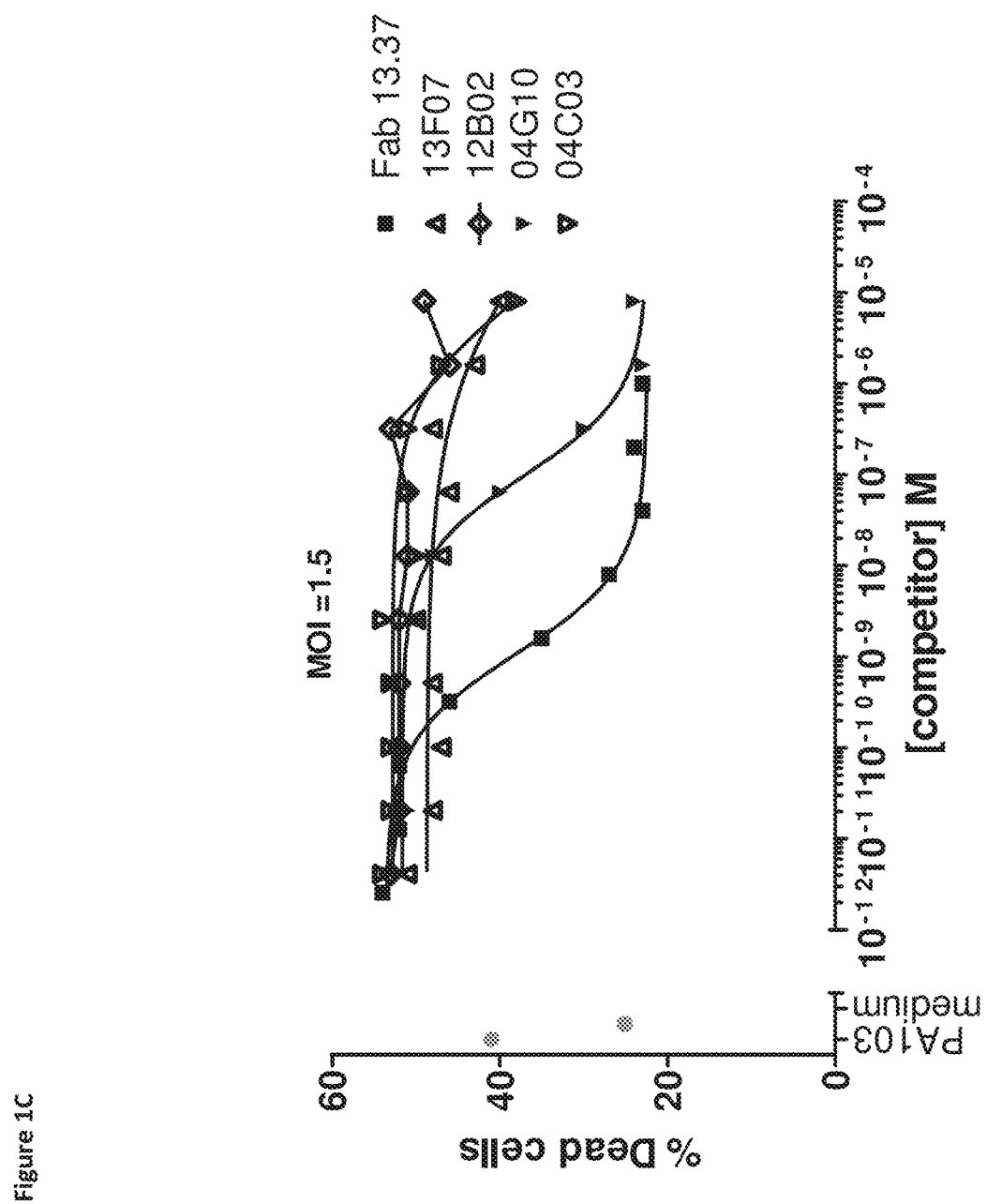
Figure 1D:
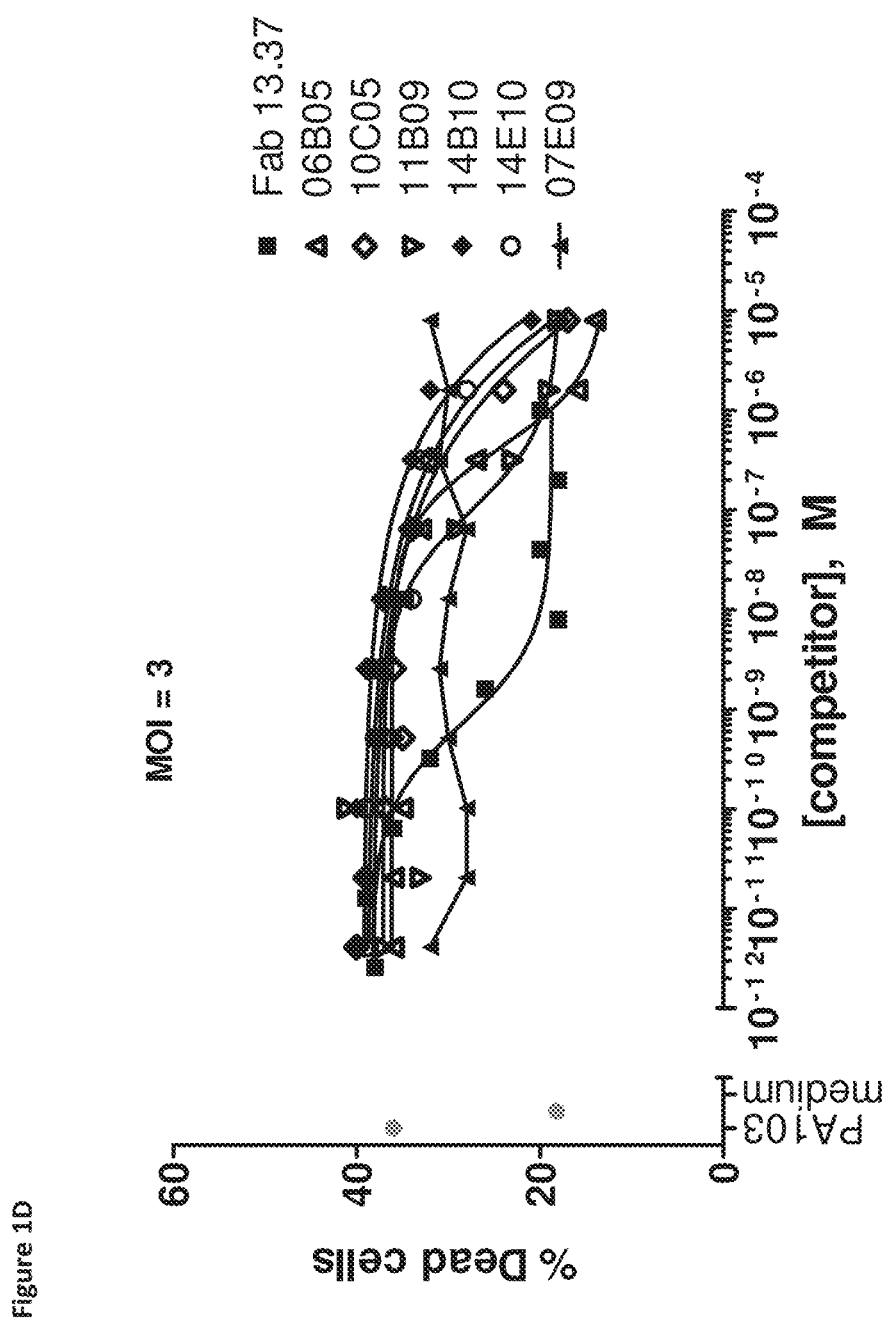

Specification includes a Sequence Listing.

(56) References Cited

OTHER PUBLICATIONS

Faure et al., Effects of monoclonal anti-PcrV antibody on Pseudomonas aeruginosa-induced acute lung injury in a rat model. J Immune Based Ther Vaccines. Aug. 13, 2003;1(1):2.

Fitzsimmons, The changing epidemiology of cystic fibrosis. J Pediatr. Jan. 1993;122(1):1-9.

Frank et al., Generation and characterization of a protective monoclonal antibody to Pseudomonas aeruginosa PcrV. J Infect Dis. Jul. 1, 2002;186(1):64-73. Epub Jun. 14, 2002.

Ghahroudi et al., Selection and identification of single domain antibody fragments from camel heavy-chain antibodies; FEBS. 1997;414:521-52.

Giamarellou et al., Current therapies for pseudomonas aeruginosa. Crit Care Clin. Apr. 2008;24(2):261-78, viii. doi: 10.1016/j.ccc.2007.12.004.

Greenspan et al., Defining epitopes: It's not as easy as it seems; Nature Biotechnology. 1999;17:936-937.

Jones et al., Replacing the complementarity-determining regions in a human antibody with those from a mouse. Nature. May 29-Jun. 4, 1986;321(6069):522-5.

Kerem et al., Pulmonary function and clinical course in patients with cystic fibrosis after pulmonary colonization with Pseudomonas aeruginosa. J Pediatr. May 1990;116(5):714-9.

Kontermann, Dual targeting strategies with bispecific antibodies. MAbs. Mar.-Apr. 2012;4(2):182-97. doi: 10.4161/mabs.4.2.19000. Epub Mar. 1, 2012.

Lee et al., Activities of Pseudomonas aeruginosa effectors secreted by the Type III secretion system in vitro and during infection. Infect Immun. Mar. 2005;73(3):1695-705.

Lee, Eradication of early Pseudomonas infection in cystic fibrosis. Chron Respir Dis. 2009;6(2):99-107. doi: 10.1177/1479972309104661.

Luyt et al., Aerosolized antibiotics to treat ventilator-associated pneumonia. Curr Opin Infect Dis. Apr. 2009;22(2):154-8. doi: 10.1097/QCO.0b013e328322a006.

Lyczak et al., Lung infections associated with cystic fibrosis. Clin Microbiol Rev. Apr. 2002;15(2):194-222.

Lynch et al., Polymorphisms in the Pseudomonas aeruginosa type III secretion protein, PcrV-implications for anti-PcrV immunotherapy. Microb Pathog. Jun. 2010;48(6):197-204. doi: 10.1016/j.micpath.2010.02.008. Epub Mar. 6, 2010.

Moriyama et al., Protective effects of affinity-purified antibody and truncated vaccines against Pseudomonas aeruginosa V-antigen in neutropenic mice. Microbiol Immunol. Nov. 2009;53(11):587-94. doi: 10.1111/j.1348-0421.2009.00165.x.

Murphy, Pseudomonas aeruginosa in adults with chronic obstructive pulmonary disease. Curr Opin Pulm Med. Mar. 2009;15(2):138-42. doi: 10.1097/MCP.0b013e328321861a.

Muyldermans et al., Unique single-domain antigen binding fragments derived from naturally occurring camel heavy-chain antibodies. J Mol Recognit. Mar.-Apr. 1999;12(2):131-40.

Muyldermans Single domain camel antibodies: current status. J Biotechnol. Jun. 2001;74(4):277-302.

Page et al., Prospects for the next anti-Pseudomonas drug. Curr Opin Pharmacol. Oct. 2009;9(5):558-65. doi: 10.1016/j.coph.2009.08.006. Epub Sep. 12, 2009.

Papalia et al., High-resolution characterization of antibody fragment/antigen interactions using Biacore T100. Anal Biochem. Dec. 1, 2006;359(1):112-9. Epub Sep. 22, 2006.

Rajpal et al., A general method for greatly improving the affinity of antibodies by using combinatorial libraries. Proc Natl Acad Sci USA. Jun. 14, 2005;102(24):8466-71. Epub Jun. 6, 2005.

Riechmann et al., Single domain antibodies: comparison of camel VH and camelised human VH domains. J Immunol Methods. Dec. 10, 1999;231(1-2):25-38.

Riechmann, Rearrangement of the former VL interface in the solution structure of a camelised, single antibody VH domain. J Mol Biol. Jun. 28, 1996;259(5):957-69.

Roux et al., Novel therapies for Pseudomonas aeruginosa pneumonia. Infect Disord Drug Targets. Aug. 2011;11(4):389-94.

Rudikoff et al. 1982 (Single amino acid substitution altering antigen-binding specificity; PNAS, USA, 79(6):1979-1983).

Sato et al., Modified needle-tip PcrV proteins reveal distinct phenotypes relevant to the control of type III secretion and intoxication by Pseudomonas aeruginosa. PLoS One. Mar. 29, 2011;6(3):e18356. doi: 10.1371/journal.pone.0018356.

Sato et al., Multi-functional characteristics of the Pseudomonas aeruginosa type III needle-tip protein, PcrV; comparison to orthologs in other Gram-negative bacteria. Front Microbiol. Jul. 4, 2011;2:142. doi: 10.3389/fmicb.2011.00142. eCollection2011.

Scott et al., Next generation antibody therapeutics: Antibody fragments, dual-targeting strategies, and beyond. Euro Pharma Rev. Oct. 9, 2009.

Sela-Culang et al. 2013 (The structural basis of antibody-antigen recognition; Frontiers in Immunology 4(302):1-13).

Spinelli et al., The crystal structure of a llama heavy chain variable domain. Nat Struct Biol. Sep. 1996;3(9):752-7.

Velasco et al., Bloodstream infection surveillance in a cancer centre: a prospective look at clinical microbiology aspects. Clin Microbiol Infect. Jun. 2004;10(6):542-9.

Wernery et al. 2002; Infectious Disease in Camelids; 2nd edition, Blackwell Science, Berlin (ISBN 3-8263-3304-7).

Wesolowski et al., Single domain antibodies: promising experimental and therapeutic tools in infection and immunity. Med Microbiol Immunol. Aug. 2009;198(3):157-74. doi: 10.1007/s00430-009-0116-7. Epub Jun. 16, 2009.

PCTEP2013054262, Sep. 12, 2014, International Preliminary Report on Patentability.

PCTEP2013054262, Jun. 28, 2013, International Search Report and Written Opinion.

\* cited by examiner

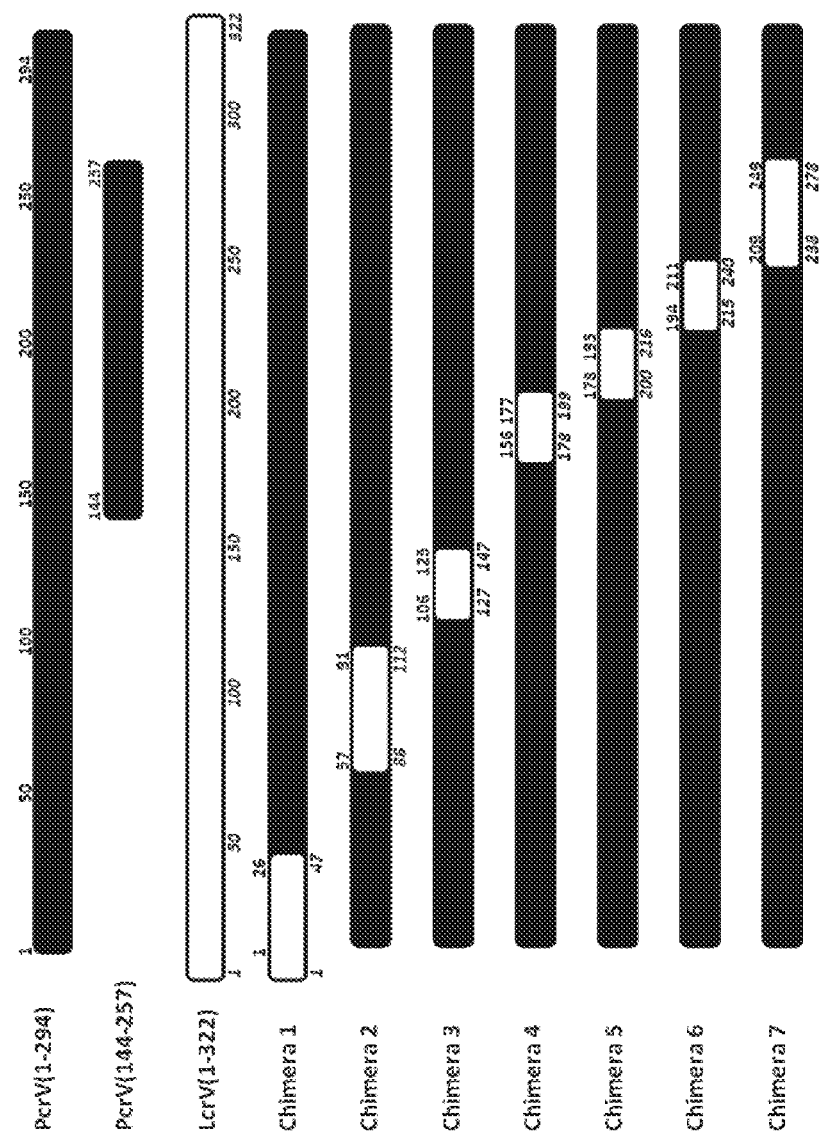

SEQUENCE LISTING

```
<160> NUMBER OF SEQ ID NOS: 207

<210> SEQ ID NO 1
<211> LENGTH: 126
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Thr Ser Asn Ser Gly Ser Thr Tyr Tyr Gly Gly Ser Val Lys
    50                  55                  60

Gly Arg Phe Thr Ala Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Val
                85                  90                  95

Ala Thr Ile Gly Cys Ala Thr Leu Gly Gly Thr Leu Asp Val Gln Arg
            100                 105                 110

Tyr Tyr Tyr Arg Gly Gln Gly Thr Gln Val Thr Val Ser Ser
        115                 120                 125
```

```
<210> SEQ ID NO 2
<211> LENGTH: 120
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Ala Gly
1               5                   10                  15

Ser Leu Arg Leu Ser Cys Thr Ala Ser Gly Arg Thr Leu Ser Ser Tyr
            20                  25                  30

Thr Met Gly Trp Phe Arg Gln Ala Pro Gly Thr Glu Arg Glu Phe Val
            35                  40                  45

Ala Ala Met Thr Arg Ser Gly Phe Asn Thr Tyr Tyr Ala Asp Ser Val
        50                  55                  60

Lys Gly Arg Phe Thr Ile Ser Arg Asp Ser Thr Glu Asn Thr Met Ala
65                  70                  75                  80

Leu Gln Met Ser Ser Leu Lys Pro Glu Asp Thr Ala Val Tyr Tyr Cys
                85                  90                  95

Thr Ala Gly Arg Gly Leu Thr Ser Tyr Arg Ala Asp Tyr Trp Gly Gln
            100                 105                 110

Gly Thr Leu Val Thr Val Ser Ser
        115                 120

<210> SEQ ID NO 3
<211> LENGTH: 111
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Arg Ser Val Asn
            20                  25                  30

Pro Met Ala Trp Phe Arg Gln Ala Pro Gly Arg Gln Arg Glu Trp Val
            35                  40                  45

Ala Thr Ile Ser Arg Ser Gly Tyr Ala Thr Tyr Ala Asp Ser Val Lys
        50                  55                  60

Gly Arg Phe Thr Ile Ser Gly Asp Asn Ala Lys Ser Ser Val Tyr Leu
65                  70                  75                  80

Gln Met Asn Ser Leu Lys Pro Glu Asp Thr Ala Val Tyr Tyr Cys Val
                85                  90                  95

Thr Gly Thr Tyr Trp Gly Gln Gly Thr Leu Val Thr Val Ser Ser
            100                 105                 110

<210> SEQ ID NO 4
<211> LENGTH: 121
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Pro Gly Asp
1               5                   10                  15

Ser Leu Arg Leu Ser Cys Ala Ala Ser Gly Arg Ile Leu Ser Ile Asn
```

```
                    20                  25                  30
Asn Met Val Trp Tyr Arg Gln Ala Pro Gly Lys Gln Arg Glu Leu Val
            35                  40                  45
Ala His Ile Thr Ser Ser Gly Ser Thr Gly Tyr Ala Asp Ser Val Lys
        50                  55                  60
Gly Arg Phe Thr Ile Ser Arg Asp Asn Ala Lys Asn Thr Phe Tyr Leu
65                  70                  75                  80
Gln Met Thr Asn Leu Asn Pro Glu Asp Thr Ala Val Tyr Tyr Cys Asn
                85                  90                  95
Cys Trp Val Ser Ser Asp Ser Asn Ala Pro Leu Lys Asn Tyr Trp Gly
                100                 105                 110
Gln Gly Thr Gln Val Thr Val Ser Ser
            115                 120

<210> SEQ ID NO 5
<211> LENGTH: 121
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Ser Ile Asn
            20                  25                  30
Asn Met Gly Trp Tyr Arg Gln Ala Pro Gly Lys Gln Arg Glu Leu Val
            35                  40                  45
Thr Val Val Thr Ser Asn Leu Ile Thr Thr Tyr Ala Asp Ser Val Lys
        50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala Trp Ala Arg Ser Val Gly Ser Val Pro Tyr Ser Gln Phe Trp Gly
                100                 105                 110
Gln Gly Thr Leu Val Thr Val Ser Ser
            115                 120

<210> SEQ ID NO 6
<211> LENGTH: 114
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Phe Gly Asp Asn Tyr
            20                  25                  30
Glu Leu Tyr Ala Met Thr Trp Phe Arg Gln Ala Pro Gly Glu Arg Arg
            35                  40                  45
Asp Phe Val Ala Ser Val Thr Gly Asp Gly Ser Thr Ser Tyr Ala Asp
        50                  55                  60
Ser Val Lys Asp Arg Phe Thr Ile Ser Arg Asp Asn Ala Lys Lys Leu
65                  70                  75                  80
```

```
Met Tyr Leu Gln Met Asn Ser Leu Lys Pro Glu Asp Thr Ala Val Tyr
                85                  90                  95

Tyr Cys Arg Leu Leu Asn Tyr Trp Gly Gln Gly Thr Leu Val Thr Val
            100                 105                 110

Ser Ser

<210> SEQ ID NO 7
<211> LENGTH: 121
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
            35                  40                  45

Ser Thr Ile Thr Ser Asn Leu Val Pro His Tyr Ala Asp Ser Val Gln
50                  55                  60

Gly Arg Phe Thr Ile Ser Arg Asp Asn Ala Arg Asn Thr Val Tyr Leu
65                  70                  75                  80

Gln Met Asn Ser Leu Lys Pro Gln Asp Thr Ala His Tyr Tyr Cys Asn
                85                  90                  95

Ala Trp Ala Arg Ser Ser Gly Ala Thr Pro Tyr Thr Asn Tyr Trp Gly
            100                 105                 110

Gln Gly Thr Leu Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Asp Leu Val
            35                  40                  45

Ala Ser Ile Thr Met Asn Gln Val Pro Asn Tyr Ala Asp Ser Val Gln
50                  55                  60

Gly Arg Phe Thr Ile Ser Arg Asp Asn Val Arg Asn Thr Val His Leu
65                  70                  75                  80

Gln Met Asn Ala Val Lys Pro Glu Asp Thr Ala Asp Tyr Phe Cys Asn
                85                  90                  95

Ala Trp Val Arg Ser Ser Gly Ala Ser Pro Tyr Thr Asn Tyr Trp Gly
            100                 105                 110

Gln Gly Thr Gln Val Thr Val Ser Ser
            115                 120

<210> SEQ ID NO 9
<211> LENGTH: 122
```

```
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Ala Ala Ser Arg Leu Thr Phe Asn His Tyr
            20                  25                  30

Asn Met Gly Trp Phe Arg Gln Ala Pro Gly Lys Glu Arg Glu Arg Val
        35                  40                  45

Ala Glu Val Thr Trp Ser Gly Asp Lys Ile Tyr Tyr Val Asp Ser Val
    50                  55                  60

Lys Gly Arg Phe Thr Ile Ser Arg Asp Asn Thr Pro Asn Pro Val Tyr
65                  70                  75                  80

Leu Tyr Leu Gln Met Asn Ser Leu Lys Pro Glu Asp Thr Ala Val Tyr
                85                  90                  95

Tyr Cys Ala Thr Ala Pro Arg Gly Leu Pro Tyr Ala Asn Gly Tyr Trp
            100                 105                 110

Gly Gln Gly Thr Gln Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Ile Asn
            20                  25                  30

Thr Met Gly Trp Tyr Arg Gln Ala Pro Gly Lys Gln Arg Glu Leu Val
        35                  40                  45

Ala Gly Val Thr Ile Asn Ala Ile Thr Asn Tyr Ala Asp Ser Val Lys
    50                  55                  60

Gly Arg Phe Thr Ile Ser Arg Asp Asn Ala Lys Asn Thr Val Trp Leu
65                  70                  75                  80

Gln Met Asn Ser Leu Lys Pro Glu Asp Thr Ala Val Tyr Tyr Cys His
                85                  90                  95

Ala Trp Ala Arg Ser Ser Gly Ser Ala Pro Tyr Ser Gln Asn Trp Gly
            100                 105                 110

Gln Gly Thr Gln Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
```

```
                    20                  25                  30
Ile Met Gly Trp Phe Arg Gln Ala Pro Gly Lys Ala Arg Glu Phe Val
                35                  40                  45
Ala Asp Ile Thr Trp Gly Gln Arg Pro Tyr Tyr Ala Asp Ser Val Lys
     50                  55                  60
Gly Arg Phe Thr Ile Ser Arg Asp Asn Ala Lys Asn Thr Val Tyr Leu
 65                  70                  75                  80
Glu Met Asn Ser Leu Lys Pro Glu Asp Thr Ala Val Tyr Tyr Cys Ala
                85                  90                  95
Ala Asp Leu Gly Val Val Ile Arg Glu His Ala Tyr Trp Gly Gln
                100                 105                 110
Gly Thr Leu Val Thr Val Ser Ser
            115                 120

<210> SEQ ID NO 12
<211> LENGTH: 117
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Ala Gly Gly
 1               5                  10                  15
Ser Leu Arg Leu Ser Cys Ala Ala Ser Gly Asn Thr Phe Ser Thr Asn
                20                  25                  30
Pro Met Tyr Trp Tyr Arg Gln Ala Glu Gly Lys Gln Arg Glu Leu Val
                35                  40                  45
Ala Ser Ile Ser Ser Arg Gly Ile Thr Asn Tyr Ala Asp Ser Val Arg
     50                  55                  60
Gly Arg Phe Ser Ile Ser Arg Asp Asn Thr Lys Asp Thr Val Tyr Leu
 65                  70                  75                  80
Gln Met Asn Ser Leu Lys Pro Glu Asp Thr Ala Val Tyr Tyr Cys Arg
                85                  90                  95
Leu Ala Ser Leu Ser Ser Gly Thr Val Tyr Trp Gly Lys Gly Thr Leu
                100                 105                 110
Val Thr Val Ser Ser
        115

<210> SEQ ID NO 13
<211> LENGTH: 127
<212> TYPE: PRT
<213> ORGANISM: Artificial Sequence
<220> FEATURE:
<223> OTHER INFORMATION: Nanobody sequence

<400> SEQUENCE: 13

Glu Val Gln Leu Val Glu Ser Gly Gly Gly Leu Val Gln Ala Gly Gly
 1               5                  10                  15
Ser Leu Arg Leu Ser Cys Ala Ala Ser Gly Phe Thr Phe Asp Asp Tyr
                20                  25                  30
Val Ile Gly Trp Phe Arg Gln Ala Pro Gly Lys Glu Arg Glu Gly Val
                35                  40                  45
Ser Cys Ile Ser Arg Leu Asp Gly Arg Thr Tyr Tyr Thr Asp Ser Val
     50                  55                  60
Lys Gly Arg Phe Thr Ile Ser Asp Asn Ala Lys Asn Thr Val Tyr
 65                  70                  75                  80
```

```
Leu Gln Met Asn Ser Leu Lys Pro Glu Asp Thr Ala Val Tyr Tyr Cys
                85                  90                  95

Ala Leu Glu Pro Arg Tyr Thr Gly Asp Tyr Tyr Pro Val His Pro Glu
            100                 105                 110

Leu Tyr Asp Tyr Trp Gly Gln Gly Thr Gln Val Thr Val Ser Ser
        115                 120                 125

<210> SEQ ID NO 14
<211> LENGTH: 126
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Val Glu Ser Gly Gly Gly Leu Val Gln Ala Gly Gly
1               5                   10                  15

Ser Leu Arg Leu Ser Cys Val Ile Ser Ala Ser Thr Val Arg Asn Tyr
            20                  25                  30

Asp Met Gly Trp Phe Arg Gln Ala Pro Gly Lys Glu Arg Glu Phe Val
        35                  40                  45

Ala Ala Ile Asp Trp Ser Gly Gly Ser Thr Arg Tyr Ala Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Ala Gly Phe Tyr Asn Asn Tyr Leu Arg Thr Ala Pro Asn Asp
            100                 105                 110

Trp Asn Tyr Trp Gly Gln Gly Thr Leu Val Thr Val Ser Ser
        115                 120                 125

<210> SEQ ID NO 15
<211> LENGTH: 126
<212> TYPE: PRT
<213> ORGANISM: Artificial Sequence
<220> FEATURE:
<223> OTHER INFORMATION: Nanobody sequence

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Val Ile Ser Glu Asp Gly Val Arg Asn Tyr
            20                  25                  30

Asp Met Gly Trp Phe Arg Gln Ala Pro Gly Lys Glu Arg Glu Phe Val
        35                  40                  45

Ala Thr Ile Asn Trp Ser Gly Gly Ser Thr Asn Tyr Ala Asp Ser Val
    50                  55                  60

Lys Gly Arg Phe Thr Val Ser Arg Asp Asn Ala Lys Asn Thr Met Tyr
65                  70                  75                  80

Leu Gln Met Asp Ser Leu Lys Pro Glu Asp Thr Ala Val Tyr Tyr Cys
                85                  90                  95

Val Ala Ala Gly Phe Tyr Asn Asn Tyr Leu Arg Thr Ala Pro Asn Asp
            100                 105                 110

Trp Asn Asp Trp Gly Gln Gly Thr Gln Val Thr Val Ser Ser
        115                 120                 125

<210> SEQ ID NO 16
```

```
<211> LENGTH: 123
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Gly Val Phe
            20                  25                  30

Ala Ile Gly Trp Phe Arg Gln Ala Pro Gly Lys Glu Arg Glu Gly Val
        35                  40                  45

Ser Cys Ile Asp Ser Ser Asp Gly Arg Thr Thr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asp Ile Glu Thr Asp Val Cys Ser Gly Ala Gly Trp Gly Phe
            100                 105                 110

Trp Gly Gln Gly Thr Gln Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Ile Asn
            20                  25                  30

Asn Met Gly Trp Tyr His Gln Ala Pro Gly Lys Gln Arg Glu Leu Val
        35                  40                  45

Ala Thr Ile Thr Met Asn Gly Ile Thr Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Cys Trp Val Arg Ser Ser Gly Gly Asp Pro Tyr Arg Asp Tyr Trp Gly
            100                 105                 110

Gln Gly Thr Gln Val Thr Val Ser Ser
        115                 120

<210> SEQ ID NO 18
<211> LENGTH: 125
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Leu Val Gln Ala Gly Gly
1               5                   10                  15
```

```
Ser Leu Arg Leu Ser Cys Thr Ala Ser Gly His Thr Phe Ser Ser Tyr
            20                  25                  30

Thr Met Gly Trp Phe Arg Gln Ala Pro Gly Lys Glu Arg Glu Phe Val
            35                  40                  45

Ala Ala Met Thr Arg Ser Gly Phe Asn Thr His Tyr Ser Asp Ser Val
 50                  55                  60

Lys Gly Arg Phe Thr Ile Ser Arg Asp Asn Thr Ser Arg Asp Asn Thr
 65                  70                  75                  80

Lys Ile Thr Met Ala Leu Gln Met Asn Ser Leu Lys Pro Glu Asp Thr
                85                  90                  95

Ala Val Tyr Tyr Cys Thr Thr Gly Arg Gly Leu Thr Ser Tyr Val Ala
                100                 105                 110

Asn Phe Trp Gly Gln Gly Thr Gln Val Thr Val Ser Ser
                115                 120                 125
```

<210> SEQ ID NO 19
<211> LENGTH: 126
<212> TYPE: PRT
<213> ORGANISM: Artificial Sequence
<220> FEATURE:
<223> OTHER INFORMATION: Nanobody sequence

<400> SEQUENCE: 19

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Ile Thr Leu Asp Ser Ile
            20                  25                  30

Ala Ile Cys Trp Phe Arg Gln Ala Pro Gly Lys Glu Arg Glu Gly Val
            35                  40                  45

Ser Cys Ser Arg Gly Ser Asp Gly Ser Thr Tyr Tyr Ala Asp Ser Val
 50                  55                  60

Lys Gly Arg Phe Thr Ile Ser Arg Val Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Ala Pro Ser Ile Phe Tyr Ser Gly Tyr Phe Pro Ser Gly
                100                 105                 110

Met Asp Tyr Trp Gly Lys Gly Thr Gln Val Thr Val Ser Ser
                115                 120                 125
```

<210> SEQ ID NO 20
<211> LENGTH: 10
<212> TYPE: PRT
<213> ORGANISM: Artificial Sequence
<220> FEATURE:
<223> OTHER INFORMATION: CDR sequence

<400> SEQUENCE: 20

```
Gly Ser Thr Leu Asp Tyr Tyr Ala Ile Gly
 1               5                   10
```

<210> SEQ ID NO 21
<211> LENGTH: 10
<212> TYPE: PRT
<213> ORGANISM: Artificial Sequence
<220> FEATURE:
<223> OTHER INFORMATION: CDR sequence

<400> SEQUENCE: 21

Gly Arg Thr Leu Ser Ser Tyr Thr Met Gly

```
1               5                   10

<210> SEQ ID NO 22
<211> LENGTH: 10
<212> TYPE: PRT
<213> ORGANISM: Artificial Sequence
<220> FEATURE:
<223> OTHER INFORMATION: CDR sequence

<400> SEQUENCE: 22

Gly Ser Thr Arg Ser Val Asn Pro Met Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: CDR sequence

<400> SEQUENCE: 23

Gly Arg Ile Leu Ser Ile Asn Asn Met Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: CDR sequence

<400> SEQUENCE: 24

Gly Ser Ile Phe Ser Ile Asn Asn Met Gly
1               5                   10

<210> SEQ ID NO 25
<211> LENGTH: 13
<212> TYPE: PRT
<213> ORGANISM: Artificial Sequence
<220> FEATURE:
<223> OTHER INFORMATION: CDR sequence

<400> SEQUENCE: 25

Gly Ser Phe Gly Asp Asn Tyr Glu Leu Tyr Ala Met Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: CDR sequence

<400> SEQUENCE: 26

Gly Ser Ile Phe Ser Ile Asn Thr Met Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: CDR sequence

<400> SEQUENCE: 27

Arg Leu Thr Phe Asn His Tyr Asn Met Gly
1               5                   10
```

```
<210> SEQ ID NO 28
<211> LENGTH: 10
<212> TYPE: PRT
<213> ORGANISM: Artificial Sequence
<220> FEATURE:
<223> OTHER INFORMATION: CDR sequence

<400> SEQUENCE: 28

Gly Arg Ile Phe Ser Ile Asn Thr Met Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: CDR sequence

<400> SEQUENCE: 29

Gly Arg Thr Phe Ser Ser Tyr Ile Met Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: CDR sequence

<400> SEQUENCE: 30

Gly Asn Thr Phe Ser Thr Asn Pro Met Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: CDR sequence

<400> SEQUENCE: 31

Gly Phe Thr Phe Asp Asp Tyr Val Ile Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: CDR sequence

<400> SEQUENCE: 32

Ala Ser Thr Val Arg Asn Tyr Asp Met Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: CDR sequence

<400> SEQUENCE: 33

Glu Asp Gly Val Arg Asn Tyr Asp Met Gly
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: CDR sequence

<400> SEQUENCE: 34

Gly Phe Ser Leu Gly Val Phe Ala Ile Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CDR sequence

<400> SEQUENCE: 35

Gly Arg Ile Phe Ser Ile Asn Asn Met Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: CDR sequence

<400> SEQUENCE: 36

Gly His Thr Phe Ser Ser Tyr Thr Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: CDR sequence

<400> SEQUENCE: 37

Gly Ile Thr Leu Asp Ser Ile Ala Ile Cys
1               5                   10

<210> SEQ ID NO 38
<211> LENGTH: 9
<212> TYPE: PRT
<213> ORGANISM: Artificial Sequence
<220> FEATURE:
<223> OTHER INFORMATION: CDR sequence

<400> SEQUENCE: 38

Cys Thr Ser Asn Ser Gly Ser Thr Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: CDR sequence

<400> SEQUENCE: 39

Ala Met Thr Arg Ser Gly Phe Asn Thr Tyr
1               5                   10
```

```
<210> SEQ ID NO 40
<211> LENGTH: 9
<212> TYPE: PRT
<213> ORGANISM: Artificial Sequence
<220> FEATURE:
<223> OTHER INFORMATION: CDR sequence

<400> SEQUENCE: 40

Thr Ile Ser Arg Ser Gly Tyr Ala Thr
1               5

<210> SEQ ID NO 41
<211> LENGTH: 9
<212> TYPE: PRT
<213> ORGANISM: Artificial Sequence
<220> FEATURE:
<223> OTHER INFORMATION: CDR sequence

<400> SEQUENCE: 41

His Ile Thr Ser Ser Gly Ser Thr Gly
1               5

<210> SEQ ID NO 42
<211> LENGTH: 9
<212> TYPE: PRT
<213> ORGANISM: Artificial Sequence
<220> FEATURE:
<223> OTHER INFORMATION: CDR sequence

<400> SEQUENCE: 42

Val Val Thr Ser Asn Leu Ile Thr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: CDR sequence

<400> SEQUENCE: 43

Ser Val Thr Gly Asp Gly Ser Thr Ser
1               5

<210> SEQ ID NO 44
<211> LENGTH: 9
<212> TYPE: PRT
<213> ORGANISM: Artificial Sequence
<220> FEATURE:
<223> OTHER INFORMATION: CDR sequence

<400> SEQUENCE: 44

Thr Ile Thr Ser Asn Leu Val Pro His
1               5

<210> SEQ ID NO 45
<211> LENGTH: 9
<212> TYPE: PRT
<213> ORGANISM: Artificial Sequence
<220> FEATURE:
<223> OTHER INFORMATION: CDR sequence

<400> SEQUENCE: 45

Ser Ile Thr Met Asn Gln Val Pro Asn
1               5

<210> SEQ ID NO 46
```

```
<211> LENGTH: 10
<212> TYPE: PRT
<213> ORGANISM: Artificial Sequence
<220> FEATURE:
<223> OTHER INFORMATION: CDR sequence

<400> SEQUENCE: 46

Glu Val Thr Trp Ser Gly Asp Lys Ile Tyr
1               5                   10

<210> SEQ ID NO 47
<211> LENGTH: 9
<212> TYPE: PRT
<213> ORGANISM: Artificial Sequence
<220> FEATURE:
<223> OTHER INFORMATION: CDR sequence

<400> SEQUENCE: 47

Gly Val Thr Ile Asn Ala Ile Thr Asn
1               5

<210> SEQ ID NO 48
<211> LENGTH: 9
<212> TYPE: PRT
<213> ORGANISM: Artificial Sequence
<220> FEATURE:
<223> OTHER INFORMATION: CDR sequence

<400> SEQUENCE: 48

Asp Ile Thr Trp Gly Gln Arg Pro Tyr
1               5

<210> SEQ ID NO 49
<211> LENGTH: 9
<212> TYPE: PRT
<213> ORGANISM: Artificial Sequence
<220> FEATURE:
<223> OTHER INFORMATION: CDR sequence

<400> SEQUENCE: 49

Ser Ile Ser Ser Arg Gly Ile Thr Asn
1               5

<210> SEQ ID NO 50
<211> LENGTH: 10
<212> TYPE: PRT
<213> ORGANISM: Artificial Sequence
<220> FEATURE:
<223> OTHER INFORMATION: CDR sequence

<400> SEQUENCE: 50

Cys Ile Ser Arg Leu Asp Gly Arg Thr Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: CDR sequence

<400> SEQUENCE: 51

Ala Ile Asp Trp Ser Gly Gly Ser Thr Arg
1               5                   10

<210> SEQ ID NO 52
<211> LENGTH: 10
```

```
<212> TYPE: PRT
<213> ORGANISM: Artificial Sequence
<220> FEATURE:
<223> OTHER INFORMATION: CDR sequence

<400> SEQUENCE: 52

Thr Ile Asn Trp Ser Gly Gly Ser Thr Asn
1               5                   10

<210> SEQ ID NO 53
<211> LENGTH: 10
<212> TYPE: PRT
<213> ORGANISM: Artificial Sequence
<220> FEATURE:
<223> OTHER INFORMATION: CDR sequence

<400> SEQUENCE: 53

Cys Ile Asp Ser Ser Asp Gly Arg Thr Thr
1               5                   10

<210> SEQ ID NO 54
<211> LENGTH: 9
<212> TYPE: PRT
<213> ORGANISM: Artificial Sequence
<220> FEATURE:
<223> OTHER INFORMATION: CDR sequence

<400> SEQUENCE: 54

Thr Ile Thr Met Asn Gly Ile Thr Thr
1               5

<210> SEQ ID NO 55
<211> LENGTH: 15
<212> TYPE: PRT
<213> ORGANISM: Artificial Sequence
<220> FEATURE:
<223> OTHER INFORMATION: CDR sequence

<400> SEQUENCE: 55

Ala Met Thr Arg Ser Gly Phe Asn Thr His Tyr Ser Asp Ser Val
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: CDR sequence

<400> SEQUENCE: 56

Cys Ser Arg Gly Ser Asp Gly Ser Thr Tyr
1               5                   10

<210> SEQ ID NO 57
<211> LENGTH: 18
<212> TYPE: PRT
<213> ORGANISM: Artificial Sequence
<220> FEATURE:
<223> OTHER INFORMATION: CDR sequence

<400> SEQUENCE: 57

Thr Ile Gly Cys Ala Thr Leu Gly Gly Thr Leu Asp Val Gln Arg Tyr
1               5                   10                  15

Tyr Tyr

<210> SEQ ID NO 58
```

```
<211> LENGTH: 11
<212> TYPE: PRT
<213> ORGANISM: Artificial Sequence
<220> FEATURE:
<223> OTHER INFORMATION: CDR sequence

<400> SEQUENCE: 58

Gly Arg Gly Leu Thr Ser Tyr Arg Ala Asp Tyr
1               5                   10

<210> SEQ ID NO 59
<211> LENGTH: 3
<212> TYPE: PRT
<213> ORGANISM: Artificial Sequence
<220> FEATURE:
<223> OTHER INFORMATION: CDR sequence

<400> SEQUENCE: 59

Gly Thr Tyr
1

<210> SEQ ID NO 60
<211> LENGTH: 13
<212> TYPE: PRT
<213> ORGANISM: Artificial Sequence
<220> FEATURE:
<223> OTHER INFORMATION: CDR sequence

<400> SEQUENCE: 60

Trp Val Ser Ser Asp Ser Asn Ala Pro Leu Lys Asn Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: CDR sequence

<400> SEQUENCE: 61

Trp Ala Arg Ser Val Gly Ser Val Pro Tyr Ser Gln Phe
1               5                   10

<210> SEQ ID NO 62
<211> LENGTH: 3
<212> TYPE: PRT
<213> ORGANISM: Artificial Sequence
<220> FEATURE:
<223> OTHER INFORMATION: CDR sequence

<400> SEQUENCE: 62

Leu Asn Tyr
1

<210> SEQ ID NO 63
<211> LENGTH: 13
<212> TYPE: PRT
<213> ORGANISM: Artificial Sequence
<220> FEATURE:
<223> OTHER INFORMATION: CDR sequence

<400> SEQUENCE: 63

Trp Ala Arg Ser Ser Gly Ala Thr Pro Tyr Thr Asn Tyr
1               5                   10

<210> SEQ ID NO 64
<211> LENGTH: 13
```

```
<212> TYPE: PRT
<213> ORGANISM: Artificial Sequence
<220> FEATURE:
<223> OTHER INFORMATION: CDR sequence

<400> SEQUENCE: 64

Trp Val Arg Ser Ser Gly Ala Ser Pro Tyr Thr Asn Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: CDR sequence

<400> SEQUENCE: 65

Ala Pro Arg Gly Leu Pro Tyr Ala Asn Gly Tyr
1               5                   10

<210> SEQ ID NO 66
<211> LENGTH: 13
<212> TYPE: PRT
<213> ORGANISM: Artificial Sequence
<220> FEATURE:
<223> OTHER INFORMATION: CDR sequence

<400> SEQUENCE: 66

Trp Ala Arg Ser Ser Gly Ser Ala Pro Tyr Ser Gln Asn
1               5                   10

<210> SEQ ID NO 67
<211> LENGTH: 12
<212> TYPE: PRT
<213> ORGANISM: Artificial Sequence
<220> FEATURE:
<223> OTHER INFORMATION: CDR sequence

<400> SEQUENCE: 67

Asp Leu Gly Val Val Ile Arg Glu Glu His Ala Tyr
1               5                   10

<210> SEQ ID NO 68
<211> LENGTH: 9
<212> TYPE: PRT
<213> ORGANISM: Artificial Sequence
<220> FEATURE:
<223> OTHER INFORMATION: CDR sequence

<400> SEQUENCE: 68

Ala Ser Leu Ser Ser Gly Thr Val Tyr
1               5

<210> SEQ ID NO 69
<211> LENGTH: 18
<212> TYPE: PRT
<213> ORGANISM: Artificial Sequence
<220> FEATURE:
<223> OTHER INFORMATION: CDR sequence

<400> SEQUENCE: 69

Glu Pro Arg Tyr Thr Gly Asp Tyr Tyr Pro Val His Pro Glu Leu Tyr
1               5                   10                  15

Asp Tyr

<210> SEQ ID NO 70
```

```
<211> LENGTH: 17
<212> TYPE: PRT
<213> ORGANISM: Artificial Sequence
<220> FEATURE:
<223> OTHER INFORMATION: CDR sequence

<400> SEQUENCE: 70

Ala Gly Phe Tyr Asn Asn Tyr Leu Arg Thr Ala Pro Asn Asp Trp Asn
1               5                   10                  15

Tyr

<210> SEQ ID NO 71
<211> LENGTH: 17
<212> TYPE: PRT
<213> ORGANISM: Artificial Sequence
<220> FEATURE:
<223> OTHER INFORMATION: CDR sequence

<400> SEQUENCE: 71

Ala Gly Phe Tyr Asn Asn Tyr Leu Arg Thr Ala Pro Asn Asp Trp Asn
1               5                   10                  15

Asp

<210> SEQ ID NO 72
<211> LENGTH: 14
<212> TYPE: PRT
<213> ORGANISM: Artificial Sequence
<220> FEATURE:
<223> OTHER INFORMATION: CDR sequence

<400> SEQUENCE: 72

Asp Ile Glu Thr Asp Val Cys Ser Gly Ala Gly Trp Gly Phe
1               5                   10

<210> SEQ ID NO 73
<211> LENGTH: 13
<212> TYPE: PRT
<213> ORGANISM: Artificial Sequence
<220> FEATURE:
<223> OTHER INFORMATION: CDR sequence

<400> SEQUENCE: 73

Trp Val Arg Ser Ser Gly Gly Asp Pro Tyr Arg Asp Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: CDR sequence

<400> SEQUENCE: 74

Gly Arg Gly Leu Thr Ser Tyr Val Ala Asn Phe
1               5                   10

<210> SEQ ID NO 75
<211> LENGTH: 17
<212> TYPE: PRT
<213> ORGANISM: Artificial Sequence
<220> FEATURE:
<223> OTHER INFORMATION: CDR sequence

<400> SEQUENCE: 75

Ala Pro Ser Ile Phe Tyr Ser Gly Gly Tyr Phe Pro Ser Gly Met Asp
1               5                   10                  15
```

Tyr

```
<210> SEQ ID NO 76
<211> LENGTH: 25
<212> TYPE: PRT
<213> ORGANISM: Artificial Sequence
<220> FEATURE:
<223> OTHER INFORMATION: Framework sequence

<400> SEQUENCE: 76
```

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 77
<211> LENGTH: 25
<212> TYPE: PRT
<213> ORGANISM: Artificial Sequence
<220> FEATURE:
<223> OTHER INFORMATION: Framework sequence

<400> SEQUENCE: 77
```

Glu Val Gln Leu Val Glu Ser Gly Gly Gly Leu Val Gln Ala Gly Gly
1               5                   10                  15

Ser Leu Arg Leu Ser Cys Thr Ala Ser
            20                  25

```
<210> SEQ ID NO 78
<211> LENGTH: 25
<212> TYPE: PRT
<213> ORGANISM: Artificial Sequence
<220> FEATURE:
<223> OTHER INFORMATION: Framework sequence

<400> SEQUENCE: 78
```

Glu Val Gln Leu Val Glu Ser Gly Gly Gly Leu Val Gln Pro Gly Asp
1               5                   10                  15

Ser Leu Arg Leu Ser Cys Ala Ala Ser
            20                  25

```
<210> SEQ ID NO 79
<211> LENGTH: 25
<212> TYPE: PRT
<213> ORGANISM: Artificial Sequence
<220> FEATURE:
<223> OTHER INFORMATION: Framework sequence

<400> SEQUENCE: 79
```

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

```
<210> SEQ ID NO 80
<211> LENGTH: 25
<212> TYPE: PRT
<213> ORGANISM: Artificial Sequence
<220> FEATURE:
<223> OTHER INFORMATION: Framework sequence

<400> SEQUENCE: 80
```

Glu Val Gln Leu Val Glu Ser Gly Gly Gly Leu Val Gln Ala Gly Gly
1               5                   10                  15

```
Ser Leu Arg Leu Ser Cys Val Ile Ser
            20                  25

<210> SEQ ID NO 81
<211> LENGTH: 14
<212> TYPE: PRT
<213> ORGANISM: Artificial Sequence
<220> FEATURE:
<223> OTHER INFORMATION: Framework sequence

<400> SEQUENCE: 81

Trp Phe Arg Gln Ala Pro Gly Lys Glu Arg Glu Gly Val Ser
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Framework sequence

<400> SEQUENCE: 82

Trp Phe Arg Gln Ala Pro Gly Thr Glu Arg Glu Phe Val Ala
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Framework sequence

<400> SEQUENCE: 83

Trp Phe Arg Gln Ala Pro Gly Arg Gln Arg Glu Trp Val Ala
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Framework sequence

<400> SEQUENCE: 84

Trp Tyr Arg Gln Ala Pro Gly Lys Gln Arg Glu Leu Val Ala
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Framework sequence

<400> SEQUENCE: 85

Trp Tyr Arg Gln Ala Pro Gly Lys Gln Arg Glu Leu Val Thr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Framework sequence

<400> SEQUENCE: 86
```

Trp Phe Arg Gln Ala Pro Gly Glu Arg Arg Asp Phe Val Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Framework sequence

<400> SEQUENCE: 87

Trp Tyr Arg Gln Ala Pro Gly Lys Gln Arg Glu Leu Val Ser
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Framework sequence

<400> SEQUENCE: 88

Trp Tyr Arg Gln Ala Pro Gly Lys Gln Arg Asp Leu Val Ala
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Framework sequence

<400> SEQUENCE: 89

Trp Phe Arg Gln Ala Pro Gly Lys Glu Arg Glu Arg Val Ala
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Framework sequence

<400> SEQUENCE: 90

Trp Phe Arg Gln Ala Pro Gly Lys Ala Arg Glu Phe Val Ala
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Framework sequence

<400> SEQUENCE: 91

Trp Tyr Arg Gln Ala Glu Gly Lys Gln Arg Glu Leu Val Ala
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Framework sequence

<400> SEQUENCE: 92

Trp Phe Arg Gln Ala Pro Gly Lys Glu Arg Glu Phe Val Ala

-continued

```
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Framework sequence

<400> SEQUENCE: 93

Trp Tyr His Gln Ala Pro Gly Lys Gln Arg Glu Leu Val Ala
1               5                   10

<210> SEQ ID NO 94
<211> LENGTH: 39
<212> TYPE: PRT
<213> ORGANISM: Artificial Sequence
<220> FEATURE:
<223> OTHER INFORMATION: Framework sequence

<400> SEQUENCE: 94

Tyr Gly Gly Ser Val Lys Gly Arg Phe Thr Ala Ser Arg Asp Asn Ala
1               5                   10                  15

Lys Asn Thr Val Tyr Leu Gln Met Asn Ser Leu Arg Pro Glu Asp Thr
            20                  25                  30

Ala Val Tyr Tyr Cys Val Ala
        35

<210> SEQ ID NO 95
<211> LENGTH: 39
<212> TYPE: PRT
<213> ORGANISM: Artificial Sequence
<220> FEATURE:
<223> OTHER INFORMATION: Framework sequence

<400> SEQUENCE: 95

Tyr Ala Asp Ser Val Lys Gly Arg Phe Thr Ile Ser Arg Asp Ser Thr
1               5                   10                  15

Glu Asn Thr Met Ala Leu Gln Met Ser Ser Leu Lys Pro Glu Asp Thr
            20                  25                  30

Ala Val Tyr Tyr Cys Thr Ala
        35

<210> SEQ ID NO 96
<211> LENGTH: 39
<212> TYPE: PRT
<213> ORGANISM: Artificial Sequence
<220> FEATURE:
<223> OTHER INFORMATION: Framework sequence

<400> SEQUENCE: 96

Tyr Ala Asp Ser Val Lys Gly Arg Phe Thr Ile Ser Gly Asp Asn Ala
1               5                   10                  15

Lys Ser Ser Val Tyr Leu Gln Met Asn Ser Leu Lys Pro Glu Asp Thr
            20                  25                  30

Ala Val Tyr Tyr Cys Val Thr
        35

<210> SEQ ID NO 97
<211> LENGTH: 39
<212> TYPE: PRT
<213> ORGANISM: Artificial Sequence
<220> FEATURE:
<223> OTHER INFORMATION: Framework sequence
```

<400> SEQUENCE: 97

Tyr Ala Asp Ser Val Lys Gly Arg Phe Thr Ile Ser Arg Asp Asn Ala
1               5                   10                  15

Lys Asn Thr Phe Tyr Leu Gln Met Thr Asn Leu Asn Pro Glu Asp Thr
            20                  25                  30

Ala Val Tyr Tyr Cys Asn Cys
        35

<210> SEQ ID NO 98
<211> LENGTH: 39
<212> TYPE: PRT
<213> ORGANISM: Artificial Sequence
<220> FEATURE:
<223> OTHER INFORMATION: Framework sequence

<400> SEQUENCE: 98

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Asn Ala
        35

<210> SEQ ID NO 99
<211> LENGTH: 39
<212> TYPE: PRT
<213> ORGANISM: Artificial Sequence
<220> FEATURE:
<223> OTHER INFORMATION: Framework sequence

<400> SEQUENCE: 99

Tyr Ala Asp Ser Val Lys Asp Arg Phe Thr Ile Ser Arg Asp Asn Ala
1               5                   10                  15

Lys Lys Leu Met Tyr Leu Gln Met Asn Ser Leu Lys Pro Glu Asp Thr
            20                  25                  30

Ala Val Tyr Tyr Cys Arg Leu
        35

<210> SEQ ID NO 100
<211> LENGTH: 39
<212> TYPE: PRT
<213> ORGANISM: Artificial Sequence
<220> FEATURE:
<223> OTHER INFORMATION: Framework sequence

<400> SEQUENCE: 100

Tyr Ala Asp Ser Val Gln Gly Arg Phe Thr Ile Ser Arg Asp Asn Ala
1               5                   10                  15

Arg Asn Thr Val Tyr Leu Gln Met Asn Ser Leu Lys Pro Gln Asp Thr
            20                  25                  30

Ala His Tyr Tyr Cys Asn Ala
        35

<210> SEQ ID NO 101
<211> LENGTH: 39
<212> TYPE: PRT
<213> ORGANISM: Artificial Sequence
<220> FEATURE:
<223> OTHER INFORMATION: Framework sequence

<400> SEQUENCE: 101

```
Tyr Ala Asp Ser Val Gln Gly Arg Phe Thr Ile Ser Arg Asp Asn Val
1               5                   10                  15

Arg Asn Thr Val His Leu Gln Met Asn Ala Val Lys Pro Glu Asp Thr
            20                  25                  30

Ala Asp Tyr Phe Cys Asn Ala
        35
```

<210> SEQ ID NO 102
<211> LENGTH: 41
<212> TYPE: PRT
<213> ORGANISM: Artificial Sequence
<220> FEATURE:
<223> OTHER INFORMATION: Framework sequence

<400> SEQUENCE: 102

```
Tyr Val Asp Ser Val Lys Gly Arg Phe Thr Ile Ser Arg Asp Asn Thr
1               5                   10                  15

Pro Asn Pro Val Tyr Leu Tyr Leu Gln Met Asn Ser Leu Lys Pro Glu
            20                  25                  30

Asp Thr Ala Val Tyr Tyr Cys Ala Thr
        35                  40
```

<210> SEQ ID NO 103
<211> LENGTH: 39
<212> TYPE: PRT
<213> ORGANISM: Artificial Sequence
<220> FEATURE:
<223> OTHER INFORMATION: Framework sequence

<400> SEQUENCE: 103

```
Tyr Ala Asp Ser Val Lys Gly Arg Phe Thr Ile Ser Arg Asp Asn Ala
1               5                   10                  15

Lys Asn Thr Val Trp Leu Gln Met Asn Ser Leu Lys Pro Glu Asp Thr
            20                  25                  30

Ala Val Tyr Tyr Cys His Ala
        35
```

<210> SEQ ID NO 104
<211> LENGTH: 39
<212> TYPE: PRT
<213> ORGANISM: Artificial Sequence
<220> FEATURE:
<223> OTHER INFORMATION: Framework sequence

<400> SEQUENCE: 104

```
Tyr Ala Asp Ser Val Lys Gly Arg Phe Thr Ile Ser Arg Asp Asn Ala
1               5                   10                  15

Lys Asn Thr Val Tyr Leu Glu Met Asn Ser Leu Lys Pro Glu Asp Thr
            20                  25                  30

Ala Val Tyr Tyr Cys Ala Ala
        35
```

<210> SEQ ID NO 105
<211> LENGTH: 39
<212> TYPE: PRT
<213> ORGANISM: Artificial Sequence
<220> FEATURE:
<223> OTHER INFORMATION: Framework sequence

<400> SEQUENCE: 105

```
Tyr Ala Asp Ser Val Arg Gly Arg Phe Ser Ile Ser Arg Asp Asn Thr
1               5                   10                  15
```

Lys Asp Thr Val Tyr Leu Gln Met Asn Ser Leu Lys Pro Glu Asp Thr
            20                  25                  30

Ala Val Tyr Tyr Cys Arg Leu
        35

<210> SEQ ID NO 106
<211> LENGTH: 39
<212> TYPE: PRT
<213> ORGANISM: Artificial Sequence
<220> FEATURE:
<223> OTHER INFORMATION: Framework sequence

<400> SEQUENCE: 106

Tyr Thr Asp Ser Val Lys Gly Arg Phe Thr Ile Ser Ser Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Leu
        35

<210> SEQ ID NO 107
<211> LENGTH: 39
<212> TYPE: PRT
<213> ORGANISM: Artificial Sequence
<220> FEATURE:
<223> OTHER INFORMATION: Framework sequence

<400> SEQUENCE: 107

Tyr Ala Asp Ser Val Lys Gly Arg Phe Thr Val Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Val Ala
        35

<210> SEQ ID NO 108
<211> LENGTH: 39
<212> TYPE: PRT
<213> ORGANISM: Artificial Sequence
<220> FEATURE:
<223> OTHER INFORMATION: Framework sequence

<400> SEQUENCE: 108

Tyr Ala Asp Ser Val Lys Gly Arg Phe Thr Val Ser Arg Asp Asn Ala
1               5                   10                  15

Lys Asn Thr Met Tyr Leu Gln Met Asp Ser Leu Lys Pro Glu Asp Thr
            20                  25                  30

Ala Val Tyr Tyr Cys Val Ala
        35

<210> SEQ ID NO 109
<211> LENGTH: 39
<212> TYPE: PRT
<213> ORGANISM: Artificial Sequence
<220> FEATURE:
<223> OTHER INFORMATION: Framework sequence

<400> SEQUENCE: 109

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

-continued

Ala Val Tyr Tyr Cys Ala Thr
        35

<210> SEQ ID NO 110
<211> LENGTH: 39
<212> TYPE: PRT
<213> ORGANISM: Artificial Sequence
<220> FEATURE:
<223> OTHER INFORMATION: Framework sequence

<400> SEQUENCE: 110

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ser Cys
        35

<210> SEQ ID NO 111
<211> LENGTH: 39
<212> TYPE: PRT
<213> ORGANISM: Artificial Sequence
<220> FEATURE:
<223> OTHER INFORMATION: Framework sequence

<400> SEQUENCE: 111

Lys Gly Arg Phe Thr Ile Ser Arg Asp Asn Ser Arg Asp Asn Thr
1               5                   10                  15

Lys Ile Thr Met Ala Leu Gln Met Asn Ser Leu Lys Pro Glu Asp Thr
            20                  25                  30

Ala Val Tyr Tyr Cys Thr Thr
        35

<210> SEQ ID NO 112
<211> LENGTH: 39
<212> TYPE: PRT
<213> ORGANISM: Artificial Sequence
<220> FEATURE:
<223> OTHER INFORMATION: Framework sequence

<400> SEQUENCE: 112

Tyr Ala Asp Ser Val Lys Gly Arg Phe Thr Ile Ser Arg Val Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35

<210> SEQ ID NO 113
<211> LENGTH: 11
<212> TYPE: PRT
<213> ORGANISM: Artificial Sequence
<220> FEATURE:
<223> OTHER INFORMATION: Framework sequence

<400> SEQUENCE: 113

Arg Gly Gln Gly Thr Gln Val Thr Val Ser Ser
1               5                   10

<210> SEQ ID NO 114
<211> LENGTH: 11
<212> TYPE: PRT
<213> ORGANISM: Artificial Sequence
<220> FEATURE:

```
<223> OTHER INFORMATION: Framework sequence

<400> SEQUENCE: 114

Trp Gly Gln Gly Thr Leu Val Thr Val Ser Ser
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Framework sequence

<400> SEQUENCE: 115

Trp Gly Gln Gly Thr Gln Val Thr Val Ser Ser
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Framework sequence

<400> SEQUENCE: 116

Trp Gly Lys Gly Thr Leu Val Thr Val Ser Ser
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Framework sequence

<400> SEQUENCE: 117

Trp Gly Lys Gly Thr Gln Val Thr Val Ser Ser
1               5                   10

<210> SEQ ID NO 118
<211> LENGTH: 272
<212> TYPE: PRT
<213> ORGANISM: Artificial Sequence
<220> FEATURE:
<223> OTHER INFORMATION: Nanobody sequence

<400> SEQUENCE: 118

Glu Val Gln Leu Val Glu Ser Gly Gly Leu Val Gln Pro Gly Gly
1               5                   10                  15

Ser Leu Arg Leu Ser Cys Ala Ala Ser Gly Ser Thr Arg Ser Val Asn
                20                  25                  30

Pro Met Ala Trp Phe Arg Gln Ala Pro Gly Arg Gln Arg Glu Trp Val
            35                  40                  45

Ala Thr Ile Ser Arg Ser Gly Tyr Ala Thr Tyr Ala Asp Ser Val Lys
        50                  55                  60

Gly Arg Phe Thr Ile Ser Gly Asp Asn Ala Lys Ser Ser Val Tyr Leu
65                  70                  75                  80

Gln Met Asn Ser Leu Lys Pro Glu Asp Thr Ala Val Tyr Tyr Cys Val
                85                  90                  95

Thr Gly Thr Tyr Trp Gly Gln Gly Thr Leu Val Thr Val Ser Ser Gly
            100                 105                 110

Gly Gly Gly Ser Gly Gly Gly Ser Gly Gly Gly Gly Ser Gly Gly
        115                 120                 125
```

```
Gly Gly Ser Gly Gly Gly Ser Gly Gly Gly Ser Gly Gly Gly
    130                 135                 140
Gly Ser Gly Gly Gly Ser Glu Val Gln Leu Val Glu Ser Gly Gly
145                 150                 155                 160
Gly Leu Val Gln Pro Gly Gly Ser Leu Arg Leu Ser Cys Ala Ala Ser
                165                 170                 175
Gly Ser Ile Phe Ser Ile Asn Asn Met Gly Trp Tyr Arg Gln Ala Pro
            180                 185                 190
Gly Lys Gln Arg Glu Leu Val Thr Val Val Thr Ser Asn Leu Ile Thr
        195                 200                 205
Thr Tyr Ala Asp Ser Val Lys Gly Arg Phe Thr Ile Ser Arg Asp Asn
210                 215                 220
Ala Lys Asn Thr Val Tyr Leu Gln Met Asn Ser Leu Lys Pro Glu Asp
225                 230                 235                 240
Thr Ala Val Tyr Tyr Cys Asn Ala Trp Ala Arg Ser Val Gly Ser Val
                245                 250                 255
Pro Tyr Ser Gln Phe Trp Gly Gln Gly Thr Leu Val Thr Val Ser Ser
            260                 265                 270

<210> SEQ ID NO 119
<211> LENGTH: 283
<212> TYPE: PRT
<213> ORGANISM: Artificial Sequence
<220> FEATURE:
<223> OTHER INFORMATION: Nanobody sequence

<400> SEQUENCE: 119

Glu Val Gln Leu Val Glu Ser Gly Gly Gly Leu Val Gln Ala Gly Gly
1               5                   10                  15
Ser Leu Arg Leu Ser Cys Ala Ala Ser Arg Leu Thr Phe Asn His Tyr
            20                  25                  30
Asn Met Gly Trp Phe Arg Gln Ala Pro Gly Lys Glu Arg Glu Arg Val
        35                  40                  45
Ala Glu Val Thr Trp Ser Gly Asp Lys Ile Tyr Tyr Val Asp Ser Val
    50                  55                  60
Lys Gly Arg Phe Thr Ile Ser Arg Asp Asn Thr Pro Asn Pro Val Tyr
65                  70                  75                  80
Leu Tyr Leu Gln Met Asn Ser Leu Lys Pro Glu Asp Thr Ala Val Tyr
                85                  90                  95
Tyr Cys Ala Thr Ala Pro Arg Gly Leu Pro Tyr Ala Asn Gly Tyr Trp
            100                 105                 110
Gly Gln Gly Thr Leu Val Thr Val Ser Ser Gly Gly Gly Gly Ser Gly
        115                 120                 125
Gly Gly Gly Ser Gly Gly Gly Ser Gly Gly Gly Ser Gly Gly
    130                 135                 140
Gly Gly Ser Gly Gly Gly Ser Gly Gly Gly Ser Gly Gly Gly
145                 150                 155                 160
Gly Ser Glu Val Gln Leu Val Glu Ser Gly Gly Leu Val Gln Pro
                165                 170                 175
Gly Gly Ser Leu Arg Leu Ser Cys Ala Ala Ser Gly Ser Ile Phe Ser
            180                 185                 190
Ile Asn Thr Met Gly Trp Tyr Arg Gln Ala Pro Gly Lys Gln Arg Asp
        195                 200                 205
Leu Val Ala Ser Ile Thr Met Asn Gln Val Pro Asn Tyr Ala Asp Ser
    210                 215                 220
```

```
Val Gln Gly Arg Phe Thr Ile Ser Arg Asp Asn Val Arg Asn Thr Val
225                 230                 235                 240

His Leu Gln Met Asn Ala Val Lys Pro Glu Asp Thr Ala Asp Tyr Phe
                245                 250                 255

Cys Asn Ala Trp Val Arg Ser Ser Gly Ala Ser Pro Tyr Thr Asn Tyr
            260                 265                 270

Trp Gly Gln Gly Thr Leu Val Thr Val Ser Ser
            275                 280
```

<210> SEQ ID NO 120
<211> LENGTH: 272
<212> TYPE: PRT
<213> ORGANISM: Artificial Sequence
<220> FEATURE:
<223> OTHER INFORMATION: Nanobody sequence

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ser Thr Ile Thr Ser Asn Leu Val Pro His Tyr Ala Asp Ser Val Gln
    50                  55                  60

Gly Arg Phe Thr Ile Ser Arg Asp Asn Ala Arg Asn Thr Val Tyr Leu
65                  70                  75                  80

Gln Met Asn Ser Leu Lys Pro Gln Asp Thr Ala His Tyr Tyr Cys Asn
                85                  90                  95

Ala Trp Ala Arg Ser Ser Gly Ala Thr Pro Tyr Thr Asn Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Gly Gly Gly Gly
145                 150                 155                 160

Ser Glu Val Gln Leu Val Glu Ser Gly Gly Leu Val Gln Pro Gly
                165                 170                 175

Gly Ser Leu Arg Leu Ser Cys Ala Ala Ser Gly Ser Thr Arg Ser Val
            180                 185                 190

Asn Pro Met Ala Trp Phe Arg Gln Ala Pro Gly Arg Gln Arg Glu Trp
        195                 200                 205

Val Ala Thr Ile Ser Arg Ser Gly Tyr Ala Thr Tyr Ala Asp Ser Val
    210                 215                 220

Lys Gly Arg Phe Thr Ile Ser Gly Asp Asn Ala Lys Ser Ser Val Tyr
225                 230                 235                 240

Leu Gln Met Asn Ser Leu Lys Pro Glu Asp Thr Ala Val Tyr Tyr Cys
                245                 250                 255

Val Thr Gly Thr Tyr Trp Gly Gln Gly Thr Leu Val Thr Val Ser Ser
            260                 265                 270
```

<210> SEQ ID NO 121
<211> LENGTH: 272
<212> TYPE: PRT
<213> ORGANISM: Artificial Sequence
<220> FEATURE:
<223> OTHER INFORMATION: Nanobody sequence

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Arg Ser Val Asn
            20                  25                  30

Pro Met Ala Trp Phe Arg Gln Ala Pro Gly Arg Gln Arg Glu Trp Val
        35                  40                  45

Ala Thr Ile Ser Arg Ser Gly Tyr Ala Thr Tyr Ala Asp Ser Val Lys
    50                  55                  60

Gly Arg Phe Thr Ile Ser Gly Asp Asn Ala Lys Ser Ser Val Tyr Leu
65                  70                  75                  80

Gln Met Asn Ser Leu Lys Pro Glu Asp Thr Ala Val Tyr Tyr Cys Val
                85                  90                  95

Thr Gly Thr Tyr Trp Gly Gln Gly Thr Leu Val Thr Val Ser Ser Gly
            100                 105                 110

Gly Gly Gly Ser Gly Gly Gly Ser Gly Gly Gly Ser Gly Gly Gly Gly
        115                 120                 125

Gly Gly Ser Gly Gly Gly Ser Gly Gly Gly Ser Gly Gly Gly Gly Gly
    130                 135                 140

Gly Ser Gly Gly Gly Ser Glu Val Gln Leu Val Glu Ser Gly Gly Gly
145                 150                 155                 160

Gly Leu Val Gln Pro Gly Asp Ser Leu Arg Leu Ser Cys Ala Ala Ser
                165                 170                 175

Gly Arg Ile Leu Ser Ile Asn Asn Met Val Trp Tyr Arg Gln Ala Pro
            180                 185                 190

Gly Lys Gln Arg Glu Leu Val Ala His Ile Thr Ser Gly Ser Thr
        195                 200                 205

Gly Tyr Ala Asp Ser Val Lys Gly Arg Phe Thr Ile Ser Arg Asp Asn
    210                 215                 220

Ala Lys Asn Thr Phe Tyr Leu Gln Met Thr Asn Leu Asn Pro Glu Asp
225                 230                 235                 240

Thr Ala Val Tyr Tyr Cys Asn Cys Trp Val Ser Ser Asp Ser Asn Ala
                245                 250                 255

Pro Leu Lys Asn Tyr Trp Gly Gln Gly Thr Leu Val Thr Val Ser Ser
            260                 265                 270
```

<210> SEQ ID NO 122
<211> LENGTH: 286
<212> TYPE: PRT
<213> ORGANISM: Artificial Sequence
<220> FEATURE:
<223> OTHER INFORMATION: Nanobody sequence

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Thr Ser Asn Ser Gly Ser Thr Tyr Tyr Gly Gly Ser Val Lys
    50                  55                  60

Gly Arg Phe Thr Ala Ser Arg Asp Asn Ala Lys Asn Thr Val Tyr Leu
```

```
            65                  70                  75                  80
Gln Met Asn Ser Leu Arg Pro Glu Asp Thr Ala Val Tyr Tyr Cys Val
                85                  90                  95

Ala Thr Ile Gly Cys Ala Thr Leu Gly Gly Thr Leu Asp Val Gln Arg
            100                 105                 110

Tyr Tyr Tyr Arg Gly Gln Gly Thr Leu Val Thr Val Ser Gly Gly
            115                 120                 125

Gly Gly Ser Gly Gly Gly Ser Gly Gly Gly Ser Gly Gly Gly
        130                 135                 140

Gly Ser Gly Gly Gly Ser Gly Gly Gly Ser Gly Gly Gly
145                 150                 155                 160

Ser Gly Gly Gly Ser Glu Val Gln Leu Val Glu Ser Gly Gly
                165                 170                 175

Leu Val Gln Ala Gly Gly Ser Leu Arg Leu Ser Cys Thr Ala Ser Gly
            180                 185                 190

Arg Thr Leu Ser Ser Tyr Thr Met Gly Trp Phe Arg Gln Ala Pro Gly
            195                 200                 205

Thr Glu Arg Glu Phe Val Ala Ala Met Thr Arg Ser Gly Phe Asn Thr
    210                 215                 220

Tyr Tyr Ala Asp Ser Val Lys Gly Arg Phe Thr Ile Ser Arg Asp Ser
225                 230                 235                 240

Thr Glu Asn Thr Met Ala Leu Gln Met Ser Ser Leu Lys Pro Glu Asp
                245                 250                 255

Thr Ala Val Tyr Tyr Cys Thr Ala Gly Arg Gly Leu Thr Ser Tyr Arg
                260                 265                 270

Ala Asp Tyr Trp Gly Gln Gly Thr Leu Val Thr Val Ser Ser
            275                 280                 285

<210> SEQ ID NO 123
<211> LENGTH: 286
<212> TYPE: PRT
<213> ORGANISM: Artificial Sequence
<220> FEATURE:
<223> OTHER INFORMATION: Nanobody sequence

<400> SEQUENCE: 123

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Leu Ser Ser Tyr
            20                  25                  30

Thr Met Gly Trp Phe Arg Gln Ala Pro Gly Thr Glu Arg Glu Phe Val
        35                  40                  45

Ala Ala Met Thr Arg Ser Gly Phe Asn Thr Tyr Tyr Ala Asp Ser Val
    50                  55                  60

Lys Gly Arg Phe Thr Ile Ser Arg Asp Ser Thr Glu Asn Thr Met Ala
65                  70                  75                  80

Leu Gln Met Ser Ser Leu Lys Pro Glu Asp Thr Ala Val Tyr Tyr Cys
                85                  90                  95

Thr Ala Gly Arg Gly Leu Thr Ser Tyr Arg Ala Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
```

-continued

```
                    145                 150                 155                 160
Glu Val Gln Leu Val Glu Ser Gly Gly Gly Leu Val Gln Pro Gly Gly
                165                 170                 175

Ser Leu Arg Leu Ser Cys Ala Ala Ser Gly Ser Thr Leu Asp Tyr Tyr
                180                 185                 190

Ala Ile Gly Trp Phe Arg Gln Ala Pro Gly Lys Glu Arg Glu Gly Val
                195                 200                 205

Ser Cys Thr Ser Asn Ser Gly Ser Thr Tyr Tyr Gly Gly Ser Val Lys
            210                 215                 220

Gly Arg Phe Thr Ala Ser Arg Asp Asn Ala Lys Asn Thr Val Tyr Leu
225                 230                 235                 240

Gln Met Asn Ser Leu Arg Pro Glu Asp Thr Ala Val Tyr Tyr Cys Val
                245                 250                 255

Ala Thr Ile Gly Cys Ala Thr Leu Gly Gly Thr Leu Asp Val Gln Arg
                260                 265                 270

Tyr Tyr Tyr Arg Gly Gln Gly Thr Leu Val Thr Val Ser Ser
                275                 280                 285

<210> SEQ ID NO 124
<211> LENGTH: 277
<212> TYPE: PRT
<213> ORGANISM: Artificial Sequence
<220> FEATURE:
<223> OTHER INFORMATION: Nanobody sequence

<400> SEQUENCE: 124

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Thr Phe Ser Thr Asn
                20                  25                  30

Pro Met Tyr Trp Tyr Arg Gln Ala Glu Gly Lys Gln Arg Glu Leu Val
                35                  40                  45

Ala Ser Ile Ser Ser Arg Gly Ile Thr Asn Tyr Ala Asp Ser Val Arg
            50                  55                  60

Gly Arg Phe Ser Ile Ser Arg Asp Asn Thr Lys Asp Thr Val Tyr Leu
65              70                  75                  80

Gln Met Asn Ser Leu Lys Pro Glu Asp Thr Ala Val Tyr Tyr Cys Arg
                85                  90                  95

Leu Ala Ser Leu Ser Ser Gly Thr Val Tyr Trp Gly Lys Gly Thr Leu
                100                 105                 110

Val Thr Val Ser Ser Gly Gly Gly Gly Ser Gly Gly Gly Gly Ser Gly
                115                 120                 125

Gly Gly Ser Gly Gly Gly Gly Ser Gly Gly Gly Gly Ser Gly Gly
            130                 135                 140

Gly Gly Ser Gly Gly Gly Ser Gly Gly Gly Gly Ser Glu Val Gln
145                 150                 155                 160

Leu Val Glu Ser Gly Gly Gly Leu Val Gln Ala Gly Gly Ser Leu Arg
                165                 170                 175

Leu Ser Cys Thr Ala Ser Gly Arg Thr Leu Ser Ser Tyr Thr Met Gly
                180                 185                 190

Trp Phe Arg Gln Ala Pro Gly Thr Glu Arg Glu Phe Val Ala Ala Met
                195                 200                 205

Thr Arg Ser Gly Phe Asn Thr Tyr Tyr Ala Asp Ser Val Lys Gly Arg
            210                 215                 220

Phe Thr Ile Ser Arg Asp Ser Thr Glu Asn Thr Met Ala Leu Gln Met
```

```
                225                 230                 235                 240

Ser Ser Leu Lys Pro Glu Asp Thr Ala Val Tyr Tyr Cys Thr Ala Gly
            245                 250                 255

Arg Gly Leu Thr Ser Tyr Arg Ala Asp Tyr Trp Gly Gln Gly Thr Leu
            260                 265                 270

Val Thr Val Ser Ser
            275

<210> SEQ ID NO 125
<211> LENGTH: 280
<212> TYPE: PRT
<213> ORGANISM: Artificial Sequence
<220> FEATURE:
<223> OTHER INFORMATION: Nanobody sequence

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Gly Asp Asn Tyr
            20                  25                  30

Glu Leu Tyr Ala Met Thr Trp Phe Arg Gln Ala Pro Gly Glu Arg Arg
        35                  40                  45

Asp Phe Val Ala Ser Val Thr Gly Asp Gly Ser Thr Ser Tyr Ala Asp
    50                  55                  60

Ser Val Lys Asp Arg Phe Thr Ile Ser Arg Asp Asn Ala Lys Lys Leu
65                  70                  75                  80

Met Tyr Leu Gln Met Asn Ser Leu Lys Pro Glu Asp Thr Ala Val Tyr
                85                  90                  95

Tyr Cys Arg Leu Leu Asn Tyr Trp Gly Gln Gly Thr Leu Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
            165                 170                 175

Ala Ala Ser Gly Ser Thr Leu Asp Tyr Tyr Ala Ile Gly Trp Phe Arg
            180                 185                 190

Gln Ala Pro Gly Lys Glu Arg Glu Gly Val Ser Cys Thr Ser Asn Ser
            195                 200                 205

Gly Ser Thr Tyr Tyr Gly Gly Ser Val Lys Gly Arg Phe Thr Ala Ser
        210                 215                 220

Arg Asp Asn Ala Lys Asn Thr Val Tyr Leu Gln Met Asn Ser Leu Arg
225                 230                 235                 240

Pro Glu Asp Thr Ala Val Tyr Tyr Cys Val Ala Thr Ile Gly Cys Ala
            245                 250                 255

Thr Leu Gly Gly Thr Leu Asp Val Gln Arg Tyr Tyr Tyr Arg Gly Gln
            260                 265                 270

Gly Thr Leu Val Thr Val Ser Ser
            275                 280

<210> SEQ ID NO 126
<211> LENGTH: 282
<212> TYPE: PRT
```

```
<213> ORGANISM: Artificial Sequence
<220> FEATURE:
<223> OTHER INFORMATION: Nanobody sequence

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Leu Ser Ser Tyr
            20                  25                  30

Thr Met Gly Trp Phe Arg Gln Ala Pro Gly Thr Glu Arg Glu Phe Val
        35                  40                  45

Ala Ala Met Thr Arg Ser Gly Phe Asn Thr Tyr Tyr Ala Asp Ser Val
50                  55                  60

Lys Gly Arg Phe Thr Ile Ser Arg Asp Ser Thr Glu Asn Thr Met Ala
65                  70                  75                  80

Leu Gln Met Ser Ser Leu Lys Pro Glu Asp Thr Ala Val Tyr Tyr Cys
                85                  90                  95

Thr Ala Gly Arg Gly Leu Thr Ser Tyr Arg Ala Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Ala Gly Gly
                165                 170                 175

Ser Leu Arg Leu Ser Cys Ala Ala Ser Arg Leu Thr Phe Asn His Tyr
            180                 185                 190

Asn Met Gly Trp Phe Arg Gln Ala Pro Gly Lys Glu Arg Glu Arg Val
        195                 200                 205

Ala Glu Val Thr Trp Ser Gly Asp Lys Ile Tyr Tyr Val Asp Ser Val
    210                 215                 220

Lys Gly Arg Phe Thr Ile Ser Arg Asp Asn Thr Pro Asn Pro Val Tyr
225                 230                 235                 240

Leu Tyr Leu Gln Met Asn Ser Leu Lys Pro Glu Asp Thr Ala Val Tyr
                245                 250                 255

Tyr Cys Ala Thr Ala Pro Arg Gly Leu Pro Tyr Ala Asn Gly Tyr Trp
            260                 265                 270

Gly Gln Gly Thr Leu Val Thr Val Ser Ser
        275                 280

<210> SEQ ID NO 127
<211> LENGTH: 271
<212> TYPE: PRT
<213> ORGANISM: Artificial Sequence
<220> FEATURE:
<223> OTHER INFORMATION: Nanobody sequence

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Arg Ser Val Asn
            20                  25                  30

Pro Met Ala Trp Phe Arg Gln Ala Pro Gly Arg Gln Arg Glu Trp Val
        35                  40                  45
```

Ala Thr Ile Ser Arg Ser Gly Tyr Ala Thr Tyr Ala Asp Ser Val Lys
    50                  55                  60

Gly Arg Phe Thr Ile Ser Gly Asp Asn Ala Lys Ser Ser Val Tyr Leu
65                  70                  75                  80

Gln Met Asn Ser Leu Lys Pro Glu Asp Thr Ala Val Tyr Tyr Cys Val
                85                  90                  95

Thr Gly Thr Tyr Trp Gly Gln Gly Thr Leu Val Thr Val Ser Ser Gly
            100                 105                 110

Gly Gly Gly Ser Gly Gly Gly Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Glu Val Gln Leu Val Glu Ser Gly Gly
145                 150                 155                 160

Gly Leu Val Gln Ala Gly Gly Ser Leu Arg Leu Ser Cys Thr Ala Ser
                165                 170                 175

Gly Arg Thr Leu Ser Ser Tyr Thr Met Gly Trp Phe Arg Gln Ala Pro
            180                 185                 190

Gly Thr Glu Arg Glu Phe Val Ala Ala Met Thr Arg Ser Gly Phe Asn
            195                 200                 205

Thr Tyr Tyr Ala Asp Ser Val Lys Gly Arg Phe Thr Ile Ser Arg Asp
        210                 215                 220

Ser Thr Glu Asn Thr Met Ala Leu Gln Met Ser Ser Leu Lys Pro Glu
225                 230                 235                 240

Asp Thr Ala Val Tyr Tyr Cys Thr Ala Gly Arg Gly Leu Thr Ser Tyr
                245                 250                 255

Arg Ala Asp Tyr Trp Gly Gln Gly Thr Leu Val Thr Val Ser Ser
            260                 265                 270

<210> SEQ ID NO 128
<211> LENGTH: 278
<212> TYPE: PRT
<213> ORGANISM: Artificial Sequence
<220> FEATURE:
<223> OTHER INFORMATION: Nanobody sequence

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ser Thr Ile Thr Ser Asn Leu Val Pro His Tyr Ala Asp Ser Val Gln
    50                  55                  60

Gly Arg Phe Thr Ile Ser Arg Asp Asn Ala Arg Asn Thr Val Tyr Leu
65                  70                  75                  80

Gln Met Asn Ser Leu Lys Pro Gln Asp Thr Ala His Tyr Tyr Cys Asn
                85                  90                  95

Ala Trp Ala Arg Ser Ser Gly Ala Thr Pro Tyr Thr Asn Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Gly Gly Gly
    130                 135                 140

```
Gly Ser Gly Gly Gly Gly Ser Gly Gly Gly Ser Gly Gly Gly
145                 150                 155                 160

Ser Glu Val Gln Leu Val Glu Ser Gly Gly Gly Leu Val Gln Ala Gly
                165                 170                 175

Gly Ser Leu Arg Leu Ser Cys Ala Ala Ser Gly Asn Thr Phe Ser Thr
            180                 185                 190

Asn Pro Met Tyr Trp Tyr Arg Gln Ala Glu Gly Lys Gln Arg Glu Leu
        195                 200                 205

Val Ala Ser Ile Ser Ser Arg Gly Ile Thr Asn Tyr Ala Asp Ser Val
    210                 215                 220

Arg Gly Arg Phe Ser Ile Ser Arg Asp Asn Thr Lys Asp Thr Val Tyr
225                 230                 235                 240

Leu Gln Met Asn Ser Leu Lys Pro Glu Asp Thr Ala Val Tyr Tyr Cys
                245                 250                 255

Arg Leu Ala Ser Leu Ser Ser Gly Thr Val Tyr Trp Gly Lys Gly Thr
            260                 265                 270

Leu Val Thr Val Ser Ser
        275

<210> SEQ ID NO 129
<211> LENGTH: 283
<212> TYPE: PRT
<213> ORGANISM: Artificial Sequence
<220> FEATURE:
<223> OTHER INFORMATION: Nanobody sequence

<400> SEQUENCE: 129

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Thr Phe Ser Thr Asn
            20                  25                  30

Pro Met Tyr Trp Tyr Arg Gln Ala Glu Gly Lys Gln Arg Glu Leu Val
        35                  40                  45

Ala Ser Ile Ser Ser Arg Gly Ile Thr Asn Tyr Ala Asp Ser Val Arg
    50                  55                  60

Gly Arg Phe Ser Ile Ser Arg Asp Asn Thr Lys Asp Thr Val Tyr Leu
65                  70                  75                  80

Gln Met Asn Ser Leu Lys Pro Glu Asp Thr Ala Val Tyr Tyr Cys Arg
                85                  90                  95

Leu Ala Ser Leu Ser Ser Gly Thr Val Tyr Trp Gly Lys Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly Gly
130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Ser Thr Leu Asp Tyr Tyr Ala Ile Gly
            180                 185                 190

Trp Phe Arg Gln Ala Pro Gly Lys Glu Arg Glu Gly Val Ser Cys Thr
        195                 200                 205

Ser Asn Ser Gly Ser Thr Tyr Tyr Gly Gly Ser Val Lys Gly Arg Phe
    210                 215                 220
```

```
Thr Ala Ser Arg Asp Asn Ala Lys Asn Thr Val Tyr Leu Gln Met Asn
225                 230                 235                 240

Ser Leu Arg Pro Glu Asp Thr Ala Val Tyr Tyr Cys Val Ala Thr Ile
            245                 250                 255

Gly Cys Ala Thr Leu Gly Gly Thr Leu Asp Val Gln Arg Tyr Tyr Tyr
            260                 265                 270

Arg Gly Gln Gly Thr Leu Val Thr Val Ser Ser
            275                 280

<210> SEQ ID NO 130
<211> LENGTH: 288
<212> TYPE: PRT
<213> ORGANISM: Artificial Sequence
<220> FEATURE:
<223> OTHER INFORMATION: Nanobody sequence

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp Tyr Tyr
            20                  25                  30

Ala Ile Gly Trp Phe Arg Gln Ala Pro Gly Lys Glu Arg Glu Gly Val
            35                  40                  45

Ser Cys Thr Ser Asn Ser Gly Ser Thr Tyr Tyr Gly Gly Ser Val Lys
50                  55                  60

Gly Arg Phe Thr Ala Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Val
                85                  90                  95

Ala Thr Ile Gly Cys Ala Thr Leu Gly Gly Thr Leu Asp Val Gln Arg
            100                 105                 110

Tyr Tyr Tyr Arg Gly Gln Gly Thr Leu Val Thr Val Ser Ser Gly Gly
            115                 120                 125

Gly Gly Ser Gly Gly Gly Ser Gly Gly Gly Gly Ser Gly Gly Gly
            130                 135             140

Gly Ser Gly Gly Gly Gly Ser Gly Gly Gly Gly Ser Gly Gly Gly Gly
145                 150                 155                 160

Ser Gly Gly Gly Gly Ser Glu Val Gln Leu Val Glu Ser Gly Gly Gly
            165                 170                 175

Leu Val Gln Ala Gly Gly Ser Leu Arg Leu Ser Cys Ala Ala Ser Arg
            180                 185                 190

Leu Thr Phe Asn His Tyr Asn Met Gly Trp Phe Arg Gln Ala Pro Gly
            195                 200                 205

Lys Glu Arg Glu Arg Val Ala Glu Val Thr Trp Ser Gly Asp Lys Ile
210                 215                 220

Tyr Tyr Val Asp Ser Val Lys Gly Arg Phe Thr Ile Ser Arg Asp Asn
225                 230                 235                 240

Thr Pro Asn Pro Val Tyr Leu Tyr Leu Gln Met Asn Ser Leu Lys Pro
            245                 250                 255

Glu Asp Thr Ala Val Tyr Tyr Cys Ala Thr Ala Pro Arg Gly Leu Pro
            260                 265                 270

Tyr Ala Asn Gly Tyr Trp Gly Gln Gly Thr Leu Val Thr Val Ser Ser
            275                 280                 285

<210> SEQ ID NO 131
<211> LENGTH: 278
```

```
<212> TYPE: PRT
<213> ORGANISM: Artificial Sequence
<220> FEATURE:
<223> OTHER INFORMATION: Nanobody sequence

<400> SEQUENCE: 131

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Thr Phe Ser Thr Asn
            20                  25                  30

Pro Met Tyr Trp Tyr Arg Gln Ala Glu Gly Lys Gln Arg Glu Leu Val
        35                  40                  45

Ala Ser Ile Ser Ser Arg Gly Ile Thr Asn Tyr Ala Asp Ser Val Arg
    50                  55                  60

Gly Arg Phe Ser Ile Ser Arg Asp Asn Thr Lys Asp Thr Val Tyr Leu
65                  70                  75                  80

Gln Met Asn Ser Leu Lys Pro Glu Asp Thr Ala Val Tyr Tyr Cys Arg
                85                  90                  95

Leu Ala Ser Leu Ser Ser Gly Thr Val Tyr Trp Gly Lys Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly Gly
    130                 135                 140

Gly Gly Ser Gly Gly Gly Gly Ser Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Ser Ile Phe Ser Ile Asn Asn Met Gly
            180                 185                 190

Trp Tyr Arg Gln Ala Pro Gly Lys Gln Arg Glu Leu Val Thr Val Val
        195                 200                 205

Thr Ser Asn Leu Ile Thr Thr Tyr Ala Asp Ser Val Lys Gly Arg Phe
    210                 215                 220

Thr Ile Ser Arg Asp Asn Ala Lys Asn Thr Val Tyr Leu Gln Met Asn
225                 230                 235                 240

Ser Leu Lys Pro Glu Asp Thr Ala Val Tyr Tyr Cys Asn Ala Trp Ala
                245                 250                 255

Arg Ser Val Gly Ser Val Pro Tyr Ser Gln Phe Trp Gly Gln Gly Thr
            260                 265                 270

Leu Val Thr Val Ser Ser
        275

<210> SEQ ID NO 132
<211> LENGTH: 278
<212> TYPE: PRT
<213> ORGANISM: Artificial Sequence
<220> FEATURE:
<223> OTHER INFORMATION: Nanobody sequence

<400> SEQUENCE: 132

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Thr Phe Ser Thr Asn
            20                  25                  30

Pro Met Tyr Trp Tyr Arg Gln Ala Glu Gly Lys Gln Arg Glu Leu Val
        35                  40                  45
```

```
Ala Ser Ile Ser Ser Arg Gly Ile Thr Asn Tyr Ala Asp Ser Val Arg
        50                  55                  60

Gly Arg Phe Ser Ile Ser Arg Asp Asn Thr Lys Asp Thr Val Tyr Leu
 65                  70                  75                  80

Gln Met Asn Ser Leu Lys Pro Glu Asp Thr Ala Val Tyr Tyr Cys Arg
                85                  90                  95

Leu Ala Ser Leu Ser Ser Gly Thr Val Tyr Trp Gly Lys Gly Thr Leu
                100                 105                 110

Val Thr Val Ser Ser Gly Gly Gly Ser Gly Gly Gly Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Gly Gly Gly Ser Glu Val Gln
145                 150                 155                 160

Leu Val Glu Ser Gly Gly Gly Leu Val Gln Pro Gly Asp Ser Leu Arg
                165                 170                 175

Leu Ser Cys Ala Ala Ser Gly Arg Ile Leu Ser Ile Asn Asn Met Val
                180                 185                 190

Trp Tyr Arg Gln Ala Pro Gly Lys Gln Arg Glu Leu Val Ala His Ile
                195                 200                 205

Thr Ser Ser Gly Ser Thr Gly Tyr Ala Asp Ser Val Lys Gly Arg Phe
                210                 215                 220

Thr Ile Ser Arg Asp Asn Ala Lys Asn Thr Phe Tyr Leu Gln Met Thr
225                 230                 235                 240

Asn Leu Asn Pro Glu Asp Thr Ala Val Tyr Tyr Cys Asn Cys Trp Val
                245                 250                 255

Ser Ser Asp Ser Asn Ala Pro Leu Lys Asn Tyr Trp Gly Gln Gly Thr
                260                 265                 270

Leu Val Thr Val Ser Ser
            275

<210> SEQ ID NO 133
<211> LENGTH: 279
<212> TYPE: PRT
<213> ORGANISM: Artificial Sequence
<220> FEATURE:
<223> OTHER INFORMATION: Nanobody sequence

<400> SEQUENCE: 133

Glu Val Gln Leu Val Glu Ser Gly Gly Gly Leu Val Gln Ala Gly Gly
 1               5                  10                  15

Ser Leu Arg Leu Ser Cys Ala Ala Ser Arg Leu Thr Phe Asn His Tyr
                20                  25                  30

Asn Met Gly Trp Phe Arg Gln Ala Pro Gly Lys Glu Arg Glu Arg Val
                35                  40                  45

Ala Glu Val Thr Trp Ser Gly Asp Lys Ile Tyr Tyr Val Asp Ser Val
        50                  55                  60

Lys Gly Arg Phe Thr Ile Ser Arg Asp Asn Thr Pro Asn Pro Val Tyr
 65                  70                  75                  80

Leu Tyr Leu Gln Met Asn Ser Leu Lys Pro Glu Asp Thr Ala Val Tyr
                85                  90                  95

Tyr Cys Ala Thr Ala Pro Arg Gly Leu Pro Tyr Ala Asn Gly Tyr Trp
                100                 105                 110

Gly Gln Gly Thr Leu Val Thr Val Ser Ser Gly Gly Gly Gly Ser Gly
                115                 120                 125
```

```
Gly Gly Gly Ser Gly Gly Gly Ser Gly Gly Gly Ser Gly Gly
    130                 135                 140
Gly Gly Ser Gly Gly Gly Ser Gly Gly Gly Ser Gly Gly Gly
145                 150                 155                 160
Gly Ser Glu Val Gln Leu Val Glu Ser Gly Gly Leu Val Gln Ala
                165                 170                 175
Gly Gly Ser Leu Arg Leu Ser Cys Ala Ala Ser Gly Asn Thr Phe Ser
            180                 185                 190
Thr Asn Pro Met Tyr Trp Tyr Arg Gln Ala Glu Gly Lys Gln Arg Glu
        195                 200                 205
Leu Val Ala Ser Ile Ser Ser Arg Gly Ile Thr Asn Tyr Ala Asp Ser
    210                 215                 220
Val Arg Gly Arg Phe Ser Ile Ser Arg Asp Asn Thr Lys Asp Thr Val
225                 230                 235                 240
Tyr Leu Gln Met Asn Ser Leu Lys Pro Glu Asp Thr Ala Val Tyr Tyr
                245                 250                 255
Cys Arg Leu Ala Ser Leu Ser Ser Gly Thr Val Tyr Trp Gly Lys Gly
            260                 265                 270
Thr Leu Val Thr Val Ser Ser
        275

<210> SEQ ID NO 134
<211> LENGTH: 278
<212> TYPE: PRT
<213> ORGANISM: Artificial Sequence
<220> FEATURE:
<223> OTHER INFORMATION: Nanobody sequence

<400> SEQUENCE: 134

Glu Val Gln Leu Val Glu Ser Gly Gly Gly Leu Val Gln Ala Gly Gly
1               5                   10                  15
Ser Leu Arg Leu Ser Cys Ala Ala Ser Gly Asn Thr Phe Ser Thr Asn
            20                  25                  30
Pro Met Tyr Trp Tyr Arg Gln Ala Glu Gly Lys Gln Arg Glu Leu Val
        35                  40                  45
Ala Ser Ile Ser Ser Arg Gly Ile Thr Asn Tyr Ala Asp Ser Val Arg
    50                  55                  60
Gly Arg Phe Ser Ile Ser Arg Asp Asn Thr Lys Asp Thr Val Tyr Leu
65                  70                  75                  80
Gln Met Asn Ser Leu Lys Pro Glu Asp Thr Ala Val Tyr Tyr Cys Arg
                85                  90                  95
Leu Ala Ser Leu Ser Ser Gly Thr Val Tyr Trp Gly Lys Gly Thr Leu
            100                 105                 110
Val Thr Val Ser Ser Gly Gly Gly Gly Ser Gly Gly Gly Gly Ser Gly
        115                 120                 125
Gly Gly Ser Gly Gly Gly Gly Ser Gly Gly Gly Ser Gly Gly
    130                 135                 140
Gly Gly Ser Gly Gly Gly Ser Gly Gly Gly Ser Glu Val Gln
145                 150                 155                 160
Leu Val Glu Ser Gly Gly Gly Leu Val Gln Pro Gly Ser Leu Arg
                165                 170                 175
Leu Ser Cys Ala Ala Ser Gly Arg Ile Phe Ser Ile Asn Thr Met Gly
            180                 185                 190
Trp Tyr Arg Gln Ala Pro Gly Lys Gln Arg Glu Leu Val Ala Gly Val
        195                 200                 205
```

```
Thr Ile Asn Ala Ile Thr Asn Tyr Ala Asp Ser Val Lys Gly Arg Phe
    210                 215                 220

Thr Ile Ser Arg Asp Asn Ala Lys Asn Thr Val Trp Leu Gln Met Asn
225                 230                 235                 240

Ser Leu Lys Pro Glu Asp Thr Ala Val Tyr Tyr Cys His Ala Trp Ala
                245                 250                 255

Arg Ser Ser Gly Ser Ala Pro Tyr Ser Gln Asn Trp Gly Gln Gly Thr
            260                 265                 270

Leu Val Thr Val Ser Ser
            275

<210> SEQ ID NO 135
<211> LENGTH: 281
<212> TYPE: PRT
<213> ORGANISM: Artificial Sequence
<220> FEATURE:
<223> OTHER INFORMATION: Nanobody sequence

<400> SEQUENCE: 135

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ile Met Gly Trp Phe Arg Gln Ala Pro Gly Lys Ala Arg Glu Phe Val
        35                  40                  45

Ala Asp Ile Thr Trp Gly Gln Arg Pro Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Tyr Cys Ala
                85                  90                  95

Ala Asp Leu Gly Val Val Ile Arg Glu Glu His Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Pro Gly Gly
                165                 170                 175

Ser Leu Arg Leu Ser Cys Ala Ala Ser Gly Ser Ile Phe Ser Ile Asn
            180                 185                 190

Thr Met Gly Trp Tyr Arg Gln Ala Pro Gly Lys Gln Arg Glu Leu Val
        195                 200                 205

Ser Thr Ile Thr Ser Asn Leu Val Pro His Tyr Ala Asp Ser Val Gln
    210                 215                 220

Gly Arg Phe Thr Ile Ser Arg Asp Asn Ala Arg Asn Thr Val Tyr Leu
225                 230                 235                 240

Gln Met Asn Ser Leu Lys Pro Gln Asp Thr Ala His Tyr Tyr Cys Asn
                245                 250                 255

Ala Trp Ala Arg Ser Ser Gly Ala Thr Pro Tyr Thr Asn Tyr Trp Gly
            260                 265                 270

Gln Gly Thr Leu Val Thr Val Ser Ser
        275                 280
```

```
<210> SEQ ID NO 136
<211> LENGTH: 281
<212> TYPE: PRT
<213> ORGANISM: Artificial Sequence
<220> FEATURE:
<223> OTHER INFORMATION: Nanobody sequence

<400> SEQUENCE: 136
```

| Glu | Val | Gln | Leu | Val | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Arg | Thr | Leu | Ser | Ser | Tyr |
|---|---|---|---|---|---|---|---|---|---|---|---|---|---|---|---|
| | | | 20 | | | | | 25 | | | | | 30 | | |

| Thr | Met | Gly | Trp | Phe | Arg | Gln | Ala | Pro | Gly | Thr | Glu | Arg | Glu | Phe | Val |
|---|---|---|---|---|---|---|---|---|---|---|---|---|---|---|---|
| | | 35 | | | | | 40 | | | | | 45 | | | |

| Ala | Ala | Met | Thr | Arg | Ser | Gly | Phe | Asn | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Ser | Thr | Glu | Asn | Thr | Met | Ala |
|---|---|---|---|---|---|---|---|---|---|---|---|---|---|---|---|
| 65 | | | | | 70 | | | | | 75 | | | | | 80 |

| Leu | Gln | Met | Ser | Ser | Leu | Lys | Pro | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Ala | Gly | Arg | Gly | Leu | Thr | Ser | Tyr | Arg | Ala | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser | Gly | Gly | Gly | Ser | Gly | Gly | Gly |
|---|---|---|---|---|---|---|---|---|---|---|---|---|---|---|
| | | 115 | | | | | 120 | | | | | 125 | | |

| Gly | Ser | Gly | Gly | Gly | Gly | Ser | Gly | Gly | Gly | Ser | Gly | Gly | Gly |
|---|---|---|---|---|---|---|---|---|---|---|---|---|---|
| | 130 | | | | | 135 | | | | | 140 | | |

| Ser | Gly | Gly | Gly | Gly | Ser | Gly | Gly | Gly | Ser | Gly | Gly | Gly | Ser |
|---|---|---|---|---|---|---|---|---|---|---|---|---|---|
| 145 | | | | | 150 | | | | | 155 | | | | 160 |

| Glu | Val | Gln | Leu | Val | Glu | Ser | Gly | Gly | Leu | Val | Gln | Pro | Gly | Gly |
|---|---|---|---|---|---|---|---|---|---|---|---|---|---|---|
| | | | | 165 | | | | | 170 | | | | | 175 |

| Ser | Leu | Arg | Leu | Ser | Cys | Ala | Ala | Ser | Gly | Arg | Ile | Phe | Ser | Ile | Asn |
|---|---|---|---|---|---|---|---|---|---|---|---|---|---|---|---|
| | | | 180 | | | | | 185 | | | | | 190 | | |

| Thr | Met | Gly | Trp | Tyr | Arg | Gln | Ala | Pro | Gly | Lys | Gln | Arg | Glu | Leu | Val |
|---|---|---|---|---|---|---|---|---|---|---|---|---|---|---|---|
| | | 195 | | | | | 200 | | | | | 205 | | | |

| Ala | Gly | Val | Thr | Ile | Asn | Ala | Ile | Thr | Asn | Tyr | Ala | Asp | Ser | Val | Lys |
|---|---|---|---|---|---|---|---|---|---|---|---|---|---|---|---|
| | 210 | | | | | 215 | | | | | 220 | | | | |

| Gly | Arg | Phe | Thr | Ile | Ser | Arg | Asp | Asn | Ala | Lys | Asn | Thr | Val | Trp | Leu |
|---|---|---|---|---|---|---|---|---|---|---|---|---|---|---|---|
| 225 | | | | | 230 | | | | | 235 | | | | | 240 |

| Gln | Met | Asn | Ser | Leu | Lys | Pro | Glu | Asp | Thr | Ala | Val | Tyr | Tyr | Cys | His |
|---|---|---|---|---|---|---|---|---|---|---|---|---|---|---|---|
| | | | | 245 | | | | | 250 | | | | | 255 | |

| Ala | Trp | Ala | Arg | Ser | Ser | Gly | Ser | Ala | Pro | Tyr | Ser | Gln | Asn | Trp | Gly |
|---|---|---|---|---|---|---|---|---|---|---|---|---|---|---|---|
| | | | 260 | | | | | 265 | | | | | 270 | | |

| Gln | Gly | Thr | Leu | Val | Thr | Val | Ser | Ser |
|---|---|---|---|---|---|---|---|---|
| | | 275 | | | | | 280 | |

```
<210> SEQ ID NO 137
<211> LENGTH: 277
<212> TYPE: PRT
<213> ORGANISM: Artificial Sequence
<220> FEATURE:
<223> OTHER INFORMATION: Nanobody sequence

<400> SEQUENCE: 137
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Ser | Thr | Arg | Ser | Val | Asn |
|---|---|---|---|---|---|---|---|---|---|---|---|---|---|---|---|

```
                20                25                30
Pro Met Ala Trp Phe Arg Gln Ala Pro Gly Arg Gln Arg Glu Trp Val
            35                40                45
Ala Thr Ile Ser Arg Ser Gly Tyr Ala Thr Tyr Ala Asp Ser Val Lys
        50                55                60
Gly Arg Phe Thr Ile Ser Gly Asp Asn Ala Lys Ser Ser Val Tyr Leu
65                  70                75                  80
Gln Met Asn Ser Leu Lys Pro Glu Asp Thr Ala Val Tyr Tyr Cys Val
                85                90                95
Thr Gly Thr Tyr Trp Gly Gln Gly Thr Leu Val Thr Val Ser Ser Gly
            100               105               110
Gly Gly Gly Ser Gly Gly Gly Ser Gly Gly Gly Ser Gly Gly Gly Gly
        115               120               125
Gly Gly Ser Gly Gly Gly Ser Gly Gly Gly Ser Gly Gly Gly Gly Gly
        130               135               140
Gly Ser Gly Gly Gly Ser Glu Val Gln Leu Val Glu Ser Gly Gly Gly
145               150               155               160
Gly Leu Val Gln Pro Gly Gly Ser Leu Arg Leu Ser Cys Ala Ala Ser
                165               170               175
Gly Ser Thr Leu Asp Tyr Tyr Ala Ile Gly Trp Phe Arg Gln Ala Pro
            180               185               190
Gly Lys Glu Arg Glu Gly Val Ser Cys Thr Ser Asn Ser Gly Ser Thr
            195               200               205
Tyr Tyr Gly Gly Ser Val Lys Gly Arg Phe Thr Ala Ser Arg Asp Asn
        210               215               220
Ala Lys Asn Thr Val Tyr Leu Gln Met Asn Ser Leu Arg Pro Glu Asp
225               230               235               240
Thr Ala Val Tyr Tyr Cys Val Ala Thr Ile Gly Cys Ala Thr Leu Gly
                245               250               255
Gly Thr Leu Asp Val Gln Arg Tyr Tyr Tyr Arg Gly Gln Gly Thr Leu
            260               265               270
Val Thr Val Ser Ser
            275

<210> SEQ ID NO 138
<211> LENGTH: 278
<212> TYPE: PRT
<213> ORGANISM: Artificial Sequence
<220> FEATURE:
<223> OTHER INFORMATION: Nanobody sequence

<400> SEQUENCE: 138

Glu Val Gln Leu Val Glu Ser Gly Gly Gly Leu Val Gln Ala Gly Gly
1               5                   10                  15
Ser Leu Arg Leu Ser Cys Ala Ala Ser Gly Asn Thr Phe Ser Thr Asn
            20                  25                  30
Pro Met Tyr Trp Tyr Arg Gln Ala Glu Gly Lys Gln Arg Glu Leu Val
            35                  40                  45
Ala Ser Ile Ser Ser Arg Gly Ile Thr Asn Tyr Ala Asp Ser Val Arg
        50                  55                  60
Gly Arg Phe Ser Ile Ser Arg Asp Asn Thr Lys Asp Thr Val Tyr Leu
65                  70                  75                  80
Gln Met Asn Ser Leu Lys Pro Glu Asp Thr Ala Val Tyr Tyr Cys Arg
                85                  90                  95
Leu Ala Ser Leu Ser Ser Gly Thr Val Tyr Trp Gly Lys Gly Thr Leu
```

```
                100             105             110
Val Thr Val Ser Ser Gly Gly Gly Ser Gly Gly Gly Ser Gly
            115             120             125

Gly Gly Gly Ser Gly Gly Gly Ser Gly Gly Gly Ser Gly Gly
            130             135             140

Gly Gly Ser Gly Gly Gly Ser Gly Gly Gly Ser Glu Val Gln
145             150             155             160

Leu Val Glu Ser Gly Gly Leu Val Gln Pro Gly Gly Ser Leu Arg
            165             170             175

Leu Ser Cys Ala Ala Ser Gly Ser Ile Phe Ser Ile Asn Thr Met Gly
            180             185             190

Trp Tyr Arg Gln Ala Pro Gly Lys Gln Arg Glu Leu Val Ser Thr Ile
            195             200             205

Thr Ser Asn Leu Val Pro His Tyr Ala Asp Ser Val Gln Gly Arg Phe
            210             215             220

Thr Ile Ser Arg Asp Asn Ala Arg Asn Thr Val Tyr Leu Gln Met Asn
225             230             235             240

Ser Leu Lys Pro Gln Asp Thr Ala His Tyr Tyr Cys Asn Ala Trp Ala
            245             250             255

Arg Ser Ser Gly Ala Thr Pro Tyr Thr Asn Tyr Trp Gly Gln Gly Thr
            260             265             270

Leu Val Thr Val Ser Ser
            275
```

<210> SEQ ID NO 139
<211> LENGTH: 277
<212> TYPE: PRT
<213> ORGANISM: Artificial Sequence
<220> FEATURE:
<223> OTHER INFORMATION: Nanobody sequence

<400> SEQUENCE: 139

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp Tyr Tyr
            20                  25                  30

Ala Ile Gly Trp Phe Arg Gln Ala Pro Gly Lys Glu Arg Glu Gly Val
            35                  40                  45

Ser Cys Thr Ser Asn Ser Gly Ser Thr Tyr Tyr Gly Gly Ser Val Lys
            50                  55                  60

Gly Arg Phe Thr Ala Ser Arg Asp Asn Ala Lys Asn Thr Val Tyr Leu
65              70                  75                  80

Gln Met Asn Ser Leu Arg Pro Glu Asp Thr Ala Val Tyr Tyr Cys Val
            85                  90                  95

Ala Thr Ile Gly Cys Ala Thr Leu Gly Gly Thr Leu Asp Val Gln Arg
            100             105             110

Tyr Tyr Tyr Arg Gly Gln Gly Thr Leu Val Thr Val Ser Ser Gly Gly
            115             120             125

Gly Gly Ser Gly Gly Gly Gly Ser Gly Gly Gly Ser Gly Gly Gly
            130             135             140

Gly Ser Gly Gly Gly Ser Gly Gly Gly Ser Gly Gly Gly
145             150             155             160

Ser Gly Gly Gly Ser Glu Val Gln Leu Val Glu Ser Gly Gly Gly
            165             170             175

Leu Val Gln Pro Gly Gly Ser Leu Arg Leu Ser Cys Ala Ala Ser Gly
```

```
              180                 185                 190
Ser Thr Arg Ser Val Asn Pro Met Ala Trp Phe Arg Gln Ala Pro Gly
            195                 200                 205

Arg Gln Arg Glu Trp Val Ala Thr Ile Ser Arg Ser Gly Tyr Ala Thr
            210                 215                 220

Tyr Ala Asp Ser Val Lys Gly Arg Phe Thr Ile Ser Gly Asp Asn Ala
225                 230                 235                 240

Lys Ser Ser Val Tyr Leu Gln Met Asn Ser Leu Lys Pro Glu Asp Thr
                245                 250                 255

Ala Val Tyr Tyr Cys Val Thr Gly Thr Tyr Trp Gly Gln Gly Thr Leu
            260                 265                 270

Val Thr Val Ser Ser
            275

<210> SEQ ID NO 140
<211> LENGTH: 287
<212> TYPE: PRT
<213> ORGANISM: Artificial Sequence
<220> FEATURE:
<223> OTHER INFORMATION: Nanobody sequence

<400> SEQUENCE: 140

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Thr Leu Asp Tyr Tyr
            20                  25                  30

Ala Ile Gly Trp Phe Arg Gln Ala Pro Gly Lys Glu Arg Glu Gly Val
            35                  40                  45

Ser Cys Thr Ser Asn Ser Gly Ser Thr Tyr Tyr Gly Gly Ser Val Lys
        50                  55                  60

Gly Arg Phe Thr Ala Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Val
                85                  90                  95

Ala Thr Ile Gly Cys Ala Thr Leu Gly Gly Thr Leu Asp Val Gln Arg
            100                 105                 110

Tyr Tyr Tyr Arg Gly Gln Gly Thr Leu Val Thr Val Ser Ser Gly Gly
        115                 120                 125

Gly Gly Ser Gly Gly Gly Ser Gly Gly Gly Ser Gly Gly
        130                 135                 140

Gly Ser Gly Gly Gly Ser Gly Gly Gly Ser Gly Gly Gly Gly
145                 150                 155                 160

Ser Gly Gly Gly Ser Glu Val Gln Leu Val Glu Ser Gly Gly Gly
                165                 170                 175

Leu Val Gln Pro Gly Gly Ser Leu Arg Leu Ser Cys Ala Ala Ser Gly
            180                 185                 190

Ser Ile Phe Ser Ile Asn Asn Met Gly Trp Tyr Arg Gln Ala Pro Gly
        195                 200                 205

Lys Gln Arg Glu Leu Val Thr Val Thr Ser Asn Leu Ile Thr Thr
            210                 215                 220

Tyr Ala Asp Ser Val Lys Gly Arg Phe Thr Ile Ser Arg Asp Asn Ala
225                 230                 235                 240

Lys Asn Thr Val Tyr Leu Gln Met Asn Ser Leu Lys Pro Glu Asp Thr
                245                 250                 255

Ala Val Tyr Tyr Cys Asn Ala Trp Ala Arg Ser Val Gly Ser Val Pro
```

```
                   260                 265                 270
Tyr Ser Gln Phe Trp Gly Gln Gly Thr Leu Val Thr Val Ser Ser
            275                 280                 285

<210> SEQ ID NO 141
<211> LENGTH: 280
<212> TYPE: PRT
<213> ORGANISM: Artificial Sequence
<220> FEATURE:
<223> OTHER INFORMATION: Nanobody sequence

<400> SEQUENCE: 141

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ile Met Gly Trp Phe Arg Gln Ala Pro Gly Lys Ala Arg Glu Phe Val
        35                  40                  45

Ala Asp Ile Thr Trp Gly Gln Arg Pro Tyr Tyr Ala Asp Ser Val Lys
50                  55                  60

Gly Arg Phe Thr Ile Ser Arg Asp Asn Ala Lys Asn Thr Val Tyr Leu
65                  70                  75                  80

Glu Met Asn Ser Leu Lys Pro Glu Asp Thr Ala Val Tyr Tyr Cys Ala
                85                  90                  95

Ala Asp Leu Gly Val Val Ile Arg Glu His Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Gly Gly Gly Gly Ser
145                 150                 155                 160

Glu Val Gln Leu Val Glu Ser Gly Gly Gly Leu Val Gln Ala Gly Gly
                165                 170                 175

Ser Leu Arg Leu Ser Cys Thr Ala Ser Gly Arg Thr Leu Ser Ser Tyr
            180                 185                 190

Thr Met Gly Trp Phe Arg Gln Ala Pro Gly Thr Glu Arg Glu Phe Val
        195                 200                 205

Ala Ala Met Thr Arg Ser Gly Phe Asn Thr Tyr Tyr Ala Asp Ser Val
    210                 215                 220

Lys Gly Arg Phe Thr Ile Ser Arg Asp Ser Thr Glu Asn Thr Met Ala
225                 230                 235                 240

Leu Gln Met Ser Ser Leu Lys Pro Glu Asp Thr Ala Val Tyr Tyr Cys
                245                 250                 255

Thr Ala Gly Arg Gly Leu Thr Ser Tyr Arg Ala Asp Tyr Trp Gly Gln
            260                 265                 270

Gly Thr Leu Val Thr Val Ser Ser
        275                 280

<210> SEQ ID NO 142
<211> LENGTH: 124
<212> TYPE: PRT
<213> ORGANISM: Artificial Sequence
<220> FEATURE:
<223> OTHER INFORMATION: Antibody fragment

<400> SEQUENCE: 142
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
            35                  40                  45

Ser Phe Ile Ser Tyr Asp Gly Ser Glu Lys Tyr Tyr Ala Ser Ser Val
    50                  55                  60

Lys Gly Arg Phe Thr Ile Ser Arg Asp Asn Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
            115                 120
```

<210> SEQ ID NO 143
<211> LENGTH: 107
<212> TYPE: PRT
<213> ORGANISM: Artificial Sequence
<220> FEATURE:
<223> OTHER INFORMATION: Antibody fragment

<400> SEQUENCE: 143

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
            20                  25                  30

Val Ala Trp Tyr Gln Gln Arg Pro Gly Lys Ala Pro Asn Leu Leu Ile
            35                  40                  45

Tyr Asp Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Phe Trp Gly Thr Pro Tyr
                85                  90                  95

Thr Phe Gly Gln Gly Thr Lys Leu Glu Ile Lys
            100                 105
```

<210> SEQ ID NO 144
<211> LENGTH: 124
<212> TYPE: PRT
<213> ORGANISM: Artificial Sequence
<220> FEATURE:
<223> OTHER INFORMATION: Antibody fragment

<400> SEQUENCE: 144

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
            35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Thr Val Thr Val Ser Ser
        115                 120

<210> SEQ ID NO 145
<211> LENGTH: 107
<212> TYPE: PRT
<213> ORGANISM: Artificial Sequence
<220> FEATURE:
<223> OTHER INFORMATION: Antibody fragment

<400> SEQUENCE: 145

Asp Ile Gln Leu Thr Gln Ser Pro Ser Thr Leu Ser Ala Ser Val Gly
1               5                   10                  15

Asp Ser Val Thr Ile Thr Cys Arg Ala Ser Glu Gly Val Asp Arg Trp
            20                  25                  30

Leu Ala Trp Tyr Gln Gln Lys Pro Gly Arg Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Val Ala Thr Tyr Tyr Cys Gln His Phe Trp Gly Thr Pro Tyr
                85                  90                  95

Thr Phe Gly Gln Gly Thr Lys Leu Glu Ile Lys
            100                 105

<210> SEQ ID NO 146
<211> LENGTH: 124
<212> TYPE: PRT
<213> ORGANISM: Artificial Sequence
<220> FEATURE:
<223> OTHER INFORMATION: Antibody fragment

<400> SEQUENCE: 146

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Tyr Trp Gly Gln Gly Thr Thr Val Thr Val Ser Ser
        115                 120

<210> SEQ ID NO 147
<211> LENGTH: 107
<212> TYPE: PRT

<213> ORGANISM: Artificial Sequence
<220> FEATURE:
<223> OTHER INFORMATION: Antibody fragment

<400> SEQUENCE: 147

```
Asp Ile Gln Leu Thr Gln Ser Pro Ser Thr Leu Ser Ala Ser Val Gly
1               5                   10                  15

Asp Ser Val Thr Ile Thr Cys Arg Ala Ser Glu Gly Val Asp Arg Trp
            20                  25                  30

Leu Ala Trp Tyr Gln Gln Lys Pro Gly Arg Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Val Ala Thr Tyr Tyr Cys Gln His Phe Trp Ser Thr Pro Tyr
                85                  90                  95

Thr Phe Gly Gln Gly Thr Lys Leu Glu Ile Lys
            100                 105
```

<210> SEQ ID NO 148
<211> LENGTH: 103
<212> TYPE: PRT
<213> ORGANISM: Artificial Sequence
<220> FEATURE:
<223> OTHER INFORMATION: Antibody fragment

<400> SEQUENCE: 148

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 149
<211> LENGTH: 107
<212> TYPE: PRT
<213> ORGANISM: Artificial Sequence
<220> FEATURE:
<223> OTHER INFORMATION: Antibody fragment

<400> SEQUENCE: 149

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 150
<211> LENGTH: 24
<212> TYPE: DNA
<213> ORGANISM: Artificial Sequence
<220> FEATURE:
<223> OTHER INFORMATION: Primer sequence

<400> SEQUENCE: 150
gaggtgcaat tggtggagtc tggg        24

<210> SEQ ID NO 151
<211> LENGTH: 30
<212> TYPE: DNA
<213> ORGANISM: Artificial Sequence
<220> FEATURE:
<223> OTHER INFORMATION: Primer sequence

<400> SEQUENCE: 151
accgcctccg gaggagaccg tgaccagggt        30

<210> SEQ ID NO 152
<211> LENGTH: 34
<212> TYPE: DNA
<213> ORGANISM: Artificial Sequence
<220> FEATURE:
<223> OTHER INFORMATION: Primer sequence

<400> SEQUENCE: 152
tcttggatcc gaggtgcagc tggtggagtc tggg        34

<210> SEQ ID NO 153
<211> LENGTH: 21
<212> TYPE: DNA
<213> ORGANISM: Artificial Sequence
<220> FEATURE:
<223> OTHER INFORMATION: Primer sequence

<400> SEQUENCE: 153
tgaggagacg gtgaccaggg t        21

<210> SEQ ID NO 154
<211> LENGTH: 24
<212> TYPE: DNA
<213> ORGANISM: Artificial Sequence
<220> FEATURE:
<223> OTHER INFORMATION: Primer sequence

<400> SEQUENCE: 154
gaggtgcaat tggtggagtc tggg        24

<210> SEQ ID NO 155
<211> LENGTH: 35
<212> TYPE: DNA
<213> ORGANISM: Artificial Sequence
<220> FEATURE:
<223> OTHER INFORMATION: Primer sequence

<400> SEQUENCE: 155

-continued acttgaagac ctccggagga gaccgtgacc agggt                35

<210> SEQ ID NO 156
<211> LENGTH: 41
<212> TYPE: DNA
<213> ORGANISM: Artificial Sequence
<220> FEATURE:
<223> OTHER INFORMATION: Primer sequence

<400> SEQUENCE: 156
acttgaagac tggatccgag gtgcagttgg tggagtctgg g                41

<210> SEQ ID NO 157
<211> LENGTH: 21
<212> TYPE: DNA
<213> ORGANISM: Artificial Sequence
<220> FEATURE:
<223> OTHER INFORMATION: Primer sequence

<400> SEQUENCE: 157
tgaggagacg gtgaccaggg t                21

<210> SEQ ID NO 158
<211> LENGTH: 40
<212> TYPE: PRT
<213> ORGANISM: Artificial Sequence
<220> FEATURE:
<223> OTHER INFORMATION: Linker sequence

<400> SEQUENCE: 158

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 159
<211> LENGTH: 294
<212> TYPE: PRT
<213> ORGANISM: Pseudomonas aeruginosa

<400> SEQUENCE: 159

Met Glu Val Arg Asn Leu Asn Ala Ala Arg Glu Leu Phe Leu Asp Glu
1               5                   10                  15

Leu Leu Ala Ala Ser Ala Ala Pro Ala Ser Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val

```
                130                 135                 140
Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Ser Asn Leu Asp Thr Phe Ser Gly Lys Leu Ser Ile Lys
                195                 200                 205

Asp Phe Leu Ser Gly Ser Pro Lys Gln Ser Gly Glu Leu Lys Gly Leu
                210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285

Asp Ile Leu Ser Ala Ile
    290

<210> SEQ ID NO 160
<211> LENGTH: 294
<212> TYPE: PRT
<213> ORGANISM: Pseudomonas aeruginosa

<400> SEQUENCE: 160

Met Glu Val Arg Asn Leu Asn Ala Ala Arg Glu Leu Phe Leu Asp Glu
1               5                   10                  15

Leu Leu Ala Ala Ser Ala Pro Ala Ser Ala Glu Gln Glu Glu Leu
                20                  25                  30

Leu Ala Leu Leu Arg Ser Glu Arg Ile Val Leu Ala His Ala Gly Gln
                35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
                115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Ser Asn Leu Asp Thr Phe Ser Gly Lys Leu Ser Ile Lys
                195                 200                 205
```

```
Asp Phe Leu Ser Gly Ser Pro Lys Gln Ser Gly Glu Leu Lys Gly Leu
    210                 215                 220

Gly Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285

Asp Ile Leu Ser Ala Ile
            290
```

<210> SEQ ID NO 161
<211> LENGTH: 294
<212> TYPE: PRT
<213> ORGANISM: Pseudomonas aeruginosa

<400> SEQUENCE: 161

```
Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Leu
                20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65              70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Asn Asn Leu Asp Thr Phe Ser Gly Lys Leu Ser Ile Lys
            195                 200                 205

Asp Phe Val Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285
```

```
Asp Ile Leu Ser Ala Ile
    290

<210> SEQ ID NO 162
<211> LENGTH: 294
<212> TYPE: PRT
<213> ORGANISM: Pseudomonas aeruginosa

<400> SEQUENCE: 162

Met Glu Val Arg Asn Leu Asn Ala Ala Arg Glu Leu Phe Leu Asp Glu
1               5                   10                  15

Leu Leu Ala Ala Ser Ala Ala Pro Ala Ser Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290

<210> SEQ ID NO 163
<211> LENGTH: 294
<212> TYPE: PRT
<213> ORGANISM: Pseudomonas aeruginosa

<400> SEQUENCE: 163

Met Glu Val Arg Asn Leu Asn Ala Ala Arg Glu Leu Phe Leu Asp Glu
1               5                   10                  15
```

```
Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu Tyr Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290

<210> SEQ ID NO 164
<211> LENGTH: 294
<212> TYPE: PRT
<213> ORGANISM: Pseudomonas aeruginosa

<400> SEQUENCE: 164

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
```

```
                85                  90                  95
Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
        130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Phe
        210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
        290

<210> SEQ ID NO 165
<211> LENGTH: 294
<212> TYPE: PRT
<213> ORGANISM: Pseudomonas aeruginosa

<400> SEQUENCE: 165

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu His Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
        130                 135                 140

Tyr Ser Val Ile Gln Ser Gln Ile Asn Ala Ala Leu Ser Ala Lys Gln
145                 150                 155                 160
```

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 166
<211> LENGTH: 294
<212> TYPE: PRT
<213> ORGANISM: Pseudomonas aeruginosa

<400> SEQUENCE: 166

Met Glu Val Arg Asn Phe Asn Ala Gly Arg Glu Leu Phe Leu Asp Glu
1               5                   10                  15

Leu Leu Ala Ala Pro Ala Ala Pro Ala Ser Ala Glu Gln Glu Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
            50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Arg Asp Glu Tyr Pro Phe Glu Lys Asp Asn Asn Pro Val Gly Asn Phe
225                 230                 235                 240

```
Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
        260                 265                 270

Val Glu Ala Leu Asn Arg Phe Ile Gln Lys Tyr Asp Ser Val Leu Arg
            275                 280                 285

Asp Ile Leu Ser Ala Ile
        290

<210> SEQ ID NO 167
<211> LENGTH: 294
<212> TYPE: PRT
<213> ORGANISM: Pseudomonas aeruginosa

<400> SEQUENCE: 167

Met Glu Val Arg Asn Phe Asn Ala Ala Arg Glu Leu Phe Leu Asp Glu
1               5                   10                  15

Leu Leu Ala Ala Pro Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290
```

<210> SEQ ID NO 168
<211> LENGTH: 294
<212> TYPE: PRT
<213> ORGANISM: Pseudomonas aeruginosa

<400> SEQUENCE: 168

```
Met Glu Val Arg Asn Phe Asn Ala Gly Arg Glu Leu Phe Leu Asp Glu
1               5                   10                  15

Leu Leu Ala Ala Pro Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
210                 215                 220

Lys Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
        290
```

<210> SEQ ID NO 169
<211> LENGTH: 294
<212> TYPE: PRT
<213> ORGANISM: Pseudomonas aeruginosa

<400> SEQUENCE: 169

```
Met Glu Val Arg Asn Phe Asn Ala Ala Arg Glu Leu Phe Leu Asp Glu
1               5                   10                  15

Leu Leu Ala Ala Pro Ala Ala Pro Ala Ser Ala Glu Gln Glu Glu Leu
            20                  25                  30

Leu Ala Leu Leu Arg Ser Glu Arg Ile Val Leu Ala His Ala Gly Gln
```

```
            35                  40                  45
Pro Leu Ser Glu Ala Gln Val Leu Lys Ala Leu Ala Trp Leu Leu Ala
 50                  55                  60
Ala Asn Pro Ser Ala Pro Pro Gly Gln Gly Leu Glu Val Leu Arg Glu
 65                  70                  75                  80
Val Leu Gln Ala Arg Arg Gln Pro Gly Ala Gln Trp Asp Leu Arg Glu
                 85                  90                  95
Phe Leu Val Ser Ala Tyr Phe Ser Leu His Gly Arg Leu Asp Glu Asp
                100                 105                 110
Val Ile Gly Val Tyr Lys Asp Val Leu Gln Thr Gln Asp Gly Lys Arg
                115                 120                 125
Lys Ala Leu Leu Asp Glu Leu Lys Ala Leu Thr Ala Glu Leu Lys Val
130                 135                 140
Tyr Ser Val Ile Gln Ser Gln Ile Asn Ala Ala Leu Ser Ala Lys Gln
145                 150                 155                 160
Gly Ile Arg Ile Asp Ala Gly Gly Ile Asp Leu Val Asp Pro Thr Leu
                165                 170                 175
Tyr Gly Tyr Ala Val Gly Asp Pro Arg Trp Lys Asp Ser Pro Glu Ser
                180                 185                 190
Ala Leu Leu Ser Asn Leu Asp Thr Phe Ser Gly Lys Leu Ser Ile Lys
                195                 200                 205
Asp Phe Leu Ser Gly Ser Pro Lys Gln Ser Gly Glu Leu Lys Gly Leu
210                 215                 220
Lys Asp Glu Tyr Pro Phe Glu Lys Asp Asn Asn Pro Val Gly Asn Phe
225                 230                 235                 240
Ala Thr Thr Val Ser Asp Arg Ser Arg Pro Leu Asn Asp Lys Val Asn
                245                 250                 255
Glu Lys Thr Thr Leu Leu Asn Asp Thr Ser Ser Arg Tyr Asn Ser Ala
                260                 265                 270
Val Glu Ala Leu Asn Arg Phe Ile Gln Lys Tyr Asp Ser Val Leu Arg
                275                 280                 285
Asp Ile Leu Ser Ala Ile
                290

<210> SEQ ID NO 170
<211> LENGTH: 294
<212> TYPE: PRT
<213> ORGANISM: Pseudomonas aeruginosa

<400> SEQUENCE: 170

Met Glu Val Arg Asn Phe Asn Ala Ala Arg Glu Leu Phe Leu Asp Glu
 1                   5                  10                  15
Leu Leu Asp Ala Pro Ala Ala Pro Ala Ser Ala Glu Gln Glu Glu Leu
                 20                  25                  30
Leu Ala Leu Leu Arg Ser Glu Arg Ile Val Leu Ala His Ala Gly Gln
                 35                  40                  45
Pro Leu Ser Glu Ala Gln Val Leu Lys Ala Leu Ala Trp Leu Leu Ala
 50                  55                  60
Ala Asn Pro Ser Ala Pro Pro Gly Gln Gly Leu Glu Val Leu Arg Glu
 65                  70                  75                  80
Val Leu Gln Ala Arg Arg Gln Pro Gly Ala Gln Trp Asp Leu Arg Glu
                 85                  90                  95
Phe Leu Val Ser Ala Tyr Phe Ser Leu His Gly Arg Leu Asp Glu Asp
                100                 105                 110
```

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
    290

<210> SEQ ID NO 171
<211> LENGTH: 294
<212> TYPE: PRT
<213> ORGANISM: Pseudomonas aeruginosa

<400> SEQUENCE: 171

Met Glu Val Arg Asn Leu Asn Ala Gly Arg Glu Leu Phe Leu Asp Glu
1               5                   10                  15

Leu Leu Ala Ala Pro Ala Pro Ala Ser Ala Glu Gln Glu Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
        50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

```
Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 172
<211> LENGTH: 294
<212> TYPE: PRT
<213> ORGANISM: Pseudomonas aeruginosa

<400> SEQUENCE: 172

Met Glu Val Arg Asn Phe Asn Ala Gly Arg Glu Leu Phe Leu Asp Glu
1               5                   10                  15

Leu Leu Ala Ala Pro Ala Pro Ala Ser Ala Glu Gln Lys Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
```

```
                260                 265                 270
Val Glu Ala Leu Asn Arg Phe Ile Gln Lys Tyr Asp Ser Val Leu Arg
            275                 280                 285

Asp Ile Leu Ser Ala Ile
        290

<210> SEQ ID NO 173
<211> LENGTH: 294
<212> TYPE: PRT
<213> ORGANISM: Pseudomonas aeruginosa

<400> SEQUENCE: 173

Met Glu Val Arg Asn Phe Asn Ala Ser Arg Glu Leu Phe Leu Asp Glu
1               5                   10                  15

Leu Leu Ala Ala Pro Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290

<210> SEQ ID NO 174
<211> LENGTH: 294
<212> TYPE: PRT
<213> ORGANISM: Pseudomonas aeruginosa
```

<400> SEQUENCE: 174

Met Glu Val Arg Asn Leu Asn Ala Ala Arg Glu Leu Phe Leu Asp Glu
1               5                   10                  15

Leu Leu Ala Ala Ser Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65              70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Ser Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
            290

<210> SEQ ID NO 175
<211> LENGTH: 294
<212> TYPE: PRT
<213> ORGANISM: Pseudomonas aeruginosa

<400> SEQUENCE: 175

Met Glu Val Arg Asn Phe Asn Ala Ala Arg Glu Leu Phe Leu Asp Glu
1               5                   10                  15

Leu Leu Ala Ala Pro Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

-continued

```
Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                 85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
210                 215                 220

Lys Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
        290

<210> SEQ ID NO 176
<211> LENGTH: 294
<212> TYPE: PRT
<213> ORGANISM: Pseudomonas aeruginosa

<400> SEQUENCE: 176

Met Glu Val Arg Asn Leu Asn Ala Ala Arg Glu Leu Phe Leu Asp Glu
 1               5                  10                  15

Leu Leu Ala Ala Pro Ala Ala Pro Ala Ser Ala Glu Gln Gly Glu Leu
                20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
        50                  55                  60

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                 85                  90                  95

Phe Leu Val Ser Ala Tyr Phe Ser Leu His Gly Arg Leu Asp Glu Asn
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
130                 135                 140
```

```
Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Lys Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 177
<211> LENGTH: 294
<212> TYPE: PRT
<213> ORGANISM: Pseudomonas aeruginosa

<400> SEQUENCE: 177

Met Glu Val Arg Asn Phe Asn Ala Gly Arg Glu Leu Phe Leu Asp Glu
1               5                   10                  15

Leu Leu Ala Ala Pro Ala Pro Ala Ser Ala Glu Gln Glu Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Val Leu Lys Gly Leu
```

```
            210                 215                 220
Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285

Asp Ile Leu Ser Ala Ile
                290

<210> SEQ ID NO 178
<211> LENGTH: 294
<212> TYPE: PRT
<213> ORGANISM: Pseudomonas aeruginosa

<400> SEQUENCE: 178

Met Glu Val Arg Asn Leu Asn Ala Gly Arg Glu Leu Phe Leu Asp Glu
1               5                   10                  15

Leu Leu Ala Ala Pro Ala Pro Ala Ser Ala Glu Gln Lys Glu Leu
                20                  25                  30

Leu Ala Leu Leu Arg Ser Glu Arg Ile Val Leu Ala His Ala Gly Gln
                35                  40                  45

Pro Leu Ser Glu Ala Gln Val Leu Lys Ala Leu Ala Trp Leu Leu Ala
        50                  55                  60

Ala Asn Pro Ser Ala Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu Arg Gly Arg Leu Asp Glu Asp
                100                 105                 110

Val Ile Gly Val Tyr Lys Asp Val Leu Gln Thr Gln Asp Gly Lys Arg
                115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Ser Asn Leu Asp Thr Phe Ser Gly Lys Leu Ser Ile Lys
                195                 200                 205

Asp Phe Leu Ser Gly Ser Pro Lys Gln Ser Gly Glu Leu Lys Gly Leu
                210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285
```

```
Asp Ile Leu Ser Ala Ile
    290

<210> SEQ ID NO 179
<211> LENGTH: 294
<212> TYPE: PRT
<213> ORGANISM: Pseudomonas aeruginosa

<400> SEQUENCE: 179

Met Glu Val Arg Asn Phe Asn Ala Gly Arg Glu Leu Phe Leu Asp Glu
1               5                   10                  15

Leu Leu Ala Ala Pro Ala Ala Pro Ala Ser Ala Glu Gln Glu Glu Leu
            20                  25                  30

Met Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Arg Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290

<210> SEQ ID NO 180
<211> LENGTH: 294
<212> TYPE: PRT
<213> ORGANISM: Pseudomonas aeruginosa

<400> SEQUENCE: 180

Met Glu Val Arg Asn Leu Asn Ala Gly Arg Glu Leu Phe Leu Asp Glu
1               5                   10                  15
```

```
Leu Leu Ala Ala Pro Ala Pro Ala Ser Ala Glu Gln Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
 50                  55                  60

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
                180                 185                 190

Ala Leu Leu Ser Asn Leu Asp Thr Phe Ser Gly Lys Leu Ser Ile Lys
                195                 200                 205

Asp Phe Leu Ser Gly Ser Pro Lys Gln Ser Gly Glu Leu Lys Gly Leu
210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
                260                 265                 270

Val Glu Ala Leu Asn Arg Phe Ile Gln Lys Tyr Asp Ser Val Leu Arg
                275                 280                 285

Asp Ile Leu Ser Ala Ile
                290

<210> SEQ ID NO 181
<211> LENGTH: 294
<212> TYPE: PRT
<213> ORGANISM: Pseudomonas aeruginosa

<400> SEQUENCE: 181

Met Glu Val Arg Asn Phe Asn Ala Ala Arg Glu Leu Phe Leu Asp Glu
 1               5                  10                  15

Leu Leu Ala Ala Ser Ala Ala Pro Ala Ser Ala Glu Gln Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
 50                  55                  60

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                85                  90                  95
```

Phe Leu Val Ser Ala Tyr Phe Ser Leu His Gly Arg Leu Asp Glu Asp
                100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
                195                 200                 205

Asp Phe Leu Ser Gly Ser Pro Lys Gln Ser Gly Glu Leu Lys Gly Leu
            210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
                275                 280                 285

Asp Ile Leu Ser Ala Ile
    290

<210> SEQ ID NO 182
<211> LENGTH: 5
<212> TYPE: PRT
<213> ORGANISM: Artificial Sequence
<220> FEATURE:
<223> OTHER INFORMATION: Primer sequence

<400> SEQUENCE: 182

Gly Gly Gly Gly Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Primer sequence

<400> SEQUENCE: 183

Ser Gly Gly Ser Gly Gly Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Primer sequence

<400> SEQUENCE: 184

Gly Gly Gly Gly Cys Gly Gly Gly Ser
1               5

<210> SEQ ID NO 185
<211> LENGTH: 9
<212> TYPE: PRT
<213> ORGANISM: Artificial Sequence
<220> FEATURE:
<223> OTHER INFORMATION: Primer sequence

<400> SEQUENCE: 185

Gly Gly Gly Gly Ser Gly Gly Gly Ser
1               5

<210> SEQ ID NO 186
<211> LENGTH: 10
<212> TYPE: PRT
<213> ORGANISM: Artificial Sequence
<220> FEATURE:
<223> OTHER INFORMATION: Primer sequence

<400> SEQUENCE: 186

Gly Gly Gly Gly Ser Gly Gly Gly Gly Ser
1               5                   10

<210> SEQ ID NO 187
<211> LENGTH: 15
<212> TYPE: PRT
<213> ORGANISM: Artificial Sequence
<220> FEATURE:
<223> OTHER INFORMATION: Primer sequence

<400> SEQUENCE: 187

Gly Gly Gly Gly Ser Gly Gly Gly Gly Ser Gly Gly Gly Gly Ser
1               5                   10                  15

<210> SEQ ID NO 188
<211> LENGTH: 18
<212> TYPE: PRT
<213> ORGANISM: Artificial Sequence
<220> FEATURE:
<223> OTHER INFORMATION: Primer sequence

<400> SEQUENCE: 188

Gly Gly Gly Gly Ser Gly Gly Gly Gly Ser Gly Gly Gly Gly Gly
1               5                   10                  15

Gly Ser

<210> SEQ ID NO 189
<211> LENGTH: 20
<212> TYPE: PRT
<213> ORGANISM: Artificial Sequence
<220> FEATURE:
<223> OTHER INFORMATION: Primer sequence

<400> SEQUENCE: 189

Gly Gly Gly Gly Ser Gly Gly Gly Gly Ser Gly Gly Gly Gly Ser Gly
1               5                   10                  15

Gly Gly Gly Ser
            20

<210> SEQ ID NO 190
<211> LENGTH: 25
<212> TYPE: PRT
<213> ORGANISM: Artificial Sequence
<220> FEATURE:
<223> OTHER INFORMATION: Primer sequence

<400> SEQUENCE: 190

Gly Gly Gly Gly Ser Gly Gly Gly Ser Gly Gly Gly Ser Gly
1               5                   10                  15

Gly Gly Gly Ser Gly Gly Gly Ser
            20                  25

<210> SEQ ID NO 191
<211> LENGTH: 30
<212> TYPE: PRT
<213> ORGANISM: Artificial Sequence
<220> FEATURE:
<223> OTHER INFORMATION: Primer sequence

<400> SEQUENCE: 191

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 192
<211> LENGTH: 35
<212> TYPE: PRT
<213> ORGANISM: Artificial Sequence
<220> FEATURE:
<223> OTHER INFORMATION: Primer sequence

<400> SEQUENCE: 192

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 193
<211> LENGTH: 40
<212> TYPE: PRT
<213> ORGANISM: Artificial Sequence
<220> FEATURE:
<223> OTHER INFORMATION: Primer sequence

<400> SEQUENCE: 193

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 194
<211> LENGTH: 15
<212> TYPE: PRT
<213> ORGANISM: Artificial Sequence
<220> FEATURE:
<223> OTHER INFORMATION: Primer sequence

<400> SEQUENCE: 194

Glu Pro Lys Ser Cys Asp Lys Thr His Thr Cys Pro Pro Cys Pro
1               5                   10                  15

<210> SEQ ID NO 195
<211> LENGTH: 24
<212> TYPE: PRT
<213> ORGANISM: Artificial Sequence
<220> FEATURE:
<223> OTHER INFORMATION: Primer sequence

<400> SEQUENCE: 195

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 196
<211> LENGTH: 12
<212> TYPE: PRT
<213> ORGANISM: Artificial Sequence
<220> FEATURE:
<223> OTHER INFORMATION: Primer sequence

<400> SEQUENCE: 196

Glu Pro Lys Thr Pro Lys Pro Gln Pro Ala Ala Ala
1               5                   10

<210> SEQ ID NO 197
<211> LENGTH: 62
<212> TYPE: PRT
<213> ORGANISM: Artificial Sequence
<220> FEATURE:
<223> OTHER INFORMATION: Primer sequence

<400> SEQUENCE: 197

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 198
<211> LENGTH: 141
<212> TYPE: PRT
<213> ORGANISM: Pseudomonas aeruginosa

<400> SEQUENCE: 198

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Val Tyr Ser Val Ile
            20                  25                  30

Gln Ser Gln Ile Asn Ala Ala Leu Ser Ala Lys Gln Gly Ile Arg Ile
        35                  40                  45

Asp Ala Gly Gly Ile Asp Leu Val Asp Pro Thr Leu Tyr Gly Tyr Ala
    50                  55                  60

Val Gly Asp Pro Arg Trp Lys Asp Ser Pro Glu Tyr Ala Leu Leu Ser
65                  70                  75                  80

Asn Leu Asp Thr Phe Ser Gly Lys Leu Ser Ile Lys Asp Phe Leu Ser
                85                  90                  95

Gly Ser Pro Lys Gln Ser Gly Glu Leu Lys Gly Leu Ser Asp Glu Tyr
            100                 105                 110

Pro Phe Glu Lys Asp Asn Asn Pro Val Gly Asn Phe Ala Thr Thr Val
        115                 120                 125

Ser Asp Arg Ser Arg Pro Leu Asn Asp Lys Val Asn Glu
    130                 135                 140

130             135             140

<210> SEQ ID NO 199
<211> LENGTH: 315
<212> TYPE: PRT
<213> ORGANISM: Artificial Sequence
<220> FEATURE:
<223> OTHER INFORMATION: Chimeric sequence

<400> SEQUENCE: 199

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ala
        35                  40                  45

Glu Gln Glu Glu Leu Leu Ala Leu Leu Arg Ser Glu Arg Ile Val Leu
    50                  55                  60

Ala His Ala Gly Gln Pro Leu Ser Glu Ala Gln Val Leu Lys Ala Leu
65                  70                  75                  80

Ala Trp Leu Leu Ala Ala Asn Pro Ser Ala Pro Pro Gly Gln Gly Leu
                85                  90                  95

Glu Val Leu Arg Glu Val Leu Gln Ala Arg Arg Gln Pro Gly Ala Gln
            100                 105                 110

Trp Asp Leu Arg Glu Phe Leu Val Ser Ala Tyr Phe Ser Leu His Gly
        115                 120                 125

Arg Leu Asp Glu Asp Val Ile Gly Val Tyr Lys Asp Val Leu Gln Thr
    130                 135                 140

Gln Asp Gly Lys Arg Lys Ala Leu Leu Asp Glu Leu Lys Ala Leu Thr
145                 150                 155                 160

Ala Glu Leu Lys Val Tyr Ser Val Ile Gln Ser Gln Ile Asn Ala Ala
                165                 170                 175

Leu Ser Ala Lys Gln Gly Ile Arg Ile Asp Ala Gly Gly Ile Asp Leu
            180                 185                 190

Val Asp Pro Thr Leu Tyr Gly Tyr Ala Val Gly Asp Pro Arg Trp Lys
        195                 200                 205

Asp Ser Pro Glu Tyr Ala Leu Leu Ser Asn Leu Asp Thr Phe Ser Gly
    210                 215                 220

Lys Leu Ser Ile Lys Asp Phe Leu Ser Gly Ser Pro Lys Gln Ser Gly
225                 230                 235                 240

Glu Leu Lys Gly Leu Ser Asp Glu Tyr Pro Phe Glu Lys Asp Asn Asn
                245                 250                 255

Pro Val Gly Asn Phe Ala Thr Thr Val Ser Asp Arg Ser Arg Pro Leu
            260                 265                 270

Asn Asp Lys Val Asn Glu Lys Thr Thr Leu Leu Asn Asp Thr Ser Ser
        275                 280                 285

Arg Tyr Asn Ser Ala Val Glu Ala Leu Asn Arg Phe Ile Gln Lys Tyr
    290                 295                 300

Asp Ser Val Leu Arg Asp Ile Leu Ser Ala Ile
305                 310                 315

<210> SEQ ID NO 200
<211> LENGTH: 286
<212> TYPE: PRT
<213> ORGANISM: Artificial Sequence
<220> FEATURE:
<223> OTHER INFORMATION: Chimeric sequence

<400> SEQUENCE: 200

```
Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Gly Gly His Tyr Asp Asn Gln
50                  55                  60

Leu Gln Asn Gly Ile Lys Arg Val Lys Glu Phe Leu Glu Ser Ser Pro
65              70                  75                  80

Asn Thr Gln Trp Asp Leu Arg Glu Phe Leu Val Ser Ala Tyr Phe Ser
                85                  90                  95

Leu His Gly Arg Leu Asp Glu Asp Val Ile Gly Val Tyr Lys Asp Val
            100                 105                 110

Leu Gln Thr Gln Asp Gly Lys Arg Lys Ala Leu Leu Asp Glu Leu Lys
        115                 120                 125

Ala Leu Thr Ala Glu Leu Lys Val Tyr Ser Val Ile Gln Ser Gln Ile
130                 135                 140

Asn Ala Ala Leu Ser Ala Lys Gln Gly Ile Arg Ile Asp Ala Gly Gly
145             150                 155                 160

Ile Asp Leu Val Asp Pro Thr Leu Tyr Gly Tyr Ala Val Gly Asp Pro
                165                 170                 175

Arg Trp Lys Asp Ser Pro Glu Tyr Ala Leu Leu Ser Asn Leu Asp Thr
            180                 185                 190

Phe Ser Gly Lys Leu Ser Ile Lys Asp Phe Leu Ser Gly Ser Pro Lys
        195                 200                 205

Gln Ser Gly Glu Leu Lys Gly Leu Ser Asp Glu Tyr Pro Phe Glu Lys
210                 215                 220

Asp Asn Asn Pro Val Gly Asn Phe Ala Thr Thr Val Ser Asp Arg Ser
225             230                 235                 240

Arg Pro Leu Asn Asp Lys Val Asn Glu Lys Thr Thr Leu Leu Asn Asp
                245                 250                 255

Thr Ser Arg Tyr Asn Ser Ala Val Glu Ala Leu Asn Arg Phe Ile
            260                 265                 270

Gln Lys Tyr Asp Ser Val Leu Arg Asp Ile Leu Ser Ala Ile
        275                 280                 285
```

<210> SEQ ID NO 201
<211> LENGTH: 295
<212> TYPE: PRT
<213> ORGANISM: Artificial Sequence
<220> FEATURE:
<223> OTHER INFORMATION: Chimeric sequence

<400> SEQUENCE: 201

```
Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
50                  55                  60
```

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                 85                  90                  95

Phe Leu Val Ser Ala Tyr Phe Ser Leu Thr Ala Asp Arg Ile Asp Asp
             100                 105                 110

Asp Ile Leu Lys Val Ile Val Asp Ser Met Asn His His Gly Gly Lys
         115                 120                 125

Arg Lys Ala Leu Leu Asp Glu Leu Lys Ala Leu Thr Ala Glu Leu Lys
130                 135                 140

Val Tyr Ser Val Ile Gln Ser Gln Ile Asn Ala Ala Leu Ser Ala Lys
145                 150                 155                 160

Gln Gly Ile Arg Ile Asp Ala Gly Gly Ile Asp Leu Val Asp Pro Thr
                165                 170                 175

Leu Tyr Gly Tyr Ala Val Gly Asp Pro Arg Trp Lys Asp Ser Pro Glu
            180                 185                 190

Tyr Ala Leu Leu Ser Asn Leu Asp Thr Phe Ser Gly Lys Leu Ser Ile
        195                 200                 205

Lys Asp Phe Leu Ser Gly Ser Pro Lys Gln Ser Gly Glu Leu Lys Gly
210                 215                 220

Leu Ser Asp Glu Tyr Pro Phe Glu Lys Asp Asn Asn Pro Val Gly Asn
225                 230                 235                 240

Phe Ala Thr Thr Val Ser Asp Arg Ser Arg Pro Leu Asn Asp Lys Val
                245                 250                 255

Asn Glu Lys Thr Thr Leu Leu Asn Asp Thr Ser Ser Arg Tyr Asn Ser
            260                 265                 270

Ala Val Glu Ala Leu Asn Arg Phe Ile Gln Lys Tyr Asp Ser Val Leu
        275                 280                 285

Arg Asp Ile Leu Ser Ala Ile
290                 295

<210> SEQ ID NO 202
<211> LENGTH: 294
<212> TYPE: PRT
<213> ORGANISM: Artificial Sequence
<220> FEATURE:
<223> OTHER INFORMATION: Chimeric sequence

<400> SEQUENCE: 202

Met Glu Val Arg Asn Leu Asn Ala Ala Arg Glu Leu Phe Leu Asp Glu
1               5                   10                  15

Leu Leu Ala Ala Ser Ala Ala Pro Ser Ala Glu Gln Glu Leu
             20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
 50                  55                  60

Ala Asn Pro Ser Ala Pro Pro Gly Gln Gly Leu Glu Val Leu Arg Glu
 65                  70                  75                  80

Val Leu Gln Ala Arg Arg Gln Pro Gly Ala Gln Trp Asp Leu Arg Glu
                 85                  90                  95

Phe Leu Val Ser Ala Tyr Phe Ser Leu His Gly Arg Leu Asp Glu Asp
             100                 105                 110

Val Ile Gly Val Tyr Lys Asp Val Leu Gln Thr Gln Asp Gly Lys Arg
         115                 120                 125

```
Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ser Ser Gly
145                 150                 155                 160

Thr Ile Asn Ile His Asp Lys Ser Ile Asn Leu Met Asp Lys Asn Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
            290

<210> SEQ ID NO 203
<211> LENGTH: 293
<212> TYPE: PRT
<213> ORGANISM: Artificial Sequence
<220> FEATURE:
<223> OTHER INFORMATION: Chimeric sequence

<400> SEQUENCE: 203

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
        50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Thr Asp Glu Glu Ile Phe Lys Ala Ser Ala Glu Tyr Lys
            180                 185                 190
```

```
Ile Leu Ser Asn Leu Asp Thr Phe Ser Gly Lys Leu Ser Ile Lys Asp
            195                 200                 205

Phe Leu Ser Gly Ser Pro Lys Gln Ser Gly Glu Leu Lys Gly Leu Ser
    210                 215                 220

Asp Glu Tyr Pro Phe Glu Lys Asp Asn Asn Pro Val Gly Asn Phe Ala
225                 230                 235                 240

Thr Thr Val Ser Asp Arg Ser Arg Pro Leu Asn Asp Lys Val Asn Glu
                245                 250                 255

Lys Thr Thr Leu Leu Asn Asp Thr Ser Ser Arg Tyr Asn Ser Ala Val
                260                 265                 270

Glu Ala Leu Asn Arg Phe Ile Gln Lys Tyr Asp Ser Val Leu Arg Asp
            275                 280                 285

Ile Leu Ser Ala Ile
        290

<210> SEQ ID NO 204
<211> LENGTH: 302
<212> TYPE: PRT
<213> ORGANISM: Artificial Sequence
<220> FEATURE:
<223> OTHER INFORMATION: Chimeric sequence

<400> SEQUENCE: 204

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Ile Leu Glu Lys Met Pro Gln Thr Thr Ile Gln Val Asp Gly Ser
        195                 200                 205

Glu Lys Lys Ile Val Ser Ile Lys Asp Phe Leu Ser Gly Ser Pro Lys
    210                 215                 220

Gln Ser Gly Glu Leu Lys Gly Leu Ser Asp Glu Tyr Pro Phe Glu Lys
225                 230                 235                 240

Asp Asn Asn Pro Val Gly Asn Phe Ala Thr Thr Val Ser Asp Arg Ser
                245                 250                 255
```

Arg Pro Leu Asn Asp Lys Val Asn Glu Lys Thr Thr Leu Leu Asn Asp
            260                 265                 270

Thr Ser Ser Arg Tyr Asn Ser Ala Val Glu Ala Leu Asn Arg Phe Ile
        275                 280                 285

Gln Lys Tyr Asp Ser Val Leu Arg Asp Ile Leu Ser Ala Ile
    290                 295                 300

<210> SEQ ID NO 205
<211> LENGTH: 294
<212> TYPE: PRT
<213> ORGANISM: Artificial Sequence
<220> FEATURE:
<223> OTHER INFORMATION: Chimeric sequence

<400> SEQUENCE: 205

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Gly Ser Glu Asn Lys Arg Thr Gly Ala Leu Gly Asn Leu
    210                 215                 220

Lys Asn Ser Tyr Ser Tyr Asn Lys Asp Asn Glu Leu Ser His Phe
225                 230                 235                 240

Ala Thr Thr Cys Ser Asp Lys Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile
    290

<210> SEQ ID NO 206
<211> LENGTH: 17

```
<212> TYPE: PRT
<213> ORGANISM: Artificial Sequence
<220> FEATURE:
<223> OTHER INFORMATION: Myc-tag

<400> SEQUENCE: 206

Ala Ala Ala Glu Gln Lys Leu Ile Ser Glu Glu Asp Leu Asn Gly Ala
1               5                   10                  15

Ala

<210> SEQ ID NO 207
<211> LENGTH: 408
<212> TYPE: PRT
<213> ORGANISM: Artificial Sequence
<220> FEATURE:
<223> OTHER INFORMATION: Nanobody sequence

<400> SEQUENCE: 207

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Ala Gly Gly Ser Leu Ser Ile Ser Cys
    290                 295                 300
```

-continued

```
Ala Ala Ser Gly Gly Ser Leu Ser Asn Tyr Val Leu Gly Trp Phe Arg
305             310             315             320

Gln Ala Pro Gly Lys Glu Arg Glu Phe Val Ala Ala Ile Asn Trp Arg
            325             330             335

Gly Asp Ile Thr Ile Gly Pro Pro Asn Val Glu Gly Arg Phe Thr Ile
            340             345             350

Ser Arg Asp Asn Ala Lys Asn Thr Gly Tyr Leu Gln Met Asn Ser Leu
        355             360             365

Ala Pro Asp Asp Thr Ala Val Tyr Tyr Cys Gly Ala Gly Thr Pro Leu
    370             375             380

Asn Pro Gly Ala Tyr Ile Tyr Asp Trp Ser Tyr Asp Tyr Trp Gly Arg
385             390             395             400

Gly Thr Gln Val Thr Val Ser Ser
                405
```

PSEUDOMONAS AERUGINOSA PCRV BINDING SINGLE VARIABLE DOMAIN ANTIBODIES

RELATED APPLICATION

This application is a divisional of U.S. patent application Ser. No. 14/382,027, filed Aug. 29, 2014, which is a national stage filing under 35 U.S.C. § 371 of international application PCT/EP2013/054262, filed Mar. 4, 2013, which was published under PCT Article 21(2) in English, and claims the benefit under 35 U.S.C. § 119(e) of U.S. provisional application Ser. No. 61/606,094, filed Mar. 2, 2012, the disclosures of which are incorporated by reference herein in their entireties.

FIELD OF THE INVENTION

The present invention relates to polypeptides that bind the PcrV protein of *Pseudomonas aeruginosa*. More specifically, the present invention relates to multiparatopic polypeptides (also referred to herein as "multiparatopic polypeptide(s) of the invention") that bind PcrV and neutralize *P. aeruginosa*. The invention further relates to monovalent polypeptides (also referred to herein as "monovalent polypeptide(s) of the invention") for use as building blocks in the preparation of the multiparatopic polypeptides of the invention.

The invention also relates to nucleic acids encoding such polypeptides (also referred to herein as "nucleic acid(s) of the invention"; to methods for preparing such polypeptides; to host cells expressing or capable of expressing such polypeptides; to compositions, and in particular to pharmaceutical compositions, that comprise such polypeptides, nucleic acids and/or host cells; and to uses of polypeptides, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND ART

*Pseudomonas aeruginosa* is an environmental Gram-negative bacterium, associated with a broad spectrum of infections in humans. It has a very large genome which is remarkably flexible metabolically, explaining why it can be found in very diverse environments. This opportunistic pathogen can cause acute lung injury and mortality through the delivery of exotoxins by the type III secretion system (TTSS).

The Type III Secretion System (TTSS) of *P. aeruginosa* is a complex multi-protein structure crossing the complete cell wall. It is a specialised hollow needle-like molecular structure secreting only TTSS proteins and pathogenicity related toxins. Many different proteins form the TTSS, both on the bacterial cytoplasmic side and externally. Externally, only the single 'barrel' homopolymeric forming protein and the 'needle tip' protein are accessible to antibodies. The needle protein PcrV is thought to form a ring-type structure on the tip of the needle. The TTSS complex can inject various exotoxins, produced by the bacterium, directly into the cytoplasm of host cells.

The involvement of this translocation apparatus in pathogenesis may not be limited to the transport of exotoxins, as indeed mutants expressing TTSS but not the toxins are cytotoxic as well (Lee et al. Infect. Immun. 73: 1695-1705, 2005). The translocation pore itself is sufficient to cause the death of host cells, either directly through pore-mediated increases in membrane permeability, or indirectly through the activation of broad cellular defence responses. The TTSS virulence mechanism on the bacteria's external surface enables *P. aeruginosa* to evade human immune defences by killing white blood cells and epithelial cells and triggering tissue-damaging inflammation.

Under normal circumstances, the bacterium is perfectly harmless. However, under certain circumstances, the bacterium can colonise hosts with a weakened immune system. It is recognized as a major cause of nosocomial bacteremia and infections associated with invasive devices, mechanical ventilation, burn wounds, or surgery in the immunocompromised and the immunocompetent patients (Giamarellou and Kanellakopoulou Crit. Care Clin. 24: 261-278, 2008), such as bone marrow transplant patients (Velasco et al. Clin. Microbiol. Infect. 10: 542-549, 2004). *P. aeruginosa* typically causes nosocomial infections of the pulmonary tract, urinary tract, (burn) wounds and also sepsis.

In Cystic Fibrosis (CF) patients, *P. aeruginosa* infection follows a well-established pattern of recurrent pulmonary infection in early childhood leading to the establishment of chronic infection in older CF patients, where it is a major contributing factor in the progressive decline in lung function and disease exacerbations leading to respiratory failure (FitzSimmons J. Pediatr. 122: 1-9, 1993; Kerem et al. J. Pediatr. 116: 714-719, 1990; Lyczak et al. Clin. Microb. Rev. 15: 194-222, 2002). Once chronic *P. aeruginosa* pulmonary infection is established, eradication of the organism appears impossible using current therapies (Lee Chronic Respiratory Disease 6: 99-107, 2009).

*P. aeruginosa* has several different manifestations in the setting of chronic obstructive pulmonary disease (COPD). The organism is a colonizer that is cleared quickly, causes acute exacerbations and also may cause chronic infections in a subset of adults with COPD (Murphy Curr. Opin. Pulm. Med. 15: 138-142, 2009).

A good overview on the current treatment of *P. aeruginosa* pneumonia is given by Giamarellou and Kanellakopoulou (Crit. Care Clin. 24: 261-278, 2008), Malcolm and Heim (Curr. Opin. Pharmacol. 9: 558-565, 2009), El Solh and Alhajhusain (J. Antimicrobial Chemotherapy 64: 229-238, 2009) and Roux and Ricard (Infectious Disorders—Drug Targets 11: 389-394, 2011). Current treatment for patients still relies on antibiotics. Antibiotics of the four major structural classes are in use against *P. aeruginosa* infection (Giamarellou and Kanellakopoulou Crit. Care Clin. 24: 261-278, 2008). Importantly, once *P. aeruginosa* colonisation has been established, it cannot be successfully cleared using antibiotics due to biofilm formation. Biofilm limits the access of certain antibiotics to the deeper layers of the film (diffusion limiting). More importantly, the deeper layers of biofilm contain many *P. aeruginosa* bacteria which are live but virtually completely inactive for lack of nutrient access. Antibiotics of various classes act on cell division or highly active metabolic pathways, and are thus unable to kill these dormant bacteria. Once therapy is tapered back or withdrawn, these cells rapidly re-colonise the patient.

Furthermore, *P. aeruginosa* has the ability to evade new antimicrobial therapies and develop resistance, being on one hand intrinsically resistant to many drugs, on the other hand rapidly acquiring resistance via a number of mechanisms (Malcolm and Heim Curr. Opin. Pharmacol. 9: 558-565, 2009). Because of the versatility and the large size of *P. aeruginosa* genome, various resistance mechanisms can be present simultaneously, causing cross-resistance to several antipseudomonal agents (Giamarellou and Kanellakopoulou Crit. Care Clin. 24: 261-278, 2008). Novel variants on the same basic antibiotic structures are in development and may alleviate current resistance to some extent, but are very likely to give rise to novel resistance once in widespread clinical use. No novel classes of antibiotics are known to be in clinical development. Because the development of new classes of antibiotics has lagged far behind our growing need for such drugs, we now face a post-antibiotic era with limited capacity to combat these infections.

Topical administration of existing antibiotics (e.g., aerosol administration of tobramycin or colistin) has been used to deliver higher local concentrations of antibiotics without exposing the patient to high systemic levels which may be toxic to the patient (Luyt et al. Curr. Opin. Infect. Dis. 22: 154-158, 2009). However, continued concerns are raised about its efficacy and potential emergence of resistance as well (El Solh and Alhajhusain J. Antimicrobial Chemotherapy 64: 229-238, 2009; Roux and Ricard Infectious Disorders—Drug Targets 11: 389-394, 2011).

With the pipeline of new antimicrobial agents running dry, treatment of *P. aeruginosa* continues to rely on the theoretical advantages of combination therapy and the revival of old drugs previously abandoned because of serious toxicity, like polymyxins (Giamarellou and Kanellakopoulou Crit. Care Clin. 24: 261-278, 2008; El Solh and Alhajhusain J. Antimicrobial Chemotherapy 64: 229-238, 2009). However, resistance to such treatment is rapidly emerging with very worrisome latest resistance rates, and the appearance of *Pseudomonas* strains with multidrug-resistant, or even pan-resistant, phenotypes (Malcolm and Heim Curr. Opin. Pharmacol. 9: 558-565, 2009). Based on the reported resistance surveillance data, it is evident that the current therapeutic approach for *P. aeruginosa* infections is approaching its limits (Giamarellou and Kanellakopoulou Crit. Care Clin. 24: 261-278, 2008).

There are currently no non-antibiotic based treatments on the market. However, there are a number of drug candidates in development.

Various monoclonal antibodies, mostly directed to *P. aeruginosa* flagellin or strain-specific LPS have been described. Most did not reach clinical stage. One LPS-reactive IgM (Kenta (Berna/Crucell) is listed as in active Phase II development. However, the serotype specificity of this antibody underscores the need for a quick assay to determine the serotype of the infectious agent in the hospital setting and the development of antibodies specific for other clinic-relevant serotypes (Roux and Ricard Infectious Disorders—Drug Targets 11: 389-394, 2011).

A mouse monoclonal anti-PcrV antibody, monoclonal antibody (Mab) 166, with potent neutralizing activity in mouse and rat models of *Pseudomonas* infection had been described by Frank et al. (J. Infect. Dis. 186: 64-73, 2002) and Faure et al (J. Immune based Therapies and Vaccines 1: 2, 2003). WO 2009/073631 A2 and Baer et al. (Infection and Immunity 77: 1083-1090) describes several engineered human antibody Fab fragments (amongst which Fab1A8) specific for *P. aeruginosa* PcrV protein and which compete with MAb 166 for binding to the same epitope on PcrV. These Fabs show potent neutralization activity against the *P. aeruginosa* Type III secretion system. KB001 (KaloBios, US) is a Humaneered™ anti-PcrV PEGylated antibody Fab' fragment (Anti-PcrV Program Fact Sheet, KaloBios) that showed potent Type III Secretion System (TTSS) neutralising activity in cellular cytotoxicity assays. KB001 is being developed for the prevention of Pa ventilator-associated pneumonia (VAP) and for the treatment of CF. Preliminary evidence of activity and safety has been demonstrated in both indications in Phase ½ trials conducted by KaloBios. It still remains to be determined, however, whether or not escape mutants will develop to this monospecific monoclonal antibody once administered to patients.

Taken together, the increased incidence in certain types of infections, the increased use of invasive devices in the hospital as well as the increased frequency of multi-resistant *Pseudomonas* strains, have clearly let to a shortage of treatment options for nosocomial *Pseudomonas* infections. Despite the above efforts, management of *P. aeruginosa* infection represents a difficult therapeutic challenge for critical care physicians (El Solh and Alhajhusain J. Antimicrobial Chemotherapy 64: 229-238, 2009). For patients with multi-drug resistant strains, very few clinical options remain. It is therefore considered imperative to discover and develop novel anti-*Pseudomonas* drugs to fill a dangerous void in the anti-bacterial armamentarium of the clinician (Malcolm and Heim Curr. Opin. Pharmacol. 9: 558-565, 2009).

SUMMARY OF THE INVENTION

The present invention provides polypeptides with improved prophylactic, therapeutic and/or pharmacological properties, in addition to other advantageous properties (such as, for example, improved ease of preparation, good stability, and/or reduced costs of goods), compared to the prior art amino acid sequences and antibodies. More particularly, the present invention provides multivalent polypeptides comprising two or more immunoglobulin single variable domains that show improved properties for neutralizing PcrV compared to the PcrV neutralizing molecules described in the prior art. The inventors surprisingly observed that biparatopic polypeptides comprising two different PcrV-binding immunoglobulin single variable domains showed a significant increase in PcrV-neutralizing efficacy as compared to the PcrV neutralizing capacity of the monovalent PcrV-binding building blocks alone. For this purpose, the present invention in addition also makes available a number of highly advantageous immunoglobulin single variable domains (i.e., monovalent polypeptides) that specifically bind PcrV and/or that are capable of significantly inhibiting or neutralizing PcrV. These PcrV-binding immunoglobulin single variable domains and polypeptides comprising the same form further aspects of the invention.

Accordingly, the present invention provides polypeptides comprising or essentially consisting of two or more immunoglobulin single variable domains that specifically bind to the PcrV protein of *P. aeruginosa* (herein referred to as "PcrV"). Such polypeptides are also referred to herein as "multivalent polypeptide(s) of the invention". The two or more immunoglobulin single variable domains may optionally be linked via one or more peptidic linkers.

Preferably, the multivalent polypeptide comprises two or more immunoglobulin single variable domains directed against PcrV, wherein the "first" immunoglobulin single variable domain directed against PcrV and the "second" immunoglobulin single variable domain directed against PcrV have a different paratope. Such polypeptides are also referred to herein as "multiporotopic polypeptide(s) of the invention". Accordingly, the present invention relates to a polypeptide comprising or consisting of two or more immunoglobulin single variable domains that are directed against PcrV, wherein the "first" immunoglobulin single variable domain directed against PcrV and the "second" immunoglobulin single variable domain directed against PcrV have different paratopes. Such polypeptides comprise or consist of two or more immunoglobulin single variable domains that are directed against different epitopes on PcrV. More specifically, such polypeptides comprise at least one "first" immunoglobulin single variable domain that is directed against a first epitope on PcrV and at least one "second" immunoglobulin single variable domain that is directed against a second epitope on PcrV different from the first epitope on PcrV. Preferably, these multiparatopic polypeptides of the invention are biparatopic or triparatopic polypeptides (also referred to herein as "bipaorotopic polypeptide(s) of the invention" and "triparatopic polypeptide(s) of the invention"), as further defined herein.

Multiparatopic (such as the biparatopic or triparatopic) polypeptides as described herein, showed improved properties for neutralizing PcrV compared to the PcrV neutralizing molecules described in the prior art. The multiparatopic (such as biparatopic or triparatopic) polypeptide of the invention is capable of neutralizing PcrV with 100% efficacy in a cytotoxicity assay, such as e.g., a cytotoxicity assay with P3X63 cells as target at an MOI of 12. Apart from this and/or in addition, the multiparatopic (such as biparatopic or triparatopic) polypeptide of the invention is capable of neutralizing PcrV with an IC50 of $5.0 \times 10^{-10}$ M or lower in a cytotoxicity assay (such as e.g., a cytotoxicity assay with P3X63 cells as target at an MOI of 12. Apart from this and/or in addition, the multiparatopic (such as biparatopic or triparatopic) polypeptide of the invention has a decrease in potency after 24 hours in the presence of *P. aeruginosa* elastase (3 ug/ug polypeptide) of maximal 5 fold (e.g., 5 fold, 3 fold, 2 fold or lower). Apart from this and/or in addition, the multiparatopic (such as biparatopic or triparatopic) polypeptide of the invention has a decrease in potency after 24 hours in the presence of human neutrophil elastase (1-2 ug/ug polypeptide) of maximal 15 fold (e.g., 10 fold, 5 fold, 3 fold, 2 fold or lower).

Preferred multiparatopic (such as biparatopic or triparatopic) polypeptides of the invention comprise or essentially consist of two or more immunoglobulin single variable domains, wherein at least one immunoglobulin single variable domain consists of 4 framework regions (FR1 to FR4, respectively) and 3 complementarity determining regions (CDR1 to CDR3, respectively), in which (see Table A-6):
CDR1 is chosen from the group consisting of:
a) the amino acid sequences of SEQ ID NOs: 20-37;
b) amino acid sequences that have at least 80% amino acid identity with at least one of the amino acid sequences of SEQ ID NOs: 20-37;
c) amino acid sequences that have 3, 2, or 1 amino acid difference with at least one of the amino acid sequences of SEQ ID NOs: 20-37;
and/or
CDR2 is chosen from the group consisting of:
d) the amino acid sequences of SEQ ID NOs: 38-56;
e) amino acid sequences that have at least 80% amino acid identity with at least one of the amino acid sequences of SEQ ID NOs: 38-56;
f) amino acid sequences that have 3, 2, or 1 amino acid difference with at least one of the amino acid sequences of SEQ ID NOs: 38-56;
and/or
CDR3 is chosen from the group consisting of:
g) the amino acid sequences of SEQ ID NOs: 57-75;
h) amino acid sequences that have at least 80% amino acid identity with at least one of the amino acid sequences of SEQ ID NOs: 57-75;
i) amino acid sequences that have 3, 2, or 1 amino acid difference with at least one of the amino acid sequences of SEQ ID NOs: 57-75.

More particularly, the multiparatopic (such as biparatopic or triparatopic) polypeptide of the invention comprise or essentially consist of two or more immunoglobulin single variable domains, wherein at least one of the immunoglobulin single variable domains consists of 4 framework regions (FR1 to FR4, respectively) and 3 complementarity determining regions (CDR1 to CDR3, respectively), in which:
CDR1 is chosen from the group consisting of:
a) the amino acid sequences of SEQ ID NOs: 20-37;
b) amino acid sequences that have at least 80% amino acid identity with at least one of the amino acid sequences of SEQ ID NOs: 20-37;
c) amino acid sequences that have 3, 2, or 1 amino acid difference with at least one of the amino acid sequences of SEQ ID NOs: 20-97];
and
CDR2 is chosen from the group consisting of:
d) the amino acid sequences of SEQ ID NOs: 38-56;
e) amino acid sequences that have at least 80% amino acid identity with at least one of the amino acid sequences of SEQ ID NOs: 38-56;
f) amino acid sequences that have 3, 2, or 1 amino acid difference with at least one of the amino acid sequences of SEQ ID NOs: 38-56;
and
CDR3 is chosen from the group consisting of:
g) the amino acid sequences of SEQ ID NOs: 57-75;
h) amino acid sequences that have at least 80% amino acid identity with at least one of the amino acid sequences of SEQ ID NOs: 57-75;
i) amino acid sequences that have 3, 2, or 1 amino acid difference with at least one of the amino acid sequences of SEQ ID NOs: 57-75.

Preferred multiparatopic (such as biparatopic or triparatopic) polypeptides of the invention comprise or essentially consist of two or more immunoglobulin single variable domains wherein, in at least one of the immunoglobulin single variable domains, the CDR sequences have at least 70% amino acid identity, preferably at least 80% amino acid identity, more preferably at least 90% amino acid identity, such as 95% amino acid identity or more, or even essentially 100% amino acid identity with the CDR sequences of at least one of the immunoglobulin single variable domains with SEQ ID NOs: 1-19 (Table A-4).

In a preferred aspect, the multiparatopic (such as biparatopic or triparatopic) polypeptides of the invention comprise or essentially consist of two or more immunoglobulin single variable domains, wherein at least one of the immunoglobulin single variable domains cross-blocks the binding to PcrV of at least one of the immunoglobulin single variable domains with SEQ ID NOs: 1-19 and/or is cross-blocked from binding to PcrV by at least one of the immunoglobulin single variable domains with SEQ ID NOs: 1-19.

In a preferred aspect, each of the two or more immunoglobulin single variable domains present in the multiparatopic (such as biparatopic or triparatopic) polypeptides of the invention are as defined above. Examples of multiparatopic (such as biparatopic or triparatopic) polypeptides of the invention are SEQ ID NOs 118-151 (Table A-5).

In a preferred aspect, each of the two or more immunoglobulin single variable domains of the multiparatopic (such as biparatopic or triparatopic) polypeptide of the invention, that is directed against PcrV belongs to a different epitope bin. Accordingly, the present invention relates to a polypeptide comprising or essentially consisting of two or more immunoglobulin single variable domains directed against PcrV, wherein each of the two or more immunoglobulin single variable domains that are directed against PcrV belong to a different epitope bin. Immunoglobulin single variable domains that belong to a different epitope bin, by definition do not cross-compete with each other for binding the target, PcrV. Accordingly, the present invention relates to a polypeptide comprising or essentially consisting of two or more immunoglobulin single variable domains against PcrV, wherein the first immunoglobulin single variable domain does not cross-block the binding to PcrV of the second immunoglobulin single variable domain and/or wherein the first immunoglobulin single variable is not cross-blocked from binding to PcrV by the second immunoglobulin single variable domain.

Preferred combination of immunoglobulin single variable domains present in the multiparatopic (such as biparatopic or triparatopic) polypeptide of the invention may encompass any of the following:

- the first immunoglobulin single variable domain cross-blocks the binding to PcrV of at least one of the immunoglobulin single variable domains with SEQ ID NOs: 3-10 [epitope bin1] and/or is cross-blocked from binding to PcrV by at least one of the immunoglobulin single variable domains with SEQ ID NOs: 3-10 [epitope bin1]; and the second immunoglobulin single variable domain cross-blocks the binding to PcrV of at least one of the immunoglobulin single variable domains with SEQ ID NOs: 1-2 [epitope bin2] and/or is cross-blocked from binding to PcrV by at least one of immunoglobulin single variable domains with SEQ ID NOs: 1-2 [epitope bin2];
- the first immunoglobulin single variable domain cross-blocks the binding to PcrV of at least one of the immunoglobulin single variable domains with SEQ ID NOs: 3-10 [epitope bin1] and/or is cross-blocked from binding to PcrV by at least one of the immunoglobulin single variable domains with SEQ ID NOs: 3-10 [epitope bin1]; and the second immunoglobulin single variable domain cross-blocks the binding to PcrV of at least one of the immunoglobulin single variable domains with SEQ ID NOs: 11-12 [epitope bin3] and/or is cross-blocked from binding to PcrV by at least one of the immunoglobulin single variable domains with SEQ ID NOs: 11-12 [epitope bin3];
- the first immunoglobulin single variable domain cross-blocks the binding to PcrV of at least one of the immunoglobulin single variable domains with SEQ ID NOs: 1-2 [epitope bin2] and/or is cross-blocked from binding to PcrV by at least one of the immunoglobulin single variable domains with SEQ ID NOs: 1-2 [epitope bin2]; and the second immunoglobulin single variable domain cross-blocks the binding to PcrV of at least one of the immunoglobulin single variable domains with SEQ ID NOs: 11-12 [epitope bin3] and/or is cross-blocked from binding to PcrV by at least one of the immunoglobulin single variable domains with SEQ ID NOs: 11-12 [epitope bin3];
- the first immunoglobulin single variable domain cross-blocks the binding to PcrV of at least one of the immunoglobulin single variable domains with SEQ ID NOs: 11-12 [epitope bin3] and/or is cross-blocked from binding to PcrV by at least one of immunoglobulin single variable domains with SEQ ID NOs: 11-12 [epitope bin3]; and the second immunoglobulin single variable domain cross-blocks the binding to PcrV of at least one of the immunoglobulin single variable domains with SEQ ID NOs: 3-10 [epitope bin1] and/or is cross-blocked from binding to PcrV by at least one of the immunoglobulin single variable domains with SEQ ID NOs: 3-10 [epitope bin1]; or
- the first immunoglobulin single variable domain cross-blocks the binding to PcrV of at least one of the immunoglobulin single variable domains with SEQ ID NOs: 11-12 [epitope bin3] and/or is cross-blocked from binding to PcrV by at least one of the immunoglobulin single variable domains with SEQ ID NOs: 11-12 [epitope bin3]; and the second immunoglobulin single variable domain cross-blocks the binding to PcrV of at least one of the immunoglobulin single variable domains with SEQ ID NOs: 1-2 [epitope bin2] and/or is cross-blocked from binding to PcrV by at least one of the immunoglobulin single variable domains with SEQ ID NOs: 1-2 [epitope bin2].

Preferred multiparatopic (such as biparatopic or triparatopic) polypeptides of the invention may comprise or essentially consist of one of the following combinations of immunoglobulin single variable domains:

- the first immunoglobulin single variable domain is a polypeptide that belongs to epitope bin 1 and is selected from any one of:
  - a polypeptide that binds full length PcrV (SEQ ID NO: 159) and that shows reduced binding (30-90% compared to full length PcrV) or no binding to chimera 4 (SEQ ID NO: 202) and chimera 6 (SEQ ID NO: 204);
  - a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 3-10;
  - a polypeptide that cross-blocks the binding to PcrV of at least one of the immunoglobulin single variable domains with SEQ ID NOs: 3-10 and/or that is cross-blocked from binding to PcrV by at least one of the immunoglobulin single variable domains with SEQ ID NOs: 3-10; and
  - a polypeptide that is any of SEQ ID NOs: 3-10;

and the second immunoglobulin single variable domain is a polypeptide that belongs to epitope bin 2 and is selected from any one of:
  - a polypeptide that binds to full length PcrV (SEQ ID NO: 159) and that shows reduced binding (30-90% compared to full length PcrV) or no binding to chimera 7 (SEQ ID NO: 205);

a polypeptide, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2;

a polypeptide that cross-blocks the binding to PcrV of at least one of the immunoglobulin single variable domains with SEQ ID NOs: 1 and 2 and/or that is cross-blocked from binding to PcrV by at least one of the immunoglobulin single variable domains with SEQ ID NOs: 1 and 2; and a polypeptide that is any of SEQ ID NOs: 1 and 2;

the first immunoglobulin single variable domain is a polypeptide that belongs to epitope bin 1 and is selected from any one of:

a polypeptide that binds full length PcrV (SEQ ID NO: 159) and that shows reduced binding (30-90% compared to full length PcrV) or no binding to chimera 4 (SEQ ID NO: 202) and chimera 6 (SEQ ID NO: 204);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 3-10;

a polypeptide that cross-blocks the binding to PcrV of at least one of the immunoglobulin single variable domains with SEQ ID NOs: 3-10 and/or that is cross-blocked from binding to PcrV by at least one of the immunoglobulin single variable domains with SEQ ID NOs: 3-10; and a polypeptide that is any of SEQ ID NOs: 3-10;

and the second immunoglobulin single variable domain is a polypeptide that belongs to epitope bin 3 and is selected from any one of:

a polypeptide that binds full length PcrV (SEQ ID NO: 159) and that shows reduced binding (30-90% compared to full length PcrV) or no binding to chimera 2 (SEQ ID NO: 200);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;

a polypeptide that cross-blocks the binding to PcrV of at least one of the immunoglobulin single variable domains with SEQ ID NOs: 11 and 12 and/or that is cross-blocked from binding to PcrV by at least one of the immunoglobulin single variable domains with SEQ ID NOs: 11 and 12; and a polypeptide that is any of SEQ ID NOs: 11 and 12;

the first immunoglobulin single variable domain is a polypeptide that belongs to epitope bin 2 and is selected from any one of:

a polypeptide that binds to full length PcrV (SEQ ID NO: 159) and that shows reduced binding (30-90% compared to full length PcrV) or no binding to chimera 7 (SEQ ID NO: 205);

a polypeptide, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2;

a polypeptide that cross-blocks the binding to PcrV of at least one of the immunoglobulin single variable domains with SEQ ID NOs: 1 and 2 and/or that is cross-blocked from binding to PcrV by at least one of the immunoglobulin single variable domains with SEQ ID NOs: 1 and 2; and a polypeptide that is any of SEQ ID NOs: 1 and 2;

and the second immunoglobulin single variable domain is a polypeptide that belongs to epitope bin 1 and is selected from any one of:

a polypeptide that binds full length PcrV (SEQ ID NO: 159) and that shows reduced binding (30-90% compared to full length PcrV) or no binding to chimera 4 (SEQ ID NO: 202) and chimera 6 (SEQ ID NO: 204);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 3-10;

a polypeptide that cross-blocks the binding to PcrV of at least one of the immunoglobulin single variable domains with SEQ ID NOs: 3-10 and/or that is cross-blocked from binding to PcrV by at least one of the immunoglobulin single variable domains with SEQ ID NOs: 3-10; and a polypeptide that is any of SEQ ID NOs: 3-10;

the first immunoglobulin single variable domain is a polypeptide that belongs to epitope bin 2 and is selected from any one of:

a polypeptide that binds to full length PcrV (SEQ ID NO: 159) and that shows reduced binding (30-90% compared to full length PcrV) or no binding to chimera 7 (SEQ ID NO: 205);

a polypeptide, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2;

a polypeptide that cross-blocks the binding to PcrV of at least one of the immunoglobulin single variable domains with SEQ ID NOs: 1 and 2 and/or that is cross-blocked from binding to PcrV by at least one of the immunoglobulin single variable domains with SEQ ID NOs: 1 and 2; and a polypeptide that is any of SEQ ID NOs: 1 and 2;

and the second immunoglobulin single variable domain is a polypeptide that belongs to epitope bin 3 and is selected from any one of:

a polypeptide that binds full length PcrV (SEQ ID NO: 159) and that shows reduced binding (30-90% compared to full length PcrV) or no binding to chimera 2 (SEQ ID NO: 200);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;

a polypeptide that cross-blocks the binding to PcrV of at least one of the immunoglobulin single variable domains with SEQ ID NOs: 11 and 12 and/or that is cross-blocked from binding to PcrV by at least one of the immunoglobulin single variable domains with SEQ ID NOs: 11 and 12; and a polypeptide that is any of SEQ ID NOs: 11 and 12;

the first immunoglobulin single variable domain is a polypeptide that belongs to epitope bin 3 and is selected from any one of:

a polypeptide that binds full length PcrV (SEQ ID NO: 159) and that shows reduced binding (30-90% compared to full length PcrV) or no binding to chimera 2 (SEQ ID NO: 200);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;

a polypeptide that cross-blocks the binding to PcrV of at least one of the immunoglobulin single variable domains with SEQ ID NOs: 11 and 12 and/or that is cross-blocked from binding to PcrV by at least one of the immunoglobulin single variable domains with SEQ ID NOs: 11 and 12; and a polypeptide that is any of SEQ ID NOs: 11 and 12;

and the second immunoglobulin single variable domain is a polypeptide that belongs to epitope bin 1 and is selected from any one of:

a polypeptide that binds full length PcrV (SEQ ID NO: 159) and that shows reduced binding (30-90% compared to full length PcrV) or no binding to chimera 4 (SEQ ID NO: 202) and chimera 6 (SEQ ID NO: 204);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 3-10;

a polypeptide that cross-blocks the binding to PcrV of at least one of the immunoglobulin single variable domains with SEQ ID NOs: 3-10 and/or that is cross-blocked from binding to PcrV by at least one of the immunoglobulin single variable domains with SEQ ID NOs: 3-10; and a polypeptide that is any of SEQ ID NOs: 3-10; or the first immunoglobulin single variable domain is a polypeptide that belongs to epitope bin 3 and is selected from any one of:

a polypeptide that binds full length PcrV (SEQ ID NO: 159) and that shows reduced binding (30-90% compared to full length PcrV) or no binding to chimera 2 (SEQ ID NO: 200);

a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;

a polypeptide that cross-blocks the binding to PcrV of at least one of the immunoglobulin single variable domains with SEQ ID NOs: 11 and 12 and/or that is cross-blocked from binding to PcrV by at least one of the immunoglobulin single variable domains with SEQ ID NOs: 11 and 12; and a polypeptide that is any of SEQ ID NOs: 11 and 12;

and the second immunoglobulin single variable domain is a polypeptide that belongs to epitope bin 2 and is selected from any one of:

a polypeptide that binds to full length PcrV (SEQ ID NO: 159) and that shows reduced binding (30-90% compared to full length PcrV) or no binding to chimera 7 (SEQ ID NO: 205);

a polypeptide, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2;

a polypeptide that cross-blocks the binding to PcrV of at least one of the immunoglobulin single variable domains with SEQ ID NOs: 1 and 2 and/or that is cross-blocked from binding to PcrV by at least one of the immunoglobulin single variable domains with SEQ ID NOs: 1 and 2; and a polypeptide that is any of SEQ ID NOs: 1 and 2.

Preferred polypeptides of the invention are selected from any of SEQ ID NOs: 124-141 (Table A-5).

In a preferred aspect, the invention relates to a polypeptide as defined above, wherein the first immunoglobulin single variable domain is SEQ ID NO: 12. In another preferred aspect, the invention relates to a polypeptide wherein the second immunoglobulin single variable domain is selected from any of SEQ ID NOs: 1 and 10. In another preferred aspect, the invention relates to a polypeptide which is selected from any of SEQ ID NOs: 129 and 134. In another preferred aspect, the invention relates to a polypeptide, wherein the second immunoglobulin single variable domain is SEQ ID NO: 1. In another preferred aspect, the invention relates to a polypeptide, wherein the first immunoglobulin single variable domain is selected from any of SEQ ID NOs: 3 and 12. In another preferred aspect, the invention relates to a polypeptide which is selected from any of SEQ ID NOs: 129 and 137.

In a further aspect, each of the two or more immunoglobulin single variable domains of the multiparatopic (such as biparatopic or triparatopic) polypeptide of the invention, that are directed against PcrV belong to the same epitope bin. Accordingly, the present invention also relates to a polypeptide comprising or essentially consisting of two or more immunoglobulin single variable domains directed against PcrV, wherein each of the two or more immunoglobulin single variable domains that are directed against PcrV belong to the same epitope bin. Immunoglobulin single variable domains that belong to the same epitope bin, by definition cross-compete with each other for binding the target, PcrV. Accordingly, the present invention relates to a polypeptide comprising or essentially consisting of two or more immunoglobulin single variable domains directed against PcrV, wherein the first immunoglobulin single variable domain cross-blocks the binding to PcrV of the second immunoglobulin single variable domain and/or wherein the first immunoglobulin single variable is cross-blocked from binding to PcrV by the second immunoglobulin single variable domain.

Preferred combinations of immunoglobulin single variable domains present in such multiparatopic (such as biparatopic or triparatopic) polypeptide of the invention may encompass any of the following:

the first and the second immunoglobulin single variable domains cross-block the binding to PcrV of at least one of immunoglobulin single variable domains with SEQ ID NOs: 3-10 [epitope bin1] and/or the first and the second immunoglobulin single variable domains are cross-blocked from binding to PcrV by at least one of the immunoglobulin single variable domains with SEQ ID NOs: 3-10 [epitope bin1];

the first and the second immunoglobulin single variable domains cross-block the binding to PcrV of at least one of the immunoglobulin single variable domains with SEQ ID NOs: 1-2 [epitope bin2] and/or the first and the second immunoglobulin single variable domains are cross-blocked from binding to PcrV by at least one of the immunoglobulin single variable domains with SEQ ID NOs: 1-2 [epitope bin2]; or the first and the second immunoglobulin single variable domains cross-block the binding to PcrV of at least one of the immunoglobulin single variable domains with SEQ ID NOs: 11-12 [epitope bin3] and/or the first and the second immunoglobulin single variable domains are cross-blocked from binding to PcrV by at least one of the immunoglobulin single variable domains with SEQ ID NOs: 11-12 [epitope bin3].

Such preferred multiparatopic (such as biparatopic or triparatopic) polypeptides of the invention may comprise or essentially consist of one of the following combinations of immunoglobulin single variable domains:

the first and the second immunoglobulin single variable domains are polypeptides that belong to epitope bin 1 and are selected from any one of:
a polypeptide that binds full length PcrV (SEQ ID NO: 159) and that shows reduced binding (30-90% as compared to full length PcrV) or no binding to chimera 4 (SEQ ID NO: 202) and chimera 6 (SEQ ID NO: 204);
a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 3-10;
a polypeptide that cross-blocks the binding to PcrV of at least one of the immunoglobulin single variable domains with SEQ ID NOs: 3-10 and/or that is cross-blocked from binding to PcrV by at least one of the immunoglobulin single variable domains with SEQ ID NOs: 3-10; and
a polypeptide that is any of SEQ ID NOs: 3-10;

the first and the second immunoglobulin single variable domains are polypeptides that belong to epitope bin 2 and are selected from any one of:
a polypeptide that binds to full length PcrV (SEQ ID NO: 159) and that shows reduced binding (30-90% as compared to full length PcrV) or no binding to chimera 7 (SEQ ID NO: 205);
a polypeptide, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2;
a polypeptide that cross-blocks the binding to PcrV of at least one of the immunoglobulin single variable domains with SEQ ID NOs: 1 and 2 and/or that is cross-blocked from binding to PcrV by at least one of the immunoglobulin single variable domains with SEQ ID NOs: 1 and 2; and
a polypeptide that is any of SEQ ID NOs: 1 and 2; or the first and the second immunoglobulin single variable domains are polypeptides that belong to epitope bin 3 and are selected from any one of:
a polypeptide that binds full length PcrV (SEQ ID NO: 159) and that shows reduced binding (30-90% as compared to full length PcrV) or no binding to chimera 2 (SEQ ID NO: 200);
a polypeptide in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;
a polypeptide that cross-blocks the binding to PcrV of at least one of the immunoglobulin single variable domains with SEQ ID NOs: 11 and 12 and/or that is cross-blocked from binding to PcrV by at least one of the immunoglobulin single variable domains with SEQ ID NOs: 11 and 12; and
a polypeptide that is any of SEQ ID NOs: 11 and 12.

In a preferred aspect, the invention relates to a polypeptide as defined above, which is selected from any of SEQ ID NOs: 118-123 (Table A-5).

In another preferred aspect, the invention relates to a polypeptide as defined above, wherein at least one immunoglobulin single variable domain is SEQ ID NO: 3. In another preferred aspect, the invention relates to a polypeptide as defined above, which is selected from any of SEQ ID NOs: 118, 120 and 121. In another preferred aspect, the invention relates to a polypeptide as defined above, wherein at least one immunoglobulin single variable domain is SEQ ID NO: 1. In another preferred aspect, the invention relates to a polypeptide as defined above, which is selected from any of SEQ ID NOs: 122 and 123.

The two or more immunoglobulin single variable domains present in the polypeptide of the invention may consist of a light chain variable domain sequence (e.g., a $V_L$-sequence) or of a heavy chain variable domain sequence (e.g., a $V_H$-sequence). They may consist of a heavy chain variable domain sequence that is derived from a conventional four-chain antibody or of a heavy chain variable domain sequence that is derived from heavy chain antibody. They may consist of a domain antibody (or an amino acid that is suitable for use as a domain antibody), of a single domain antibody (or an amino acid that is suitable for use as a single domain antibody), of a "dAb" (or an amino acid that is suitable for use as a dAb) or of a Nanobody (including but not limited to a V$_{HH}$). In a preferred aspect, the two or more immunoglobulin single variable domains consist of a partially or fully humanized Nanobody or a partially or fully humanized VHH.

The multivalent, such as multiparatopic, polypeptides of the invention can generally be provided (and in particular, purposefully designed for a specific biological action) by suitably linking (optionally via suitable linkers) or combining two or more (monovalent) immunoglobulin single variable domains (or by suitably linking or combining nucleotide sequences encoding such (monovalent) immunoglobulin single variable domains to provide a nucleic acid that encodes the desired multivalent construct, and then suitably expressing said multivalent construct). Thus, it is clear that the invention not only makes available the multivalent, preferably multiparatopic, polypeptides described herein, but also provides—by making available the monovalent polypeptides described herein—the skilled person with a range of different "binding domains" or "binding units" that can be used as "building blocks" to provide a range of different multivalent, preferably multiparatopic (and in particular, biparatopic and triparatopic) polypeptides (which may have different binding affinities, avidities, specificities, potencies and/or efficacies) through the use of suitable "building blocks" as described herein.

Consequently, the various immunoglobulin single variable domains and/or monovalent polypeptides of the invention (and/or nucleotide sequences and/or nucleic acids encoding the same) and their use of as "building blocks" in or for preparation of multivalent and/or multiparatopic polypeptides (or nucleotide sequences/nucleic acids encoding the same) form an important aspect of the invention.

Accordingly, in a further aspect, the invention also relates to a polypeptide (also referred to herein as "monovalent polypeptide(s) of the invention") that comprises at least one stretch of amino acid residues that chosen from the group consisting of:
CDR1 sequences:
a) SEQ ID NOs: 20-37;
b) stretches of amino acid sequences that have at least 80% amino acid identity with at least one of the amino acid sequences of SEQ ID NOs: 20-37;
c) stretches of amino acid sequences that have 3, 2, or 1 amino acid difference with at least one of the amino acid sequences of SEQ ID NOs: 20-37;
and/or
CDR2 sequences:
d) SEQ ID NOs: 38-56;
e) stretches of amino acid sequences that have at least 80% amino acid identity with at least one of the amino acid sequences of SEQ ID NOs: 38-56;
f) stretches of amino acid sequences that have 3, 2, or 1 amino acid difference with at least one of the amino acid sequences of SEQ ID NOs: 38-56;
and/or
CDR3 sequences:
g) SEQ ID NOs: 57-75;
h) stretches of amino acid sequences that have at least 80% amino acid identity with at least one of the amino acid sequences of SEQ ID NOs: 57-75;
i) stretches of amino acid sequences that have 3, 2, or 1 amino acid difference with at least one of the amino acid sequences of SEQ ID NOs: 57-75.

Monovalent polypeptides comprising one or more of the above specified stretches of amino acid residues show improved properties such as e.g. improved binding characteristics (suitably measured and/or expressed as a K$_D$-value (actual or apparent), a K$_A$-value (actual or apparent), a k$_{on}$-rate and/or a k$_{off}$-rate, or alternatively as an IC$_{50}$ value, as further described herein), improved affinity and/or improved avidity for PcrV and/or improved efficacy and/or potency for neutralizing PcrV.

For example, in a TTSS-dependent cytotoxicity assay with P3X63 cells as the target at an average MOI of 2.8, the monovalent polypeptides of the invention may have IC50 values between 1 nM and 10000 nM, between 5 nM and 1000 nM, preferably between 5 nM and 500 nM, more preferably between 5 nM and 200 nM, such as between 5 nM and 50 nM or less.

Apart from this and/or in addition, in such a TTSS-dependent cytotoxicity assay, the monovalent polypeptides of the invention may have an efficacy (% inhibition; see Example 4.4) of 50% or more, preferably 90% or more, such as 100%.

In a preferred aspect, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. Accordingly, the present invention also relates to a monovalent polypeptide that essentially consists of 4 framework regions (FR1 to FR4, respectively) and 3 complementarity determining regions (CDR1 to CDR3, respectively), in which:
CDR1 is chosen from the group consisting of:
a) the amino acid sequences of SEQ ID NOs: 20-37;
b) amino acid sequences that have at least 80% amino acid identity with at least one of the amino acid sequences of SEQ ID NOs: 20-37;
c) amino acid sequences that have 3, 2, or 1 amino acid difference with at least one of the amino acid sequences of SEQ ID NOs: 20-37;
and/or
CDR2 is chosen from the group consisting of:
d) the amino acid sequences of SEQ ID NOs: 38-56;
e) amino acid sequences that have at least 80% amino acid identity with at least one of the amino acid sequences of SEQ ID NOs: 38-56;
f) amino acid sequences that have 3, 2, or 1 amino acid difference with at least one of the amino acid sequences of SEQ ID NOs: 38-56;
and/or
CDR3 is chosen from the group consisting of:
g) the amino acid sequences of SEQ ID NOs: 57-75;
h) amino acid sequences that have at least 80% amino acid identity with at least one of the amino acid sequences of SEQ ID NOs: 57-75;
i) amino acid sequences that have 3, 2, or 1 amino acid difference with at least one of the amino acid sequences of SEQ ID NOs: 57-75.

Preferred monovalent polypeptides essentially consist of 4 framework regions (FR1 to FR4, respectively) and 3 complementarity determining regions (CDR1 to CDR3, respectively), in which:
CDR1 is chosen from the group consisting of:
a) the amino acid sequences of SEQ ID NOs: 20-37;
b) amino acid sequences that have at least 80% amino acid identity with at least one of the amino acid sequences of SEQ ID NOs: 20-37;

c) amino acid sequences that have 3, 2, or 1 amino acid difference with at least one of the amino acid sequences of SEQ ID NOs: 20-37;

and

CDR2 is chosen from the group consisting of:
d) the amino acid sequences of SEQ ID NOs: 38-56;
e) amino acid sequences that have at least 80% amino acid identity with at least one of the amino acid sequences of SEQ ID NOs: 38-56;
f) amino acid sequences that have 3, 2, or 1 amino acid difference with at least one of the amino acid sequences of SEQ ID NOs: 38-56;

and

CDR3 is chosen from the group consisting of:
g) the amino acid sequences of SEQ ID NOs: 57-75;
h) amino acid sequences that have at least 80% amino acid identity with at least one of the amino acid sequences of SEQ ID NOs: 57-75;
i) amino acid sequences that have 3, 2, or 1 amino acid difference with at least one of the amino acid sequences of SEQ ID NOs: 57-75.

In a preferred monovalent polypeptide of the invention, the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1-19.

The invention also relates to monovalent polypeptides directed against PcrV, that cross-block the binding to PcrV of at least one of the immunoglobulin single variable domains with SEQ ID NOs: 1-19 and/or that are cross-blocked from binding to PcrV by at least one of the immunoglobulin single variable domains with SEQ ID NOs: 1-19.

Preferred monovalent polypeptides of the invention are selected from any of SEQ ID NOs: 1-19.

The present inventors furthermore observed that immunoglobulins belonging to certain epitope bins are particularly suited for binding to PcrV, neutralization of *P. aeruginosa* and/or as a binding unit for the preparation of multiparatopic, such as e.g. biparatopic or triparatopic polypeptides. Preferred immunoglobulins belong to epitope bins 1, 2 or 3 (as further defined herein).

Accordingly, in a further aspect, the present invention relates to an immunoglobulin that belongs to epitope bin 1 and that has one or more of the following features:
- it cross-blocks the binding to PcrV of at least one of the immunoglobulin single variable domains with SEQ ID NOs: 3-10;
- it is cross-blocked from binding to PcrV by at least one of the immunoglobulin single variable domains with SEQ ID NOs: 3-10;
- it binds full length PcrV (SEQ ID NO: 159) while showing reduced (30-90% as compared to full length PcrV) or no (lower than 30% as compared to full length PcrV) binding to chimera 4 (SEQ ID NO: 202) and chimera 6 (SEQ ID NO: 204);
- it consists of 4 framework regions (FR1 to FR4, respectively) and 3 complementarity determining regions (CDR1 to CDR3, respectively), in which:

CDR1 is chosen from the group consisting of:
a) the amino acid sequences of SEQ ID NOs: 22-28;
b) amino acid sequences that have at least 80% amino acid identity with at least one of the amino acid sequences of SEQ ID NOs: 22-28;
c) amino acid sequences that have 3, 2, or 1 amino acid difference with at least one of the amino acid sequences of SEQ ID NOs: 22-28;

and

CDR2 is chosen from the group consisting of:
d) the amino acid sequences of SEQ ID NOs: 40-47;
e) amino acid sequences that have at least 80% amino acid identity with at least one of the amino acid sequences of SEQ ID NOs: 40-47;
f) amino acid sequences that have 3, 2, or 1 amino acid difference with at least one of the amino acid sequences of SEQ ID NOs: 40-47;

and

CDR3 is chosen from the group consisting of:
g) the amino acid sequences of SEQ ID NOs: 59-66;
h) amino acid sequences that have at least 80% amino acid identity with at least one of the amino acid sequences of SEQ ID NOs: 59-66;
i) amino acid sequences that have 3, 2, or 1 amino acid difference with at least one of the amino acid sequences of SEQ ID NOs: 59-66;

its CDR sequences have at least 70% amino acid identity, preferably at least 80% amino acid identity, more preferably at least 90% amino acid identity, such as 95% amino acid identity or more, or even essentially 100% amino acid identity with the CDR sequences of at least one of the immunoglobulin single variable domains with SEQ ID NOs: 3-10; or it is selected from any of SEQ ID NOs: 3-10.

In another aspect, the present invention relates to an immunoglobulin that belongs to epitope bin 2 and that has one or more of the following features:
- it cross-blocks the binding to PcrV of at least one of the immunoglobulin single variable domains with SEQ ID NOs: 1 and 2;
- it is cross-blocked from binding to PcrV by at least one of the immunoglobulin single variable domains with SEQ ID NOs: 1 and 2;
- it binds to full length PcrV (SEQ ID NO: 159), while it shows reduced (30-90% as compared to full length PcrV) or no (below 30% as compared to full length PcrV) binding to chimera 7 (SEQ ID NO: 205);
- it consists of 4 framework regions (FR1 to FR4, respectively) and 3 complementarity determining regions (CDR1 to CDR3, respectively), in which:

CDR1 is chosen from the group consisting of:
a) the amino acid sequences of SEQ ID NOs: 20-21;
b) amino acid sequences that have at least 80% amino acid identity with at least one of the amino acid sequences of SEQ ID NOs: 20-21;
c) amino acid sequences that have 3, 2, or 1 amino acid difference with at least one of the amino acid sequences of SEQ ID NOs: 20-21;

and

CDR2 is chosen from the group consisting of:
d) the amino acid sequences of SEQ ID NOs: 38-39;
e) amino acid sequences that have at least 80% amino acid identity with at least one of the amino acid sequences of SEQ ID NOs: 38-39;
f) amino acid sequences that have 3, 2, or 1 amino acid difference with at least one of the amino acid sequences of SEQ ID NOs: 38-39;

and

CDR3 is chosen from the group consisting of:
g) the amino acid sequences of SEQ ID NOs: 57-58;
h) amino acid sequences that have at least 80% amino acid identity with at least one of the amino acid sequences of SEQ ID NOs: 57-58;

i) amino acid sequences that have 3, 2, or 1 amino acid difference with at least one of the amino acid sequences of SEQ ID NOs: 57-58;

its CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 1 and 2; or it is selected from any of SEQ ID NOs: 1 and 2.

In another aspect, the present invention relates to an immunoglobulin that belongs to epitope bin 3 and that has one or more of the following features:

it cross-blocks the binding to PcrV of at least one of the immunoglobulin single variable domain with SEQ ID NOs: 11 and 12;

it is cross-blocked from binding to PcrV by at least one of the immunoglobulin single variable domains with SEQ ID NOs: 11 and 12;

it binds to full length PcrV (SEQ ID NO: 159), while it shows reduced (30-90% as compared to full length PcrV) or no (below 30% as compared to full length PcrV) binding to chimera 2 (SEQ ID NO: 200);

it consists of 4 framework regions (FR1 to FR4, respectively) and 3 complementarity determining regions (CDR1 to CDR3, respectively), in which:

CDR1 is chosen from the group consisting of:
a) the amino acid sequences of SEQ ID NOs: 29-30;
b) amino acid sequences that have at least 80% amino acid identity with at least one of the amino acid sequences of SEQ ID NOs: 29-30;
c) amino acid sequences that have 3, 2, or 1 amino acid difference with at least one of the amino acid sequences of SEQ ID NOs: 29-30;
and CDR2 is chosen from the group consisting of:
d) the amino acid sequences of SEQ ID NOs: 48-49;
e) amino acid sequences that have at least 80% amino acid identity with at least one of the amino acid sequences of SEQ ID NOs: 48-49;
f) amino acid sequences that have 3, 2, or 1 amino acid difference with at least one of the amino acid sequences of SEQ ID NOs: 48-49;
and CDR3 is chosen from the group consisting of:
g) the amino acid sequences of SEQ ID NOs: 67-68;
h) amino acid sequences that have at least 80% amino acid identity with at least one of the amino acid sequences of SEQ ID NOs: 67-68;
i) amino acid sequences that have 3, 2, or 1 amino acid difference with at least one of the amino acid sequences of SEQ ID NOs: 67-68;

its CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains with SEQ ID NOs: 11 and 12;

it is selected from any of SEQ ID NOs: 11 and 12.

The monovalent polypeptides of the invention may essentially consist of an immunoglobulin single variable domain selected from a light chain variable domain sequence (e.g., a $V_L$-sequence) and from a heavy chain variable domain sequence (e.g., a V-sequence). The monovalent polypeptides of the invention may essentially consists of an immunoglobulin single variable domain selected from a heavy chain variable domain sequence that is derived from a conventional four-chain antibody and from a heavy chain variable domain sequence that is derived from heavy chain antibody. The monovalent polypeptides of the invention may essentially consists of an immunoglobulin single variable domain selected from a domain antibody (or an amino acid that is suitable for use as a domain antibody), a single domain antibody (or an amino acid that is suitable for use as a single domain antibody), a "dAb" (or an amino acid that is suitable for use as a dAb) or a Nanobody (including but not limited to a $V_{HH}$). In a preferred aspect, the monovalent polypeptide of the invention essentially consists of a partially or fully humanized Nanobody, such as a partially or fully humanized VHH.

As described above, the invention also relates to the use of a monovalent polypeptide as described herein in preparing a multivalent, preferably multiparatopic polypeptide of the invention. Accordingly, the present invention relates to the use of a monovalent polypeptide of the invention as a binding domain or binding unit in preparing a multivalent polypeptide of the invention.

The invention further relates to a polypeptides (also referred to herein as a "polypeptide(s) of the invention") that comprises or essentially consists of one or more monovalent polypeptide or one or more multivalent, preferably multiparatopic, polypeptide of the invention, and optionally further comprises one or more other groups, residues, moieties or binding units, optionally linked via one or more peptidic linkers. As will become clear to the skilled person from the further disclosure herein, such further groups, residues, moieties, binding units or amino acid sequences may or may not provide further functionality to the monovalent or multivalent, preferably multiparatopic, polypeptide of the invention and may or may not modify the properties of the monovalent or multivalent polypeptide of the invention.

The invention also relates to nucleic acids or nucleotide sequences that encode a polypeptide of the invention. Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

Nucleic acids encoding a monovalent polypeptide of the invention can be linked to obtain a nucleic acid encoding a multivalent, preferably multiparatopic, polypeptide of the invention. Accordingly, the present invention also relates to the use of a nucleic acid or nucleotide sequence that encodes a monovalent polypeptide of the invention for the preparation of a genetic construct that encodes a multivalent, preferably multiparatopic, polypeptide of the invention.

The invention further relates to a host or host cell that expresses (or that under suitable circumstances is capable of expressing) a polypeptide of the invention; and/or that contains a nucleic acid of the invention. Some preferred but non-limiting examples of such hosts or host cells will become clear from the further description herein.

The invention further relates to a composition containing or comprising at least one polypeptide of the invention and/or at least one nucleic acid of the invention, and optionally one or more further components of such compositions known per se, i.e. depending on the intended use of the composition. Such a composition may for example be a pharmaceutical composition (as described herein) or a veterinary composition. Some preferred but non-limiting examples of such compositions will become clear from the further description herein.

The invention further relates to methods for preparing polypeptides, nucleic acids, host cells, and compositions described herein.

The invention further relates to applications and uses of the polypeptides, nucleic acids, host cells, and compositions described herein, as well as to methods for the prevention and/or treatment of P. aeruginosa infections. Some preferred but non-limiting applications and uses will become clear from the further description herein.

As such, polypeptides and compositions of the present invention can be used for the prevention and/or treatment of P. P. aeruginosa infections. Patient groups susceptible to P. aeruginosa infections will be clear to the skilled person and for example include (without being limiting) ventilator-associated pneumonia (VAP), burn victims, mechanical ventilated patients, Cystic Fibrosis (CF) patients, hematopoietic cell transplantation patients, bone marrow transplant patients, patients undergoing surgery, patients with chronic obstructive pulmonary disease (COPD), patients with bronchiectasis, patients with sepsis and patients with cancer-associated neutropenia.

Accordingly, the present invention also relates to a method for the prevention and/or treatment of P. aeruginosa infections in least one of ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia, said method comprising administering, to a subject in need thereof, a pharmaceutically active amount of at least one polypeptide of the invention or composition of the invention.

The invention also relates to the use of a polypeptide of the invention in the preparation of a pharmaceutical composition for the prevention and/or treatment of P. aeruginosa infections in least one of ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia; and/or for use in one or more of the methods described herein.

The invention also relates to a polypeptide of the invention or a composition of the invention for prevention and/or treatment of P. aeruginosa infections in least one of ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia.

Other applications and uses of the polypeptides and compositions of the invention will become clear to the skilled person from the further disclosure herein.

FIGURE LEGENDS

FIGS. 1A-1D: Analysis of monovalent anti-PcrV Nanobodies in cytotoxicity assay with P3X63 cells as target as described in Example 5.

Figure 2A:
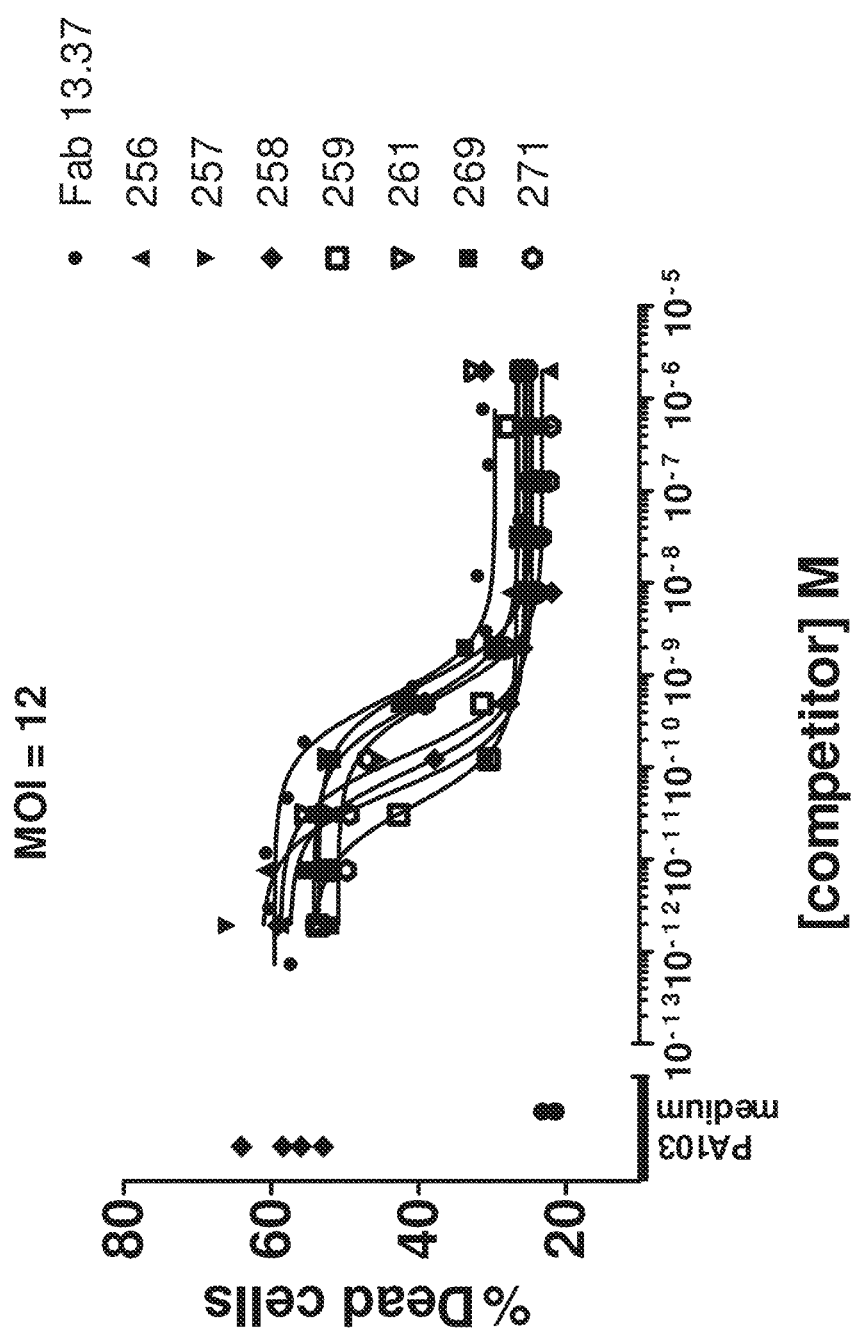
Figure 2B:
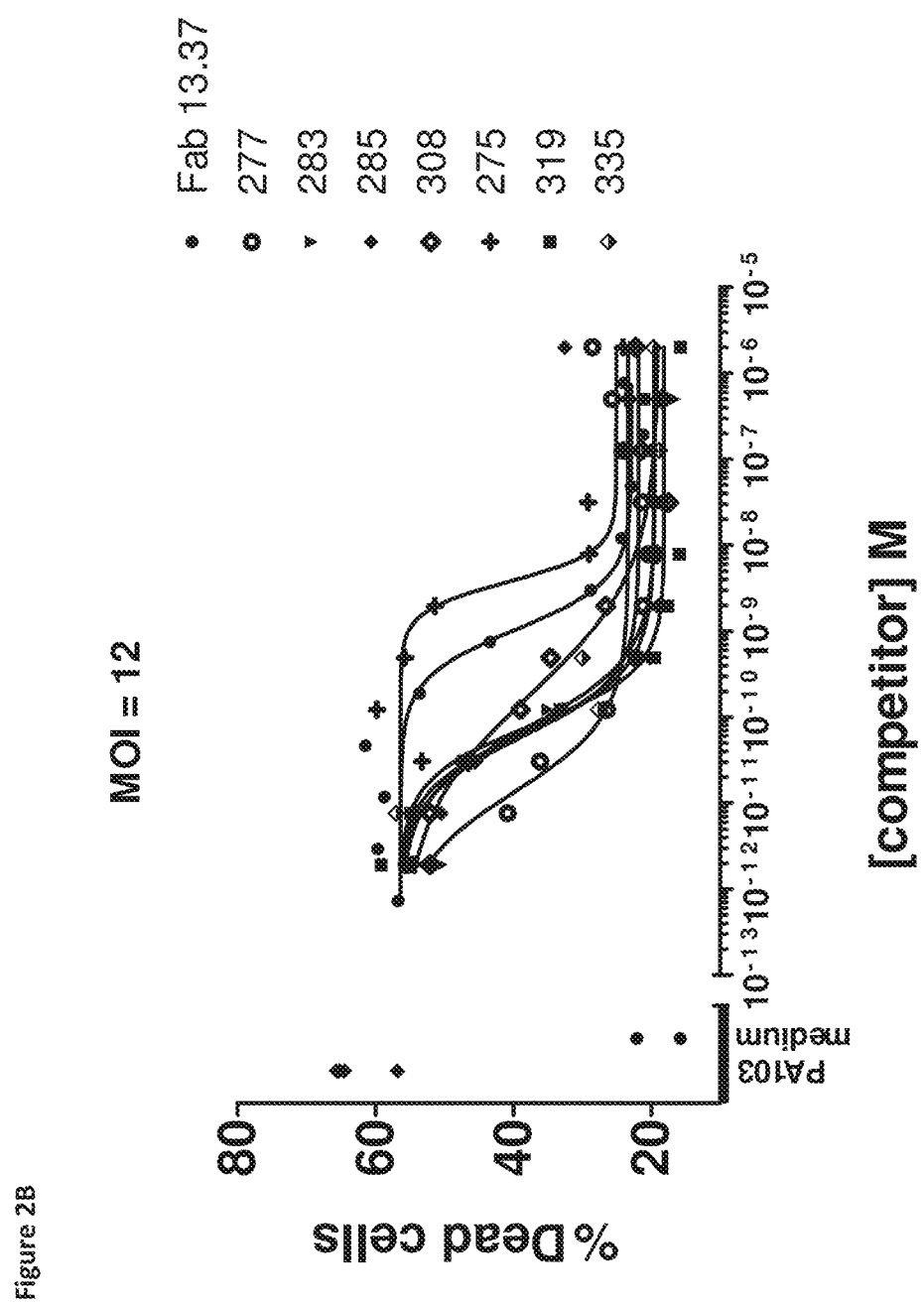

FIGS. 2A-2B: Analysis of bivalent/biparatopic anti-PcrV Nanobodies in cytotoxicity assay with P3X63 cells as target as described in Example 7.

FIG. 3: Schematic representation of molecules used for epitope mapping. The PcrV-LcrV chimera design was based on primary sequence and structural (particularly secondary structure) information. Seven different chimeric molecules were designed by introducing seven fragments of LcrV (transparent bars) of length between 17 and 47 amino acid residues in replacement of the structurally corresponding counterparts of PcrV (black bars). A PcrV fragment (amino acids 144-257) described by Frank et al. (The Journal of infectious diseases 186: 64-73, 2002 and U.S. Pat. No. 6,827,935) was also generated. Numbers above and below the bars indicate PcrV or LcrV amino acid residue numbers, respectively. The amino acid sequence of the different constructs is given in Table A-7.

Figure 4A:
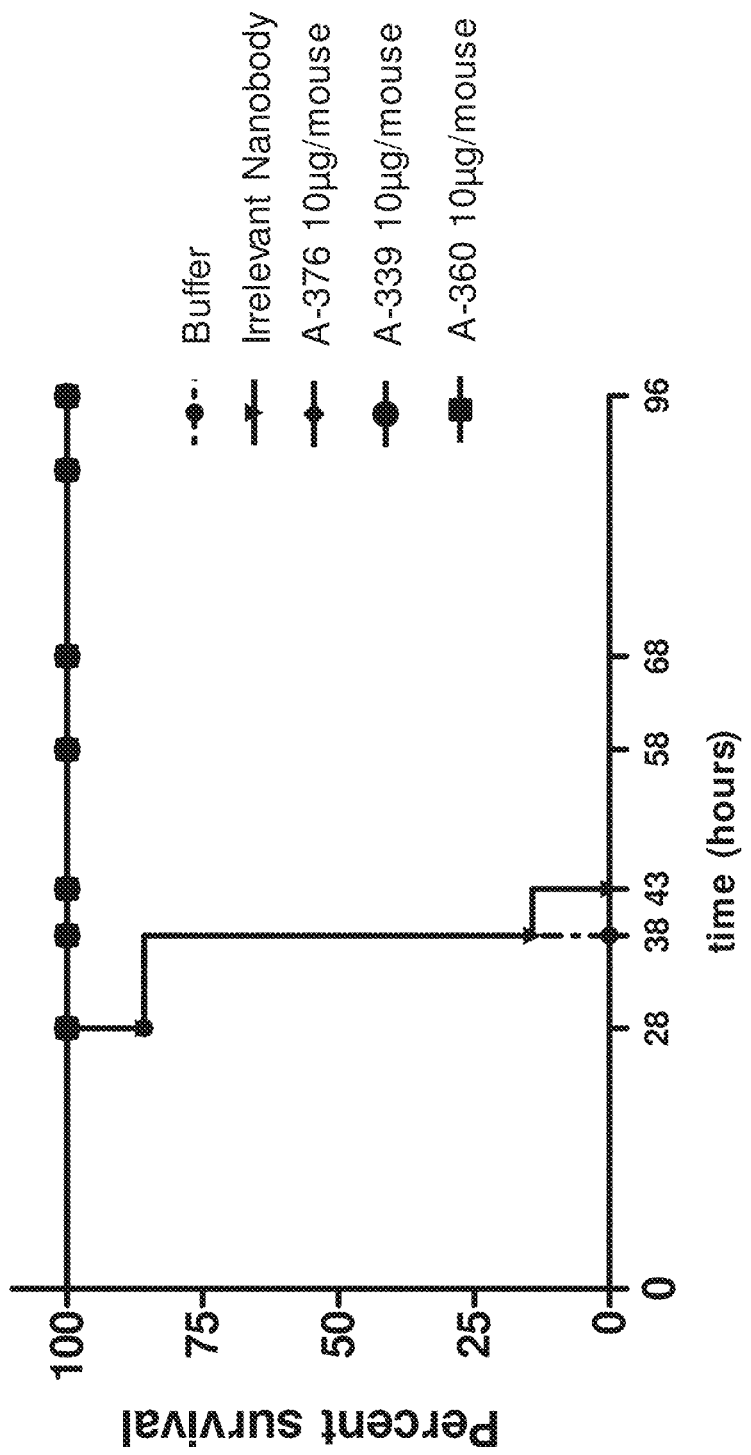
Figure 4B:
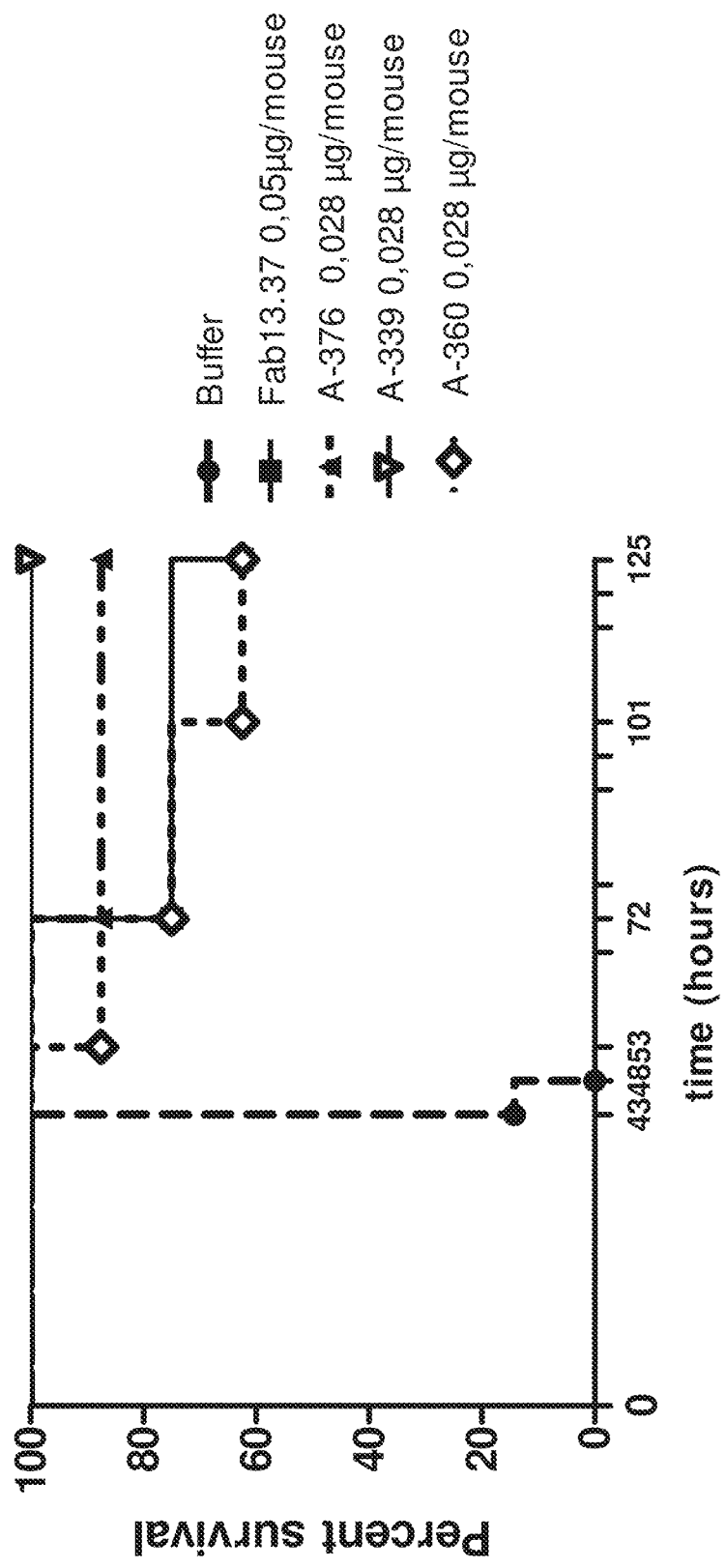

FIGS. 4A-4B: Survival curves obtained in acute P. aeruginosa infection mouse model after inoculation with Nanobodies 339, 360 and 376. 7 to 8 C57Bl/6 mice per group were intranasally challenged with a premix of either Nanobody, Fab 13.37 or buffer alone premixed with Pseudomonas aeruginosa. The mice were monitored for survival during 96 hours or 125 hours.

Figure 5A:
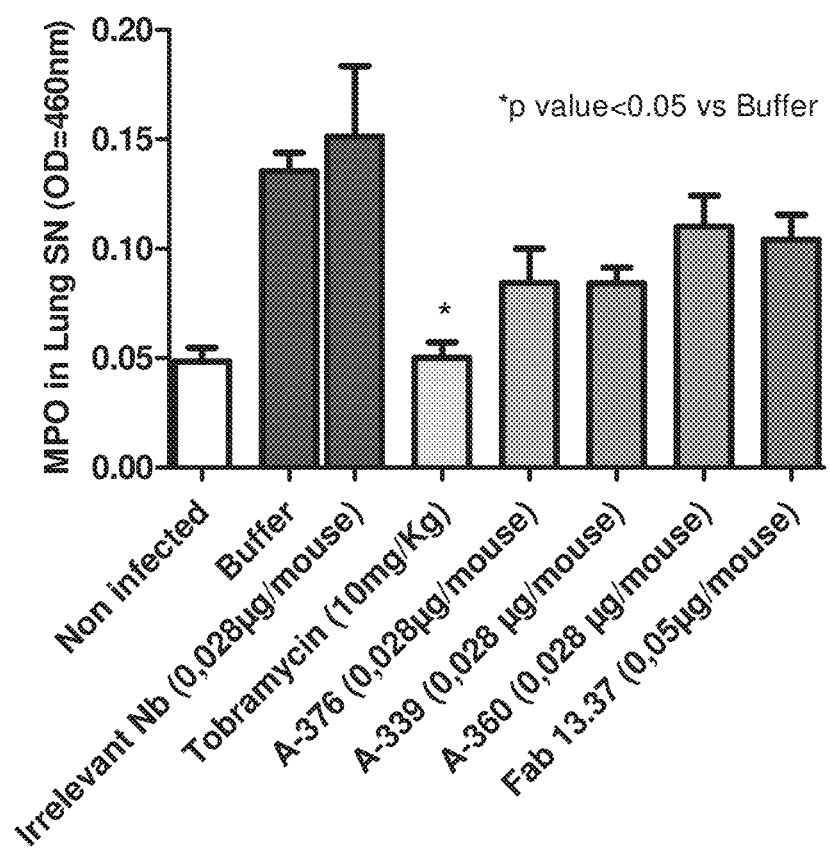
Figure 5B:
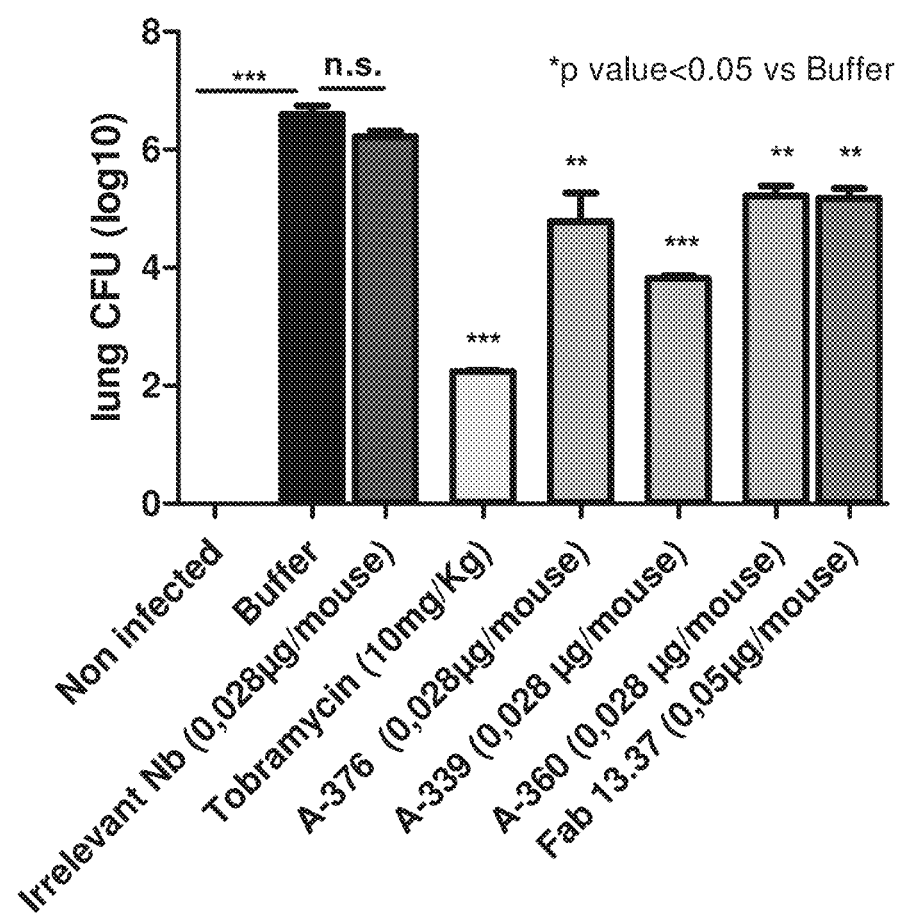
Figure 5C:
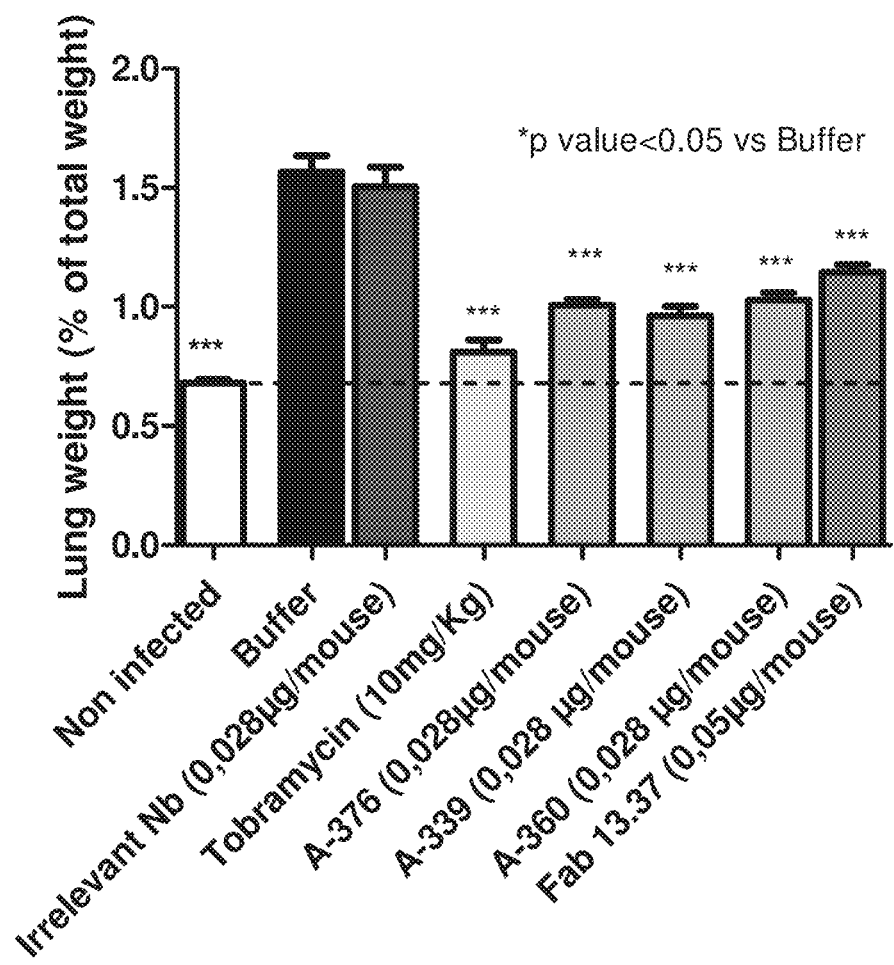

FIGS. 5A-5C: Lung inflammation parameters and bacterial burden. 3 to 5 C57Bl/6 mice per group were intranasally challenged with a premix of either Nanobody, Fab 13.37 or buffer alone premixed with Pseudomonas aeruginosa. An additional group received Tobramycin at 10 mg/kg i.p. to serve as positive control. All the mice were sacrificed at 24 hours post-infection following which myeloperoxidase activity (A), bacterial burden (B) and percentage lung weights to total body weight (C) were assessed. Results are depicted as mean±SEM. Statistics were performed using a one-way ANOVA with a post-hoc Bonferroni's multiple comparison test. P-values <0.05 were considered statistically significant.

Figure 6:
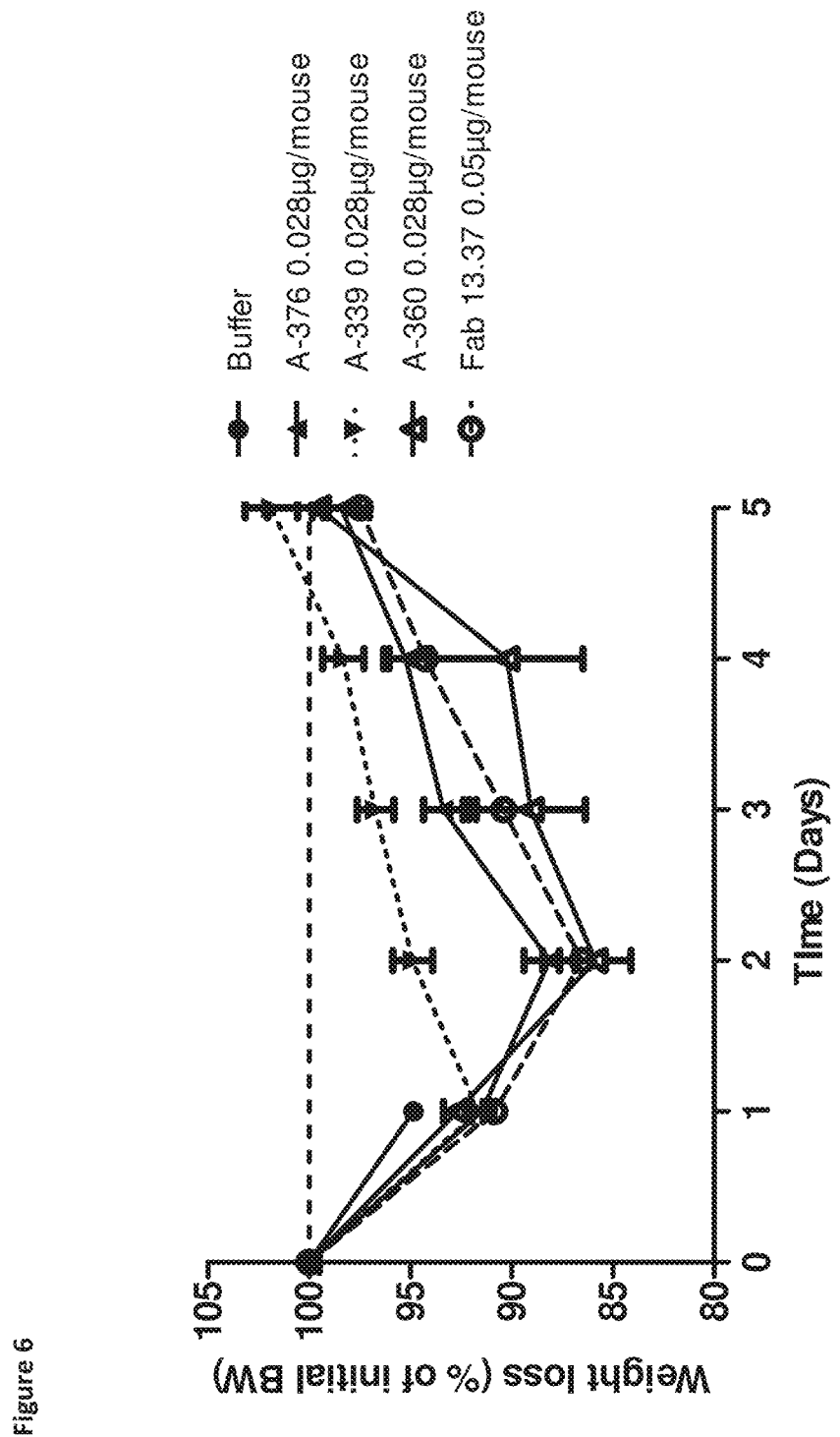

FIG. 6: Relative weight loss. 7 to 8 C57Bl/6 mice per group were intranasally challenged with a premix of either Nanobody, Fab 13.37 or buffer alone premixed with Pseudomonas aeruginosa. The mice were monitored for 5 days and body weights were recorded daily at 1 pm. Results are depicted as mean±SEM.

Figure 7:
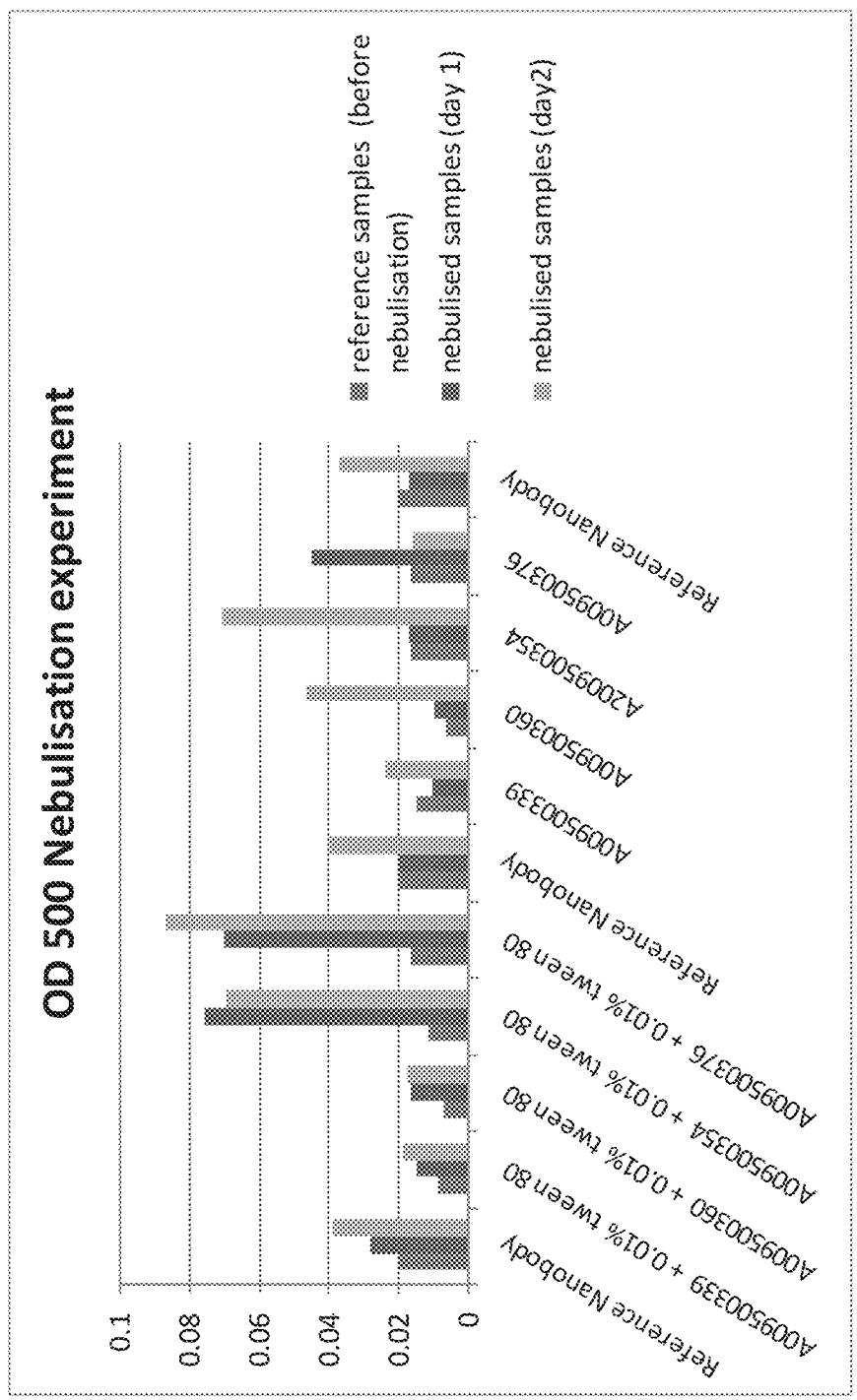

FIG. 7. OD500 values of the Nanobody samples before and after nebulisation. The polypeptides 339, 360, 354 and 376 (in D-PBS with and without Tween80) were nebulized by the AKITA$^2$® APIXNEB nebulizer system (Activaero). The nebulisation experiment was performed in duplicate. 500 ⍰ l of sample was nebulised continuously via a mesh nebulizer with a 4 um membrane. The aerosol was collected in a 100 mL glass bottle and then analysed.

DETAILED DESCRIPTION

Definitions

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd. Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, Calif., 1981); Roitt et al. (Immunology (6th. Ed.) Mosby/Elsevier, Edinburgh, 2001), Roitt et al. (Roitt's Essential Immunology (10$^{th}$ Ed.) Blackwell Publishing, UK, 2001), and Janeway et al. (Immunobiology (6th Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid difference" refers to an insertion, deletion or substitution of a single amino acid residue on a position of the CDR sequence specified in c), f) or i), compared to the CDR sequence of respectively a), d) or g); it being understood that the CDR sequence of c), f) and i) can contain one, two or maximal three such amino acid differences compared to the CDR sequence of respectively a), d) or g).

The "amino acid difference" can be any one, two or maximal three substitutions, deletions or insertions, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind PcrV with the same, about the same, or a higher affinity compared to the polypeptide comprising the one or more CDR sequences without the one, two or maximal three substitutions, deletions or insertions, said affinity as measured by surface plasmon resonance.

In this respect, the amino acid sequence according to c), f) and/or i) may be an amino acid sequence that is derived from an amino acid sequence according to a), d) and/or g) respectively by means of affinity maturation using one or more techniques of affinity maturation known per se.

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-PcrV).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent polypeptide of the invention will bind to the desired antigen with an affinity less than 500 nM, preferably less than 200 nM, more preferably less than 10 nM, such as e.g., between 10 and 5 nM or less. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less, such as 10000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays. One particularly suitable quantitative cross-blocking assay uses a Biacore instrument which can measure the extent of interactions using surface plasmon resonance technology. Another suitable quantitative cross-blocking assay uses an ELISA-based approach to measure competition between immunoglobulins, antibodies, immunoglobulin single variable domains, polypeptides or other binding agents in terms of their binding to the target.

The following generally describes a suitable Biacore assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The Biacore instrument (for example the Biacore 3000) is operated in line with the manufacturer's recommendations. Thus in one cross-blocking assay, the target protein (e.g. PcrV) is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test binding agents (termed A* and B*) to be assessed for their ability to cross-block each other are mixed at a one to one molar ratio of binding sites in a suitable buffer to create the test mixture. When calculating the concentrations on a binding site basis the molecular weight of a binding agent is assumed to be the total molecular weight of the binding agent divided by the number of target binding sites on that binding agent. The concentration of each binding agent in the test mix should be high enough to readily saturate the binding sites for that binding agent on the target molecules captured on the Biacore chip. The binding agents in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound binding agents without damaging the chip-bound target. Typically this is done by treating the chip with 30 mM HCl for 60 seconds. The solution of A* alone is then passed over the target-coated surface and the amount of binding recorded. The chip is again treated to remove all of the bound binding agents without damaging the chip-bound target. The solution of B* alone is then passed over the target-coated surface and the amount of binding recorded. The maximum theoretical binding of the mixture of A* and B* is next calculated, and is the sum of the binding of each binding agent when passed over the target surface alone. If the actual recorded binding of the mixture is less than this theoretical maximum then the two binding agents are said to cross-block each other. Thus, in general, a cross-blocking immunoglobulin, antibody, immunoglobulin single variable domain, polypeptide or other binding agent according to the invention is one which will bind to the target in the above Biacore cross-blocking assay such that during the assay and in the presence of a second immunoglobulin, antibody, immunoglobulin single variable domain, polypeptide or other binding agent the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two immunoglobulins, antibodies, immunoglobulin single variable domains, polypeptides or binding agents in combination. The Biacore assay described above is a primary assay used to determine if immunoglobulins, antibodies, immunoglobulin single variable domains, polypeptide or other binding agents cross-block each other according to the invention. On rare occasions particular immunoglobulins, antibodies, immunoglobulin single variable domains, polypeptides or other binding agents may not bind to a target coupled via amine chemistry to a CM5 Biacore chip (this usually occurs when the relevant binding site on the target is masked or destroyed by the coupling to the chip). In such cases cross-blocking can be determined using a tagged version of the target, for example a N-terminal His-tagged version. In this particular format, an anti-His antibody would be coupled to the Biacore chip and then the His-tagged target would be passed over the surface of the chip and captured by the anti-His antibody. The cross blocking analysis would be carried out essentially as described above, except that after each chip regeneration cycle, new His-tagged target would be loaded back onto the anti-His antibody coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an immunoglobulin, antibody, immunoglobulin single variable domain, polypeptide or other binding agent directed against a target (e.g., PcrV) cross-blocks or is capable of cross-blocking as defined herein. It will be appreciated that the assay can be used with any of the immunoglobulins, antibodies, immunoglobulin single variable domains, polypeptides or other binding agents described herein. The general principal of the assay is to have an immunoglobulin, antibody, immunoglobulin single variable domain, polypeptide or binding agent that is directed against the target coated onto the wells of an ELISA plate. An excess amount of a second, potentially cross-blocking, anti-target immunoglobulin, antibody, immunoglobulin single variable domain, polypeptide or other binding agent is added in solution (i.e. not bound to the ELISA plate). A limited amount of the target is then added to the wells. The coated immunoglobulin, antibody, immunoglobulin single variable domain, polypeptide or other binding agent and the immunoglobulin, antibody, immunoglobulin single variable domain, polypeptide or other binding agent in solution compete for binding of the limited number of target molecules. The plate is washed to remove excess target that has not been bound by the coated immunoglobulin, antibody, immunoglobulin single variable domain, polypeptide or other binding agent and to also remove the second, solution phase immunoglobulin, antibody, immunoglobulin single variable domain, polypeptide or other binding agent as well as any complexes formed between the second, solution phase immunoglobulin, antibody, immunoglobulin single variable domain, polypeptide or other binding agent and target. The amount of bound target is then measured using a reagent that is appropriate to detect the target. An immunoglobulin, antibody, immunoglobulin single variable domain, polypeptide or other binding agent in solution that is able to cross-block the coated immunoglobulin, antibody, immunoglobulin single variable domain, polypeptide or other binding agent will be able to cause a decrease in the number of target molecules that the coated immunoglobulin, antibody, immunoglobulin single variable domain, polypeptide or other binding agent can bind relative to the number of target molecules that the coated immunoglobulin, antibody, immunoglobulin single variable domain, polypeptide or other binding agent can bind in the absence of the second, solution phase, immunoglobulin, antibody, immunoglobulin single variable domain, polypeptide or other binding agent. In the instance where the first immunoglobulin, antibody, immunoglobulin single variable domain, polypeptide or other binding agent, e.g., an Ab-X, is chosen to be the immobilized immunoglobulin, antibody, immunoglobulin single variable domain, polypeptide or other binding agent, it is coated onto the wells of the ELISA plate, after which the plates are blocked with a suitable blocking solution to minimize non-specific binding of reagents that are subsequently added. An excess amount of the second immunoglobulin, antibody, immunoglobulin single variable domain, polypeptide or other binding agent, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target immunoglobulin, antibody, immunoglobulin single variable domain, polypeptide or other binding agent (in this case Ab-X). The background signal for the assay is defined as the signal obtained in wells with the coated immunoglobulin, antibody, immunoglobulin single variable domain, polypeptide or other binding agent (in this case Ab-X), second solution phase immunoglobulin single variable domain, polypeptide or other binding agent (in this case Ab-Y), target buffer only (i.e., without target) and target detection reagents. The positive control signal for the assay is defined as the signal obtained in wells with the coated immunoglobulin, antibody, immunoglobulin single variable domain, polypeptide or other binding agent (in this case Ab-X), second solution phase immunoglobulin, antibody, immunoglobulin single variable domain, polypeptide or other binding agent buffer only (i.e., without second solution phase immunoglobulin, antibody, immunoglobulin single variable domain, polypeptide or other binding agent), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which immunoglobulin, antibody, immunoglobulin single variable domain, polypeptide or other binding agent to use as the coating immunoglobulin, antibody, immunoglobulin single variable domain, polypeptide or other binding agent and which to use as the second (competitor) immunoglobulin, antibody, immunoglobulin single variable domain, polypeptide or other binding agent, the cross-blocking assay may to be run in two formats: 1) format 1 is where Ab-X is the immunoglobulin, antibody, immunoglobulin single variable domain, polypeptide or other binding agent that is coated onto the ELISA plate and Ab-Y is the competitor immunoglobulin, antibody, immunoglobulin single variable domain, polypeptide or other binding agent that is in solution and 2) format 2 is where Ab-Y is the immunoglobulin, antibody, immunoglobulin single variable domain, polypeptide or other binding agent that is coated onto the ELISA plate and Ab-X is the competitor immunoglobulin, antibody, immunoglobulin single variable domain, polypeptide or other binding agent that is in solution. Ab-X and Ab-Y are defined as cross-blocking if, either in format 1 or in format 2, the solution phase anti-target immunoglobulin, antibody, immunoglobulin single variable domain, polypeptide or other binding agent is able to cause a reduction of between 60% and 100%, specifically between 70% and 100%, and more specifically between 80% and 100%, of the target detection signal (i.e., the amount of target bound by the coated immunoglobulin, antibody, immunoglobulin single variable domain, polypeptide or other binding agent) as compared to the target detection signal obtained in the absence of the solution phase anti-target immunoglobulin, antibody, immunoglobulin single variable domain, polypeptide or other binding agent (i.e., the positive control wells).

Other methods for determining whether an immunoglobulin, antibody, immunoglobulin single variable domain, polypeptide or other binding agent directed against a target cross-blocks, is capable of cross-blocking, competitively binds or is cross-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 5.4).

"Epitope binning" refers to the use of competitive binding assays or cross-blocking assays to identify pairs of immunoglobulins, antibodies, immunoglobulin single variable domains, polypeptides, or other binding agents that are, or are not, capable of binding the target (e.g., PcrV) simultaneously thereby identifying immunoglobulins, antibodies, immunoglobulin single variable domains, polypeptides or other binding agents that bind to the same, or overlapping epitopes on the target.

An "epitope bin" as used in the present specification therefore is a family of immunoglobulins, antibodies, immunoglobulin single variable domains, polypeptides, or other binding agents having the same or overlapping binding specificity. As described above, the sorting of the immunoglobulins, antibodies, immunoglobulin single variable domains, polypeptides, or other binding agents into epitope bins is based on cross-competition (cross-blocking) of the immunoglobulins, antibodies, immunoglobulin single variable domains, polypeptides, or other binding agents for antigen binding. The cross-competition (cross-blocking) assay analyzes the simultaneous binding (pairing) of the immunoglobulins, antibodies, immunoglobulin single variable domains, polypeptides or other binding agents to the antigen and groups together immunoglobulins, antibodies, immunoglobulin single variable domains, polypeptides, or other binding agents with similar pairing profiles. Immunoglobulins, antibodies, immunoglobulin single variable domains, polypeptides or other binding agents with similar profiles (i.e. belonging to the same epitope bin) may bind to the same, closely related and/or overlapping epitopes.

An amino acid sequence is said to be "cross-reactive" for two different antigens or antigenic determinants (such as e.g., serum albumin from two different species of mammal, such as e.g., human serum albumin and cyno serum albumin, such as e.g., PcrV from different strains of $P.$ $aeruginosa$) if it is specific for (as defined herein) both these different antigens or antigenic determinants.

The term "PcrV" as used herein refers to the needle protein PcrV present in the Type III Secretion System (TTSS) of $Pseudomonas$ $aeruginosa$ ($P.$ $aeruginosa$).

The term "potency" of a polypeptide of the invention, as used herein, is a function of the amount of polypeptide of the invention required for its specific effect to occur. It is measured simply as the inverse of the $IC_{50}$ for that polypeptide. It refers to the capacity of said polypeptide of the invention to neutralize $P.$ $aeruginosa$; such as to modulate, inhibit and/or prevent infectivity of $P.$ $aeruginosa$, to modulate, inhibit and/or prevent colonization of the host by $P.$ $aeruginosa$, to modulate, inhibit and/or prevent TTSS virulence mechanisms of $P.$ $aeruginosa$, to modulate, inhibit and/or prevent injection by $P.$ $aeruginosa$ into the host cell of various exotoxins, to modulate, inhibit and/or prevent pore-mediated increases in host cell membrane permeability induced by $P.$ $aeruginosa$, to modulate, inhibit and/or prevent activation of broad cellular defence responses induced by $P.$ $aeruginosa$ and/or to modulate, inhibit and/or prevent triggering of tissue-damaging inflammation induced by $P.$ $aeruginosa$. The potency may be measured by any suitable assay known in the art or described herein, such as e.g., an in vitro cytotoxicity assay (e.g., as described by Frank et al., The Journal of infectious diseases 186: 64-73, 2002; Vance et al. Infection and Immunity 73: 1706-1713, 2005; El Solh et al. Am. J. Respir. Crit. Care Med. 178: 513-519, 2008; and/or the cytoxicity assays as described in the Example section) and/or in vivo assays (e.g., the acute mouse model described by Secher et al., Journal of Antimicrobial Chemotherapy 66: 1100-1109, 2011).

In contrast, the "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the standard handbooks, such as Kenneth et al (Chemical Stability of Pharmaceuticals: A Handbook for Pharmacists, John Wiley & Sons Inc, 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t½-beta, either with or without an increase in the t½-alpha and/or the AUC or both.

Unless indicated otherwise, the term "immunoglobulin"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_H$H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in Figure 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, in at least one of the framework residues) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e., against the same or another epitope on PcrV and/or against one or more other antigens, proteins or targets than PcrV).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprises three immunoglobulin single variable domains, optionally linked via two linker sequences; etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., PcrV) and at least one binding unit is directed against a second antigen (i.e., different from PcrV) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., PcrV) and at least one further immunoglobulin single variable domain directed against a second antigen (i.e., different from PcrV), whereas a "trispecific" polypeptide of the invention is a polypeptide that comprises at least one immunoglobulin single variable domain directed against a first antigen (i.e., PcrV), at least one further immunoglobulin single variable domain directed against a second antigen (i.e., different from PcrV) and at least one further immunoglobulin single variable domain directed against a third antigen (i.e., different from both PcrV and the second antigen); etc.

"Multiparatopic polypeptides", such as e.g., "biparatopic polypeptides" or "triparatopic polypeptides", comprise or essentially consist of two or more binding units that each have a different paratope (as will be further described herein; see chapter on multivalent polypeptides of the invention).

Monovalent Polypeptides of the Invention

The present invention provides stretches of amino acid residues (SEQ ID NOs: 20-37, SEQ ID NOs: 38-56 and SEQ ID NOs: 57-75; Table A-6) that are particularly suited for binding to PcrV. These stretches of amino acid residues may be present in, and/or may be incorporated into, a polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against PcrV. These stretches of amino acid residues are also referred to herein as "CDR sequence(s) of the invention" (i.e., as "CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in a polypeptide of the invention, as long as these stretches of amino acid residues allow the polypeptide of the invention to bind to PcrV with a certain affinity and potency (as defined herein). Thus, generally, the invention in its broadest sense provides monovalent polypeptides (also referred to herein as "monovalent polypeptide(s) of the invention") that are capable of binding to PcrV with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to PcrV. It should however also be noted that the presence of only one such CDR sequence in a monovalent polypeptide of the invention may by itself already be sufficient to provide the monovalent polypeptide of the invention the capacity of binding to PcrV; reference is for example again made to the so-called "Expedite fragments" described in WO 03/050531.

Thus, in a specific, but non-limiting aspect, the monovalent polypeptide of the invention may comprise at least one stretch of amino acid residues that is chosen from the group consisting of:

CDR1 sequences:
a) SEQ ID NOs: 20-37;
b) stretches of amino acid sequences that have at least 80% amino acid identity with at least one of the amino acid sequences of SEQ ID NOs: 20-37;
c) stretches of amino acid sequences that have 3, 2, or 1 amino acid difference with at least one of the amino acid sequences of SEQ ID NOs: 20-37;

and/or

CDR2 sequences:
d) SEQ ID NOs: 38-56;
e) stretches of amino acid sequences that have at least 80% amino acid identity with at least one of the amino acid sequences of SEQ ID NOs: 38-56;
f) stretches of amino acid sequences that have 3, 2, or 1 amino acid difference with at least one of the amino acid sequences of SEQ ID NOs: 38-56;

and/or

CDR3 sequences:
g) SEQ ID NOs: 57-75;
h) stretches of amino acid sequences that have at least 80% amino acid identity with at least one of the amino acid sequences of SEQ ID NOs: 57-75;
i) stretches of amino acid sequences that have 3, 2, or 1 amino acid difference with at least one of the amino acid sequences of SEQ ID NOs: 57-75.

Monovalent polypeptides comprising one or more of the above specified stretches of amino acid residues show improved properties such as e.g., improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for PcrV and/or improved efficacy and/or potency for neutralizing PcrV.

More in particular, the monovalent polypeptides of the invention comprising one or more of the above specified stretches of amino acid residues can bind to protein PcrV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to PcrV with a dissociation constant ($K_D$) of 1000 nM to 1 nM or less, preferably 100 nM to 1 nM or less, more preferably 15 nM to 1 nM or even 10 nM to 1 nM or less;

and/or such that they:

bind to PcrV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;

and/or such that they:

bind to PcrV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Some preferred $IC_{50}$ values for binding of the monovalent polypeptides of the invention to PcrV will become clear from the further description and examples herein.

Assays to determine the $IC_{50}$ include binding in ELISA or, more preferably, cytotoxicity assays such as the TTSS-dependent cytotoxicity assay described by Frank et al. (The Journal of infectious diseases 186: 64-73, 2002), Vance et al. (Infection and Immunity 73: 1706-1713, 2005), El Solh et al. (Am. J. Respir. Crit. Care Med. 178: 513-519, 2008), modifications of these assays such as e.g. described in Example 4.4, or a cytotoxicity assay with human lung epithelial cells (A549 cells) as described in Example 7.2, and modifications thereof.

For example, in a TTSS-dependent cytotoxicity assay with P3X63 cells as the target at an average MOI of 2.8, the monovalent polypeptides of the invention may have $IC_{50}$ values between 1 nM and 10000 nM, between 5 nM and 1000 nM, preferably between 5 nM and 500 nM, more preferably between 5 nM and 200 nM, such as between 5 nM and 50 nM or less.

In such a TTSS-dependent cytotoxicity assay, the monovalent polypeptides of the invention may have an efficacy (% inhibition; see Example 4.4) of 50% or more, preferably 90% or more, such as 100%.

In particular, a monovalent polypeptide of the invention may be a monovalent polypeptide that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the monovalent polypeptide of the invention comprises more than one, such as two or more stretches of amino acid residues chosen from the group consisting of the CDR1 sequences of the invention, the CDR2 sequences of the invention and/or the CDR3 sequences of the invention. Preferably, the monovalent polypeptide of the invention comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the monovalent polypeptides of the invention are listed in Table A-6.

It should be noted that the invention is not limited as to the origin of the monovalent polypeptide of the invention (or of the nucleic acid of the invention used to express it), nor as to the way that the monovalent polypeptide or nucleic acid of the invention is (or has been) generated or obtained. Thus, the monovalent polypeptides of the invention may be naturally occurring monovalent polypeptides (from any suitable species) or synthetic or semi-synthetic monovalent polypeptides.

Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In said monovalent polypeptides of the invention, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's.

According to a preferred, but non-limiting embodiment, the monovalent polypeptides of the invention comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. In such a monovalent polypeptide of the invention, the framework sequences may be any suitable framework sequences, and examples of suitable framework sequences will be clear to the skilled person, for example on the basis the standard handbooks and the further disclosure and prior art mentioned herein.

Accordingly, the present invention also relates to a monovalent polypeptide against PcrV which essentially consists of 4 framework regions (FR1 to FR4, respectively) and 3 complementarity determining regions (CDR1 to CDR3, respectively), in which:

CDR1 is chosen from the group consisting of:

a) the amino acid sequences of SEQ ID NOs: 20-37;

b) amino acid sequences that have at least 80% amino acid identity with at least one of the amino acid sequences of SEQ ID NOs: 20-37;

c) amino acid sequences that have 3, 2, or 1 amino acid difference with at least one of the amino acid sequences of SEQ ID NOs: 20-37;

and/or

CDR2 is chosen from the group consisting of:

d) the amino acid sequences of SEQ ID NOs: 38-56;

e) amino acid sequences that have at least 80% amino acid identity with at least one of the amino acid sequences of SEQ ID NOs: 38-56;

f) amino acid sequences that have 3, 2, or 1 amino acid difference with at least one of the amino acid sequences of SEQ ID NOs: 38-56;

and/or

CDR3 is chosen from the group consisting of:

g) the amino acid sequences of SEQ ID NOs: 57-75;

h) amino acid sequences that have at least 80% amino acid identity with at least one of the amino acid sequences of SEQ ID NOs: 57-75;

i) amino acid sequences that have 3, 2, or 1 amino acid difference with at least one of the amino acid sequences of SEQ ID NOs: 57-75.

In particular, according to this preferred but non-limiting aspect, the invention relates to a monovalent polypeptide against PcrV, which consists of 4 framework regions (FR1 to FR4 respectively) and 3 complementarity determining regions (CDR1 to CDR3 respectively), in which:

CDR1 is chosen from the group consisting of:

a) the amino acid sequences of SEQ ID NOs: 20-37;

b) amino acid sequences that have at least 80% amino acid identity with at least one of the amino acid sequences of SEQ ID NOs: 20-37;

c) amino acid sequences that have 3, 2, or 1 amino acid difference with at least one of the amino acid sequences of SEQ ID NOs: 20-37;

and

CDR2 is chosen from the group consisting of:

d) the amino acid sequences of SEQ ID NOs: 38-56;

e) amino acid sequences that have at least 80% amino acid identity with at least one of the amino acid sequences of SEQ ID NOs: 38-56;

f) amino acid sequences that have 3, 2, or 1 amino acid difference with at least one of the amino acid sequences of SEQ ID NOs: 38-56;

and

CDR3 is chosen from the group consisting of:

g) the amino acid sequences of SEQ ID NOs: 57-75;

h) amino acid sequences that have at least 80% amino acid identity with at least one of the amino acid sequences of SEQ ID NOs: 57-75;

i) amino acid sequences that have 3, 2, or 1 amino acid difference with at least one of the amino acid sequences of SEQ ID NOs: 57-75.

The invention also relates to a monovalent polypeptide in which the CDR sequences have at least 70% amino acid identity, preferably at least 80% amino acid identity, more preferably at least 90% amino acid identity, such as 95% amino acid identity or more or even (essentially) 100% amino acid identity with the CDR sequences of at least one of the amino acid sequences of SEQ ID NOs: 1-19.

In one specific, but non-limiting aspect, the monovalent polypeptide of the invention may be a monovalent polypeptide that comprises an immunoglobulin fold or a monovalent polypeptide that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding PcrV.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the monovalent polypeptide of the invention is an immunoglobulin single variable domain such as a Domain antibody (or an amino acid sequence that is suitable for use as a domain antibody); is a single domain antibody (or an amino acid that is suitable for use as a single domain antibody); is a "dAb" (or an amino acid that is suitable for use as a dAb); or is a Nanobody® (including but not limited to $V_{HH}$). Again, suitable framework sequences will be clear to the skilled person, for example on the basis the standard handbooks and the further disclosure and prior art mentioned herein.

In particular, the framework sequences present in the monovalent polypeptides of the invention may contain one or more of Hallmark residues (as defined in WO 08/020079 (Tables A-3 to A-8)), such that the monovalent polypeptide of the invention is a Nanobody. Some preferred, but non-limiting examples of (suitable combinations of) such framework sequences will become clear from the further disclosure herein (see e.g., Table A-6). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3).

More in particular, a Nanobody can be an immunoglobulin single variable domain and/or polypeptide with the (general) structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and which:
  i) have at least 80% amino acid identity with at least one of the amino acid sequences of SEQ ID NOs: 1-19 (see Table A-4), in which for the purposes of determining the degree of amino acid identity, the amino acid residues that form the CDR sequences are disregarded. In this respect, reference is also made to Table A-6, which lists the framework 1 sequences (SEQ ID NOs: 76-80), framework 2 sequences (SEQ ID NOs: 81-93), framework 3 sequences (SEQ ID NOs: 94-112) and framework 4 sequences (SEQ ID NOs: 113-117) of the immunoglobulin single variable domains of SEQ ID NOs: 1-19 (see Table A-4); or
  ii) combinations of framework sequences as depicted in Table A-6;
  and in which:
  iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

In a preferred aspect, the present invention provides an immunoglobulin single variable domain or monovalent polypeptide that is selected from any of SEQ ID NOs: 1-19.

The present invention also provides monovalent polypeptides that belong to the same epitope bin as any one of the immunoglobulin single variable domains with SEQ ID NOs: 1-19. Accordingly, the present invention also relates to monovalent polypeptides directed against PcrV, that cross-blocks the binding to PcrV of at least one of the immunoglobulin single variable domains with SEQ ID NOs: 1-19 and/or that are cross-blocked from binding to PcrV by at least one of the immunoglobulin single variable domains with SEQ ID NOs: 1-19.

Again, such monovalent polypeptides may be an immunoglobulin single variable domain derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin single variable domain comprises a $V_{HH}$ sequence, said immunoglobulin single variable domain may be suitably humanized, as further described herein, so as to provide one or more further (partially or fully) humanized immunoglobulin single variable domains of the invention. Similarly, when an immunoglobulin single variable domain comprises a synthetic or semi-synthetic sequence (such as a partially humanized sequence), said immunoglobulin single variable domain may optionally be further suitably humanized, again as described herein, again so as to provide one or more further (partially or fully) humanized immunoglobulin single variable domains of the invention.

These monovalent polypeptides of the invention, and in particular the immunoglobulin single variable domains comprising the CDR sequences of the invention are particularly suited for use as building block or binding unit for the preparation of multivalent polypeptides.

Accordingly, the monovalent polypeptides of the invention that bind PcrV can be in essentially isolated form (as defined herein), or they may form part of a protein or polypeptide, which may comprise or essentially consist of one or more monovalent polypeptides that bind PcrV and which may optionally further comprise one or more further amino acid sequences (all optionally linked via one or more suitable linkers). The present invention also relates to a protein or polypeptide that comprises or essentially consists of one or more monovalent polypeptides of the invention (or suitable fragments thereof).

The one or more monovalent polypeptides of the invention are thus used as a binding unit or building block in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of one monovalent polypeptide of the invention. The present invention thus also relates to a polypeptide which is a multivalent polypeptide, such as e.g., a bivalent or trivalent polypeptide comprising or essentially consisting of two or more monovalent polypeptides of the invention (for multivalent and multispecific polypeptides containing one or more VHH domains and their preparation, reference is also made to Conrath et al., J. Biol. Chem. 276: 7346-7350, 2001, as well as to for example WO 96/34103, WO 99/23221 and WO 2010/115998).

Immunoglobulins Belonging to Preferred Epitope Bins

The present inventors furthermore found that immunoglobulins belonging to certain epitope bins are particularly suited for binding to PcrV, neutralization of *P. aeruginosa* and/or as a binding unit for the preparation of the multiparatopic, such as e.g., biparatopic or triparatopic, polypeptides of the invention. Preferred immunoglobulins include immunoglobulins (such as heavy chain antibodies, conventional 4-chain antibodies (such as IgG, IgM, IgA, IgD or IgE molecules), Fab fragments, F(ab')2 fragments, Fv fragments such as disulphide linked Fv or scFv fragments, or diabodies derived from such conventional 4-chain antibody, the individual chains thereof, as well as all parts, domains or fragments thereof (including but not limited to antigen-binding domains or fragments such as immunoglobulin single variable domains), monovalent polypeptides of the invention, or other binding agents) that belong to epitope bins 1, 2 or 3 (as further defined).

Accordingly, in a first aspect, the present invention relates to an immunoglobulin that belongs to epitope bin 1. Epitope bin 1 encompasses a family of immunoglobulins (including monovalent polypeptides of the invention) that have the same or overlapping binding specificity, based on cross-competition (cross-blocking) of the immunoglobulins. More particularly, immunoglobulins belonging to epitope bin 1 cross-block the binding to PcrV of at least one of the immunoglobulin single variable domains with SEQ ID NOs: 3-10 and/or are cross-blocked from binding to PcrV by at least one of the immunoglobulin single variable domains with SEQ ID NOs: 3-10.

The immunoglobulins belonging to epitope bin 1 are expected to bind to the same, closely related and/or overlapping epitopes. More particularly, the immunoglobulins belonging to epitope bin 1 bind full length PcrV (SEQ ID NO: 159) while showing reduced (30-90% as compared to full length PcrV) or no (lower than 30% as compared to full length PcrV) binding to chimera 4 (SEQ ID NO: 202) and chimera 6 (SEQ ID NO: 204).

Preferred immunoglobulins belonging to epitope bin 1 include monovalent polypeptides of the invention (as defined above) in which:

CDR1 is chosen from the group consisting of:
a) the amino acid sequences of SEQ ID NOs: 22-28;
b) amino acid sequences that have at least 80% amino acid identity with at least one of the amino acid sequences of SEQ ID NOs: 22-28;
c) amino acid sequences that have 3, 2, or 1 amino acid difference with at least one of the amino acid sequences of SEQ ID NOs: 22-28;
and/or
CDR2 is chosen from the group consisting of:
d) the amino acid sequences of SEQ ID NOs: 40-47;
e) amino acid sequences that have at least 80% amino acid identity with at least one of the amino acid sequences of SEQ ID NOs: 40-47;
f) amino acid sequences that have 3, 2, or 1 amino acid difference with at least one of the amino acid sequences of SEQ ID NOs: 40-47;
and/or
CDR3 is chosen from the group consisting of:
g) the amino acid sequences of SEQ ID NOs: 59-66;
h) amino acid sequences that have at least 80% amino acid identity with at least one of the amino acid sequences of SEQ ID NOs: 59-66;
i) amino acid sequences that have 3, 2, or 1 amino acid difference with at least one of the amino acid sequences of SEQ ID NOs: 59-66.

More particularly, monovalent polypeptides in which:
CDR1 is chosen from the group consisting of:
a) the amino acid sequences of SEQ ID NOs: 22-28;
b) amino acid sequences that have at least 80% amino acid identity with at least one of the amino acid sequences of SEQ ID NOs: 22-28;
c) amino acid sequences that have 3, 2, or 1 amino acid difference with at least one of the amino acid sequences of SEQ ID NOs: 22-28;
and
CDR2 is chosen from the group consisting of:
d) the amino acid sequences of SEQ ID NOs: 40-47;
e) amino acid sequences that have at least 80% amino acid identity with at least one of the amino acid sequences of SEQ ID NOs: 40-47;
f) amino acid sequences that have 3, 2, or 1 amino acid difference with at least one of the amino acid sequences of SEQ ID NOs: 40-47;
and
CDR3 is chosen from the group consisting of:
g) the amino acid sequences of SEQ ID NOs: 59-66;
h) amino acid sequences that have at least 80% amino acid identity with at least one of the amino acid sequences of SEQ ID NOs: 59-66;
i) amino acid sequences that have 3, 2, or 1 amino acid difference with at least one of the amino acid sequences of SEQ ID NOs: 59-66.

More particularly, the present invention relates to monovalent polypeptides of the invention that belong to epitope bin 1, in which the CDR sequences of said monovalent polypeptides have at least 70% amino acid identity, preferably at least 80% amino acid identity, more preferably at least 90% amino acid identity, such as 95% amino acid identity or more, or even (essentially) 100% amino acid identity with the CDR sequences of at least one of the immunoglobulin single variable domains with SEQ ID NOs: 3-10.

Preferred monovalent polypeptides of the invention belonging to epitope bin 1 are selected from any of SEQ ID NOs: 3-10.

In another aspect, the present invention relates to an immunoglobulin that belongs to epitope bin 2. Epitope bin 2 encompasses a family of immunoglobulins that have the same or overlapping binding specificity, based on cross-competition (cross-blocking) of the immunoglobulins. More particularly, immunoglobulins belonging to epitope bin 2 cross-block the binding to PcrV of at least one of the immunoglobulin single variable domains with SEQ ID NOs: 1 and 2 and/or are cross-blocked from binding to PcrV by at least one of the immunoglobulin single variable domains with SEQ ID NOs: 1 and 2.

The immunoglobulins belonging to epitope bin 2 are expected to bind to the same, closely related and/or overlapping epitopes. More particularly, the immunoglobulins belonging to epitope bin 2 bind to full length PcrV (SEQ ID NO: 159), while they show reduced (30-90% as compared to full length PcrV) or no (below 30% as compared to full length PcrV) binding to chimera 7 (SEQ ID NO: 205).

Preferred immunoglobulins belonging to epitope bin 2 include monovalent polypeptides of the invention (as defined above) in which:

CDR1 is chosen from the group consisting of:
a) the amino acid sequences of SEQ ID NOs: 20-21;
b) amino acid sequences that have at least 80% amino acid identity with at least one of the amino acid sequences of SEQ ID NOs: 20-21;
c) amino acid sequences that have 3, 2, or 1 amino acid difference with at least one of the amino acid sequences of SEQ ID NOs: 20-21;
and/or
CDR2 is chosen from the group consisting of:
d) the amino acid sequences of SEQ ID NOs: 38-39;
e) amino acid sequences that have at least 80% amino acid identity with at least one of the amino acid sequences of SEQ ID NOs: 38-39;
f) amino acid sequences that have 3, 2, or 1 amino acid difference with at least one of the amino acid sequences of SEQ ID NOs: 38-39;
and/or
CDR3 is chosen from the group consisting of:
g) the amino acid sequences of SEQ ID NOs: 57-58;
h) amino acid sequences that have at least 80% amino acid identity with at least one of the amino acid sequences of SEQ ID NOs: 57-58;
i) amino acid sequences that have 3, 2, or 1 amino acid difference with at least one of the amino acid sequences of SEQ ID NOs: 57-58.

More particularly, monovalent polypeptides in which:
CDR1 is chosen from the group consisting of:
a) the amino acid sequences of SEQ ID NOs: 20-21;
b) amino acid sequences that have at least 80% amino acid identity with at least one of the amino acid sequences of SEQ ID NOs: 20-21;
c) amino acid sequences that have 3, 2, or 1 amino acid difference with at least one of the amino acid sequences of SEQ ID NOs: 20-21;
and
CDR2 is chosen from the group consisting of:
d) the amino acid sequences of SEQ ID NOs: 38-39;
e) amino acid sequences that have at least 80% amino acid identity with at least one of the amino acid sequences of SEQ ID NOs: 38-39;
f) amino acid sequences that have 3, 2, or 1 amino acid difference with at least one of the amino acid sequences of SEQ ID NOs: 38-39;
and
CDR3 is chosen from the group consisting of:
g) the amino acid sequences of SEQ ID NOs: 57-58;
h) amino acid sequences that have at least 80% amino acid identity with at least one of the amino acid sequences of SEQ ID NOs: 57-58;
i) amino acid sequences that have 3, 2, or 1 amino acid difference with at least one of the amino acid sequences of SEQ ID NOs: 57-58.

More particularly, the present invention relates to monovalent polypeptides of the invention that belong to epitope bin 2, in which the CDR sequences of said monovalent polypeptide have at least 70% amino acid identity, preferably at least 80% amino acid identity, more preferably at least 90% amino acid identity, such as 95% amino acid identity or more or even (essentially) 100% amino acid identity with the CDR sequences of at least one of the immunoglobulin single variable domains with SEQ ID NOs: 1 and 2.

Preferred monovalent polypeptides of the invention belonging to epitope bin 2 are selected from any of SEQ ID NOs: 1 and 2.

In another aspect, the present invention relates to an immunoglobulin that belongs to epitope bin 3. Epitope bin 3 encompasses a family of immunoglobulins that have the same or overlapping binding specificity, based on cross-competition (cross-blocking) of the immunoglobulins. More particularly, immunoglobulins belonging to epitope bin 3 cross-block the binding to PcrV of at least one of the immunoglobulin single variable domain with SEQ ID NOs: 11 and 12 and/or are cross-blocked from binding to PcrV by at least one of the immunoglobulin single variable domains with SEQ ID NOs: 11 and 12.

The immunoglobulins belonging to epitope bin 3 are expected to bind to the same, closely related and/or overlapping epitopes. More particularly, the immunoglobulins belonging to epitope bin 3 bind to full length PcrV (SEQ ID NO: 159), while they show reduced (30-90% as compared to full length PcrV) or no (below 30% as compared to full length PcrV) binding to chimera 2 (SEQ ID NO: 200).

Preferred immunoglobulins belonging to epitope bin 3 include monovalent polypeptides of the invention (as defined above) in which:
CDR1 is chosen from the group consisting of:
a) the amino acid sequences of SEQ ID NOs: 29-30;
b) amino acid sequences that have at least 80% amino acid identity with at least one of the amino acid sequences of SEQ ID NOs: 29-30;
c) amino acid sequences that have 3, 2, or 1 amino acid difference with at least one of the amino acid sequences of SEQ ID NOs: 29-30;
and/or
CDR2 is chosen from the group consisting of:
d) the amino acid sequences of SEQ ID NOs: 48-49;
e) amino acid sequences that have at least 80% amino acid identity with at least one of the amino acid sequences of SEQ ID NOs: 48-49;
f) amino acid sequences that have 3, 2, or 1 amino acid difference with at least one of the amino acid sequences of SEQ ID NOs: 48-49;
and/or
CDR3 is chosen from the group consisting of:
g) the amino acid sequences of SEQ ID NOs: 67-68;
h) amino acid sequences that have at least 80% amino acid identity with at least one of the amino acid sequences of SEQ ID NOs: 67-68;
i) amino acid sequences that have 3, 2, or 1 amino acid difference with at least one of the amino acid sequences of SEQ ID NOs: 67-68.

More particularly, monovalent polypeptides in which:
CDR1 is chosen from the group consisting of:
a) the amino acid sequences of SEQ ID NOs: 29-30;
b) amino acid sequences that have at least 80% amino acid identity with at least one of the amino acid sequences of SEQ ID NOs: 29-30;
c) amino acid sequences that have 3, 2, or 1 amino acid difference with at least one of the amino acid sequences of SEQ ID NOs: 29-30;
and
CDR2 is chosen from the group consisting of:
d) the amino acid sequences of SEQ ID NOs: 48-49;
e) amino acid sequences that have at least 80% amino acid identity with at least one of the amino acid sequences of SEQ ID NOs: 48-49;

f) amino acid sequences that have 3, 2, or 1 amino acid difference with at least one of the amino acid sequences of SEQ ID NOs: 48-49;
and
CDR3 is chosen from the group consisting of:
g) the amino acid sequences of SEQ ID NOs: 67-68;
h) amino acid sequences that have at least 80% amino acid identity with at least one of the amino acid sequences of SEQ ID NOs: 67-68;
i) amino acid sequences that have 3, 2, or 1 amino acid difference with at least one of the amino acid sequences of SEQ ID NOs: 67-68.

More particularly, the present invention relates to monovalent polypeptides of the invention that belong to epitope bin 3, in which the CDR sequences of said monovalent polypeptide have at least 70% amino acid identity, preferably at least 80% amino acid identity, more preferably at least 90% amino acid identity, such as 95% amino acid identity or more, or even (essentially) 100% amino acid identity with the CDR sequences of at least one of the immunoglobulin single variable domains with SEQ ID NOs: 11 and 12.

Preferred monovalent polypeptides of the invention belonging to epitope bin 3 are selected from SEQ ID NOs: 11 and 12.

Multivalent Polypeptides of the Invention

The invention further relates to a multivalent polypeptide (also referred to herein as a "multivalent polypeptide(s) of the invention") that comprises or (essentially) consists of two or more immunoglobulin single variable domains (or suitable fragments thereof) directed against PcrV. The multivalent polypeptide of the invention preferably is a multiparatopic polypeptide (also referred to herein as "multiparatopic polypeptide(s) of the invention"), such as e.g., (a) "biparatopic polypeptide(s) of the invention" or "triparatopic polypeptide(s) of the invention". The term "multiparatopic" (antigen-)binding molecule or "multiparatopic" polypeptide as used herein shall mean a polypeptide comprising at least two (i.e. two or more) immunoglobulin single variable domains, wherein a "first" immunoglobulin single variable domain is directed against PcrV and a "second" immunoglobulin single variable domain is directed against PcrV, and wherein these "first" and "second" immunoglobulin single variable domains have a different paratope. Accordingly, the multiparatopic polypeptide comprises or consists of two or more immunoglobulin single variable domains that are directed against PcrV, wherein at least one "first" immunoglobulin single variable domain is directed against a first epitope on PcrV and at least one "second" immunoglobulin single variable domain is directed against a second epitope on PcrV different from the first epitope on PcrV.

In a preferred aspect, the polypeptide of the invention is a biparatopic polypeptide. The term "biparatopic" (antigen-)binding molecule or "biparatopic" polypeptide as used herein shall mean a polypeptide comprising a "first" immunoglobulin single variable domain directed against PcrV and a "second" immunoglobulin single variable domain directed against PcrV, wherein these "first" and "second" immunoglobulin single variable domains have a different paratope. Accordingly, the biparatopic polypeptide comprises or consists of two or more immunoglobulin single variable domains that are directed against PcrV, a "first" immunoglobulin single variable domain is directed against a first epitope on PcrV and a "second" immunoglobulin single variable domain is directed against a second epitope on PcrV different from the first epitope on PcrV.

The biparatopic polypeptides of the invention show improved properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for PcrV and/or improved efficacy and/or potency for neutralizing PcrV.

More in particular, the biparatopic polypeptides of the invention can bind to PcrV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to PcrV with a dissociation constant ($K_D$) of 1000 nM to 1 nM or less, preferably 100 nM to 1 nM or less, more preferably 15 nM to 1 nM or even 10 nM to 1 nM or less;

and/or such that they:

bind to PcrV with a ken-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;

and/or such that they:

bind to PcrV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower;

Some preferred $IC_{50}$ values for binding of the biparatopic polypeptides of the invention to PcrV will become clear from the further description and examples herein.

Assays to determine the $IC_{50}$ include binding in ELISA or more preferably cytotoxicity assays such as the TTSS-dependent cytotoxicity assay described by Frank et al. (The Journal of infectious diseases 186: 64-73, 2002), Vance et al. (Infection and Immunity 73: 1706-1713, 2005), El Solh et al. (Am. J. Respir. Crit. Care Med. 178: 513-519, 2008), modifications of this assay such as e.g. described in Example 4.4, or a cytotoxicity assay with human lung epithelial cells (A549 cells) as described in Example 7.2, and modifications thereof.

For example, in a TTSS-dependent cytotoxicity assay with P3X63 cells as the target at an MOI of 12, the biparatopic polypeptides of the invention may have $IC_{50}$ values between 0.01 nM and 50 nM, between 0.01 nM and 10 nM, preferably between 0.01 nM and 5 nM, more preferably between 0.01 nM and 1 nM, such as between 0.01 nM and 0.1 nM or less.

Apart from this and/or in addition, in such a TTSS-dependent cytotoxicity assay, the biparatopic polypeptides of the invention have an efficacy (% inhibition; see Example 4.4) of 100%.

Moreover, the biparatopic polypeptides of the invention were shown to be stable and maintained functionality in the presence of elastases.

After 24 hours in the presence of P. aeruginosa elastase, the biparatopic polypeptides of the invention may have a decrease in potency of maximal 10 fold, preferably maximal 5 fold, such as 3 fold, 2 fold, 1 fold or lower. After 24 hours in the presence of human neutrophil Elastase, the biparatopic polypeptides of the invention may have a decrease in potency of maximal 100 fold, preferably maximal 30 fold, such as 15 fold, 10 fold, 5 fold, 3 fold, 2 fold or lower.

In another preferred aspect, the polypeptide of the invention is a triparatopic polypeptide. The term "triparatopic" (antigen-)binding molecule or "triparatopic" polypeptide as used herein shall mean a polypeptide comprising a "first"

immunoglobulin single variable domain directed against PcrV, a "second" immunoglobulin single variable domain directed against PcrV and a "third" immunoglobulin single variable domain directed against PcrV, wherein these "first", "second" and "third" immunoglobulin single variable domains have a different paratope. Accordingly, the tri-paratopic polypeptide comprises or consists of three or more immunoglobulin single variable domains that are directed against PcrV, wherein a "first" immunoglobulin single variable domain is directed against a first epitope on PcrV, a "second" immunoglobulin single variable domain is directed against a second epitope on PcrV different from the first epitope on PcrV, and a "third" immunoglobulin single variable domain is directed against a third epitope on PcrV different from the first and second epitope on PcrV.

The two or more immunoglobulin single variable domains present in the multiparatopic polypeptide of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a Domain antibody), of a single domain antibody (or an amino acid that is suitable for use as a single domain antibody), of a "dAb" (or an amino acid that is suitable for use as a dAb) or of a Nanobody (including but not limited to a $V_{HH}$). The two or more immunoglobulin single variable domains may consist of a partially or fully humanized Nanobody or a partially or fully humanized VHH. In a preferred aspect of the invention, the immunoglobulin single variable domains encompassed in the multiparatopic polypeptide of the invention are one or more monovalent polypeptides of the invention, as defined herein.

In a preferred aspect of the invention, the first immunoglobulin single variable domain and the second immunoglobulin single variable domain present in the multiparatopic (preferably biparatopic or triparatopic) polypeptide of the invention do not (cross)-compete with each other for binding to PcrV and, as such, belong to different epitope bins. Accordingly, the present invention relates to a multiparatopic (preferably biparatopic or triparatopic) polypeptide comprising two or more immunoglobulin single variable domains wherein each immunoglobulin single variable domain belongs to a different epitope bin. Accordingly, the first immunoglobulin single variable domain of this preferred multiparatopic (preferably biparatopic or triparatopic) polypeptide of the invention does not cross-block the binding to PcrV of the second immunoglobulin single variable domain of this preferred multiparatopic (preferably biparatopic or triparatopic) polypeptide of the invention and/or the first immunoglobulin single variable is not cross-blocked from binding to PcrV by the second immunoglobulin single variable domain.

Different epitope bins (1 to 3) have been identified amongst the monovalent polypeptides of the invention (see Tables B-4 and B-10). Accordingly, the present invention relates to a multiparatopic polypeptide comprising two or more immunoglobulin single variable domains wherein each immunoglobulin single variable domain belongs to a different epitope bin as defined herein. In a preferred aspect, following combination of two or more immunoglobulin single variable domains are envisaged in the multiparatopic (preferably biparatopic or triparatopic) polypeptide of the invention:

| "first" immunoglobulin single variable domain belongs to: | "second" immunoglobulin single variable domain belongs to: |
|---|---|
| Epitope bin 1 | Epitope bin 2 |
| Epitope bin 1 | Epitope bin 3 |
| Epitope bin 2 | Epitope bin 1 |
| Epitope bin 2 | Epitope bin 3 |
| Epitope bin 3 | Epitope bin 1 |
| Epitope bin 3 | Epitope bin 2 |

Preferred immunoglobulin single variable domains for use in these multiparatopic, (preferably biparatopic or triparatopic) polypeptides of the invention are the monovalent polypeptides of the invention (as described above), belonging to the respective epitope bins. In another preferred aspect, the multiparatopic polypeptide of the invention is selected from any of SEQ ID NOs: 124-141.

Preferred combination of immunoglobulin single variable domains for use in the multiparatopic (preferably biparatopic or triparatopic) polypeptides of the invention are:
    immunoglobulin single variable domains belonging to epitope bins 1 and 2;
    immunoglobulin single variable domains belonging to epitope bins 3 and 1;
    immunoglobulin single variable domains belonging to epitope bins 3 and 2.

Preferred immunoglobulin single variable domains for use in these multiparatopic (preferably biparatopic or triparatopic) polypeptides of the invention are the monovalent polypeptides of the invention (as described above) belonging to the respective epitope bins. In a preferred aspect the first immunoglobulin single variable domain belongs to epitope bin 3, and is preferably SEQ ID NO: 12. In another preferred aspect the second immunoglobulin single variable domain belongs to epitope bin 2, and is preferably SEQ ID NO: 1. In yet another preferred aspect, the multiparatopic polypeptide of the invention is selected from any of SEQ ID NOs: 129, 134 and 137.

In another aspect, the first immunoglobulin single variable domain and the second immunoglobulin single variable domain present in the multiparatopic (preferably biparatopic or triparatopic) polypeptides of the invention belong to the same epitope bin. Accordingly, the present invention relates to a multiparatopic (preferably biparatopic or triparatopic) polypeptide comprising two or more immunoglobulin single variable domains wherein both immunoglobulin single variable domains belong to the same epitope bin. While these immunoglobulin single variable domains have different paratopes, these immunoglobulin single variable domains bind to closely related and/or overlapping epitopes and, as such, (cross)-compete with each other for binding to PcrV. Accordingly, the first immunoglobulin single variable domain of these multiparatopic (preferably biparatopic or triparatopic) polypeptides of the invention cross-blocks the binding to PcrV of the second immunoglobulin single variable domain of these multiparatopic (preferably biparatopic or triparatopic) polypeptides of the invention and/or the first immunoglobulin single variable is cross-blocked from binding to PcrV by the second immunoglobulin single variable domain.

In a preferred aspect the immunoglobulin single variable domains present in such multiparatopic (preferably biparatopic or triparatopic) polypeptides of the invention belong to an epitope bin (1 to 3) as defined herein (see Tables B-4 and B-10). Accordingly, the present invention relates to a multiparatopic polypeptide comprising two or more immunoglobulin single variable domains wherein both immunoglobulin single variable domains belong to the same epitope bin as defined herein.

Preferred immunoglobulin single variable domains for use in these multiparatopic (preferably biparatopic or triparatopic) polypeptides of the invention are the monovalent polypeptides of the invention (as described earlier) belonging to the respective epitope bins. In another preferred aspect, the multiparatopic polypeptide of the invention is selected from any of SEQ ID NOs: 118-123.

Preferred combination for use in the multiparatopic (preferably biparatopic or triparatopic) polypeptides of the invention are:
two immunoglobulin single variable domains belonging to epitope bin 1;
two immunoglobulin single variable domains belonging to epitope bin 2.

Preferred immunoglobulin single variable domains for use in these multiparatopic (preferably biparatopic or triparatopic) polypeptides of the invention are the monovalent polypeptides of the invention (as described earlier) belonging to the respective epitope bins. In a preferred aspect, two immunoglobulin single variable domain present in the multiparatopic polypeptide of the invention belong to epitope bin 1, and one of the two or more immunoglobulin single variable domains is preferably SEQ ID NO: 3. Preferred multiparatopic polypeptides of the invention include SEQ ID NOs: 118, 120 and 121. In another preferred aspect, two immunoglobulin single variable domain present in the multiparatopic polypeptide of the invention belong to epitope bin 2, and one of the two or more immunoglobulin single variable domains is preferably SEQ ID NO: 1. Preferred multiparatopic polypeptides of the invention include SEQ ID NOs: 122 and 123.

Polypeptides of the Invention

The monovalent polypeptide of the invention and the multivalent (multiparatopic) polypeptide of the invention, may or may not further comprise one or more other groups, residues, moieties or binding units (these monovalent polypeptides as well as multivalent (multiparatopic) polypeptides (with or without additional groups, residues, moieties or binding units) are all referred to as "polypeptide(s) of the invention"). If present, such further groups, residues, moieties or binding units may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are immunoglobulin single variable domains chosen from the group consisting of Domain antibodies, amino acids that are suitable for use as a domain antibody, single domain antibodies, amino acids that are suitable for use as a single domain antibody, "dAb"'s, amino acids that are suitable for use as a dAb, or Nanobodies (such as e.g. VHH, humanized VHH).

As described above, additional binding units, such as immunoglobulin single variable domains having different antigen specificity can be linked to form multispecific polypeptides. By combining immunoglobulin single variable domains of two or more specificities, bispecific, trispecific etc. constructs can be formed. For example, a polypeptide according to the invention may comprise one, two or more immunoglobulin single variable domains directed against PcrV and one immunoglobulin single variable domain against another target. Such constructs and modifications thereof, which the skilled person can readily envisage, are all encompassed by the term "polypeptide of the invention" as used herein.

In the polypeptides described above, the one, two or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In one specific aspect of the invention, a polypeptide is prepared that has an increased half-life, compared to the corresponding polypeptide of the invention. Examples of polypeptides of the invention that comprise such half-life extending moieties for example include, without limitation, polypeptides in which the immunoglobulin single variable domains are suitable linked to one or more serum proteins or fragments thereof (such as (human) serum albumin or suitable fragments thereof) or to one or more binding units that can bind to serum proteins (such as, for example, Domain antibodies, amino acids that are suitable for use as a domain antibody, single domain antibodies, amino acids that are suitable for use as a single domain antibody, "dAb"'s, amino acids that are suitable for use as a dAb, or Nanobodies) that can bind to serum proteins (such as serum albumin (such as human serum albumin)), serum immunoglobulins (such as IgG), transferrin or one of the other serum proteins listed in WO 04/003019; polypeptides in which the immunoglobulin single variable domain is linked to an Fc portion (such as a human Fc) or a suitable part or fragment thereof; or polypeptides in which the one or more immunoglobulin single variable domains are suitable linked to one or more small proteins or peptides that can bind to serum proteins (such as, without limitation, the proteins and peptides described in WO 91/01743, WO 01/45746 or WO 02/076489). Reference is also made to the dAb's described in WO 03/002609 and WO 04/003019 and to Harmsen et al. (Vaccine 23: 4926-42, 2005); to EP 0368684, as well as to WO 08/028977, WO 08/043821, WO 08/043822 by Ablynx N.V. and WO 08/068280.

According to a specific, but non-limiting aspect of the invention, the polypeptides of the invention may contain, besides the two or more immunoglobulin single variable domains and/or monovalent polypeptides of the invention against PcrV, at least one Nanobody against human serum albumin. These Nanobodies against human serum albumin may be as generally described in the applications by Ablynx N.V. cited above (see for example WO 04/062551). Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred, as well as the Nanobodies disclosed in WO 2012/175400 (SEQ ID NOs: 1-11 of WO 2012/175400).

The polypeptide of the invention may, for example, be a trivalent, bispecific polypeptide, comprising two immunoglobulin single variable domains, preferably monovalent polypeptides of the invention against PcrV and a third immunoglobulin single variable domain directed against (human) serum albumin, in which said first, second and third immunoglobulin single variable domain may optionally be linked via one or more, and in particular two, linker sequences.

According to one specific aspect, one or more polypeptides of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068628. Coupling of a polypeptide of the invention to an Fc portion may also lead to an increased half-life, compared to the corresponding polypeptide of the invention. For some applications, the use of an Fc portion and/or of constant domains (i.e., $C_H2$ and/or $C_H3$ domains) that confer increased half-life without any biologically significant effector function may also be suitable or even preferred. Other suitable constructs comprising one or more polypeptides of the invention and one or more constant domains with increased half-life in vivo will be clear to the skilled person, and may for example comprise polypeptides linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, the polypeptides of the invention may be linked (optionally via a suitable linker or hinge region) to naturally occurring, synthetic or semi-synthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al. (J. Biol. Chem. 271: 7494, 1996), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

Generally, the polypeptides of the invention with increased half-life preferably have a half-life that is increased with more than 1 hours, preferably more than 2 hours, more preferably more than 6 hours, such as more than 12 hours, or even more than 24, 48 or 72 hours, compared to the half-life of the corresponding immunoglobulin single variable domain or polypeptide of the invention per se.

In another preferred, but non-limiting aspect, such polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.
b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;
c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 206);
d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

The multivalent (such as biparatopic or triparatopic) polypeptides of the invention can generally be prepared by a method which comprises at least the step of suitably linking the immunoglobulin single variable domain and/or monovalent polypeptide of the invention to one or more further immunoglobulin single variable domains and/or monovalent polypeptides of the invention, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multiparatopic polypeptides of the invention may comprise at least the steps of linking two or more immunoglobulin single variable domains and/or monovalent polypeptides of the invention and for example one or more linkers together in a suitable manner. The immunoglobulin single variable domains and/or monovalent polypeptides of the invention (and linkers) can be coupled by any method known in the art and as further described herein. Preferred techniques include the linking of the nucleic acid sequences that encode the immunoglobulin single variable domains and/or monovalent polypeptides of the invention (and linkers) to prepare a genetic construct that expresses the multiparatopic polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an immunoglobulin single variable domain and/or monovalent polypeptide of the invention in preparing a multivalent, preferably multiparatopic polypeptide of the invention. The method for the preparation of a multivalent polypeptide will comprise the linking of an immunoglobulin single variable domain and/or monovalent polypeptide of the invention to at least one further immunoglobulin single variable domain and/or monovalent polypeptide of the invention, optionally via one or more linkers. The immunoglobulin single variable domain and/or monovalent polypeptide of the invention is then used as a binding domain or binding unit in providing and/or preparing the multivalent, preferably multiparatopic polypeptide comprising two (e.g., in a bivalent polypeptide), three (e.g., in a trivalent polypeptide) or more (e.g., in a multivalent polypeptide) binding units. In this respect, the immunoglobulin singe variable domain and/or the monovalent polypeptide of the invention may be used as a binding domain or binding unit in providing and/or preparing a multivalent (preferably multiparatopic), such as bivalent (preferably biparatopic) or trivalent (preferably triparatopic) polypeptide of the invention comprising two, three or more binding units.

Accordingly, the present invention also relates to the use of an immunoglobulin single variable domain and/or particularly, a monovalent polypeptide of the invention (as described herein) in preparing a multivalent, preferably multiparatopic polypeptide. The method for the preparation of the multivalent, preferably multiparatopic polypeptide will comprise the linking of the immunoglobulin single variable domain and/or monovalent polypeptide of the invention to at least one further immunoglobulin single variable domain and/or monovalent polypeptide of the invention, optionally via one or more linkers.

Suitable spacers or linkers for use in multivalent, preferably multiparatopic polypeptides of the invention will be clear to the skilled person, and may generally be any linker or spacer used in the art to link amino acid sequences. Preferably, said linker or spacer is suitable for use in constructing polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, hinge-like regions such as the hinge regions of naturally occurring heavy chain antibodies or similar sequences (such as described in WO 94/04678).

Some other particularly preferred linkers are mentioned in Table A-8, of which GS40 (SEQ ID NO: 193) is particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for PcrV, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g., as described herein for the derivatives of the polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three of more amino acid sequences or Nanobodies, it is possible to link them by use of a linker with three or more "arms", which each "arm" being linked to an amino acid sequence or Nanobody, so as to provide a "star-shaped" construct. It is also possible, although usually less preferred, to use circular constructs.

Also encompassed in the present invention are fused immunoglobulin sequences, comprising tags or other functional moieties, e.g., toxins, labels, radiochemicals, etc.

Alternatively, the additional groups, residues, moieties or binding units may for example be chemical groups, residues, moieties, which may or may not by themselves be biologically and/or pharmacologically active. For example, and without limitation, such groups may be linked to the two or more immunoglobulin single variable domains or monovalent polypeptides so as to provide a "derivative" of the polypeptide of the invention.

Accordingly, the invention in its broadest sense also comprises derivatives of the polypeptides of the invention. Such derivatives can generally be obtained by modification, and in particular by chemical and/or biological (e.g., enzymatical) modification, of the polypeptides of the invention and/or of one or more of the amino acid residues that form polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g., by covalent linking or in any other suitable manner) of one or more functional groups, residues or moieties into or onto the polypeptide of the invention, and in particular of one or more functional groups, residues or moieties that confer one or more desired properties or functionalities to the polypeptide of the invention. Example of such functional groups will be clear to the skilled person.

For example, such modification may comprise the introduction (e.g., by covalent binding or in any other suitable manner) of one or more functional groups that that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, 16th ed., Mack Publishing Co., Easton, Pa., 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, iso-thiocyanate, rhodamine, phycoerythrin, phycocyanin, allo-phycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{62}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example are the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the derivatives are such that they bind to PcrV, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention). Such derivatives will usually also have a PcrV neutralization efficacy and/or potency as defined herein.

Such polypeptides of the invention and derivatives thereof may also be in essentially isolated form (as defined herein).

The invention further relates to methods for preparing the polypeptides, nucleic acids, host cells, and compositions described herein.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:

the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:

isolating and/or purifying the polypeptide of the invention thus obtained.

In particular, such a method may comprise the steps of:

cultivating and/or maintaining a host of the invention under conditions that are such that said host of the invention expresses and/or produces at least one polypeptide of the invention;

optionally followed by:

isolating and/or purifying the polypeptide of the invention thus obtained.

Accordingly, the present invention also relates to a nucleic acid or nucleotide sequence that encodes a polypeptide of the invention (also referred to as "nucleic acid of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding an immunoglobulin single variable domain or a monovalent polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g., a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e., under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g., in a specific part or organelle of a cell and/or in (a) specific cell(s), tissue(s), organ(s) or part(s) of a multicellular organism. Such reporter genes may also be expressed as a protein fusion with the amino acid sequence or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1085089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtillis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojoae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
- an amphibian cell or cell line, such as *Xenopus* oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein.

The polypeptides of the invention may also be expressed as so-called "intrabodies", as for example described in WO 94/02610, WO 95/22618 and U.S. Pat. No. 7,004,940; WO 03/014960; in Cattaneo and Biocca ("Intracellular Antibodies: Development and Applications" Landes and Springer-Verlag, 1997); and in Kontermann (Methods 34: 163-170, 2004).

The polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing polypeptide therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the kind, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting embodiment of the invention, the polypeptide of the invention is glycosylated. According to another non-limiting embodiment of the invention, the polypeptide of the invention is non-glycosylated.

According to one preferred, but non-limiting embodiment of the invention, the polypeptide of the invention is produced in a bacterial cell, in particular a bacterial cell suitable for large scale pharmaceutical production, such as cells of the strains mentioned above.

According to another preferred, but non-limiting embodiment of the invention, the polypeptide of the invention is produced in a yeast cell, in particular a yeast cell suitable for large scale pharmaceutical production, such as cells of the species mentioned above.

According to yet another preferred, but non-limiting embodiment of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the polypeptides of the invention, the polypeptides of the invention can be produced either intracellularly (e.g., in the cytosol, in the periplasma or in inclusion bodies) and then isolated from the host cells and optionally further purified; or can be produced extracellularly (e.g., in the medium in which the host cells are cultured) and then isolated from the culture medium and optionally further purified. When eukaryotic host cells are used, extracellular production is usually preferred since this considerably facilitates the further isolation and downstream processing of the polypeptides obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a polypeptide of the invention, can be used.

Thus, according to one non-limiting embodiment of the invention, the polypeptide of the invention is a polypeptide that has been produced intracellularly and that has been isolated from the host cell, and in particular from a bacterial cell or from an inclusion body in a bacterial cell. According to another non-limiting embodiment of the invention, the polypeptide of the invention is a polypeptide that has been produced extracellularly, and that has been isolated from the medium in which the host cell is cultivated.

Some preferred, but non-limiting promoters for use with these host cells include:

for expression in *E. coli*: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in *Pichia pastoris*: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1a (hEF-1a) promoter from human, chimpanzee, mouse or rat; the SV40 early promoter; HIV-1 long terminal repeat promoter; 3-actin promoter;

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and *Pichia* expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:

for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Suc), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide of the invention, e.g., using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g., when the nucleotide sequences of the invention are under the control of an inducible promoter); all of which may be selected by the skilled person. Again, under such conditions, the polypeptides of the invention may be expressed in a constitutive manner, in a transient manner, or only when suitably induced.

It will also be clear to the skilled person that the polypeptide of the invention may (first) be generated in an immature form (as mentioned above), which may then be subjected to post-translational modification, depending on the host cell/host organism used. Also, the polypeptide of the invention may be glycosylated, again depending on the host cell/host organism used.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

Compositions of the Invention

The invention further relates to a product or composition containing or comprising at least one polypeptide of the invention, and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one polypeptide of the invention and at least one suitable carrier, diluent or excipient (i.e., suitable for pharmaceutical use), and optionally one or more further active substances. In a particular aspect, the invention relates to a pharmaceutical composition that contains a polypeptide of the invention selected from any of SEQ ID NOs: 118-141 and at least one suitable carrier, diluent or excipient (i.e. suitable for pharmaceutical use), and optionally one or more further active substances.

Generally, the polypeptides of the invention can be formulated and administered in any suitable manner known per se, for which reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18[1] Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

For example, the polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration).

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The polypeptides of the invention may be administered intravenously or intraperitoneally by infusion or injection. Solutions of the polypeptides of the invention can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptides of the invention in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

In a preferred aspect, the polypeptides of the invention and/or compositions comprising the same are administered to the pulmonary tissue. In the context of the present invention, "pulmonary tissue" is for the purposes of this invention equivalent with lung tissue or lung. The lung comprises 2 distinct zones: a conducting and a respiratory zone, within which the airway and vascular compartments lie (see e.g., "Pulmonary Drug Delivery", Edited by Karoline Bechtold-Peters and Henrik Luessen, ISBN 978-3-87193-322-6 pp. 16-28, 2007).

For pulmonary delivery, the polypeptides of the invention may be applied in pure form, i.e., when they are liquids or a dry powder. However, it will be preferred to administer them to the pulmonary tissue as composition or formulation comprising a polypeptide of the invention and a carrier suitable for pulmonary delivery. Accordingly, the present invention also relates to a pharmaceutical composition comprising the polypeptide of the invention and a carrier suitable for pulmonary delivery. Carriers suitable for pulmonary delivery are known in the art.

The polypeptides of the invention may also be administered as micro- or nanoparticles of pure drugs with particle sizes and distributions favorable for pulmonary delivery.

Accordingly, the present invention also relates to a pharmaceutical device suitable for the pulmonary delivery of the polypeptides of the invention and suitable in the use of a composition comprising the same. This device may be an inhaler for liquids (e.g., a suspension of fine solid particles or droplets) comprising the polypeptide of the invention. Preferably this device is an aerosol, nebulizer or metered dose inhaler comprising the polypeptide of the invention. The device may also be a dry powder inhaler comprising the polypeptide of the invention in the form of a dry powder.

In a preferred method, the administration to the pulmonary tissue is performed by inhaling the polypeptides of the invention and/or the composition comprising the same in an aerosol cloud. According to the invention, inhaling of the aerosol cloud can be performed by an inhaler device. The device should generate from a formulation comprising the polypeptides of the invention (and/or composition comprising the same) an aerosol cloud of the desired particle size (distribution) at the appropriate moment of the mammal's inhalation cycle, containing the right dose of the polypeptides of the invention ("Pulmonary drug delivery", Bechtold-Peters and Luessen, eds., ISBN 978-3-87193-322-6, page 125, 2007).

In the context of the present invention, "aerosol" denotes a suspension of fine solid particles or liquid droplets (or a combination thereof) in a gas wherein, for the purposes of this invention, the particles and/or droplets comprise the polypeptides of the invention.

The device should generate from the formulation an aerosol cloud of the desired particle size (distribution) at the appropriate moment of the mammal's inhalation cycle, containing the right dose of polypeptides of the invention.

Various inhalation systems are e.g. described on pages 129 to 148 in the review ("Pulmonary Drug Delivery", Bechtold-Peters and Luessen, eds., supra) and include, but are not limited to, nebulizers, metered dose inhalers, metered dose liquid inhalers, and dry powder inhalers. Devices taking into account optimized and individualized breathing pattern for controlled inhalation manoeuvres may also be used (see AKITA® technology on page 157 of "Pulmonary Drug Delivery", Bechtold-Peters and Luessen, eds., supra).

However, not only the device is important to pulmonary delivery of the polypeptides of the invention but also the right formulation is critical to achieve an effective delivery. This can be in principle achieved by using one of the following approaches:

- Administration of aqueous solutions or suspensions comprising the polypeptides of the invention (e.g., nasal drops) into the nasal cavities;
- Nebulisation of aqueous solutions or suspensions comprising the polypeptides of the invention;
- Atomization by means of liquefied propellants; and
- Dispersion of dry powders.

Hence formulations of the polypeptides of the invention have to be adopted and adjusted to the chosen inhalation device. Appropriate formulations, i.e. the excipients in addition to the polypeptides of the invention, are e.g., described in chapter IV of "Pulmonary Drug Delivery", Bechtold-Peters and Luessen, eds., supra. In this respect, reference is also made to WO 2010/081856.

The amount of the polypeptides of the invention required for use in treatment will vary not only with the particular polypeptide selected but also with the route of administration, the nature of the condition being treated and the age and condition of the patient and will be ultimately at the discretion of the attendant physician or clinician. Also the dosage of the polypeptides of the invention will vary.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

Uses of the Polypeptides of the Invention

The invention further relates to applications and uses of the polypeptides, nucleic acids, host cells, and compositions described herein, as well as to methods for the prevention and/or treatment *P. aeruginosa* infection. Some preferred but non-limiting applications and uses will become clear from the further description herein.

The polypeptides and compositions of the present invention can generally be used to neutralize *P. aeruginosa*; such as to modulate, inhibit and/or prevent infectivity of *P. aeruginosa*, to modulate, inhibit and/or prevent colonization of the host by *P. aeruginosa*, to modulate, inhibit and/or prevent TTSS virulence mechanisms of *P. aeruginosa*, to modulate, inhibit and/or prevent injection by *P. aeruginosa* into the host cell of various exotoxins, to modulate, inhibit and/or prevent pore-mediated increases in host cell membrane permeability induced by *P. aeruginosa*, to modulate, inhibit and/or prevent activation of broad cellular defence responses induced by *P. aeruginosa* and/or to modulate, inhibit and/or prevent triggering of tissue-damaging inflammation induced by *P. aeruginosa.*

In one aspect, the polypeptides, and compositions of the present invention can neutralize *P. aeruginosa* infectivity at least 1%, preferably at least 5%, such as at least 10% or at least 25%, preferably, at least 50%, at least 60%, at least 70%, at least 80%, or at least 90% or more, such as 100% compared to the *P. aeruginosa* infectivity under the same conditions but without the presence of the polypeptide of the invention, measured in any suitable manner known per se, for example using one of the assays described herein (such as the TTSS-dependent cytotoxicity assay as described in the Example section).

The invention also relates to a method for the prevention and/or treatment of infection with *P. aeruginosa*, said method comprising administering, to a subject in need thereof, a pharmaceutically active amount of a polypeptide of the invention, and/or of a pharmaceutical composition comprising the same.

As such, the polypeptides and compositions of the present invention can be used for the prevention and/or treatment of *P. aeruginosa* infection. Examples of patient groups susceptible to P. *aeruginosa* infection will be clear to the skilled person based on the disclosure herein, and for example include (without being limiting) the following patient groups: ventilator-associated pneumonia (VAP), burn victims, mechanical ventilated patients, Cystic Fibrosis (CF) patients, hematopoietic cell transplantation patients, bone marrow transplant patients, patients undergoing surgery, patients with chronic obstructive pulmonary disease (COPD), patients with bronchiectasis, patients with sepsis and patients with cancer-associated neutropenia.

Accordingly, the present invention also relates to a method for the prevention and/or treatment of *P. aeruginosa* infections in ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia, said method comprising administering, to a subject in need thereof, a pharmaceutically active amount of at least one polypeptide of the invention or a composition of the invention.

The invention also relates to the use of a polypeptide of the invention in the preparation of a pharmaceutical composition for prevention and/or treatment of *P. aeruginosa* infection including but not limited to *P. aeruginosa* infections in ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia; and/or for use in one or more of the methods described herein.

The invention also relates to a polypeptide of the invention, or a composition comprising the same for prevention and/or treatment of *P. aeruginosa* infection such as *P. aeruginosa* infections including (but not limited to) *P. aeruginosa* infections in ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia.

In the context of the present invention, the term "prevention and/or treatment" not only comprises preventing and/or treating the infection, but also generally comprises slowing or reversing the progress of the infection, reducing the severity and/or the duration of the infection and/or preventing a further increase in the severity of the infection, and generally any pharmacological action that is beneficial to the patient being treated.

In another aspect, the invention relates to a method for immunotherapy, and in particular for passive immunotherapy, which method comprises administering, to a subject suffering from or at risk of *P. aeruginosa* infection, a pharmaceutically active amount of a polypeptide of the invention, and/or of a pharmaceutical composition comprising the same.

The subject to be treated may be any warm-blooded animal, but is in particular a mammal, and more in particular a human being. As will be clear to the skilled person, the subject to be treated will in particular be a person suffering from, or at risk of *P. aeruginosa* infection, including but not limited to the patient groups susceptible to *P. aeruginosa* infection mentioned herein.

Thus, in general, the polypeptides according to the invention and/or the compositions comprising the same can be administered in any suitable manner. For example (but not limited thereto) the polypeptides according to the invention and compositions comprising the same can be administered intranasally, intratracheally, by inhalation and/or by any other suitable form of pulmonary delivery. Methods for pulmonary delivery, intranasal delivery, intratracheally and/or delivery by inhalation of a polypeptide of the invention will be known to the skilled person and are e.g. described in the handbook "Drug Delivery: Principles and Applications" (2005) by Binghe Wang, Teruna Siahaan and Richard Soltero (Eds. Wiley Interscience (John Wiley & Sons)); in "Pharmacology PreTest™ Self-Assessment and Review" (11$^{th}$ Edition) by Rosenfeld G. C., Loose-Mitchell D. S.; and in "Pharmacology" (3$^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing.

Accordingly, the present invention also relates to a method for administering an effective amount of a polypeptide of the invention and/or a composition comprising the same, wherein said method comprises the step of administering the polypeptide and/or composition comprising the same to the pulmonary tissue. In such method, the polypeptide and/or a composition comprising the same can be administered by any method known in the art for pulmonary delivery such as e.g., by use of an inhaler (aerosol, metered dose inhaler, nebulizer) or intranasal delivery device.

In a preferred aspect of the invention, the polypeptide will bind and/or neutralize *P. aeruginosa* present in the pulmonary tissue. Preferably in such method for pulmonary delivery at least 5%, preferably at least 10%, 20%, 30%, 40%, more preferably at least 50%, 60%, 70%, and even more preferably at least 80% or more of the polypeptide of the invention is stable in the pulmonary tissue for at least 12 hours, preferably at least 24 hours more preferably at least 48 hours.

Accordingly, the invention relates to a method for delivering a polypeptide of the invention to the pulmonary tissue of a subject without being inactivated, said method comprising the step of pulmonary administering said polypeptide of the invention to said subject.

The invention also relates to a method for the prevention and/or treatment of *P. aeruginosa* infection, said method comprising administering to the pulmonary tissue of a subject in need thereof, a pharmaceutically active amount of a polypeptide of the invention and/or of a pharmaceutical composition comprising the same.

More in particular, the invention relates to a method for the prevention and/or treatment of *P. aeruginosa* infections in ventilator-associated pneumonia (VAP), burn victims, mechanical ventilated patients, Cystic Fibrosis (CF) patients, hematopoietic cell transplantation patients, bone marrow transplant patients, surgery, chronic obstructive pulmonary disease (COPD), bronchiectasis, sepsis, cancer-associated neutropenia, said method comprising administering, to the pulmonary tissue of a subject in need thereof, a pharmaceutically active amount of a polypeptide of the invention and/or of a pharmaceutical composition comprising the same.

The polypeptides of the invention and/or the compositions comprising the same are administered according to a regime of treatment that is suitable for preventing and/or treating the *P. aeruginosa* infection. The clinician will generally be able to determine a suitable treatment regimen, depending on factors such as the patient group to be treated, the severity of the infection and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the *P. aeruginosa* infection and depending on the specific patient group to be treated, the potency of the polypeptide of the invention to be used, the specific route of administration and the specific pharmaceutical formulation or composition used, the polypeptides of the invention will generally be administered in an amount between 1 gram and 1 microgram per kg body weight per day, preferably between 0.1 gram and 10 microgram per kg body weight per day, most preferably between 0.01 gram and 100 microgram per kg body weight per day such as about 0.1, 0.5, 1, 2, 5 or 10 milligram per kg body weight per day, either continuously (e.g. by infusion), as a single daily dose or as multiple divided doses during the day. Polypeptides of the invention that contain a half-life extending moiety may be administered in an amount between 1 milligram and 100 milligram per kg body weight, preferably between 1 milligram and 50 milligram per kg body weight, such as about 10, 15, 20 or 30 milligram per kg body weight once or twice a month. The clinician will generally be able to determine a suitable daily dose, depending on the factors mentioned herein. It will also be clear that in specific cases, the clinician may choose to deviate from these amounts, for example on the basis of the factors cited above and his expert judgment.

When the polypeptide and/or a composition comprising the same is administered to the pulmonary tissue the treatment regime may be once or twice daily, preferably once daily, or once every 2, 3, 4, 5, 6, or 7 days.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of P. aeruginosa infection, as a result of which a synergistic effect may or may not be obtained. Examples of such compounds and principles, as well as routes, methods and pharmaceutical formulations or compositions for administering them will be clear to the clinician and include (without being limiting): Aminoglycosides (tobramycin, gentamicin, sisomycin, amikacin, netilmicin), Fluoroquinolones (sitafloxacin, ciprofloxacin, levofloxacin, ofloxacin), Polymyxins (polymyxin A, polymyxin B, polymyxin C, polymyxin D, polymyxin E (colistin; colimycin)), UDP-N-acetylglucosamine-3-enolpyruvyl-transferase (NAM; MurA) inhibitors (fosfomycin), Macrolides (azithromycin), Oxazolidinones (linezolid), Penicillins (methicillin; Carboxypenicillins: ticarcillin; Ureidopenicillins: piperacillin, azlocillin), Carbapenems (doripenem, biapenem, imipenem, meropenem, topopenem), Cephalosporins (ceftazidime, cefepime, aztreonam, ceftobiprole, CXA-101 (Calixa)), or other beta-lactamase inhibitors such as clavulanate, and beta-lactamase inhibitor combinations (combination of piperacillin and tazobactam, combination of ticarcillin and clavulanic acid, combination of imipenem and cilastatin); or any combination thereof.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Further uses of the polypeptides, nucleic acids, genetic constructs and hosts and host cells of the invention will be clear to the skilled person based on the disclosure herein. For example, and without limitation, the polypeptides of the invention can be linked to a suitable carrier or solid support so as to provide a medium than can be used in a manner known per se to purify PcrV protein from P. aeruginosa from compositions and preparations comprising the same. Derivatives of the polypeptides of the invention that comprise a suitable detectable label can also be used as markers to determine (qualitatively or quantitatively) the presence of PcrV protein of P. aeruginosa in a composition or preparation.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: Materials and Methods 1.1 Generation of Recombinant PcrV Protein (rPcrV)

The gene encoding full length PcrV protein of reference strain PAO1 (amino acid residues 1-294, see Table A-1) was cloned into an in house pUC119 derived expression vector. The vector contained the LacZ promoter, a resistance gene for kanamycin, a multicloning site and the pel B leader sequence. In frame with the rPvrV coding sequence, the vector coded for a C-terminal His$_6$ tag. Upon transformation in E. coli (TG-1), expression cultures were grown and expression was induced by addition of 1 mM IPTG and allowed to continue for 4 hours at 37° C. Cells were harvested by centrifugation and cell pellets were lysed by sonication. Cytosolic fractions were isolated by centrifugation. The recombinant protein was purified from the crude extracts via immobilized metal affinity chromatography (IMAC) on HisTrap FF crude 1 ml columns and buffer exchange into D-PBS (HiPrep 26/10 column), followed by ion exchange chromatography using a Source15Q (2 ml CV)

column and finally a gel filtration with a Superdex75 10/300 GL column (GE Healthcare Bio-Sciences AB, Uppsala, Sweden). The purity and homogeneity of the protein was confirmed by SDS-PAGE and analytical size exclusion.

1.2 Generation of GST-PcrV Protein

The PcrV coding sequence from strain PAO1 (amino acid residues 1-294, see Table A-1) was cloned into the expression vector pET42a(+) (EMBBiosciences, Darmstadt, Germany) to generate a GST-PcrV genetic fusion. The resulting vector was transformed into E. coli BL21 DE3 cells (Invitrogen). GST-rPcrV fusion protein was expressed and purified from E. coli (BL21 DE3) as follows. A 1 liter culture batch of E. coli expressing GST-PcrV was grown and induced for expression by addition of 1 mM IPTG. Following further growth for 3 hrs at 37° C., bacterial cells were pelleted by centrifugation and lysed via sonication. After the lysate was cleared by centrifugation, it was passed over a glutathione sepharose column (GSTrap FF) followed by a desalting step (HiPrep26/10 column) and an additional ion exchange chromatography step using a Source15Q column (GE Healthcare Bio-Sciences AB, Uppsala, Sweden). The purity (>90%) and homogeneity of the protein was confirmed by SDS-PAGE.

1.3 Generation of PcrV Sequence Variants

To determine whether anti-PcrV therapy is universally applicable to a variety of P. aeruginosa clinical isolates, Lynch (Microbial pathogenesis 48: 197-204, 2010) determined the genetic heterogeneity of PcrV by sequencing PcrV from 90 clinical isolates collected from 3 distinct geographical areas. This way, they identified 14 different PcrV variants (see Table A-1, PcrV variant 01-PcrV variant 15).

Using a similar approach, 207 clinical isolates—collected over geographically well spread locations (Prof. Vaneechoutte, UGent, Belgium)—were used to provide additional information about the genetic heterogeneity of PcrV. Eight novel PcrV sequence variants were identified this way (see Table A-1, PcrV variant 16-PcrV variant 23).

For the generation of all PcrV sequence variants, genes encoding the 23 different PcrV variants (amino acid residues 1-294, see Table A-1) were cloned together with the gene coding for the $His_6$ tag into the pET42a(+) vector (EMB-Biosciences, Darmstadt, Germany) to generate GST-PcrV-$His_6$ genetic fusions. GST-PcrV-$His_6$ fusion protein was expressed and purified from E. coli (BL21 DE3) transformed with pET42a(+)-PcrV-$His_6$ as follows. A 1 liter culture was grown and induced for expression by addition of 1 mM IPTG. Following further growth for 3 hrs at 37° C., bacterial cells were pelleted by centrifugation and lysed via sonication. After the lysate was cleared by centrifugation, it was passed over a GSTrap FF column (GE Healthcare Bio-Sciences AB, Uppsala, Sweden) and buffer exchanged to D-PBS, after which pure proteins (>90%) were obtained.

1.4 Generation of Anti-PcrV Fab Molecules

The gene segments encoding VL and VH from 3 Fab molecules, Fab 13.37 (WO 2009/073631; SEQ ID NOs: 13 and 37), Fab 26.24 (WO 2009/073631; SEQ ID NOs: 26 and 24) and Fab 35.36 (WO 2009/073631; SEQ ID NOs: 35 and 36) were cloned into an in-house human IgG1/K Fab expression vector. This vector contained the LacZ promoter, a resistance gene for kanamycine, two separate cloning sites preceded by a pelB (light chain) or a gene 3 (heavy chain) leader sequence. In frame with the heavy chain coding sequence, the expression vector encoded a C-terminal HA tag and a $His_6$ tag. The Fab fragments were expressed in E. coli and purified under native, non-reducing conditions via immobilized metal affinity chromatography (IMAC) on His-Trap FF crude 1 ml (GE healthcare, Buckinghamshire, United Kingdom) followed by affinity chromatography for the human Fabκ light chain (CaptureSelect LC-kappa (Hu), BAC) and size exclusion chromatography on a Superdex75 10/300 GL column (GE Healthcare GE healthcare, Buckinghamshire, United Kingdom) or desalting via Zeba spin columns (Pierce, Rockford, Ill., USA). Amino acid sequences of the variable heavy and variable light chain of the 3 Fabs are shown in Table A-2. The amino acid sequences of the constant heavy and light chain are shown in Table A-3.

Example 2: Immunization of Llamas with rPcrV Protein, Cloning of the Heavy Chain-Only Antibody Fragment Repertoires and Preparation of Phage 2.1 Immunizations After approval of the Ethical Committee of the faculty of Veterinary Medicine (University Ghent, Belgium), 4 llamas (designated No. 504, 505, 506 and 507) were immunized with 4 intramuscular injections (25 or 10 ug/dose at two weekly intervals) of rPcrV protein formulated in Stimune (Prionics, Lelystad, the Netherlands).

2.2 Cloning of Heavy Chain-Only Antibody Fragment Repertoires and Preparation of Phage Following the final immunogen injection, two 150-mL blood samples, collected 4 and 8 days after the last antigen injection were collected per animal. From the blood samples, peripheral blood mononuclear cells (PBMCs) were prepared using Ficoll-Hypaque according to the manufacturer's instructions (Amersham Biosciences, Piscataway, N.J., USA). From the PBMCs, total RNA was extracted and used as starting material for RT-PCR to amplify the VHH/Nanobody-encoding DNA segments. The PCR-amplified VHH repertoire was cloned via specific restriction sites into a vector designed to facilitate phage display of the VHH library. The vector was derived from pUC119 and contained the LacZ promoter, a M13 phage gIII protein coding sequence, a resistance gene for ampicillin or carbenicillin, a multiple cloning site and a hybrid gIII-pelB leader sequence. In frame with the VHH/Nanobody coding sequence, the vector encoded a C-terminal triple Flag tag and a $His_6$ tag. Phage were prepared according to standard protocols (see for example WO 04/041865, WO 04/041863, WO 04/062551, WO 05/044858 and other prior art and applications filed by Ablynx N.V. cited herein) and stored after filter sterilization at 4° C. for further use.

Example 3: Selection of PcrV Specific VHHs Via Phage Display

VHH repertoires obtained from all llamas and cloned in phage library were used in two selection strategies. In a first selection strategy, rPcrV protein (in house produced, see Example 1, section 1.1) was immobilized at a concentration of 15 ug/ml on a Nunc Maxisorp plate next to a negative control of 0 ug/ml antigen. Following incubation with the phage libraries and extensive washing, bound phages were eluted with trypsin (1 mg/mL). Eluted phages were amplified and applied in a second round of selection on 10 ug/ml rPcrV and 0 ug/ml (control).

In a second selection strategy, 50 nM and 5 nM of biotinylated rPcrV protein (bio-rPcrV; biotinylated according to the manufacturer instructions using Sulfo-NHS-LC-Biotin (Pierce, Rockford, Ill., USA)) were captured on a neutravidin coated (1 ug/ml) Nunc Maxisorp plate, next to a negative control of only neutravidin (1 ug/ml). Following incubation with the phage libraries and extensive washing, bound phages were eluted with trypsin (1 mg/mL). Eluted phages were used to infect *E. coli*. Infected *E. coli* cells were either used to prepare phage for the next selection round on 5 nM, 0.5 nM, 0.05 nM, 0.005 nM bio-rPcrV and a control (neutravidin 1 ug/ml) or plated on agar plates (LB+amp+ glucose2%) for analysis of individual VHH clones.

Outputs of all selection rounds were analyzed for enrichment factor (number of phages present in eluate relative to controls) and the best selection conditions were chosen for further analysis. In order to screen a selection output for specific binders, single colonies were picked from the agar plates and grown in 1 mL 96-deep-well plates. LacZ-controlled VHH expression was induced by addition of IPTG (1 mM final) in the absence of glucose. Periplasmic extracts (in a volume of ~80 uL) were prepared according to standard protocols (see for example WO 03/035694, WO 04/041865, WO 04/041863, WO 04/062551 and other prior art and applications filed by Ablynx N.V. cited herein).

Example 4: Screening of Periplasmic Extracts for Functional Blocking Nanobodies 4.1 Screening in ELISA In a first step, periplasmic extracts were tested for binding to bio-rPcrV by binding ELISA. In brief, 10 nM bio-rPcrV protein was captured on neutravidin (2 ug/ml) coated 96-well MaxiSorp plates (Nunc, Wiesbaden, Germany). Wells were blocked with a casein solution (1%). After addition of a 10-fold dilution of the periplasmic extracts, Nanobody binding was detected using a mouse anti-Flag-HRP conjugate (Sigma) and a subsequent enzymatic reaction in the presence of the substrate esTMB (3,3',5,5'-tetramentylbenzidine) (SDT, Brussels, Belgium). Clones showing ELISA signals of >2-fold above background were considered to encode positive PcrV binding Nanobodies.

4.2 Sequence Determination

The DNA sequence of the positive clones was determined. The amino acid sequences of the anti-PcrV Nanobodies are shown in Table A-4.

4.3 Off-Rate Determination

Off-rate analysis of all unique PcrV-binding Nanobodies was done by means of surface plasmon resonance on a ProteOn instrument (BioRad). To this end, recombinant PcrV protein was covalently bound to a GLC ProteOn Sensor chip via amine coupling on one ligand channel after which remaining reactive groups were inactivated. Periplasmic extracts prepared from *E. coli* cells expressing anti-PcrV Nanobodies were diluted 10-fold and injected at a flow rate of 45 uL/min during 2 minutes for binding to the immobilized rPcrV. Between sample injections, the surface was regenerated with ProteOn Phosphoric acid solution, 0.85%. Off-rates were determined by fitting a 1:1 interaction model (Langmuir model) onto the individual dissociation curves. Determined off-rates ranged from below detection limit of $3 \times 10^{-5}$ s$^{-1}$ to $4 \times 10^{-2}$ s$^{-1}$, with the vast majority of the clones having off-rates in the range of $1 \times 10^{-3}$-$1 \times 10^{-4}$ s$^{-1}$.

4.4 Analysis in TTSS-Dependent Cytotoxicity Assay

To identify Nanobodies able to prevent *Pseudomonas aeruginosa* TTSS-mediated infection, representative clones were tested in a TTSS-dependent cytotoxicity assay using P3-X63-Ag8 (P3X63) mouse myeloma cells (ECACC Cell line) as the target. Examples of *Pseudomonas aeruginosa* cytotoxicity assays are e.g. provided in Frank et al. (The Journal of infectious diseases 186: 64-73, 2002), Vance et al. (Infection and Immunity 73: 1706-1713, 2005), El Solh et al. (Am. J. Respir. Crit. Care Med. 178: 513-519, 2008). A total of $2 \times 10^5$ P3X63 cells/well were seeded in 96 well plates. Periplasmic extracts (diluted 1/4) containing PcrV binding Nanobodies were pre-incubated with *P. aeruginosa* strain PA103, which was grown under calcium-depleted conditions (LB medium+5 mM EGTA; Kim, Microbiology 151: 3575-3587, 2005) to induce expression of the TTSS. Following pre-incubation, the mixtures of periplasmic extracts and bacteria were added to the P3X63 cells and after an incubation step of 3 h at 37° C., P3X63 cells were stained with Propidium Iodide (Sigma-Aldrich, St Louis, Mo.) and fixated with 2% formaldehyde (Sigma-Aldrich, St Louis, Mo.). The ability to prevent *Pseudomonas aeruginosa* infection and mediated cell death was quantified by monitoring the uptake of the propidium iodide dye by dead cells using a FACS Array (Becton Dickinson, USA) and FCS Express software (Denovo, USA). Infections with strain PA103 were done at an average multiplicity of infection (MOI) of 8 bacteria to 1 myeloma cell (range 6:1-10:1). The data were analyzed using Prism5 software (Graphpad). Cytotoxicity was normalized to dead cells in untreated samples and normalized data were used to calculate the % inhibition according to the following formula:

$$100 \times \left[\frac{(y-x)}{(y-z)}\right]$$

Wherein:

y=average (% dead cells) of the PA103 treated wells, incubated with irrelevant control Nanobody z=average (% dead cells) of the untreated wells, incubated with irrelevant control Nanobody x=% of dead cells of evaluated data point A summary of the periplasmic extract screening data is given in Table B-1.

TABLE B-1

Screening of periplasmic extracts containing expressed anti-PcrV Nanobodies

| Nanobody | binding ELISA (OD 450 nm) | off-rate (s$^{-1}$) | cytotox assay (% inhibition) |
|---|---|---|---|
| 1E11 | 2.56 | $3.5 \times 10^{-04}$ | 33 |
| 2B02 | 2.40 | $3.7 \times 10^{-04}$ | 46 |
| 2B10 | 2.57 | $1.8 \times 10^{-04}$ | 38 |
| 2G09 | 2.37 | $1.0 \times 10^{-03}$ | 45 |
| 3B11 | 0.55 | $2.7 \times 10^{-03}$ | 26 |
| 3E10 | 2.51 | $1.5 \times 10^{-03}$ | 25 |
| 4C03 | 0.89 | $6.8 \times 10^{-03}$ | 22 |
| 4G10 | 2.60 | $1.3 \times 10^{-04}$ | 81 |
| 5E02 | 2.43 | $5.7 \times 10^{-04}$ | 71 |
| 5H01 | 2.69 | $4.9 \times 10^{-05}$ | 76 |
| 6B05 | 2.55 | $1.8 \times 10^{-04}$ | 32 |
| 7C10 | 2.55 | $8.2 \times 10^{-04}$ | 58 |
| 7E09 | 2.59 | $4.0 \times 10^{-04}$ | 16 |
| 10C05 | ND | $6.0 \times 10^{-04}$ | 25 |
| 11B09 | ND | $4.8 \times 10^{-03}$ | 37 |
| 12B02 | ND | $4.4 \times 10^{-05}$ | 14 |
| 13F07 | ND | $9.2 \times 10^{-04}$ | 13 |
| 14B10 | ND | $9.2 \times 10^{-04}$ | 20 |
| 14E10 | ND | $6.0 \times 10^{-04}$ | 22 |

Example 5: Characterization of Purified Monovalent Anti-PcrV Nanobodies

5.1 Preparation of Selected Nanobodies

Clones selected from the screening described in Example 4 were further characterized. Selected Nanobodies were subcloned into an in-house pUC119 derived expression vector. The vector contained the LacZ promoter, a resistance gene for kanamycin, a multicloning site and the pel B leader sequence. In frame with the Nanobody coding sequence, the vector coded for a C-terminal triple Flag and His$_6$ tag. Upon transformation in E. coli (TG-1), expression cultures were grown and expression was induced by addition of 1 mM IPTG and allowed to continue for 4 hours at 37° C. After spinning the cell cultures, periplasmic extracts were prepared by freeze-thawing the pellets followed by centrifugation. These extracts were then used as starting material for purification via IMAC on HisTrap FF crude 1 ml columns (GE healthcare, Buckinghamshire, United Kingdom) followed by desalting via Zeba spin columns (Pierce, Rockford, Ill., USA) resulting in 95% purity as assessed via SDS-PAGE.

5.2 Evaluation of PcrV Blocking Nanobodies in Cytotoxicity Assay

The ability of the Nanobodies to prevent *Pseudomonas aeruginosa* TTSS-induced cytotoxicity was tested in a cytotoxicity assay with P3X63 cells as the target. In brief, serial dilutions of purified Nanobodies were pre-incubated with *Pseudomonas aeruginosa* PA103 which was cultured under TTSS inducing conditions (LB medium+5 mM EGTA; Kim, Microbiology 151: 3575-3587, 2005). The mixtures were added to the P3X63 cells and cell mediated death was analysed as in example 4.4. Infections were done at an average MOI of 2.8 bacteria to 1 myeloma cell (range 4:1-1.5:1). Data are summarized in FIG. 1 and Table B-2.

TABLE B-2

Evaluation of monovalent anti-PcrV Nanobodies in P3X63 cytotoxicity assay

| Nanobody | MOI | IC50 (nM) | 95% CI on IC50 (nM) | % inhibition |
|---|---|---|---|---|
| 1E11 | 4 | 23 | 11-51 | 58 |
| 2B02 | 4 | 1732 | 577-5196 | 100 |
| 2B10 | 4 | 647 | 428-976 | 100 |
| 2G09 | 4 | 4 | 0.4-51 | 55 |
| 3B11 | 4 | 1145 | 640-2051 | 54 |
| 3E10 | 4 | 48 | 19-119 | 94 |
| 4C03 | 1.5 | 8890 | 5500-14300 | >20 |
| 4G10 | 4 | 105 | 39-284 | 100 |
| 5E02 | 4 | 38 | 16-91 | 100 |
| 5H01 | 4 | 7 | 4-14 | 100 |
| 6B05 | 3 | 435 | 162-1172 | 100 |
| 7C10 | 4 | 42 | 7-232 | 100 |
| 7E09 | 4 | No blocking observed in tested concentration range | | |
| 10C05 | 3 | >1000 | 0 | 100 |
| 11B09 | 3 | 100 | 29-336 | 100 |
| 12B02 | 4 | No blocking observed in tested concentration range | | |
| 13F07 | 1.5 | 35600 | 7100-178000 | >20 |
| 14B10 | 3 | >3000 | 0 | >70 |
| 14E10 | 3 | >3000 | 0 | 100 |
| Fab 13.37 | 4 | 8 | 4-15 | 100 |
|  | 1.5 | 1 | 0.7-1.5 | 100 |
|  | 3 | 1 | 0.4-1.5 | 100 |
| Fab 24.26 | 4 | 48 | 24-96 | 100 |
|  | 1.5 | 34 | 23-50 | 100 |

5.3 Affinity Determination

The kinetic binding parameters for a subset of Nanobodies was determined with Surface Plasmon Resonance (SPR) on a Biacore T100 instrument. To this end, recombinant GST-PcrV was immobilized onto a CM5 chip via amine coupling using EDC and NHS. Purified Nanobodies were injected for 2 minutes at different concentrations (between 1 and 1000 nM) and allowed to dissociate for 20 min at a flow rate of 45 ul/min. Between sample injections, the surfaces were regenerated with 10 mM glycine pH1.5 and 100 mM HCl. HBS-N(Hepes buffer pH7.4) was used as running buffer. The kinetic constants were computed from the sensorgrams using the BIAEvaluation software (1:1 interaction). The affinities of the 6 anti-PcrV Nanobodies ranged from 0.5-5 nM (Table B-3).

TABLE B-3

Affinity KD (nM) of purified Nanobodies for recombinant GST-PcrV

| Nanobody | ka (M$^{-1}$s$^{-1}$) | kd (s$^{-1}$) | KD (nM) |
|---|---|---|---|
| 2B10 | $5.10 \times 10^{+05}$ | $2.50 \times 10^{-04}$ | 0.5 |
| 3E10 | $2.70 \times 10^{+06}$ | $3.90 \times 10^{-03}$ | 1 |
| 4G10 | $1.40 \times 10^{+05}$ | $6.50 \times 10^{-04}$ | 5 |
| 5E02 | $1.80 \times 10^{+05}$ | $6.80 \times 10^{-04}$ | 4 |
| 5H01 | $1.60 \times 10^{+05}$ | $1.40 \times 10^{-04}$ | 1 |
| 7C10 | $1.20 \times 10^{+06}$ | $1.80 \times 10^{-03}$ | 2 |

5.4 Epitope Binning

To sort Nanobodies in different epitope bins, competitive binding ELISA assays were performed. In a first experiment, 1 ug/mL of GST-PcrV protein was coated in a 96-well MaxiSorp plate (Nunc, Wiesbaden, Germany). Dilution series (concentration range 100 nM-6.4 pM) of the purified Nanobodies in PBS buffer containing 0.1% casein and 0.05% Tween 20 (Sigma) were incubated in the presence of 1 nM Fab13.37 (SEQ ID NOs: 142 and 143). Residual binding of Fab13.37 (SEQ ID NO: 142 and 143) to GST-PcrV was detected using mouse anti-HA IgG (Zymed Laboratories, South San Francisco, Calif.) followed by horseradish peroxidase (HRP) conjugated rabbit anti-mouse IgG (Dako, Glostrup, Denmark) and a subsequent enzymatic reaction in the presence of the substrate esTMB (3,3',5,5'-tetramentylbenzidine) (SDT, Brussels, Belgium).

In the second experiment, 2 nM biotinylated rPcrV protein was captured on a 96-well MaxiSorp plate (Nunc, Wiesbaden, Germany) coated with 2 ug/ml neutravidin. A mixture of periplasmic extracts and Nanobody-phage particles from different Nanobodies (both prepared according to the standard protocol, see for example the prior art and applications filed by Ablynx N.V. cited herein) was incubated and residual binding of the phages to biotinylated rPcrV proteins was detected using an monoclonal anti-M13-HRP conjugate (GE healthcare, Buckinghamshire, United Kingdom) and a subsequent enzymatic reaction in the presence of the substrate esTMB (3,3',5,5'-tetramentylbenzidine) (SDT, Brussels, Belgium). Based on the results from these two approaches, Nanobodies were divided into different epitope bins (see Table B-4).

TABLE B-4

Epitope bins of anti-PcrV Nanobodies

| Nanobody | Nanobody epitope binning | Fab epitope binning | Epitope bin |
|---|---|---|---|
| 1E11 | bin 1 | non- competing | bin 1 |
| 2B02 | bin 1 | non- competing | bin 1 |
| 2B10 | bin 1 | non- competing | bin 1 |
| 2G09 | bin 1 | non- competing | bin 1 |
| 3B11 | ND | non- competing | ND/NC |

TABLE B-4-continued

Epitope bins of anti-PcrV Nanobodies

| Nanobody | Nanobody epitope binning | Fab epitope binning | Epitope bin |
|---|---|---|---|
| 3E10 | ND | competing | ND/C |
| 4C03 | ND | non- competing | ND/NC |
| 4G10 | ND | non- competing | ND/NC |
| 5E02 | ND | competing | ND/C |
| 5H01 | bin 2 | competing | bin 2 |
| 6B05 | bin 1 | non- competing | bin 1 |
| 7C10 | bin 2 | competing | bin 2 |
| 7E09 | bin 3 | non- competing | bin 3 |
| 10C05 | bin 1 | non- competing | bin 1 |
| 11B09 | bin 1 | non- competing | bin 1 |
| 12B02 | ND | non- competing | ND/NC |
| 13F07 | bin 3 | non- competing | bin 3 |
| 14B10 | ND | non- competing | ND/NC |
| 14E10 | bin 1 | non- competing | bin 1 |

ND = not determined
NC = non-competing

Example 6: Generation and Screening of Multivalent PcrV Blocking Nanobodies 6.1 Construction of a Bivalent/Biparatopic Anti-PcrV Nanobody Library A bivalent/biparatopic anti-PcrV Nanobody library was constructed as follows. The coding sequences of 18 monovalent anti-PcrV Nanobodies (Table A-4) were amplified by means of PCR in two separate reactions: N-terminal building block (5'-GAGGTGCAATTGGTG-GAGTCTGGG-3'; SEQ ID NO: 150 and 5'-ACCGCCTCCGGAGGAGACCGTGACCAGGGT-3'; SEQ ID NO: 151) and C-terminal building block (5'-TCTTGGATCCGAGGTGCAGCTGGTGGAGTCTGGG-3'; SEQ ID NO: 152 and 5'-TGAGGA-GACGGTGACCAGGGT-3'; SEQ ID NO: 153). For Nanobody 5H01 different primer sets were used for the N-terminal building block PCR (5'-GAGGTGCAAT-TGGTGGAGTCTGGG-3'; SEQ ID NO: 154 and 5'-ACTT-GAAGACCTCCGGAGGAGACCGTGACCAGGGT-3'; SEQ ID NO: 155) and C-terminal building block PCR (5'-ACTTGAAGACTGGATCCGAGGTGCAGTTGGTG-GAGTCTGGG-3'; SEQ ID NO: 156 and 5'-TGAGGA-GACGGTGACCAGGGT-3'; SEQ ID NO: 157). The N-terminal building block PCR pool of the 19 anti-PcrV Nanobodies was cloned in an expression vector upstream and in frame with the coding information of a flexible glycine-serine linker (40GS: GGGGSGGGGSGGGGS-GGGGSGGGGSGGGGSGGGGSGGGGS; SEQ ID NO: 193) whereas the C-terminal pool of the 19 anti-PcrV Nanobodies was cloned downstream and in frame of the 40GS5 linker coding sequence.

The expression vector was derived from pUC119, containing the LacZ promoter to drive transgene expression, a resistance gene for kanamycin, a multiple cloning site and the OmpA leader sequence. In frame and downstream of the multivalent Nanobody coding sequence, the vector coded for a C-terminal triple Flag tag and a $His_6$ tag. The resulting plasmid pool harbouring the bivalent/biparatopic anti-PcrV Nanobody library (with a theoretical diversity of 19×19=361) was transformed into E. coli TG1 cells and plated on agar plates (LB+Km+2% glucose). 864 single colonies (representing an expected completeness of >90% of the library) were picked from the agar plates. Periplasmic extracts were prepared as described above.

6.2 Screening of a Bivalent/Biparatopic Anti-PcrV Nanobody Library

The periplasmic extracts of the bivalent/biparatopic library were used in a screening campaign to select for the most potent functional blocking anti-PcrV Nanobodies. To this end, the periplasmic extracts (final dilution 1/150) were tested for their ability to prevent TTSS-induced P. aeruginosa infection in a cytotoxicity assay using P3X63 cells as target (as described in Example 4.4). The screening results (% inhibition) from the 48 most potent of 864 (13%) library clones are summarized in Table B-5. Table B-5 captures all 361 potential bivalent/biparatopic combinations as a function of their N-terminal and C-terminal building blocks, which are grouped by their relative epitope bins as determined in Example 5.4.

The corresponding sequences of the 48 most potent library clones were determined as shown in Table A-5. The sequence analysis revealed the following observations: within the 48 most potent constructs (i) no (0/48) monospecific bivalent Nanobodies (consisting of two identical Nanobody building blocks) were present (ii) the majority (42/48 clones) consisted of building blocks from two different epitope bins. After screening, 24 unique biparatopic Nanobodies (SEQ ID NO: 118-141) were selected for further characterization.

TABLE B-5

Screening results (% inhibition in P3X63 cytotoxicity assay) of 48 most potent bivalent anti-PcrV Nanobodies

| | | | C-terminal building block | | | | | | | | | |
|---|---|---|---|---|---|---|---|---|---|---|---|---|
| | | | bin 1 | | | | | | | | bin 2 | |
| | | | 1E11 | 2B02 | 2B10 | 2G09 | 6B05 | 10C05 | 11B09 | 14E10 | 5H01 | 7C10 |
| N-terminal building block | bin 1 | 1E11 | | 47 | 57 | | | | | | 52 | 49 |
| | | 2B02 | | | | | | | | | | |
| | | 2B10 | | | | | | | | | | |
| | | 2G09 | | | | | | | | | 66 | |
| | | 6B05 | 57 | | | | | | | | | |
| | | 10C05 | | | | | | | | | | |
| | | 11B09 | | | | | | | 66 | | | |
| | | 14E10 | | | | | | | | | | |
| | bin 2 | 5H01 | 46 | | 42 | | | | 85 | | | 68 |
| | | 7C10 | | | | | | | 61 | 43 | 63 | |
| | bin 3 | 7E09 | | | | | 45 | | | | | 48 |
| | | 13F07 | | 59 | 80 | | 46 | | | 69 | 65 | 74 |

TABLE B-5-continued

Screening results (% inhibition in P3X63 cytotoxicity assay) of 48 most potent bivalent anti-PcrV Nanobodies

| | | | | | | | |
|---|---|---|---|---|---|---|---|
| ND\|NC | 3B11 | | | | | | |
| | 4C03 | | | | | | |
| | 4G10 | | | | | | 81 |
| | 12B02 | | | | | | |
| | 14B10 | | | | | | |
| ND\|C | 3E10 | | 52 | | | | 85 |
| | 5E02 | 60 | | | | 48 | |

| | | | C-terminal building block ||||||||| |
|---|---|---|---|---|---|---|---|---|---|---|
| | | | bin 3 || ND\|NC ||||| ND\|C ||
| | | | 7E09 | 13F07 | 3B11 | 4C03 | 4G10 | 12B02 | 14B10 | 3E10 | 5E02 |
| N-terminal building block | bin 1 | 1E11 | | | | | 67 | 52 | | | 44 |
| | | 2B02 | | | | | | | | | |
| | | 2B10 | | | | | | | | | |
| | | 2G09 | | | | | | | | | 56 |
| | | 6B05 | | 41 | | | | | | 54 | |
| | | 10C05 | | | | | | | | | |
| | | 11B09 | | 82 | | | 52 | | | | 49 |
| | | 14E10 | | | | | | | | | 62 |
| | bin 2 | 5H01 | | | | | 47 | | | 57 | |
| | | 7C10 | | | | | | | | | 63 |
| | bin 3 | 7E09 | | | | | | | | | |
| | | 13F07 | | | | | 55 | 58 | 55 | | 69 |
| | ND\|NC | 3B11 | | | | | | | | | |
| | | 4C03 | | | | | | | | | |
| | | 4G10 | | 61 | | | | | | | |
| | | 12B02 | | | | | | | | | |
| | | 14B10 | | | | | | | | | |
| | ND\|C | 3E10 | | | | | 64 | | | | |
| | | 5E02 | 47 | 47 | | | | | | | |

Example 7: Characterization of Bivalent/Biparatopic Anti-PcrV Nanobodies

7.1 Preparation of Selected Nanobodies

Coding sequences from selected bivalent/biparatopic anti-PcrV Nanobodies were cloned into an in-house constructed plasmid allowing expression in *Pichia pastoris* and secretion into the cultivation medium. The expression vector was derived from pPICZa (Invitrogen) and contained the AOX1 promoter for tightly regulated, methanol induced expression, a resistance gene for Zeocin™, a multicloning site and the α-factor secretion signal. In frame with the Nanobody coding sequence, the vector coded for a C-terminal GlyAlaAla sequence followed by a triple Flag tag and a His6 tag. Upon transformation expression cultures were grown and Nanobody expression was induced by addition of methanol and allowed to continue for 48 hours at 30° C. The cleared supernatants were used as starting material for immobilized metal ion affinity chromatography (IMAC) using a HisTrap™ column (GE Healthcare). Nanobodies were eluted from the column using imidazole step gradient from 20 mM to 250 mM. In a next step, Nanobodies were buffer changed to D-PBS (Invitrogen) using HiPrep™ 26/10 desalting columns (GE Healthcare).

7.2 Evaluation of Bivalent/Biparatopic Anti-PcrV Nanobodies in Cytotoxicity Assay The bivalent/biparatopic anti-PcrV Nanobodies were tested for their ability to prevent TTSS induced *P. aeruginosa* infection in the cytotox assay with P3X63 cells as target at an MOI of 12 (as described in section 5.2). The results, shown in FIG. 2, demonstrate that all Nanobodies are able to prevent *P. aeruginosa* infection with IC50 values ranging from $1.3 \times 10^{-11}$ to $3.7 \times 10^{-09}$ M, as summarized in Table B-6.

TABLE B-6

Performance of bivalent/biparatopic anti-PcrV Nanobodies in cytotoxicity assay with P3X63 cells as target

| Nanobody | IC50 value (M) | 95% CI on IC50 value (M) | Efficacy (%) |
|---|---|---|---|
| Fab 13.37 | $5.4 \times 10^{-10}$ | $3.4 \times 10^{-10}$ to $8.8 \times 10^{-10}$ | 100 |
| 256 | $5.4 \times 10^{-11}$ | $3.5 \times 10^{-11}$ to $8.4 \times 10^{-11}$ | 100 |
| 257 | $1.3 \times 10^{-10}$ | $8.7 \times 10^{-11}$ to $2.1 \times 10^{-10}$ | 100 |
| 258 | $9.0 \times 10^{-11}$ | $5.6 \times 10^{-11}$ to $1.4 \times 10^{-10}$ | 100 |
| 259 | $3.9 \times 10^{-11}$ | $2.2 \times 10^{-11}$ to $6.8 \times 10^{-11}$ | 100 |
| 261 | $4.8 \times 10^{-10}$ | $2.9 \times 10^{-10}$ to $8.1 \times 10^{-10}$ | 100 |
| 269 | $8.2 \times 10^{-10}$ | $5.0 \times 10^{-10}$ to $1.4 \times 10^{-09}$ | 100 |
| 271 | $5.9 \times 10^{-10}$ | $3.5 \times 10^{-10}$ to $9.8 \times 10^{-10}$ | 100 |
| 275 | $3.7 \times 10^{-09}$ | $2.3 \times 10^{-09}$ to $6.0 \times 10^{-09}$ | 100 |
| 277 | $1.3 \times 10^{-11}$ | $7.5 \times 10^{-12}$ to $2.4 \times 10^{-11}$ | 100 |
| 283 | $7.6 \times 10^{-11}$ | $4.5 \times 10^{-11}$ to $1.3 \times 10^{-10}$ | 100 |
| 285 | $6.1 \times 10^{-11}$ | $3.7 \times 10^{-11}$ to $9.9 \times 10^{-11}$ | 100 |
| 308 | $1.8 \times 10^{-10}$ | $8.2 \times 10^{-11}$ to $3.9 \times 10^{-10}$ | 100 |
| 319 | $8.1 \times 10^{-11}$ | $5.3 \times 10^{-11}$ to $1.2 \times 10^{-10}$ | 100 |
| 335 | $6.4 \times 10^{-11}$ | $3.9 \times 10^{-11}$ to $1.0 \times 10^{-10}$ | 100 |

An additional cytotoxicity assay with human lung epithelial cells (A549 cells) as the target was also established and used to characterize the formatted Nanobodies. To this end, $6 \times 10^4$ A549 (ABL 161-ATCC: CCL-185) cells per well were added to a 96-well E-plate (Roche Cat No 05232368001) and placed in the xCELLigence RTCA workstation (Roche Analyser Model W380) for 6-8 h at 37° C. *P. aeruginosa* (strain PA103), grown under inducing conditions for TTSS expression, was pre-incubated during 1 h at 37° C. with 10 different concentrations of purified Nanobody and then added to the A549 cells and incubated during another 24 h at 37° C. Data were analyzed at the time points where drop in cell index of the treated wells was between 75%-90% of the cell index window. Data were normalized to the time point where the PA103 inoculum was added to the cells. Potencies of the tested bivalent/biparatopic anti-PcrV Nanobodies from three independently performed experiments are presented as ratios relative to the potency of a reference molecule Fab 13.37 (Table B-7).

TABLE B-7

Performance of bivalent/biparatopic anti-PcrV Nanobodies in cytotoxicity assay with A549 cells as target

| Nanobody | Ratio* (mean fold improvement over Fab 13.37) | Range (from three independent experiments) |
|---|---|---|
| 256 | 21 | (7-50) |
| 257 | 10 | (1-54) |
| 258 | 1 | (1-1) |
| 259 | 9 | (1-180) |
| 261 | 1 | (1-1) |
| 269 | 1 | (1-1) |
| 271 | 1 | (1-1) |
| 275 | 1 | (1-1) |
| 277 | 8 | (1-64) |
| 283 | 1 | (1-1) |
| 285 | 1 | (1-1) |
| 308 | 0.3 | (0.04-1) |
| 319 | 2 | (1-5.3) |
| 335 | 1 | (1-1) |

*Ratio = IC50 value Fab 13.37/IC50 value Nanobody 7.3 Cross-Reactivity to PcrV Clinical Variants Cross reactivity of the bivalent/biparatopic anti-PcrV Nanobodies to 23 PcrV sequence variants (see Table A-1) was evaluated by binding ELISA. To this end, microtiter plates were coated overnight with 1 ug/ml of each PcrV variant at 4° C. Nanobodies were applied as dilution series (concentration range: 5 nM-4 pM) in PBS buffer containing 0.1% casein and 0.05% Tween 20 (Sigma). Nanobody binding was detected using a mouse anti-Flag-HRP conjugate (Sigma) and a subsequent enzymatic reaction in the presence of the substrate esTMB (3,3',5,5'-tetramentylbenzidine) (SDT, Brussels, Belgium). All Nanobodies could bind to the all different PcrV variants to a very similar extent as they bind to PcrV reference from strain PAO1. The range of EC50 values against the different PcrV variants and reference strain PAO1 obtained for each Nanobody is presented in Table B-8.

TABLE B-8

Binding of bivalent/biparatopic anti-PcrV Nanobodies to PcrV clinical variants

| Nanobody | EC50 Range (M) |
|---|---|
| 256 | $7 \times 10^{-11}$-$1 \times 10^{-10}$ |
| 257 | $7 \times 10^{-11}$-$9 \times 10^{-11}$ |
| 259 | $1 \times 10^{-11}$-$2 \times 10^{-11}$ |
| 261 | $6 \times 10^{-11}$-$7 \times 10^{-11}$ |
| 271 | $6 \times 10^{-11}$-$1 \times 10^{-10}$ |
| 275 | $6 \times 10^{-10}$-$9 \times 10^{-10}$ |
| 277 | $7 \times 10^{-11}$-$1 \times 10^{-10}$ |
| 285 | $1 \times 10^{-10}$-$1 \times 10^{-10}$ |
| 319 | $8 \times 10^{-11}$-$1 \times 10^{-10}$ |
| 335 | $7 \times 10^{-11}$-$9 \times 10^{-11}$ |

7.4 Stability of Nanobodies Towards Human Neutrophil Elastase and *Pseudomonas aeruginosa* Elastase Stability and maintenance of functionality in the presence of pathogen derived protease (*Pseudomonas aeruginosa* elastase) and host cell derived protease (human neutrophil Elastase (HNE)) was tested in vitro by incubation of the Nanobodies with either HNE or *Pseudomonas aeruginosa* elastase and subsequent analysis of the degradation products by binding ELISA.

To this end, Nanobodies were incubated either with human neutrophil Elastase (1-2 U elastase/ug Nanobody) or *Pseudomonas aeruginosa* elastase (3 ug/ug Nanobody) in Tris pH 7.8, 150 mM NaCl; 10 mM $CaCl_2$ buffer at 37° C. for varying intervals of time (2 hr, 4 hr, 24 hr and 48 hr). For sample analysis, 1 ug/mL of recombinant PcrV protein was immobilized overnight at 4° C. in a 96-well MaxiSorp plate (Nunc, Wiesbaden, Germany). Wells were blocked with a casein solution (1%) and samples were applied as dilution series in PBS buffer containing 0.1% casein and 0.05% Tween 20 (Sigma). As reference, untreated Nanobody was taken along. Nanobody binding was detected using polyclonal rabbit anti-VHH antibody (Ablynx N.V.) followed by horseradish peroxidase (HRP) conjugated goat anti-rabbit IgG (Dako, Glostrup, Denmark) and a subsequent enzymatic reaction in the presence of the substrate esTMB (3,3',5,5'-tetramentylbenzidine) (SDT, Brussels, Belgium).

Results are summarized in Table B-9.

TABLE B-9

Proteolytic stability of selected bivalent/biparatopic anti-PcrV Nanobodies

| | Fold decrease in potency* | | | |
|---|---|---|---|---|
| | *Pseudomonas* elastase | | HNE | |
| Nanobody | 24 hr | 48 hr | 24 hr | 48 hr |
| 256 | 2 | 5 | 5 | 30 |
| 257 | 1 | 3 | 9 | 30 |
| 258 | 1 | 2 | 3 | 15 |
| 259 | 5 | 91 | 15 | 550 |
| 261 | 4 | 12 | 27 | 350 |
| 271 | 3 | 8 | 8 | 15 |
| 275 | 2 | 4 | 8 | 500 |
| 277 | 10 | 11 | 4 | 16 |
| 285 | 2 | 2 | 3 | 3 |
| 319 | 1 | 2 | 1 | 2 |
| 335 | 3 | 22 | 15 | 100 |

*Fold decrease in potency = EC50 value treated sample/EC50 value of untreated sample Example 8: Epitope Mapping A chimeric molecule-based strategy was used to map the conformational binding epitopes of selected monovalent anti-PcrV Nanobodies. To this end, discrete solvent-exposed parts of PcrV were replaced by their counterparts of LcrV, a PcrV homolog from *Yersinia* spp. (Sato et al. Frontiers in Microbiology 2: 142, 2011). In total 7 chimeric molecules covering the most of the sequence range of PcrV protein were generated (see FIG. 3; Table A-7).

Chimeric molecules together with full length PcrV protein (amino acids 1-294, see Table A-1) were cloned into an in house expression vector derived from pUC119 which contained the LacZ promoter, a resistance gene for kanamycin and a multicloning site. In frame with the chimera coding sequence, the vector coded for a C-terminal c-myc tag and a His6 tag. In addition, a small PcrV fragment (amino acids 144-257, see FIG. 3) described as PcrV blocking epitope (Frank et al. J. Inf. Dis. 186: 64-73, 2002; U.S. Pat. No. 6,827,935) was also cloned in the expression vector. Upon transformation in *E. coli* (TG-1), expression cultures were grown and expression was induced by addition of 1 mM IPTG and allowed to continue for 4 hours at 37° C. After spinning the cell cultures, periplasmic extracts were prepared by freeze-thawing the pellets followed by centrifugation. The remaining cell pellets were resuspended and lysed by sonication. Cytosolic fractions were isolated by centrifugation and pooled with the periplasmic extracts. The recombinant proteins were purified via immobilized metal affinity chromatography (IMAC) using Ni-Sepharose 6 Fast Flow beads (GE Healthcare, Uppsala, Sweden) followed by desalting using Zeba Desalt Spin Columns (Thermo Scientific).

To evaluate whether selected monovalent anti-PcrV Nanobodies could bind to the small PcrV fragment and the 7 chimeric molecules, a binding ELISA was carried out. In brief, Nanobodies were coated overnight at 4° C. at 3 ug/mL in a 96-well MaxiSorp plate (Nunc, Wiesbaden, Germany). Wells were blocked with a casein solution (1% in PBS). PcrV proteins were applied (1/10) and binding was detected using a biotinylated mouse anti-myc antibody (Serotec) followed by horseradish peroxidase (HRP) conjugated extravidin (Sigma, St Louis, Mo., USA) and a subsequent enzymatic reaction in the presence of the substrate esTMB (3,3',5,5'-tetramentylbenzidine) (SDT, Brussels, Belgium). As reference Fab 13.37 was taken along (9 ug/ml coating in 96 well plate). Since all tested Nanobodies bind to at least 5 out of 7 chimeric molecules with similar binding levels as on full-length PcrV, and that each chimeric molecule is bound by at least 3 out of 7 Nanobodies with similar binding levels as on full-length PcrV, it could be concluded that only discrete parts of the PcrV protein were replaced by their LcrV counterpart and that the overall ternary structure of the chimeric molecules was not dramatically affected in comparison with the full-length PcrV molecule. Comparison of the binding patterns of the anti-PcrV Nanobodies to the different PcrV molecules revealed 3 major epitope groups (see Table B-10). These data are in line with data retrieved from the epitope binning experiments as described in Example 5.4. Nanobodies from bin 1 bind to PrcV region with amino acids 156-177 and amino acids 195-211, Nanobodies from bin 3 recognize the PcrV region with amino acids 57-91 and Nanobodies from bin 2 bind to amino acids 209-249. More so, this experiment further delineated the proposed binding epitope of Fab13.37 (Frank et al. J. Inf. Dis. 186: 64-73, 2002) and U.S. Pat. No. 6,827,935) from amino acids 144-257 to amino acids 209-249. A representation of the 3 different PcrV blocking epitope regions is shown in FIG. 3

Example 9: Nebulization of the Polypeptides of the Invention 9.1 Materials and Methods Nanobodies 339, 354, 360 and 376 (tagless versions of respectively Nanobodies 256 (SEQ ID NO: 129), 319 (SEQ ID NO: 138), 259 (SEQ ID NO: 137) and 258 (SEQ ID NO: 134)) were produced using a *Pichia pastoris* X33 standard fermentation set-up at 2 L or 10 L fermentor scale depending on expected expression level. After fermentation all four Nanobodies were clarified using a generic tangential flow filtration step and further purified via resin chromatography using a capture step, polish step and preparative Size Exclusion Chromatography. The Nanobodies were then concentrated to approximately 50 mg/ml both in D-PBS and D-PBS+0.01% Tween80.

A reference Nanobody (SEQ ID NO: 207; DVQLVES-GGGLVQAGGSLSISCAGGSGSLSNYVLGWFRQ-APGKEREFVAAINWRGDITIGPPNVEGRFTISRD-NAKNTG YLQMNSLAPDDTAVYYCGAGTPLNPGAY-IYDWSYDYWGRGTQVTVSSGGGGSGGGGSGGGG-SEVQLVESGGGLVQ AGGSLSISCAASGGSLSNY-VLGWFRQAPGKEREFVAAINWRGDITIGPPNVEG-RFTISRDNAKNTGYLQMNSLAPDDTA VYYCG-AGTPLNPGAYIYDWSYDYWGRGTQVTVSSG-GGGSGGGGSGGGGSEVQLVESGGGLVQAGGSLSIS-CAASGG SLSNYVLGWFRQAPGKEREFVAAIN-WRGDITIGPPNVEGRFTISRDNAKNTGYLQMNSLAP-DDTAVYYCGAGTPLNPG AYIYDWSYDYWGRGT-QVTVSS; SEQ ID NO: 2 in WO 2011/098552) was also nebulised in parallel. This reference Nanobody was used at 55.2 mg/mL in 10 mM NaH2PO4/Na2HPO4+0.13M NaCl, pH 7.0.

The nebulisation sequence of the samples was based on OD 500 data obtained for the different Nanobodies from the stirring and freeze/thaw experiment: the most stable polypeptides were nebulised first, the polypeptides which showed more turbidity in stirring or F/T stress were nebulised later. The reference Nanobody was nebulised before, in between and afterwards as control. On day 1 all samples were nebulised according to the order (1 to 11) in Table B-11. The same experiment was repeated on day 2.

The polypeptides were nebulized by the AKITA[2]® APIX-NEB nebulizer system (Activaero) according to the manufacturers instruction. The nebulisation experiment was performed in duplicate. 500 ul of sample was nebulised

TABLE B-10

Epitope mapping of anti-PcrV Nanobodies

|  | Bin1 | | | | Bin2 | Bin3 | | |
| --- | --- | --- | --- | --- | --- | --- | --- | --- |
|  | 02B10 | 14E10 | 01E11 | 06B05 | 05H01 | 13F07 | 07E09 | Fab 13.37 |
| Full length PcrV (aa 1-294) | B | B | B | B | B | B | B | B |
| PcrV fragment (aa 144-257) | B | NB | B | B | B | NB | NB | B |
| Chimera 1 | B | B | B | B | B | B | B | B |
| Chimera 2 | B | B | B | B | B | RB | RB | B |
| Chimera 3 | B | B | B | B | B | B | B | B |
| Chimera 4 | NB | NB | NB | RB | B | B | B | B |
| Chimera 5 | B | B | B | B | B | B | B | B |
| Chimera 6 | NB | NB | RB | RB | B | B | B | B |
| Chimera 7 | B | B | B | B | RB | B | B | RB |

B: Binding: binding signal = binding signal on full length PcrV protein
NB: No binding: binding signal = background signal
RB: Reduced binding: binding signal = 30-90% reduction as compared to binding signal on full length PcrV protein continuously via a mesh nebulizer with a 4 μm membrane. The aerosol was collected in a 100 mL glass bottle and then analysed.

The samples before and after nebulisation were evaluated via turbidity measurement (OD 500) and SE-HPLC analysis.

9.2 Turbidity Measurement

OD500 was measured as a turbidity parameter. Blank setting was done with D-PBS. The OD 500 values measured for the reference samples (before nebulisation) and the nebulised samples (day 1 and day 2) are shown Table B-11.

TABLE B-11

Overview OD500 values before and after nebulisation

| | Sample | Reference | Nebulized (day 1) | Nebulized (day 2) |
|---|---|---|---|---|
| 1 | Reference Nanobody | 0.0202 | 0.0284 | 0.0391 |
| 2 | Nanobody 339 + Tween 80 | 0.0091 | 0.0149 | 0.019 |
| 3 | Nanobody 360 + Tween 80 | 0.007 | 0.0167 | 0.0181 |
| 4 | Nanobody 354 + Tween 80 | 0.012 | 0.0757 | 0.0699 |
| 5 | Nanobody 376 + Tween 80 | 0.0165 | 0.0702 | 0.0871 |
| 6 | Reference Nanobody | 0.0202 | 0.0201 | 0.04 |
| 7 | Nanobody 339 | 0.0151 | 0.0107 | 0.024 |
| 8 | Nanobody 360 | 0.0065 | 0.0099 | 0.0467 |
| 9 | Nanobody 354 | 0.0167 | 0.0171 | 0.071 |
| 10 | Nanobody 376 | 0.0168 | 0.0454 | 0.0162 |
| 11 | Reference Nanobody | 0.0202 | 0.0175 | 0.0375 |

The OD500 values of the samples before and after nebulisation are further presented in FIG. 7.

9.3 SE-HPLC Analysis

The SE-HPLC assay consisted of a BioSEC-5, 7.8×300 mm, 5 um, Agilent, 5190-2521 (SEC85) column, a mobile phase consisting of 0.3M arginin.HCl+phosphate buffer pH6 and UV detection at A280 nm. The relative amount of specific protein impurity was expressed as relative area %, and was calculated by dividing the peak area corresponding to the specific protein or protein impurity by the total integrated area. 10 ug sample was injected. The method is intended for quantification of higher molecular weight species (HMW's) which elute as pre-peaks in the chromatogram.

An overview of the SE-HPLC integration data is given in Table B-12. As is known for the Reference Nanobody (see WO 2011/098552), an increase of pre-peaks (HMW's) was induced by the nebulisation. This phenomenon was not observed in all nebulised polypeptides of the invention. Nebulisation did not affect the formation of high molecular weight molecules. The addition of Tween 80 to the samples did not seem necessary. In the last column the total peak area on SE-HPLC is given which is relative to the concentration of the injected sample. No significant differences were seen for any of the samples between the group area before and after nebulization, indicating no loss in concentration.

TABLE B-12

Overview SE-HPLC integration data of polypeptides and reference Nanobody before and after nebulisation

| Sample name | Rel. Area % Pre-peak 2 | Rel. Area % Pre-peak 1 | Rel. Area % Main-peak 1 | Rel. Area % Post-peak 1 | Group area mAU* min |
|---|---|---|---|---|---|
| Reference samples (before nebulization) | | | | | |
| Ref. Nanobody | 0.08 | 0.30 | 99.09 | 0.47 | 49.12 |
| 339 + Tween80 | na | 0.33 | 98.81 | 0.86 | 30.25 |
| 354 + Tween80 | na | 0.40 | 98.89 | 0.71 | 33.89 |
| 360 + Tween80 | 0.08 | 0.89 | 98.36 | 0.67 | 33.43 |
| 376 + Tween80 | na | 0.17 | 99.19 | 0.63 | 36.73 |
| 339 | na | 0.21 | 99.05 | 0.73 | 30.39 |
| 354 | na | 0.36 | 99.02 | 0.62 | 34.04 |
| 360 | 0.06 | 0.94 | 98.32 | 0.68 | 33.76 |
| 376 | na | 0.17 | 99.23 | 0.60 | 36.97 |
| Nebulised samples (day 1) | | | | | |
| Ref. Nanobody | 0.28 | 0.84 | 98.24 | 0.38 | 47.88 |
| 339 + Tween80 | na | 0.45 | 98.92 | 0.63 | 29.83 |
| 354 + Tween80 | na | 0.43 | 98.93 | 0.64 | 33.75 |
| 360 + Tween80 | 0.08 | 1.03 | 98.27 | 0.61 | 33.95 |
| 376 + Tween80 | na | 0.21 | 99.29 | 0.51 | 36.29 |
| 339 | na | 0.40 | 99.02 | 0.58 | 30.20 |
| 354 | na | 0.42 | 98.95 | 0.63 | 34.33 |
| 360 | 0.08 | 1.06 | 98.22 | 0.65 | 34.25 |
| 376 | na | 0.21 | 99.28 | 0.5 | 37.15 |
| Nebulised samples (day 2) | | | | | |
| Ref. Nanobody | 0.27 | 0.92 | 98.19 | 0.38 | 47.33 |
| 339 + Tween80 | na | 0.74 | 98.61 | 0.65 | 29.93 |
| 354 + Tween80 | na | 0.46 | 98.96 | 0.58 | 33.58 |
| 360 + Tween80 | 0.08 | 1.02 | 98.33 | 0.57 | 33.61 |
| 376 + Tween80 | na | 0.23 | 99.22 | 0.54 | 36.93 |
| 339 | na | 0.33 | 99.04 | 0.63 | 28.92 |
| 354 | na | 0.41 | 98.99 | 0.6 | 33.87 |
| 360 | 0.06 | 1.05 | 98.32 | 0.57 | 33.76 |
| 376 | na | 0.19 | 99.31 | 0.5 | 37.44 |

Example 10: In Vivo Efficacy of Anti-PcrV Nanobodies

An acute *P. aeruginosa* infection mouse model was used to assess the in vivo efficacy of 3 Nanobodies, namely 339, 360 and 376. The model was conducted as described in Secher et al. (Journal of Antimicrobial Chemotherapy 66: 1100-1109, 2011). In brief, *P. aeruginosa* strain PA2310.55 serotype 01 was grown at 37° C. overnight with shaking at 150 rpm in BHI medium (Brain Heart Infusion) supplemented with 10 nM nitrilotriacetic acid (Sigma). Following the exponential growth phase, the inoculums were prepared by diluting the *P. aeruginosa* to $5\times10^7$ cfu/ml. The Nanobodies or the Fab 13.37 were diluted in D-PBS to the appropriate concentrations and subsequently premixed with the *Pseudomonas aeruginosa* culture at a 1 to 1 ratio. The premix (40 μl) was immediately administered intranasally to 8-10 week old anaesthetized C57Bl/6 mice using an ultra-fine pipette tip.

The infected mice were monitored for 4 or 5 days and both survival and body weights (7-8 animals per group) were recorded daily throughout the study. Additionally, 3-5 animals per group were sacrificed at 24 hours post-infection. In these animals, the right lung and the other lobes (except the big lobe) of left lung were weighed and homogenized in 1.5 mL of isotonic saline solution using the sterile disposable homogenization system Dispomix (Medic Tools AG, 6300-Zug, Switzerland). Ten-fold serial dilutions of lung homogenates, made in isotonic saline solution were plated on BHI agar plates to determine viable bacteria in the lung (cfu). After lung homogenization for CFU determination, lung homogenates were subsequently centrifuged, the supernatant discarded and the pellet resuspended in 1 mL PBS containing 0.5% hexadecyltrimethyl ammonium bromide (HTAB) and 5 mM ethylene-diamine tetra-acetic acid (EDTA). After centrifugation, 100 μL of supernatants were placed in test tubes with 200 μL PBS-HTAB-EDTA, 1 mL Hanks' balanced salt solution (HBSS), 100 μL of o-dianisidine dihydrochloride (1.25 mg/mL), and 100 μL $H_2O_2$ 0.05%. The reaction was stopped with 100 μL $NaN_3$ 1% after 15 min of incubation at 37° C. in an agitator. The myeloperoxidase activity was determined as absorbance at 460 nm against medium.

A low (0.028 μg/mouse) and a high dose (10 μg/mouse) of each Nanobody were tested in this model. The survival curves depicted in FIG. 4 show that all the tested anti-PcrV Nanobodies completely protected the mice from *P. aeruginosa* infection-related lethality at a dose of 10 μg/mouse. In contrast, the irrelevant Nanobody treated animals and buffer treated animals all died within the first 48 hours post-infection. At the lower dose of 0.028 μg/mouse still all three Nanobodies provided complete (A339) or near complete (A360 and A376) protection.

The prolonged survival of the infected Nanobody-treated or Fab13.37 treated mice versus the infected buffer-treated mice or the infected irrelevant Nanobody-treated mice was correlated with a decrease in lung inflammation parameters. More specifically, neutrophilic lung infiltration as measured by the myeloperoxidase activity in the lung homogenates (FIG. 5A) and the relative lung weights (FIG. 5C) were clearly reduced by all the anti-PcrV Nanobodies at a dose as low as 0.028 μg/mouse. In addition to these positive effects on lung inflammation, bacterial burden at 24 hours was also reduced by more than 1.4 $\log_{10}$ CFUs (FIG. 5B). Conversely, the irrelevant control Nanobody had no effect on these parameters indicating that the observed effects were anti-PcrV Nanobody related.

Finally, also the percent weight loss was analyzed. A339 treated mice (FIG. 6) had a maximal mean percent weight loss of only 8.3% and reached this minimum already at day 1 post-infection. Mice treated with an 0.028 μg/mouse dose of A376 and A360 or an 0.05 μg/mouse dose of Fab13.37 displayed a mean percent weight loss of 11.9%, 14.1% and 13.5%, respectively which only reached a minimum at day 2 post-infection.

Tables

TABLE A4

Amino acid sequences (1-294) from PcrV variants

| PcrV variant | SEQ ID NO: | Sequence |
|---|---|---|
| 01 = PAO1 | 159 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLSDEYPFEKDNNPVGNFATTVSDRSRPLNDKVNEKTTLLNDTSSRYNSAVEAL NRFIQKYDSVLRDILSAI |
| 02 | 160 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLGDEYPFEKDNNPVGNFATTVSDRSRPLNDKVNEKTTLLNDTSSRYNSAVEAL NRFIQKYDSVLRDILSAI |
| 03 | 161 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFVSGSPKQSGELKGLSDEYPFEKDNNPVGNFATTVSDRSRPLNDKVNEKTTLLNDTSSRYNSAVEAL NRFIQKYDSVLRDILSAI |
| 04 | 162 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLRDEYPFEKDNNPVGNFATTVSDRSRPLNDKVNEKTTLLNDTSSRYNSAVEAL NRFIQKYDSVLRDILSAI |
| 05 | 163 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLYGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLSDEYPFEKDNNPVGNFATTVSDRSRPLNDKVNEKTTLLNDTSSRYNSAVEAL NRFIQKYDSVLRDILSAI |
| 06 | 164 | MEVRNLNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGFSDEYPFEKDNNPVGNFATTVSDRSRPLNDKVNEKTTLLNDTSSRYNSAVEAL NRFIQKYDSVLRDILSAI |
| 07 | 165 | MEVRNLNAARELFLDELLAASAAPASAEQEELLALLRSERIVLAHAGQPLSEAQVLKALAWLLAANPSA PPGQGLEVLREVLHARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLRDEYPFEKDNNPVGNFATTVSDRSRPLNDKVNEKTTLLNDTSSRYNSAVEAL NRFIQKYDSVLRDILSAI |
| 08 | 166 | MEVRNLNAGRELFLDELLAAPAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLRDEYPFEKDNNPVGNFATTVSDRSRPLNDKVNEKTTLLNDTSSRYNSAVEAL NRFIQKYDSVLRDILSAI |

TABLE A4-continued

Amino acid sequences (1-294) from PcrV variants

| PcrV variant | SEQ ID NO: | Sequence |
|---|---|---|
| 09 | 167 | MEVRNFNAARELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLRDEYPFEKDNNPVGNFATTVSDRSRPLNDKVNEKTTLLNDTSSRYNSAVEAL<br>NRFIQKYDSVLRDILSAI |
| 10 | 168 | MEVRNFNAGRELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLKDEYPFEKDNNPVGNFATTVSDRSRPLNDKVNEKTTLLNDTSSRYNSAVEAL<br>NRFIQKYDSVLRDILSAI |
| 11 | 169 | MEVRNFMAARELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPESALLSNLDTFSGKLSI<br>KDFLSGSPKQSGELKGLKDEYPFEKDNNPVGNFATTVSDRSRPLNDKVNEKTTLLNDTSSRYNSAVEAL<br>NRFIQKYDSVLRDILSAI |
| 12 | 170 | MEVRNFNAARELFLDELLDAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLRDEYPFEKDNNPVGNFATTVSDRSRPLNDKVNEKTTLLNDTSSRYNSAVEAL<br>NRFIQKYDSVLRDILSAI |
| 13 | 171 | MEVRNLNAGRELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLRDEYPFEKDNNPVGNFATTVSDRSRPLNDKVNEKTTLLNDTSSRYNSAVEAL<br>NRFIQKYDSVLRDILSAI |
| 14 | 172 | MEVRNFNAGRELFLDELLAAPAAPASAEQKELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLRDEYPFEKDNNPVGNFATTVSDRSRPLNDKVNEKTTLLNDTSSRYNSAVEAL<br>NRFIQKYDSVLRDILSAI |
| 15 | 173 | MEVRNFNASRELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLRDEYPFEKDNNPVGNFATTVSDRSRPLNDKVNEKTTLLNDTSSRYNSAVEAL<br>NRFIQKYDSVLRDILSAI |
| 16 | 174 | MEVRNLNAARELFLDELLAASAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLSDEYSFEKDNNPVGNFATTVSDRSRPLNDKVNEKTTLLNDTSSRYNSAVEAL<br>NRFIQKYDSVLRDILSAI |
| 17 | 175 | MEVRNFNAARELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLKDEYPFEKDNNPVGNFATTVSDRSRPLNDKVNEKTTLLNDTSSRYNSAVEAL<br>NRFIQKYDSVLRDILSAI |
| 18 | 176 | MEVRNLNAARELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDENVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGELKGLKDEYPFEKDNNPVGNFATTVSDRSRPLNDKVNEKTTLLNDTSSRYNSAVEAL<br>NRFIQKYDSVLRDILSAI |
| 19 | 177 | MEVRNFNAGRELFLDELLAAPAAPASAEQEELLALLRSERIVLAHAGQPLSEAQVLKALAWLLAANPSA<br>PPGQGLEVLREVLQARRQPGAQWDLREFLVSAYFSLHGRLDEDVIGVYKDVLQTQDGKRKALLDELKAL<br>TAELKVYSVIQSQINAALSAKQGIRIDAGGIDLVDPTLYGYAVGDPRWKDSPEYALLSNLDTFSGKLSI<br>KDFLSGSPKQSGVLKGLRDEYPFEKDNNPVGNFATTVSDRSRPLNDKVNEKTTLLNDTSSRYNSAVEAL<br>NRFIQKYDSVLRDILSAI |

TABLE A4-continued

| Amino acid sequences (1-294) from PcrV variants | | |
|---|---|---|
| PcrV variant | SEQ ID NO: | Sequence |
| 20 | 178 | MEVRNLNAGRELFLDELLAAPAAPASAEQKELLALLRSERIVLAHAGQPLSEAQVLKALAWLLAANPSA PPGQGLEVLREVLQARRQPGAQWDLREFLVSAYFSLRGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLRDEYPFEKDNNPVGNFATTVSDRSRPLNDKVNEKTTLLNDTSSRYNSAVEAL NRFIQKYDSVLRDILSAI |
| 21 | 179 | MEVRNFNAGRELFLDELLAAPAAPASAEQEELMALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLRDEYPFEKDNNPVGNFATTVSDRSRPLNDKVNEKTTLLNDTSSRYNSAVEAL NRFIQKYDSVLRDILSAI |
| 22 | 180 | MEVRNLNAGRELFLDELLAAPAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLSDEYPFEKDNNPVGNFATTVSDRSRPLNDKVNEKTTLLNDTSSRYNSAVEAL NRFIQKYDSVLRDILSAI |
| 23 | 181 | MEVRNFNAARELFLDELLAASAAPASAEQEELLALLRSERIVLAHAGQPLSEAQVLKALAWLLAANPSA PPGQGLEVLREVLQARRQPGAQWDLREFLVSAYFSLHGRLDEDVIGVYKDVLQTQDGKRKALLDELKAL TAELKVYSVIQSQINAALSAKQGIRIDAGGIDLVDPTLYGYAVGDPRWKDSPEYALLSNLDTFSGKLSI KDFLSGSPKQSGELKGLSDEYPFEKDNNPVGNFATTVSDRSRPLNDKVNEKTTLLNDTSSRYNSAVEAL NRFIQKYDSVLRDILSAI |

TABLE A-2

| Amino acid sequences of VH and VL regions present in 3 anti-PcrV Fab molecules (WO 2009/073631) | | | |
|---|---|---|---|
| ID Fab | | SEQ ID NO: | Sequence |
| Fab 13.37 | $V_H$ | 142 | QVQLVESGGGVVQPGRSLRLSCAASGFTFSSYPLHWVRQAPGKGLEWVSFISYDG SEKYYASSVKGRFTISRDNSENTLYLQMNSLRPEDTAVYYCARNRGDIYYDFTYA MDIWGGTMVTVSS |
| | $V_L$ | 143 | DIQMTQSPSSLSASVGDRVTITCRASQSISRWVAWYQQRPGKAPNLLIYDASSLK SGVPSRFSGSGSGTEFTLTISSLQPEDIATYYCQQFWGTPYTFGQGTKLEIK |
| Fab 26.24 | $V_H$ | 144 | EVQLVESGGGVVQPGRSLRLSCAASGFTFSNYPMHWVRQAPGKGLEWVAVISYDG SEKWYADSVKGRFTISRDNDKNTLYLEMNSLRPEDTAVYYCARNRGDIYYDFTYA MDIWGQGTTVTVSS |
| | $V_L$ | 145 | DIQLTQSPSTLSASVGDSVTITCRASEGVDRWLAWYQQKPGRAPKLLIYDASTLQ SGVPSRFSGSGSGTEFSLTISSLQPDDVATYYCQHFWGTPYTFGQGTKLEIK |
| Fab 35.36 | $V_H$ | 146 | EVQLVESGGGVVQPGRSLRLSCAASGFTFSNYPMHWVRQAPGKGLEWVAVISYDG SEKWYADSVKGRFTISRDNSKNTLYLEMNSLRPEDTAVYYCARNRGDIYYDFTYA MDYWGQGTTVTVSS |
| | $V_L$ | 147 | DIQLTQSPSTLSASVGDSVTITCRASEGVDRWLAWYQQKPGRAPKLLIYDASTLQ SGVPSRFSGSGSGTEFSLTISSLQPDDVATYYCQHFWSTPYTFGQGTKLEIK |

TABLE A-3

| Sequences from constant heavy and light chain (WO 2009/073631) | | |
|---|---|---|
| Region | SEQ ID NO: | Sequence |
| $C_H$ | 148 | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSC |
| $C_L$ | 149 | RTVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC |

TABLE A-4

SEQ ID NOs and amino acid sequences of monovalent anti-PcrV Nanobodies

| Nanobody | SEQ ID NO: | Sequence |
|---|---|---|
| 5H01 | 1 | EVQLVESGGGLVQPGGSLRLSCAASGSTLDYYAIGWFRQAPGKEREGVSCTSNSGSTYYGG SVKGRFTASRDNAKNTVYLQMNSLRPEDTAVYYCVATIGCATLGGTLDVQRYYYRGQGTQV TVSS |
| 7C10 | 2 | EVQLVESGGGLVQAGGSLRLSCTASGRTLSSYTMGWFRQAPGTEREFVAAMTRSGFNTYYA DSVKGRFTISRDSTENTMALQMSSLKPEDTAVYYCTAGRGLTSYRADYWGQGTLVTVSS |
| 1E11 | 3 | EVQLVESGGGLVQPGGSLRLSCAASGSTRSVNPMAWFRQAPGRQREWVATISRSGYATYAD SVKGRFTISGDNAKSSVYLQMNSLKPEDTAVYYCVTGTYWGQGTLVTVSS |
| 2B02 | 4 | EVQLVESGGGLVQPGDSLRLSCAASGRILSINNMVWYRQAPGKQRELVAHITSSGSTGYAD SVKGRFTISRDNAKNTFYLQMTNLNPEDTAVYYCNCWVSSDSNAPLKNYWGQGTQVTVSS |
| 2B10 | 5 | EVQLVESGGGLVQPGGSLRLSCAASGSIFSINNMGWYRQAPGKQRELVTVVTSNLITTYAD SVKGRFTISRDNAKNTVYLQMNSLKPEDTAVYYCNAWARSVGSVPYSQFWGQGTLVTVSS |
| 2G09 | 6 | EVQLVESGGGLVQPGGSLRLSCAASGSFGDNYELYAMTWFRQAPGERRDFVASVTGDGSTS YADSVKDRFTISRDNAKKLMYLQMNSLKPEDTAVYYCRLLNYWGQGTLVTVSS |
| 6B05 | 7 | EVQLVESGGGLVQPGGSLRLSCAASGSIFSINTMGWYRQAPGKQRELVSTITSNLVPHYAD SVQGRFTISRDNARNTVYLQMNSLKPQDTAHYYDNAWARSSGATPYTNYWGQGTLVTVSS |
| 10C05 | 8 | EVQLVESGGGLVQPGGSLRLSCAASGSIFSINTMGWYRQAPGKQRDLVASITMNQVPNYAD SVQGRFTISRDNVRNTVHLQMNAVKPEDTADYFCNAWVRSSGASPYTNYWGQGTQVTVSS |
| 11B09 | 9 | EVQLVESGGGLVQAGGSLRLSCAASRLTFNHYNMGWFRQAPGKERERVAEVTWSGDKIYYV DSVKGRFTISRDNTPNPVYLYLQMNSLKPEDTAVYYCATAPRGLPYANGYWGQGTQVTVSS |
| 14E10 | 10 | EVQLVESGGGLVQPGGSLRLSCAASGRIFSINTMGWYRQAPGKQRELVAGVTINAITNYAD SVKGRFTISRDNAKNTVWLQMNSLKPEDTAVYYCHAWARSSGSAPYSQNWGQGTQVTVSS |
| 7E09 | 11 | EVQLVESGGGLVQAGGSLRLSCAASGRTFSSYIMGWFRQAPGKAREFVADITWGQRPYYAD SVKGRFTISRDNAKNTVYLEMNSLKPEDTAVYYCAADLGVVIREEHAYWGQGTLVTVSS |
| 13F07 | 12 | EVQLVESGGGLVQAGGSLRLSCAASGNTFSTNPMYWYRQAEGKQRELVASISSRGITNYAD SVRGRFSISRDNTKDTVYLQMNSLKPEDTAVYYCRLASLSSGTVYWGKGTLVTVSS |
| 3B11 | 13 | EVQLVESGGGLVQAGGSLRLSCAASGFTFDDYVIGWFRQAPGKEREGVSCISRLDGRTYYT DSVKGRFTISSDNAKNTVYLQMNSLKPEDTAVYYCALEPRYTGDYYPVHPELYDYWGQGTQ VTVSS |
| 4C03 | 14 | EVQLVESGGGLVQAGGSLRLSCVISASTVRNYDMGWFRQAPGKEREFVAAIDWSGGSTRYA DSVKGRFTVSRDNAKNTVYLQMNSLKPEDTAVYYCVAAGFYNNYLRTAPNDWNYWGQGTLV TVSS |
| 4G10 | 15 | EVQLVESGGGLVQAGGSLRLSCVISEDGVRNYDMGWFRQAPGKEREFVATINWSGGSTNYA DSVKGRFTVSRDNAKNTMYLQMDSLKPEDTAVYYCVAAGFYNNYLRTAPNDWNDWGQGTQV TVSS |
| 12B02 | 16 | EVQLVESGGGLVQPGGSLRLSCAASGFSLGVFAIGWFRQAPGKEREGVSCIDSSDGRTTYA DSVKGRFTISRDNAKNTVYLQMNSLKPEDTAVYYCATDIETDVCSGAGWGFWGQGTQVTVS S |
| 14B10 | 17 | EVQLVESGGGLVQPGGSLRLSCAASGRIFSINNMGWYHQAPGKQRELVATITMNGITTYAD SVKGRFTISRDNAKNTVYLQMNSLKPEDTAVYYCSCWVRSSGGDPYRDYWGQGTQVTVSS |
| 3E10 | 18 | EVQLVESGGGLVQAGGSLRLSCTASGHTFSSYTMGWFRQAPGKEREFVAAMTRSGFNTHYS DSVKGRFTISRDNTSRDNTKITMALQMNSLKPEDTAVYYCTTGRGLTSYVANFWGQGTQVT VSS |
| 5E02 | 19 | EVQLVESGGGLVQPGGSLRLSCAASGITLDSIAICWFRQAPGKEREGVSCSRGSDGSTYYA DSVKGRFTISRVNAKNTVYLQMNSLKPEDTAVYYCAAAPSIFYSGGYFPSGMDYWGKGTQV TVSS |

TABLE A-5

Amino acid sequences of selected bivalent/biparatopic anti-PcrV Nanobodies

| Nanobody | SEQ ID NO: | Sequence |
|---|---|---|
| 260 (1E11-40GS-2B10) | 118 | EVQLVESGGGLVQPGGSLRLSCAASGSTRSVNPMAWFRQAPGRQREWVATISRSGYAT YADSVKGRFTISGDNAKSSVYLQMNSLKPEDTAVYYCVTGTYWGQGTLVTVSSGGGGS GGGGSGGGGSGGGGSGGGGSGGGGSGGGGSGGGGSEVQLVESGGGLVQPGGSLRLSCA ASGSIFSINNMGWYRQAPGKQRELVTVVTSNLITTYADSVKGRFTISRDNAKNTVYLQ MNSLKPEDTAVYYCNAWARSVGSVPYSQFWGQGTLVTVSS |
| 272 (11B09-40GS-10C05) | 119 | EVQLVESGGGLVQAGGSLRLSCAASRLTFNHYNMGWFRQAPGKERERVAEVTWSGDKI YYVDSVKGRFTISRDNTPNPVYLYLQMNSLKPEDTAVYYCATAPRGLPYANGYWGQGT LVTVSSGGGGSGGGGSGGGGSGGGGSGGGGSGGGGSGGGGSGGGGSEVQLVESGGGLV QPGGSLRLSCAASGSIFSINTMGWYRQAPGKQRDLVASITMNQVPNYADSVQGRFTIS RDNVRNIVHLQMNAVKPEDTADYFCNAWVRSSGASPYTNYWGQGLTVTVSS |
| 308 (6B05-40GS-1E11) | 120 | EVQLVESGGGLVQPGGSLRLSCAASGSIFSINTMGWYRQAPGKQRELVSTITSNLVPH YADSVQGRFTISRDNARNTVYLQMNSLKPQDTAHYYCNAWARSSGATPYTNYWGQGTL VTVSSGGGGSGGGGSGGGGSGGGGSGGGGSGGGGSGGGGSEVQLVESGGGLVQ PGGSLRLSCAASGSTRSVNPMAWFRQAPGRQREWVATISRSGYATYADSVKGRFTISG DNAKSSVYLQMNSLKPEDTAVYYCVTGTYWGQGTLVTVSS |
| 264 (1E11-40GS-2B02) | 121 | EVQLVESGGGLVQPGGSLRLSCAASGSTRSVNPMAWFRQAPGRQREWVATISRSGYAT YADSVKGRFTISGDNAKSSVYLQMNSLKPEDTAVYYCVTGTYWGQGTLVTVSSGGGGS GGGGSGGGGSGGGGSGGGGSGGGGSGGGGSGGGGSEVQLVESGGGLVQPGDSLRLSCA ASGRILSINNMVWYRQAPGKQRELVAHITSSGTGYADSVKGRFTISRDNAKNTFYLQ MTNLNPEDTAVYYCNCWVSSDSNAPLKNYWGQGTLVTVSS |
| 302 (5H01-40GS-7C10) | 122 | EVQLVESGGGLVQPGGSLRLSCAASGSTLDYYAIGWFRQAPGKEREGVSCTSNSGSTY YGGSVKGRFTASRDNAKNTVYLQMNSLRPEDTAVYYCVATIGCATLGGTLDVQRYYYR GQGTLVTVSSGGGGSGGGGSGGGGSGGGGSGGGGSGGGGSGGGGSGGGGSEVQLVESG GGLVQAGGSLRLSCTASGRTLSSYTMGWFRQAPGTEREFVAAMTRSGFNTYYADSVKG RFTISRDSTENTMALQMSSLKPEDTAVYYCTAGRGLTSYRADYWGQGTLVTVSS |
| 234 (7C10-40GS-5H01) | 123 | EVQLVESGGGLVQAGGSLRLSCTASGRTLSSYTMGWFRQAPGTEREFVAAMTRSGFNT YYADSVKGRFTISRDSTENTMALQMSSLKPEDTAVYYCTAGRGLTSYRADYWGQGTLV TVSSGGGGSGGGGSGGGGSGGGGSGGGGSGGGGSGGGGSGGGGSEVQLVESGGGLVQP GGSLRLSCAASGSTLDYYAIGWFRQAPGKEREGVSCTSNSGSTYYGGSVKGRFTASRD NAKNTVYLQMNSLRPEDTAVYYCVATIGCATLGGTLDVQRYYYRGQGTLVTVSS |
| 064 (13F07-40GS-7C10) | 124 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQAGGS LRLSCTASGRTLSSYTMGWFRQAPGTEREFVAAMTRSGFNTYYADSVKGRFTISRDST ENTMALQMSSLKPEDTAVYYCTAGRGLTSYRADYWGQGTLVTVSS |
| 275 (2G09-40GC-5H01) | 125 | EVQLVESGGGLVQPGGSLRLSCAASGSFGDNYELYAMTWFRQAPGERRDFVASVTGDG STSYADSVKDRFTISRDNAKKLMYLQMNSLKPEDTAVYYCRLLNYWGQGTLVTVSSGG GGSGGGGSGGGGSGGGGSGGGGSGGGGSGGGGSEVQLVESGGGLVQPGGSLRL SCAASGSTLDYYAIGWFRQAPGKEREGVSCTSNSGSTYYGGSVKGRFTASRDNAKNTV YLQMNSLRPEDTAVYYCVATIGCATLGGTLDVQRYYRGQGTLVTVSS |
| 083 (7C10-40GS-11B09) | 126 | EVQLVESGGGLVQAGGSLRLSCTASGRTLSSYTMGWFRQAPGTEREFVAAMTRSGFNT YYADSVKGRFTISRDSTENTMALQMSSLKPEDTAVYYCTAGRGLTSYRADYWGQGTLV TVSSGGGGSGGGGSGGGGSGGGGSGGGGSGGGGSGGGGSGGGGSEVQLVESGGGLVQA GGSLRLSCAASRLTFNHYNMGWFRQAPGKERERVAEVTWSGDKIYYVDSVKGRFTISR DNTPNPVYLYLQMNSLKPEDTAVYYCATAPRGLPYANGYWGQGTLVTVSS |
| 087 (1E11-40GS-7C10) | 127 | EVQLVESGGGLVQPGGSLRLSCAASGSTRSVNPMAWFRQAPGRQREWVATISRSGYAT YADSVKGRFTISGDNAKSSVYLQMNSLKPEDTAVYYCVTGTYWGQGTLVTVSSGGGGS GGGGSGGGGSGGGGSGGGGSGGGGSGGGGSGGGGSEVQLVESGGGLVQAGGSLRLSCT ASGRTLSSYTMGWFRQAPGTEREFVAAMTRSGFNTYYADSVKGRFTISRDSTENTMAL QMSSLKPEDTAVYYCTAGRGLTSYRADYWGQGTLVTVSS |
| 269 (6B05-40GS-13F07) | 128 | EVQLVESGGGLVQPGGSLRLSCAASGSIFSINWMGWYRQAPGKQRELVSTITSNLVPH YADSVQGRFTISRDNARNTVYLQMNSLKPQDTAHYYCNAWARSSGATPYTNYWGQGTL VTVSSGGGGSGGGGSGGGGSGGGGSGGGGSGGGGSGGGGSGGGGSEVQLVESGGGLVQ AGGSLRLSCAASGNTFSTNPMYWYRQAEGKQRELVASISSRGITNYADSVRGRFSISR DNTKDTVYLQMNSLKPEDTAVYYCRLASLSSGTVYWGKGTLVTVSS |
| 256 (13F07-40GS-5H01) | 129 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQPGGS LRLSCAASGSTLDYYAIGWFRQAPGKEREGVSCTSNSGSTYYGGSVKGRFTASRDNAK NTVYLQMNSLRPEDTAVYYCVATIGCATLGGTLDVQRYYRGQGTLVTVSS |

TABLE A-5-continued

Amino acid sequences of selected bivalent/biparatopic anti-PcrV Nanobodies

| Nanobody | SEQ ID NO: | Sequence |
|---|---|---|
| 277 (5H01-40GS-11B09) | 130 | EVQLVESGGGLVQPGGSLRLSCAASGSTLDYYAIGWFRQAPGKEREGVSCTSNSGSTY YGGSVKGRFTASRDNAKNTVYLQMNSLRPEDTAVYYCVATIGCATLGGTLDVQRYYYR GQGTLVTVSSGGGGSGGGGSGGGGSGGGGSGGGGSGGGGSGGGGSGGGGSEVQLVESG GGLVQAGGSLRLSCAASRLTFNHYNMGWFRQAPGKERERVAEVTWSGDKIYYVDSVKG RFTISDRNTPNPVYLYLQMNSLKPEDTAVYYCATAPRGLPYANGYWGQGTLVTVSS |
| 257 (13F07-40GS-2B10) | 131 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQPGGS LRLSCAASGSIFSINNMGWYRQAPGKQRELVTVVTSNLITTYADSVKGRFTISRDNAK NTVYLQMNSLKPEDTAVYYCNAWARSVGSVPYSQFWGQGTLVTVSS |
| 285 (13F07-40GS-2B02) | 132 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQPGDS LRLSCAASGRILSINNMVWYRQAPGKQRELVAHITSSGSTGYADSVKGRFTISRDNAK NTFYLQMTNLNPEDTAVYYCNCWVSSDSNAPLKNYWGQGTLVTVSS |
| 115 (11B09-40GS-13F07) | 133 | EVQLVESGGGLVQAGGSLRLSCAASRLTFNHYNMGWFRQAPGKERERVAEVTWSGDKI YYVDSVKGRFTISRDNTPNPVYLYLQMNSLKPEDTAVYYCATAPRGLPYANGYWGQGT LVTVSSGGGGSGGGGSGGGGSGGGGSGGGGSGGGGSGGGGSGGGGSEVQLVESGGGLV QAGGSLRLSCAASGNTFSTNPMYWYRQAEGKQRELVASISSRGITNYADSVRGRFSIS RDNTKDTVYLQMNSLKPEDTAVYYCRLASLSSGIVYWGKGTLVTVSS |
| 258 (13F07-40GS-14E10) | 134 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQPGGS LRLSCAASGRIFSINTMGWYRQAPGKQRELVAGVTINAITNYADSVKGRFTISRDNAK NTVWLQMNSLKPEDTAVYYCHAWARSSGSAPYSQNWGQGTLVTVSS |
| 283 (7E09-40GS-6B05) | 135 | EVQLVESGGGLVQAGGSLRLSCAASGRTFSSYIMGWFRQAPGKAREFVADITWGQRPY YADSVKGRFTISRDNAKNTVYLEMNSLKPEDTAVYYCAADLGVVIREEHAYWGQGTLV TVSSGGGGSGGGGSGGGGSGGGGSGGGGSGGGGSGGGGSGGGGSEVQLVESGGGLVQP GGSLRLSCAASGSIFSINTMGWYRQAPGKQRELVSTITSNLVPHYADSVQGRFTISRD NARNTVYLQMNSLKPQDTAHYYCNAQARSSGATPYTNYWGQGTLVTVSS |
| 271 (7C10-40GS-14E10) | 136 | EVQLVESGGGLVQAGGSLRLSCTASGRTLSSYTMGWFRQAPGTEREFVAAMTRSGFNT YYADSVKGRFTISRDSTENTMALQMSSLKPEDTAVYYCTAGRGLTSYRADYWGQGTLV TVSSGGGGSGGGGSGGGGSGGGGSGGGGSGGGGSGGGGSGGGGSEVQLVESGGGLVQP GGSLRLSCAASGRIFSINTMGWYRQAPGKQRELVAGVTINAITNYADSVKGRFTISRD NAKNTVWLQMNSLKPEDTAVYYCHAWARSSGSAPYSQNWGQGTLVTVSS |
| 259 (1E11-40GS-5H01) | 137 | EVQLVESGGGLVQPGGSLRLSCAASGSTRSVNPMAWFRQAPGRQREWVATISRSGYAT YADSVKGRFTISGDNAKSSVYLQMNSLKPEDTAVYYCVTGTYWGQGTLVTVSSGGGGS GGGGSGGGGSGGGGSGGGGSGGGGSGGGGSGGGGSEVQLVESGGGLVQPGGSLRLSCA ASGSTLDYYAIGWFRQAPGKEREGVSCTSNSGSTYYGGSVKGRFTASRDNAKNTVYLQ MNSLRPEDTAVYYCVATIGCATLGGTLDVQRYYYRGQGTLVTVSS |
| 319 (13F07-40GS-6B05) | 138 | EVQLVESGGGLVQAGGSLRLSCAASGNTFSTNPMYWYRQAEGKQRELVASISSRGITN YADSVRGRFSISRDNTKDTVYLQMNSLKPEDTAVYYCRLASLSSGTVYWGKGTLVTVS SGGGGSGGGGSGGGGSGGGGSGGGGSGGGGSGGGGSGGGGSEVQLVESGGGLVQPGGS LRLSCAASGSIFSINTMGWYRQAPGKQRELVSTITSNLVPHYADSVQGRFTISRDNAR NTVYLQMNSLKPQDTAHYYCNAWARSSGATPYTNYWGQGTLVTVSS |
| 335 (5H01-40GS-1E11) | 139 | EVQLVESGGGLVQPGGSLRLSCAASGSTLDYYAIGWRFQAPGKEREGVSCTSNSGSTY YGGSVKGRFTASRDNAKNTVYLQMNSLRPEDTAVYYCVATIGCATLGGTLDVQRYYYR GQGTLVTVSSGGGGSGGGGSGGGGSGGGGSGGGGSGGGGSGGGGSGGGGSEQVLVESG GGLVQPGGSLRLSCAASGSTRSVNPMAWFRQAPGRQREWVATISRSGYATYADSVKGR FTISGDNAKSSVYLQMNSLKPEDTAVYYCVTGTYWGQGTLVTVSS |
| 261 (5H01-40GS-2B10) | 140 | EVQLVESGGGLVQPGGSLRLSCAASGSTLDYYAIGWFRQAPGKEREGVSCTSNSGSTY YGGSVKGRFTASRDNAKNTVYLQMNSLRPEDTAVYYCVATIGCATLGGTLDVQRYYYR GQGTLVTVSSGGGGSGGGGSGGGGSGGGGSGGGGSGGGGSGGGGSGGGGSEVQLVESG GGLVQPGGSLRLSCAASGSIFSINNMGWYRQAPGKQRELVTVVTSNLITTYADSVKGR FTISRDNAKNTVYLQMNSLKPEDTAVYYCNAWARSVGSVPYSQFWGQGTLVTVSS |
| 262 (7E09-40GS-7C10) | 141 | EVQLVESGGGLVQAGGSLRLSCAASGRTFSSYIMGWFRQAPGKAREFVADITWGQRPY YADSVKGRFTISRDNAKNTVYLEMNSLKPEDTAVYYCAADLGVVIREEHAYWGQGTLV TVSSGGGGSGGGGSGGGGSGGGGSGGGGSGGGGSGGGGSGGGGSEVQLVESGGGLVQA GGSLRLSCTASGRTLSSYTMGWFRQAPGTEREFVAAMTRSGFNTYYADSVKGRFTISR DSTENTMALQMSSLKPEDTAVYYCTAGRGLTSYRADYWGQGTLVTVSS |

TABLE A-6

Preferred combinations of CDR sequences, preferred combinations of framework sequences, and preferred combinations of framework and CDR sequences.

| | Nanobody | FW1 | | CDR1* | | FW2 | | CDR2* | | FW3 | | CDR3* | | FW4 |
|---|---|---|---|---|---|---|---|---|---|---|---|---|---|---|
| 1 | 5H01 | EVQLVESGGGLVQ PGGSLRLSCAAS | 76 | GSTLDY YAIG | 20 | WFRRQAPG KEREGVS | 81 | CTSNS GSTY | 38 | YGGSVKGRFTASRDNAKNTVY LQMNSLRPEDTAVYYCVA | 94 | TIGCATLGG TLDVQRYYY | 113 | RGQGTQ VTVSS |
| 2 | 7C10 | EVQLVESGGGLVQ AGGSLRLSCTAS | 77 | GRTLSS YTMG | 21 | WFRQAPG TEREFVA | 82 | AMTRS GFNTY | 39 | YADSVKGRFTISRDSTENTMA LQMSSLKPEDTAVYYCTA | 95 | GRGLTSYRA DY | 114 | WGQGTL VTVSS |
| 3 | 1E11 | EVQLVESGGGLVQ PGGSLRLSCAAS | 76 | GSTRSV NPMA | 22 | WFRQAPG RQREWVA | 83 | TISRS GYAT | 40 | YADSVKGRFTISGDNAKSSVY LQMNSLKPEDTAVYYCVY | 96 | GTY | 114 | WGQGTL VTVSS |
| 4 | 2B02 | EVQLVESGGGLVQ PGDSLRLSCAAS | 78 | GRILSI NNMV | 23 | WYRQAPG KQRELVA | 84 | HITSS GSTG | 41 | YADSVKGRFTISRDNAKNTFY LQMTNLNPEDTAVYYCNC | 97 | WVSSDSNAP LKNY | 115 | WGQGTQ VTVSS |
| 5 | 2B10 | EVQLVESGGGLVQ PGGSLRLSCAAS | 76 | GSIFSI NNMG | 24 | WFRQAPG KQRELVT | 85 | VVTSN LITT | 42 | YADSVKGRFTISRDNAKNTVY LQMNSLKPEDTAVYYCNA | 98 | WARVGSVP YSQF | 114 | WGQGTL VTVSS |
| 6 | 2G09 | EVQLVESGGGLVQ PGGSLRLSCAAS | 76 | GSFGDN YELYAM T | 25 | WFRQAPG ERRDFVA | 86 | SVTGD GSTS | 43 | YADSVKDRFTISRDNAKKLMY LQMNSLKPEDTAVYYCRL | 99 | LNY | 114 | WGQGTL VTVSS |
| 7 | 6B05 | EVQLVESGGGLVQ PGGSLRLSCAAS | 76 | GSIFSI NTMG | 26 | WYRQAPG KQRELVS | 87 | TITSN LVPH | 44 | YADSVQGRFTISRDNARNTVY LQMNSLKPQDTAHYYCNA | 100 | WARSSGATP YTNY | 114 | WGQGTL VTVSS |
| 8 | 10C05 | EVQLVESGGGLVQ PGGSLRLSCAAS | 76 | GSIFSI NTMG | 26 | WYRQAPG KQRDLVA | 88 | SITMN QVPN | 45 | YADSVQGRFTISRDNVRNTVH LQMNAVKPEDTADYFCNA | 101 | WVRSSGASP YTNY | 115 | WGQGTQ VTVSS |
| 9 | 11B09 | EVQLVESGGGLVQ AGGSLRLSCAAS | 79 | RLTFNH YNMG | 27 | WFRQAPG KERERVA | 89 | EVTWS GDKIY | 46 | YVDSVKGRFTISRDNTPNPVY LYLQMNSLKPEDTAVYYCAT | 102 | APRGLPYAN GY | 115 | WGQGTQ VTVSS |
| 10 | 14E10 | EVQLVESGGGLVQ PGGSLRLSCAAS | 76 | GRIFSI NTMG | 28 | WYRQAPG KQRELVA | 84 | GVTIN AITN | 47 | YADSVKGRFTISRDNAKNTVW LQMNSLKPEDTAVYYCHA | 103 | WARSSGSAP YSQN | 115 | WGQGTQ VTVSS |

TABLE A-6-continued

Preferred combinations of CDR sequences, preferred combinations of framework sequences, and preferred combinations of framework and CDR sequences.

| | Nanobody | | FW1 | | CDR1* | | FW2 | | CDR2* | | FW3 | | CDR3* | | FW4 |
|---|---|---|---|---|---|---|---|---|---|---|---|---|---|---|---|
| 11 | 7E09 | 79 | EVQLVESGGGLVQ AGGSLRLSCAAS | 29 | GFTFSS YIMG | 90 | WFRQAPG KAREFVA | 48 | DITWG QRPY | 104 | YADSVKGRFTISRDNAKNTVY LEMNSLKPEDTAVYYCAA | 67 | DLGVIRE HAY | 114 | WGQGTL VTVSS |
| 12 | 13F07 | 79 | EVQLVESGGGLVQ AGGSLRLSCAAS | 30 | GNTFST NPMY | 91 | WYRQAEG KQRELVA | 49 | SISSR GITN | 105 | YADSVRGRFSISRDNTKDTVY LQMNSLKPEDTAVYYCRL | 68 | ASLSSGTVY | 116 | WGKGTL VTVSS |
| 13 | 3B11 | 79 | EVQLVESGGGLVQ AGGSLRLSCAAS | 31 | GFTFD YVTG | 81 | WFRRQAPG KEREGVS | 50 | CISRL DGRTY | 106 | YTDSVKGRFTISSDNAKNTVY LQMNSLKPEDTAVYYCAL | 69 | EPRYTGDYY PVHPELYDY | 115 | WGQGTQ VTVSS |
| 14 | 4C03 | 80 | EVQLVESGGGLVQ AGGSLRLSCVIS | 32 | ASTVRN YDMG | 92 | WFRQAPG KEREFVA | 51 | AIDWS GGSTR | 107 | YADSVKGRFTVSRDNAKNTVY LQMNSLKPEDTAVYYCVA | 70 | AGFYNNYLR TAPNDWNY | 114 | WGQGTL VTVSS |
| 15 | 4G10 | 80 | EVQLVESGGGLVQ AGGSLRLSCVIS | 33 | EDGVRN YDMG | 92 | WFRQAPG KEREFVA | 52 | TINWS GGSTN | 108 | YADSVRGRFTVSRDNAKNTMY LQMNSLKPEDTAVYYCVA | 71 | AGFYNNYLR TAPNDWND | 115 | WGQGTQ VTVSS |
| 16 | 12B02 | 76 | EVQLVESGGGLVQ PGGSLRLSCAAS | 34 | GFSLGV FAIG | | | 53 | CIDSS DGRTT | 109 | YADSVKGRFTISRDNAKNTVY LQMNSLKPEDTAVYYCAT | 72 | DIETDVCSG AGWGF | 115 | WGQGTQ VTVSS |
| 17 | 14B10 | 76 | EVQLVESGGGLVQ PGGSLRLSCAAS | 35 | GRIFSI NNMG | 93 | WYHQAPG KQRELVA | 54 | TITMN GITT | 110 | YADSVKGRFTISRDNAKNTVY LQMNSLKPEDTAVYYCSC | 73 | WVRSSGGDP YRDY | 115 | WGQGTQ VTVSS |
| 18 | 3E10 | 77 | EVQLVESGGGLVQ AGGSLRLSCTAS | 36 | GHTFSS YTMG | 92 | WFRQAPG KEREFVA | 55 | AMTRS GFNTH YSDSV | 11 | KGRFTISRDNTSRDNTKITMA LQMNSLKPEDTAVYYCTT | 74 | GRGLTSYVA NF | 115 | WGQGTQ VTVSS |
| 19 | 5E02 | 76 | EVQLVESGGGLVQ PGGSLRLSCAAS | 37 | GITLDS IAIC | 81 | WFRRQAPG KEREGVS | 56 | CSRGS DGSTY | 112 | YADSVKGRFTISRVNAKNTVY LQMNSLKPEDTAVYYCAA | 75 | APSIFYSGG YFPSGMDY | 117 | WGKGTQ VTVSS |

*CDR sequences were determined according to Antibody Engineering, vol 2 by Kontermann & Dübel (Eds.), Springer Verlag Heidelberg Berlin, Chapter 3: Martin pp. 33-51, 2010.

TABLE A-7

Amino acid sequences from PcrV fragment (amino acids 144-257) and chimeric molecules used for epitope mapping

| Molecule | SEQ ID NO: | Sequence |
|---|---|---|
| PcrV fragment (AA 144-257) | 198 | MEVRNLNAARELFLDELLAASAAPASAVYSVIQSQINAALSAKQGIRIDAG GIDLVDPTLYGYAVGDPRWKDSPEYALLSNLDTFSGKLSIKDFLSGSPKQS GELKGLSDEYPFEKDNNPVGNFATTVSDRSRPLNDKVNE |
| Chimera 1 | 199 | MIRAYEQNPQHFIEDLEKVRVEQLTGHGSSVLEELVQLVKDKNIDISAEQE ELLALLRSERIVLAHAGQPLSEAQVLKALAWLLAANPSAPPGQGLEVLREV LQARRQPGAQWDLREFLVSAYFSLHGRLDEDVIGVYKDVLQTQDGKRKALL DELKALTAELKVYSVIQSQINAALSAKQGIRIDAGGIDLVDPTLYGYAVGD PRWKDSPEYALLSNLDTFSGKLSIKDFLSGSPKQSGELKGLSDEYPFEKDN NPVGNFATTVSDRSRPLNDKVNEKTTLLNDTSSRYNSAVEALNRFIQKYDS VLRDILSAI |
| Chimera 2 | 200 | MEVRNLNAARELFLDELLAASAAPASAEQEELLALLRSERIVLAHAGQPLSE AQVLKGGHYDNQLQNGIKRVKEFLESSPNTQWDLREFLVSAYFSLHGRLDED VIGVYKDVLQTQDGKRKALLDELKALTAELKVYSVIQSQINAALSAKQGIRI DAGGIDLVDPTLYGYAVGDPRWKDSPEYALLSNLDTFSGKLSIKDFLSGSPK QSGELKGLSDEYPFEKDNNPVGNFATTVSDRSRPLNDKVNEKTTLLNDTSSR YNSAVEALNRFIQKYDSVLRDILSAI |
| Chimera 3 | 201 | MEVRNLNAARELFLDELLAASAAPASAEQEELLALLRSERIVLAHAGQPLS EAQVLKALAWLLAANPSAPPGQGLEVLREVLQARRQPGAQWDLREFLVSAY FSLTADRIDDDILKVIVDSMNHHGGKRKALLDELKALTAELKVYSVIQSQI NAALSAKQGIRIDAGGIDLVDPTLYGYAVGDPRWKDSPEYALLSNLDTFSG KLSIKDFLSGSPKQSGELKGLSDEYPFEKDNNPVGNFATTVSDRSRPLNDK VNEKTTLLNDTSSRYNSAVEALNRFIQKYDSVLRDILSAI |
| Chimera 4 | 202 | MEVRNLNAARELFLDELLAASAAPASAEQEELLALLRSERIVLAHAGQPLS EAQVLKALAWLLAANPSAPPGQGLEVLREVLQARRQPGAQWDLREFLVSAY FSLHGRLDEDVIGVYKDVLQTQDGKRKALLDELKALTAELKVYSVIQSQIN AALSSSGTINIHDKSINLMDKNLYGYAVGDPRWKDSPEYALLSNLDTFSGK LSIKDFLSGSPKQSGELKGLSDEYPFEKDNNPVGNFATTVSDRSRPLNDKV NEKTTLLNDTSSRYNSAVEALNRFIQKYDSVLRDILSAI |
| Chimera 5 | 203 | MEVRNLNAARELFLDELLAASAAPASAEQEELLALLRSERIVLAHAGQPLS EAQVLKALAWLLAANPSAPPGQGLEVLREVLQARRQPGAQWDLREFLVSAY FSLHGRLDEDVIGVYKDVLQTQDGKRKALLDELKALTAELKVYSVIQSQIN AALSAKQGIRIDAGGIDLVDPTLYGYTDEEIFKASAEYKILSNLDTFSGKL SIKDFLSGSPKQSGELKGLSDEYPFEKDNNPVGNFATTVSDRSRPLNDKVN EKTTLLNDTSSRYNSAVEALNRFIQKYDSVLRDILSAI |
| Chimera 6 | 204 | MEVRNLNAARELFLDELLAASAAPASAEQEELLALLRSERIVLAHAGQPLS EAQVLKALAWLLAANPSAPPGQGLEVLREVLQARRQPGAQWDLREFLVSAY FSLHGRLDEDVIGVYKDVLQTQDGKRKALLDELKALTAELKVYSVIQSQIN AALSAKQGIRIDAGGIDLVDPTLYGYAVGDPRWKDSPEYAILEKMPQTTIQ VDGSEKKIVSIKDFLSGSPKQSGELKGLSDEYPFEKDNNPVGNFATTVSDR SRPLNDKVNEKTTLLNDTSSRYNSAVEALNRFIQKYDSVLRDILSAI |
| Chimera 7 | 205 | MEVRNLNAARELFLDELLAASAAPASAEQEELLALLRSERIVLAHAGQPLS EAQVLKALAWLLAANPSAPPGQGLEVLREVLQARRQPGAQWDLREFLVSAY FSLHGRLDEDVIGVYKDVLQTQDGKRKALLDELKALTAELKVYSVIQSQIN AALSAKQGIRIDAGGIDLVDPTLYGYAVGDPRWKDSPEYALLSNLDTFSGK LSIKDFLGSENKRTGALGNLKNSYSYNKDNNELSHFATTCSDKSRPLNDKV NEKTTLLNDTSSRYNSAVEALNRFIQKYDSVLRDILSAI |

TABLE A-8

Linker sequences

| Linker | SEQ ID NO | Sequence |
|---|---|---|
| 5GS linker | 182 | GGGGS |
| 7GS linker | 183 | sggsggs |
| 8GS linker | 184 | ggggcgggs |
| 9GS linker | 185 | GGGGSGGGS |
| 10GS linker | 186 | GGGGSGGGGS |

TABLE A-8-continued

Linker sequences

| Linker | SEQ ID NO | Sequence |
|---|---|---|
| 15GS linker | 187 | GGGGSGGGGSGGGGS |
| 18GS linker | 188 | GGGGSGGGGSGCGGGGS |
| 20GS linker | 189 | GGGGSGGGGSGGGGSGGGGS |
| 25GS linker | 190 | GGGGSGGGGSGGGGSGGGGSGGGGS |
| 30GS linker | 191 | GGGGSGGGGSGGGGSGGGGSGGGGSGGGGS |
| 35GS linker | 192 | GGGGSGGGGSGGGGSGGGGSGGGGSGGGGSGGGGS |
| 40GS lInker | 193 | GGGGSGGGGSGGGGSGGGGSGGGGSGGGGSGGGGSGGGGS |
| G1 hinge | 194 | EPKSCDKTHTCPPCP |
| 9GS-G1 hinge | 195 | GGGGSGGGSEPKSCDKTHTCPPCP |
| Llama upper long hinge region | 196 | epktpkpqpaaa |
| G3 hinge | 197 | ELKTPLGDTTHTCPRCPEPKSCDTPPPCPRCPEPKSCDTPPPCPRCPEPKSCDTPPPCPRCP |

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A polypeptide comprising or consisting of two or more immunoglobulin single variable domains that are directed against PcrV, wherein a first immunoglobulin single variable domain is directed against a first epitope on PcrV and a second immunoglobulin single variable domain is directed against a second epitope on PcrV different from the first epitope on PcrV,
wherein at least one of the immunoglobulin single variable domains consists of 4 framework regions and 3 complementarity determining regions (CDR), in which:
CDR1 is the amino acid sequence of SEQ ID NO: 20; and
CDR2 is the amino acid sequence of SEQ ID NO: 38; and
CDR3 is the amino acid sequence of SEQ ID NO: 57; and
wherein the polypeptide does not comprise an immunoglobulin single variable domain that consists of 4 framework regions and 3 complementarity determining regions (CDR), in which:
CDR1 is the amino acid sequence of SEQ ID NO: 30; and
CDR2 is the amino acid sequence of SEQ ID NO: 49; and
CDR3 is the amino acid sequence of SEQ ID NO: 68.

2. The polypeptide according to claim 1, wherein each of the two or more immunoglobulin single variable domains is a domain antibody, a single domain antibody a VHH, a partially humanized VHH, or a fully humanized VHH.

3. The polypeptide according to claim 1, wherein at least one of the immunoglobulin single variable domains consists of the amino acid sequence of SEQ ID NO: 1.

4. The polypeptide according to claim 1, wherein at least one of the immunoglobulin single variable domains consists of 4 framework regions and 3 complementarity determining regions (CDR), in which:
CDR1 is selected from the group consisting of the amino acid sequences of SEQ ID NOs: 22-29 and 31-37; and
CDR2 is selected from the group consisting of the amino acid sequences of SEQ ID NOs: 40-48 and 50-56; and
CDR3 is selected from the group consisting of the amino acid sequences of SEQ ID NOs: 59-67 and 69-75.

5. The polypeptide according to claim 1, wherein the first immunoglobulin single variable domain does not cross-block the binding to PcrV of the second immunoglobulin single variable domain and/or wherein the first immunoglobulin single variable is not cross-blocked from binding to PcrV by the second immunoglobulin single variable domain and wherein:

the first immunoglobulin single variable domain cross-blocks the binding to PcrV of at least one of the immunoglobulin single variable domains with SEQ ID NOs: 3-10 and/or is cross-blocked from binding to PcrV by at least one of the immunoglobulin single variable domains with SEQ ID NOs: 3-10; and the second immunoglobulin single variable domain cross-blocks the binding to PcrV of at least one of the immunoglobulin single variable domains with SEQ ID NOs: 1-2 and/or is cross-blocked from binding to PcrV by at least one of immunoglobulin single variable domains with SEQ ID NOs: 1-2;

the first immunoglobulin single variable domain cross-blocks the binding to PcrV of at least one of the immunoglobulin single variable domains with SEQ ID NOs: 1-2 and/or is cross-blocked from binding to PcrV by at least one of the immunoglobulin single variable domains with SEQ ID NOs: 1-2; and the second immunoglobulin single variable domain cross-blocks the binding to PcrV of at least one of the immunoglobulin single variable domains with SEQ ID NOs: 3-10 and/or is cross-blocked from binding to PcrV by at least one of the immunoglobulin single variable domains with SEQ ID NOs: 3-10;

the first immunoglobulin single variable domain cross-blocks the binding to PcrV of at least one of the immunoglobulin single variable domains with SEQ ID NOs: 1-2 and/or is cross-blocked from binding to PcrV by at least one of the immunoglobulin single variable domains with SEQ ID NOs: 1-2; and the second immunoglobulin single variable domain cross-blocks the binding to PcrV of at least one of the immunoglobulin single variable domains with SEQ ID NOs: 11-12 and/or is cross-blocked from binding to PcrV by at least one of the immunoglobulin single variable domains with SEQ ID NOs: 11-12;

the first immunoglobulin single variable domain cross-blocks the binding to PcrV of at least one of the immunoglobulin single variable domains with SEQ ID NOs: 11-12 and/or is cross-blocked from binding to PcrV by at least one of the immunoglobulin single variable domains with SEQ ID NOs: 11-12; and the second immunoglobulin single variable domain cross-blocks the binding to PcrV of at least one of the immunoglobulin single variable domains with SEQ ID NOs: 1-2 and/or is cross-blocked from binding to PcrV by at least one of the immunoglobulin single variable domains with SEQ ID NOs: 1-2, or wherein:

the first immunoglobulin single variable domain is selected from a polypeptide that binds full length PcrV (SEQ ID NO: 159) and that shows reduced binding of 30-90%, relative to the binding to full length PcrV (SEQ ID NO: 159), or no binding to chimera 4 (SEQ ID NO: 202) and chimera 6 (SEQ ID NO: 204); and the second immunoglobulin single variable domain is selected from a polypeptide that binds to full length PcrV (SEQ ID NO: 159) and that shows reduced binding of 30-90%, relative to the binding to full length PcrV (SEQ ID NO: 159), or no binding to chimera 7 (SEQ ID NO: 205);

the first immunoglobulin single variable domain is selected from a polypeptide that binds to full length PcrV (SEQ ID NO: 159) and that shows reduced binding of 30-90%, relative to the binding to full length PcrV (SEQ ID NO: 159), or no binding to chimera 7 (SEQ ID NO: 205); and the second immunoglobulin single variable domain is selected from a polypeptide that binds full length PcrV (SEQ ID NO: 159) and that shows reduced binding of 30-90%, relative to the binding to full length PcrV (SEQ ID NO: 159), or no binding to chimera 4 (SEQ ID NO: 202) and chimera 6 (SEQ ID NO: 204);

the first immunoglobulin single variable domain is selected from a polypeptide that binds to full length PcrV (SEQ ID NO: 159) and that shows reduced binding of 30-90%, relative to the binding to full length PcrV (SEQ ID NO: 159), or no binding to chimera 7 (SEQ ID NO: 205); and the second immunoglobulin single variable domain is selected from a polypeptide that binds full length PcrV (SEQ ID NO: 159) and that shows reduced binding of 30-90%, relative to the binding to full length PcrV (SEQ ID NO: 159), or no binding to chimera 2 (SEQ ID NO: 200);

the first immunoglobulin single variable domain is selected from a polypeptide that binds full length PcrV (SEQ ID NO: 159) and that shows reduced binding of 30-90%, relative to the binding to full length PcrV (SEQ ID NO: 159), or no binding to chimera 2 (SEQ ID NO: 200); and the second immunoglobulin single variable domain is selected from a polypeptide that binds to full length PcrV (SEQ ID NO: 159) and that shows reduced binding of 30-90%, relative to the binding to full length PcrV (SEQ ID NO: 159), or no binding to chimera 7 (SEQ ID NO: 205).

or wherein:

the first immunoglobulin single variable domain is selected from one of the polypeptides of SEQ ID NOs: 3-10; and the second immunoglobulin single variable domain is selected from one of the polypeptides of SEQ ID NOs: 1-2;

the first immunoglobulin single variable domain consists of the amino acid sequence of SEQ ID NO: 1; and the second immunoglobulin single variable domain is selected from one of the polypeptides of SEQ ID NOs: 3-10;

the first immunoglobulin single variable domain consists of the amino acid sequence of SEQ ID NO: 1; and the second immunoglobulin single variable domain consists of the amino acid sequence of SEQ ID NO: 11; or the first immunoglobulin single variable domain consists of the amino acid sequence of SEQ ID NO: 11; and the second immunoglobulin single variable domain is selected from one of the polypeptides of SEQ ID NOs: 1-2.

6. The polypeptide according to claim 1, which comprises or consists of an amino acid sequence selected from the group consisting of SEQ ID NOs: 125, 130, 137, 139, and 140.

7. A polypeptide that specifically binds PcrV of Pseudomonas aeruginosa, comprising an immunoglobulin single variable domain that essentially consists of 4 framework regions and 3 complementarity determining regions (CDRs), in which:

CDR1 is the amino acid sequence of SEQ ID NO: 20; and
CDR2 is the amino acid sequence of SEQ ID NO: 38; and
CDR3 is the amino acid sequence of SEQ ID NO: 57; and
wherein the polypeptide does not comprise an immunoglobulin single variable domain that consists of 4 framework regions and 3 complementarity determining regions (CDR), in which:
CDR1 is the amino acid sequence of SEQ ID NO: 30; and
CDR2 is the amino acid sequence of SEQ ID NO: 49; and
CDR3 is the amino acid sequence of SEQ ID NO: 68.

8. The polypeptide according to claim 7, wherein the polypeptide comprises or consists of the amino acid sequence of SEQ ID NO: 1.

9. The polypeptide according to claim 7, wherein the polypeptide binds to full length PcrV (SEQ ID NO: 159) and shows reduced binding of 30-90%, relative to the binding to full length PcrV (SEQ ID NO: 159), or no binding to chimera 7 (SEQ ID NO: 205).

10. The polypeptide according to claim 7, wherein the polypeptide is a domain antibody, a single domain antibody a VHH, a humanized VHH, a partially humanized VHH, or a fully humanized VHH.

11. The polypeptide according to claim 1, further comprising one or more other groups, residues, moieties or binding units, optionally linked via one or more peptidic linkers.

12. The polypeptide according to claim 11, in which said one or more other groups, residues, moieties or binding units are selected from the group consisting of domain antibodies, partially humanized VHHs, and fully humanized VHHs.

13. The polypeptide according to claim 11, in which said one or more other groups, residues, moieties or binding units provide the polypeptide with increased half-life, compared to the corresponding polypeptide without said one or more other groups, residues, moieties or binding units, per se.

14. The polypeptide according to claim 13, in which said one or more other groups, residues, moieties or binding units that provide the polypeptide with increased half-life is selected from the group consisting of serum proteins fragments of serum proteins, binding units that can bind to serum proteins, an Fc portion, small proteins that can bind to serum proteins, and peptides that can bind to serum proteins.

15. The polypeptide according to claim 13, in which said one or more other binding units that provides the polypeptide with increased half-life are selected from the group consisting of binding units that can bind to serum albumin, optionally human serum albumin and binding units that can bind to a serum immunoglobulin, optionally IgG.

16. A composition comprising at least one polypeptide according to claim 1.

17. A composition according to claim 16, which is a pharmaceutical composition, that further comprises at least one pharmaceutically acceptable carrier, diluent or excipient and/or adjuvant, and that optionally comprises one or more further pharmaceutically active polypeptides and/or compounds.

18. The polypeptide according to claim 13, in which said one or more other binding units that provides the polypeptide with increased half-life are selected from the group consisting of binding units that can bind to human serum albumin and binding units that can bind to IgG.

* * * * *